United States Patent
Harriott et al.

(10) Patent No.: US 11,718,618 B2
(45) Date of Patent: Aug. 8, 2023

(54) SUBSTITUTED PYRIDO[2,1-A]ISOQUINOLINES AS VMAT2 INHIBITORS

(71) Applicant: Neurocrine Biosciences, Inc., San Diego, CA (US)

(72) Inventors: Nicole Harriott, San Diego, CA (US); Nicholas Pagano, San Diego, CA (US); Byron A. Boon, San Diego, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 0 days.

(21) Appl. No.: 18/096,073

(22) Filed: Jan. 12, 2023

(65) Prior Publication Data
US 2023/0159528 A1    May 25, 2023

Related U.S. Application Data

(63) Continuation of application No. PCT/US2022/021080, filed on Mar. 21, 2022.

(60) Provisional application No. 63/164,135, filed on Mar. 22, 2021.

(51) Int. Cl.
| | | |
|---|---|---|
| *A61K 31/4353* | (2006.01) | |
| *C07D 471/14* | (2006.01) | |
| *C07D 471/04* | (2006.01) | |
| *A61P 25/18* | (2006.01) | |

(52) U.S. Cl.
CPC ............ *C07D 471/04* (2013.01); *A61P 25/18* (2018.01)

(58) Field of Classification Search
CPC .......................... A61K 31/4353; C07D 471/14
USPC ............................................. 514/294; 546/94
See application file for complete search history.

(56) References Cited

U.S. PATENT DOCUMENTS

| | | | |
|---|---|---|---|
| 3,209,005 | A | 9/1965 | Brossi et al. |
| 7,897,768 | B2 | 3/2011 | Rishel et al. |
| 7,897,769 | B2 | 3/2011 | Amarasinghe et al. |
| 7,902,364 | B2 | 3/2011 | Rishel et al. |
| 7,910,738 | B2 | 3/2011 | Rishel et al. |
| 7,919,622 | B2 | 4/2011 | Amarasinghe et al. |
| 8,008,500 | B2 | 8/2011 | Rishel et al. |
| 8,013,161 | B1 | 9/2011 | Amarasinghe et al. |
| 8,039,627 | B2 | 10/2011 | Gano |
| 8,524,733 | B2 | 9/2013 | Gant et al. |
| 9,714,246 | B2 | 7/2017 | Ashweek et al. |
| 10,568,978 | B2 | 2/2020 | Cesati et al. |
| 10,668,030 | B2 | 6/2020 | Dwoskin et al. |
| 11,040,970 | B2 | 6/2021 | Harriott et al. |
| 11,051,777 | B2 | 7/2021 | Rosser et al. |
| 11,306,082 | B2 | 4/2022 | Li et al. |
| 2008/0108645 | A1 | 5/2008 | Tridgett et al. |
| 2010/0087475 | A1 | 4/2010 | Duffield et al. |
| 2016/0031840 | A1 | 2/2016 | Crooks et al. |
| 2020/0237688 | A1 | 7/2020 | Dwoskin et al. |
| 2020/0290948 | A1 | 9/2020 | Dwoskin et al. |
| 2021/0087191 | A1 | 3/2021 | Miller et al. |

FOREIGN PATENT DOCUMENTS

| | | |
|---|---|---|
| EP | 1716145 | 8/2008 |
| EP | 4015517 | 6/2022 |
| WO | WO 2005077946 | 8/2005 |
| WO | WO 2007130365 | 11/2007 |
| WO | WO 2008058261 | 5/2008 |
| WO | WO 2009070552 | 6/2009 |
| WO | WO 2010026436 | 3/2010 |
| WO | WO 2010044981 | 4/2010 |
| WO | WO 2011153157 | 12/2011 |
| WO | WO 2014047167 | 3/2014 |
| WO | WO 2014102593 | 7/2014 |
| WO | WO 2014120654 | 8/2014 |
| WO | WO 2014144064 | 9/2014 |
| WO | WO 2015077521 | 5/2015 |
| WO | WO 2015112707 | 7/2015 |
| WO | WO 2016127133 | 8/2016 |
| WO | WO 2017112857 | 6/2017 |
| WO | WO 2018195121 | 10/2018 |
| WO | WO 2018222549 | 12/2018 |
| WO | WO 2020086765 | 4/2020 |
| WO | WO 2021027792 | 2/2021 |
| WO | WO 2022232380 | 11/2022 |
| WO | WO 2023023593 | 2/2023 |

OTHER PUBLICATIONS

Behling et al., "Meta-Analysis: Efficacy and Tolerability of Vesicular Monoamine Transporter Type 2 Inhibitors in the Treatment of Tic Disorders," Movement Disorders, 2022, 37(4):684-693.

Benet et al., "Basic Principles of Pharmacokinetics," Toxicologic Pathology, 1995, 23(2):115-123.

Bergemann et al., "Olanzapine plasma concentration, average daily dose, and interaction with co-medication in schizophrenic patients," Pharmacopsychiatry, 2004, 37:63-68.

Boldt et al., "Synthesis of (+)-9-O-desmethyl-α-dihydrotetrabenazine, precursor for the high affinity VMAT2 imaging PET radioligand [$^{11}$C]-(+)-α-dihydrotetrabenazine," Organic Preparations and Procedures International, 2008, 40(4):379-384.

(Continued)

*Primary Examiner* — Douglas M Willis
(74) *Attorney, Agent, or Firm* — Fish & Richardson P.C.

(57) ABSTRACT

This disclosure relates generally to VMAT2 inhibitor compounds of Formula (Ia):

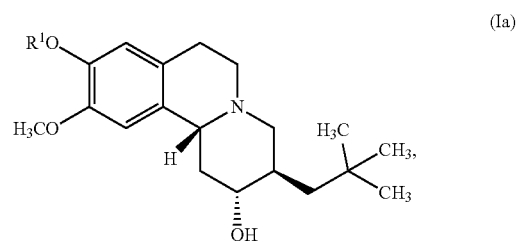

(Ia)

and pharmaceutically acceptable salts thereof, as well as compositions and methods related thereto.

28 Claims, 25 Drawing Sheets

(56) References Cited

OTHER PUBLICATIONS

Brar et al., "Pharmacokinetic and Pharmacologic Characterization of the Dihydrotetrabenazine Isomers of Deutetrabenazine and Valbenazine," Clinical Pharmacology in Drug Development, 2022, 10 pages.
Brossi et al., "No. 193: Syntheseversuche in der Emetin-Reihe. 3. Mitteilung. 2-Hydroxy-hydrobenzo[a]chinolizine," Helvetica Chimica Acta, 1958, 41(6):1793-1806 (with English Summary).
Caine, "Potassium tert-Butoxide—Dimethyl Sulfoxide," A list of General Abbreviations appears on the front Endpapers, Encyclopedia of Reagents for Organic Synthesis, 2001, 4 pages.
Chao et al., "Current Methods for Prediction of Human Hepatic Clearance Using In Vitro Intrinsic Clearance," Methods In Bioengineering—Alternative Technologies to Animal Testing, Artech House, 2010, 17 pages.
Chen et al., "Partial Rodent Genetic Models for Bipolar Disorder," Manuscript, Curr. Top. Behav. Neurosci., 2011, 5:89-106.
Cho et al., "Faster than kiss-and-run," Nature, 2013, 504(7479):220-221.
Christiansen et al., "Candidate gene polymorphisms in the serotonergic pathway: influence on depression symptomatology in an elderly population," Biological Psychiatry, 2007, 61:223-230.
Collier et al., "Radiosynthesis and in vivo evaluation of the pseudopeptide δ-opioid antagonist [$^{125}$I]ITIPP(Ψ)," J. Labelled Compd. Radiopharm., 1999, 42:S264-S266.
Demarest et al., "Comparison of dopamine synthesis regulation in the terminals of nigrostriatal, mesolimbic, tuberoinfundibular and tuberohypophyseal neurons," Journal of Neural Transmission, 1979, 46:263-277.
Dulcis et al., "Neurotransmitter switching in the adult brain regulates behavior," Science, 2013, 340(6131):449-453.
Fehr et al., "Association of VMAT2 gene polymorphisms with alcohol dependence," Journal of Neural Transmission, 2013, 120:1161-1169.
Gobira et al., "Animal models for predicting the efficacy and side effects of antipsychotic drugs," Revista Brasileira de Psiquiatria, 2013, 35:S132-S139.
Goswami et al., "Fluoroalkyl derivatives of dihydrotetrabenazine as positron emission tomography imaging agents targeting vesicular monoamine transporters," Nuclear Medicine and Biology, 2006, 33:685-694.
Grigoriadis et al., "Pharmacologic Characterization of Valbenazine (NBI-98854) and Its Metabolites," The Journal of Pharmacology and Experimental Therapeutics, 2017, 361:454-461.
Hao et al., "Pancreas-Specific Delivery of β-Cell Proliferating Small Molecules," ChemMedChem, 2016, 11:1129-1132.
Harriott et al., "VMAT2 Inhibitors and the Path to Ingrezza (Valbenazine)," Progress in Medicinal Chemistry, 2018, 57:87-111.
Hoare et al., "Conformational states of the corticotropin releasing factor 1 (CRF$_1$) receptor: detection, and pharmacological evaluation by peptide ligands," Peptides, 2003, 24(12):1881-1897.
Huang et al., "A Novel Potential Positron Emission Tomography Imaging Agent for Vesicular Monoamine Transporter Type 2," PLOS One, 2016, 11(9):e0161295, 11 pages.
Huang et al., "Effects of NBI-98782, a selective vesicular monoamine transporter 2 (VMAT2) inhibitor, on neurotransmitter efflux and phencyclidine-induced locomotor activity: Relevance to tardive dyskinesia and antipsychotic action," Pharmacology, Biochemistry and Behavior, 2020, 190:172872, 18 pages.
Kung et al., "In vivo imaging of vesicular monoamine transporter 2 in pancreas using an $^{18}$F epoxide derivative of tetrabenazine," Nuclear Medicine and Biology, 2008, 35:825-837.
Le Bas et al., "Radioiodinated analogs of EP 00652218 for the exploration of the tachykinin NK1 receptor by spect," J. Labelled Compd. Radiopharm., 2001, 44:S280-S282.
Lee et al., "In Vitro and in Vivo Studies of Benzisoquinoline Ligands for the Brain Synaptic Vesicle Monoamine Transporter," Journal of Medicinal Chemistry, 1996, 39:191-196.

Liu et al., "(+)-9-Benzyloxy-α-Dihydrotetrabenazine as an Important Intermediate for the VMAT2 Imaging Agents: Absolute Configuration and Chiral Recognition," Chirality, 2013, 25:215-223.
Login et al., "Tetrabenazine has properties of a dopamine receptor antagonist," Annals of Neurology, 1982, 12(3):257-262.
Lombardo et al., "Comprehensive Assessment of Human Pharmacokinetic Prediction Based on In Vivo Animal Pharmacokinetic Data, Part 2: Clearance," The Journal of Clinical Pharmacology, 2012, 53(2):178-191.
Milienne-Petiot et al., "The effects of reduced dopamine transporter function and chronic lithium on motivation, probabilistic learning, and neurochemistry in mice: Modeling bipolar mania," Neuropharmacology, 2017, 113:260-270.
Nag et al., "PET Imaging of VMAT2 with the Novel Radioligand [$^{18}$F]FE-DTBZ-d4 in Nonhuman Primates: Comparison with [$^{11}$C]DTBZ and [$^{18}$F]FEDTBZ," ACS Chemical Neuroscience, 2021, 12(24):4580-4586.
Near, "[$^3$H] Dihydrotetrabenazine binding to bovine striatal synaptic vesicles," Molecular Pharmacology, 1986, 30(3):252-257.
Nickell et al., "The vesicular monoamine transporter-2: an important pharmacological target for the discovery of novel therapeutics to treat methamphetamine abuse," Manuscript, Advances in Pharmacology, 2014, 69:71-106.
Niemann et al., "Real-World Experience With VMAT2 Inhibitors," Clinical Neuropharmacology, 2019, 42(2):37-41.
Nikolaus et al., "Boosted dopamine and blunted serotonin in Tourette syndrome—evidence from in vivo imaging studies," Reviews in the Neurosciences, 2022, 18 pages.
Obach et al., "The Prediction of Human Pharmacokinetic Parameters from Preclinical and In Vitro Metabolism Data," The Journal of Pharmacology and Experimental Therapeutics, 1997, 283(1):46-58.
Obach, "Prediction of human clearance of twenty-nine drugs from hepatic microsomal intrinsic clearance data: an examination of in vitro half-life approach and nonspecific binding to microsomes," Drug Metabolism and Disposition, 1999, 27(11):1350-1359.
Pettibone et al., "Tetrabenazine-induced depletion of brain monoamines: mechanism by which desmethylimipramine protects cortical norepinephrine," European Journal of Pharmacology, 1984, 102:431-436.
Price et al., "Solvent effects in the base-catalyzed isomerization of allyl to propenyl ethers," Journal of the American Chemical Society, 1961, 83(7):1773.
Reches et al., "Tetrabenazine, an amine-depleting drug, also blocks dopamine receptors in rat brain," Journal of Pharmacology and Experimental Therapeutics, 1983, 225(3):515-521.
Remington et al., "Tetrabenazine augmentation in treatment-resistant schizophrenia: a 12-week, double-blind, placebo-controlled trial," Journal of Clinical Psychopharmacology, 2012, 32(1):95-99.
Riedel et al., "Risperidone plasma levels, clinical response and side-effects," European Archives of Psychiatry and Clinical Neuroscience, 2005, 255:261-268.
Schafer et al., "Localization and expression of VMAT2 across mammalian species: a translational guide for its visualization and targeting in health and disease," Manuscript, Advances in Pharmacology, 2013, 68:319-334.
Scherman et al., "Characterization of the monoamine carrier of chromaffin granule membrane by binding of [2-$^3$H]dihydrotetrabenazine," Proc. Natl. Acad. Sci., 1983, 80:584-588.
Shamma et al., "The selective demethylation of quaternary ammonium salts," Tetrahedron Letters, 1966, 13:1375-1379.
Shen et al., "Safety and efficacy of tetrabenazine and use of concomitant medications during long-term, open-label treatment of chorea associated with Huntington's and other diseases," Tremor and Other Hyperkinetic Movements, 2013, 13 pages.
Skor et al., "Differences in Dihydrotetrabenazine Isomer Concentrations Following Administration of Tetrabenazine and Valbenazine," Drugs in R&D, 2017, 17:449-459.
Smith et al., "Clearance in drug design—miniperspective," Journal of Medicinal Chemistry, 2019, 62:2245-2255.

(56) References Cited

OTHER PUBLICATIONS

Smith et al., "The Adaptive In Combo Strategy," Comprehensive Medicinal Chemistry II, 2007, 5:957-969.
Solovieff et al., "Genetic association analysis of 300 genes identifies a risk haplotype in *SLC18A2* for post-traumatic stress disorder in two independent samples," Neuropsychopharmacology, 2014, 39:1872-1879.
Spina et al., "Relationship between plasma risperidone and 9-hydroxyrisperidone concentrations and clinical response in patients with schizophrenia," Psychopharmacology, 2001, 153:238-243.
Støve et al., "Inhibition of VMAT2 by β2-adrenergic agonists, antagonists, and the atypical antipsychotic ziprasidone," Communications Biology, 2022, 5:1283, 14 pages.
Susla et al., "Effect of Liver Disease on Pharmacokinetics," Principles of Clinical Pharmacology, 3rd Ed., Academic Press, 2012, pp. 81-96.
Tan et al., "Mood stabilizer lithium inhibits amphetamine-increased 4-hydroxynonenal-protein adducts in rat frontal cortex," International Journal of Neuropsychopharmacology, 2012, 15:1275-1285.
Teng et al., "[$^3$H] dihydrotetrabenazine binding and releases [$^3$H] dopamine from rat striatal synaptic vesicles: comparison with *d*-amphetamine," Journal of Neurochemistry, 1998, 71(1):258-265.
Turfus et al., "Chapter 25—Pharmacokinetics," Pharmacognosy, Fundamentals, Applications and Strategies, 2017, pp. 495-512.
Valvassori et al., "Lithium and valproate act on the GSK-3β signaling pathway to reverse manic-like behavior in an animal model of mania induced by ouabain," Neuropharmacology, 2017, 117:447-459.
Wadenberg et al., "The conditioned avoidance response test re-evaluated: is it a sensitive test for the detection of potentially atypical antipsychotics?," Neuroscience and Biobehavioral Reviews, 1999, 23:851-862.
Wang et al., "(+)-9-Trifluoroethoxy-α-Dihydrotetrabenazine as a Highly Potent Vesicular Monoamine Transporter 2 Inhibitor for Tardive Dyskinesia," Frontiers in Pharmacology, 2021, 12:770377, 16 pages.
Wang et al., "9-Cyclopropylmethoxy-dihydrotetrabenazine and its stereoisomers as vesicular monoamine transporter-2 inhibitors," Electronic publication ahead of print, Future Medicinal Chemistry, 2022, 13 pages.
Wang et al., "Tetrabenazine is neuroprotective in Huntington's disease mice," Molecular Neurodegeneration, 2010, 5:18, 12 pages.
Watanabe et al., "Ultrafast endocytosis at mouse hippocampal synapses," Nature, 2013, 504:242-247.
Wu et al., "The synthesis of precursor of FP- (+) DTBZ," Synthetic Communications, 2019, 49(22):3218-3225.
Xie et al., "Novel hypoglycemic dihydropyridones serendipitously discovered from O- versus C-alkylation in the synthesis of VMAT2 antagonists," Bioorganic & Medicinal Chemistry Letters, 2008, 18:5111-5114.
Xue et al., "Structural requirement of C11b chirality of tetrabenazine analogs as VMAT2 imaging ligands: synthesis and in vivo evaluation," Journal of Radioanalytical and Nuclear Chemistry, 2017, 313:419-428.
Yang et al., "Synthesis and analysis of dihydrotetrabenazine derivatives as novel vesicular monoamine transporter 2 inhibitors," European Journal of Medicinal Chemistry, 2021, 224:113718, 11 pages.
Yao et al., "Preparation and evaluation of tetrabenazine enantiomers and all eight stereoisomers of dihydrotetrabenazine as VMAT2 inhibitors," European Journal of Medicinal Chemistry, 2011, 46:1841-1848.
Young et al., "A reverse-translational approach to bipolar disorder: rodent and human studies in the Behavioral Pattern Monitor," Neuroscience & Biobehavioral Reviews, 2007, 31:882-896.
Young et al., "Investigating the mechanism(s) underlying switching between states in bipolar disorder," European Journal of Pharmacology. 2015, 759:151-162.
Zheng et al., "Synthesis and biological evaluation of 3-alkyl-dihydrotetrabenazine derivatives as vesicular monoamine transporter-2 (VMAT2) ligands," Bioorganic & Medicinal Chemistry Letters, 2011, 21:3435-3438.
Zubieta et al., "High vesicular monoamine transporter binding in asymptomatic bipolar I disorder: sex differences and cognitive correlates," American Journal of Psychiatry, 2000, 157:1619-1628.
Zubieta et al., "Vesicular monoamine transporter concentrations in bipolar disorder type I, schizophrenia, and healthy subjects," Biological Psychiatry, 2001, 49:110-116.

Representation of the crystal structure of Compound 2-B (3S,11bS)

Compound 2-B (3S,11bS)

(3S,11bS)-3-(2,2-dimethylpropyl)-9-hydroxy-10-methoxy-1H,2H,3H,4H,6H,7H,11bH-pyrido[2,1-a]isoquinolin-2-one Representation of the crystal structure of Compound 1-D (2R,3R,11bR)

Compound 1-D (2R,3R,11bR)
(2R,3R,11bR)-3-(2,2-dimethylpropyl)-10-methoxy-
1H,2H,3H,4H,6H,7H,11bH-pyrido[2,1-a]isoquinoline-2,9-diol Example 1B: Preparation of Compound 1-C (2R,3R,11bR)•DPTTA Salt Example 2: Compound 2-B (3R,11bR) and Compound 2-B (3S,11bS)

Example 7: Preparation of Compound 5-1

Example 8: Preparation of Compound 5-3

Example 9: Preparation of Compound 5-2

Example 10: Preparation of Compound 5-4

VMAT2 Ki values (nM) comparison

| Cmpd of Formula (I) vs Comparator Cmpd | Cmpd No. | Z group | VMAT Ki (nM) | Potency Improvement |
|---|---|---|---|---|
| (structure: trifluoroethoxy-dimethoxy tetrabenazine-like with neopentyl) | 4-1 | -CH(OH)- | 2.4 | 6.7x |
| | 4-1C | -N(Me)- | 16 | |
| (structure) | 4-13 | -CH(OH)- | 2.2 | 12.3x |
| | 4-13C | -N(Me)- | 27 | |
| (structure) | 4-14 | -CH(OH)- | 2.6 | 5.8x |
| | 4-14C | -N(Me)- | 15 | |

FIG. 15

VMAT2 Ki values (nM) comparison

| Cmpd of Formula (II) vs Comparator Cmpd | Cmpd No. | Z group | VMAT Ki (nM) | Potency Improvement |
|---|---|---|---|---|
| [structure with CF3 group] | 4-15 | –OH | 1.1 | 10.0x |
|  | 4-15C | N–Me | 11 |  |
| [structure with ethoxy group] | 4-17 | –OH | 1.1 | 8.1x |
|  | 4-17C | N–Me | 8.9 |  |
| [structure with fluoroethoxy group] | 4-18 | –OH | 5.5 | 5.3x |
|  | 4-18C | N–Me | 29 |  |

FIG. 16

VMAT2 Ki values (nM) comparison

| Cmpd of Formula (I) vs Comparator Cmpd | Cmpd No. | Z group | VMAT Ki (nM) | Potency Improvement |
|---|---|---|---|---|
|  | 4-22 | –OH | 14 | 6.6x |
| | 4-22C | –N–Me | 93 | |
|  | 4-26 | –OH | 14 | 12.1x |
| | 4-26C | –N–Me | 169 | |
|  | 4-28 | –OH | 0.48 | 7.1x |
| | 4-28C | –N–Me | 3.4 | |

VMAT2 Ki values (nM) comparison

| Cmpd of Formula (I) vs Comparator Cmpd | Cmpd No. | Z group | VMAT2 Ki (nM) | Potency improvement |
|---|---|---|---|---|
| (structure with oxetanyl ether) | 4-30 | CH(OH) | 12 | 20.9x |
| | 4-30C | N(Me) | 251 | |
| (structure with cyclobutyl ether) | 4-32 | CH(OH) | 0.59 | 5.8x |
| | 4-32C | N(Me) | 3.4 | |
| (structure with isopropyl ether) | 4-38 | CH(OH) | 3.7 | 7.0x |
| | 4-38C | N(Me) | 26 | |

FIG. 18

VMAT2 Ki values (nM) comparison

| Cmpd of Formula (I) vs Comparator Cmpd | Cmpd No. | Z group | VMAT Ki (nM) | Potency improvement |
|---|---|---|---|---|
|  | 4-39 |  | 12 | 15.1x |
| | 4-39C |  | 181 | |
|  | 5-1 |  | 6.6 | 4.4x |
| | 5-1C |  | 29 | |

VMAT2 Ki values (nM) comparison

| Cmpd of Formula (I) vs Comparator Cmpd | Cmpd No. | Z group | VMAT2 Ki (nM) | Potency Improvement |
|---|---|---|---|---|
| [structure with cyclopropyl-O] | 4-27 | −CH(OH)− | 1.0 | 4.4x |
|  | 4-27C | −N(Me)− | 4.4 | |
| [structure with cyclopropylmethyl-O] | 4-88 | −CH(OH)− | 0.68 | 4.1x |
|  | 4-88C | −N(Me)− | 2.8 | |
| [structure with cyclobutylmethyl-O] | 4-119 | −CH(OH)− | 0.29 | 9.7x |
|  | 4-119C | −N(Me)− | 2.8 | |

FIG. 20

VMAT2 Ki values (nM) comparison

| Cmpd of Formula (I) vs Comparator Cmpd | Cmpd No. | Z group | VMAT Ki (nM) | Potency Improvement |
|---|---|---|---|---|
| (structure with CF3-propoxy and methoxy substituents) | 4-120 | -CH(OH)- | 1.5 | 13.3x |
| | 4-120C | -CH(N-Me)- | 20 | |
| (structure with fluorocyclopropylmethoxy and methoxy substituents) | 4-121 | -CH(OH)- | 0.82 | 6.0x |
| | 4-121C | -CH(N-Me)- | 4.9 | |

FIG. 21

SUBSTITUTED PYRIDO[2,1-A]ISOQUINOLINES AS VMAT2 INHIBITORS

BACKGROUND

Technical Field

This disclosure relates generally to VMAT2 inhibitor compounds, compositions, and methods related thereto.

Description of the Related Technology

Dysregulation of dopaminergic systems is integral to several central nervous system (CNS) disorders, including neurological and psychiatric diseases and disorders. These neurological and psychiatric diseases and disorders include hyperkinetic movement disorders, and conditions, such as, schizophrenia and mood disorders. The transporter protein vesicular monoamine transporter-2 (VMAT2) plays an important role in presynaptic dopamine release and regulates monoamine uptake from the cytoplasm to the synaptic vesicle for storage and release.

(±)-Tetrabenazine ((±)-TBZ), has been used as a drug for decades. (±)-TBZ is reported as a potent, reversible inhibitor of catecholamine uptake by VMAT2 ($IC_{50}$=3.2 nM) (see, e.g., Scherman et al., Proc. Natl. Acad. Sci. USA, (1983) 80:584-8) and is currently used in the treatment of various hyperkinetic disorders. Inhibition of VMAT2 by (±)-TBZ results in depletion of brain monoamines in vivo (see, e.g., Pettibone et al., Eur. J. Pharmacol. (1984) 102:431-6). (±)-TBZ also inhibits presynaptic and postsynaptic dopamine receptors in rat brain (see, e.g., Login et al., (1982) Ann. Neurology 12:257-62; Reches et al., J. Pharmacol. Exp. Ther. (1983) 225:515-521). (±)-TBZ exhibits extensive first pass metabolism following oral administration to humans with little or no (±)-TBZ observed in systemic circulation. The pharmacological activity of (±)-TBZ is therefore thought to be mediated primarily by active metabolites. (±)-TBZ has two chiral centers and is a racemic mixture of two stereoisomers. (+)-TBZ has been determined to be rapidly and extensively metabolized in vivo by carbonyl reductase to four metabolic stereoisomers of 3-isobutyl-9,10-dimethoxy-1,3,4,6,7,11b-hexahydro-2H-pyrido[2,1-a]isoquinolin-2-ol, also known as dihydrotetrabenazine (DHTBZ). The inhibitory constants of these four metabolites for VMAT2 have been reported, such as, in WO2008/058261, Example 7. As shown, only two of the four DHTBZ isomers ([+]-alpha-DHTBZ and [+]-beta-DHTBZ) show significant potency as inhibitors of VMAT2.

| (±)-TBZ Metabolite | pKi | Ki |
| --- | --- | --- |
| [+]-alpha-DHTBZ (2R,3R,11bR) | 8.7 ± 0.2 (n = 6) | 1.9 nM |
| [+]-beta-DHTBZ (2S,3R,11bR) | 7.9 ± 0.1 (n = 5) | 13 nM |
| [−]-alpha-DHTBZ (2S,3S,11bS) | 6.7 ± 0.1 (n = 3) | 202 nM |
| [−]-beta-DHTBZ (2R,3S,11bS) | 6.1 ± 0.1 (n = 4) | 714 nM |

In patients administered (±)-TBZ, [−]-alpha-DHTBZ (2S,3S,11bS-DHTBZ) and [+]-beta-DHTBZ (2S,3R,11bR-DHTBZ) were the most abundant DHTBZ isomers, while [−]-beta-DHTBZ (2R,3S,11bS-DHTBZ) and [+]-alpha-DHTBZ (2R,3R,11bR-DHTBZ) were present as minor metabolites. The [+]-alpha-DHTBZ (2R,3R,11bR-DHTBZ) isomer was determined to be present in the least amount of all four isomers. Thus, [+]-beta-DHTBZ (2S,3R,11bR-DHTBZ) appears to be the major DHTBZ isomer contributing to the pharmacological activity of (±)-TBZ. Once formed, the half-life of [+]-beta-DHTBZ (2S,3R,11bR-DHTBZ) is relatively short (approximately 5 hours) which requires (±)-TBZ to have a sub-optimal (TID) dosing regimen.

(±)-TBZ has a narrow therapeutic window and its clinical use requires careful dose titration. Side effects associated with (±)-TBZ and/or its metabolites include neuroleptic malignant syndrome, drowsiness, fatigue, nervousness, anxiety, insomnia, agitation, confusion, orthostatic hypotension, nausea, dizziness, sedation, depression, akathisia, and Parkinsonism. Generally speaking, the probability of observing side effects is a function of the achieved plasma concentrations from a given dosing regimen. Compounds with a longer half-life ($t_{1/2}$) and lower clearance will have lower peak-to-trough fluctuations in plasma exposure given an equivalent dosing interval. These longer half-life compounds may exhibit improved tolerability by maintaining drug concentrations at levels needed for efficacy but below levels that may elicit side effects.

A fundamental and effective strategy to improve drug half-life is to reduce clearance. The term clearance describes the process of drug elimination from the body or from a single organ, defined as the volume of fluid cleared of drug from the body per unit of time. Clearance is a fundamental pharmacokinetic parameter and is commonly measured in drug research and development as this parameter impacts drug attributes such as half-life and, ultimately, the dosing regimen. When compound and dose selection is optimized, the benefits of small plasma-concentration fluctuations seen in compounds with low clearance include potentially reduced steady state peak concentrations, increased trough concentrations, and the prospect of improving medication adherence because of a possibly improved risk-benefit profile.

Despite the advances that have been made in this field, a need remains in the art for improved VMAT2 inhibitors, including compounds, compositions, and methods related thereto. The identification of long half-life/low clearance VMAT2 small molecules is advantageous for drug development, particularly when being developed for chronic administration. In certain disease populations where patient compliance and pill burden are an ongoing challenge, reduced dosing frequency is highly desirable and offers increased patient benefit.

The present disclosure fulfills these, such as, improved in vitro VMAT2 potency or improved pharmacokinetics, or both, and other needs, as evident in reference to the following disclosure.

SUMMARY

Some embodiments provide a compound of Formula (I):

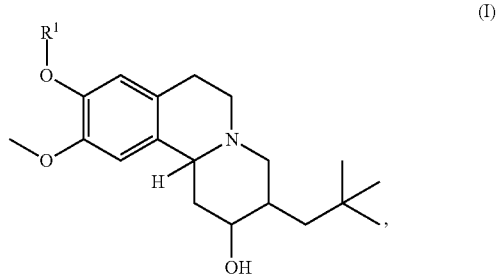

(I)

or a pharmaceutically acceptable salt thereof, wherein:

$R^1$ is $R^{2A}$, —$(CH_2)_m$—$R^{2B}$, or —$(CH_2)_n$—$OR^{2C}$;

$R^{2A}$ is $C_2$-$C_4$alkenyl, $C_1$-$C_6$alkyl, $C_3$-$C_8$cycloalkyl, or 4-7 membered heterocyclyl, each unsubstituted or substituted with one or more $R^A$;

each $R^A$ is independently selected from the group consisting of: $C_1$-$C_4$alkoxy, $C_1$-$C_4$alkyl, $C_1$-$C_4$alkylamino, $C_1$-$C_4$alkylsulfonyl, $C_2$-$C_4$dialkylamino, $C_2$-$C_4$dialkylsulfamoyl, halogen, halo$C_1$-$C_4$alkoxy, halo$C_1$-$C_4$alkyl, halo$C_2$-$C_4$dialkylamino, 4-7 membered heterocyclyl, —CN, —OH, and oxo;

$R^{2B}$ is aryl, $C_3$-$C_8$cycloalkyl, 5-10 membered heteroaryl, or 4-7 membered heterocyclyl, each unsubstituted or substituted with one or more $R^B$;

each $R^B$ is independently selected from the group consisting of: $C_1$-$C_4$alkyl, $C_1$-$C_4$alkylsulfonyl, $C_1$-$C_4$alkylsulfonyloxy, —CN, —CH$_2$CN, halogen, halo$C_1$-$C_4$alkyl, halo$C_1$-$C_4$alkylsulfonyl, oxo, and —OH;

$R^{2C}$ is $C_1$-$C_4$alkyl, $C_3$-$C_8$cycloalkyl, or 4-7 membered heterocyclyl, each unsubstituted or substituted with one or more $R^C$;

each $R^C$ is independently —CN or $C_3$-$C_6$cycloalkyl;

m is 0, 1, 2, 3, or 4; and n is 1, 2, or 3.

Also provided herein is a pharmaceutical product comprising a compound of Formula (I), or a pharmaceutically acceptable salt thereof.

Also provided herein is a pharmaceutical product selected from: a pharmaceutical composition, a formulation, a unit dosage form, and a kit; each comprising a compound of Formula (I), or a pharmaceutically acceptable salt thereof.

Also provided herein is a pharmaceutical product comprising a compound of Formula (I), or a pharmaceutically acceptable salt thereof, and at least one pharmaceutically acceptable excipient.

Also provided herein is a pharmaceutical product selected from: a pharmaceutical composition, a formulation, a unit dosage form, and a kit; each comprising a compound of Formula (I), or a pharmaceutically acceptable salt thereof, and at least one pharmaceutically acceptable excipient.

Also provided herein is a pharmaceutical composition comprising a compound of Formula (I), or a pharmaceutically acceptable salt thereof, and at least one pharmaceutically acceptable excipient.

Also provided herein is a compound of Formula (I), or a pharmaceutically acceptable salt thereof, for use in treating a neurological or psychiatric disease or disorder in a subject in need thereof.

Also provided herein is a method of inhibiting VMAT2 comprising contacting said VMAT2 with a compound of Formula (I).

Also provided herein is a method of reducing the level of monoamines in the central nervous system of a subject comprising administering to the subject an amount of a compound of Formula (I), or a pharmaceutically acceptable salt thereof, in an amount sufficient to lower the level of monoamines in the central nervous system relative to the level prior to administration.

Also provided herein is a method of treating a vesicular monoamine transporter-2 (VMAT2) disease or disorder in a subject in need thereof, comprising administering to the subject a compound of Formula (I), or a pharmaceutically acceptable salt thereof, a pharmaceutical product comprising a compound of Formula (I), or a pharmaceutically acceptable salt thereof, or a pharmaceutical composition comprising a compound of Formula (I), or a pharmaceutically acceptable salt thereof.

Also provided herein is a method of treating a neurological or psychiatric disease or disorder in a subject in need thereof, comprising administering to the subject a compound of Formula (I), or a pharmaceutically acceptable salt thereof, a pharmaceutical product comprising a compound of Formula (I), or a pharmaceutically acceptable salt thereof, or a pharmaceutical composition comprising a compound of Formula (I), or a pharmaceutically acceptable salt thereof.

Also provided herein is a method of treating a neurological or psychiatric disease or disorder in a subject comprising administering a compound of Formula (I), or a pharmaceutically acceptable salt thereof, to the subject.

Also provided herein is a method of treating a neurological or psychiatric disease or disorder in a subject in need thereof comprising administering a compound of Formula (I), or a pharmaceutically acceptable salt thereof, to the subject in combination with a further pharmaceutical agent selected from an antidepressant, an antipsychotic (typical or atypical), an antiepileptic, an antimicrobial, an antiarrhythmic, a mood stabilizer, and a gastrointestinal drug.

Also provided herein is a method of ameliorating one or more symptoms of a neurological or psychiatric disease or disorder, comprising administering to a subject in need thereof an effective amount of at least one compound of Formula (I), or a pharmaceutically acceptable salt thereof, wherein the neurological or psychiatric disease or disorder is selected from the group consisting of: hyperkinetic movement disorder, schizophrenia, schizoaffective disorder, a mood disorder, treatment-refractory obsessive-compulsive disorder, neurological dysfunction associated with Lesch-Nyhan syndrome, agitation associated with Alzheimer's disease, Fragile X syndrome or Fragile X-associated tremor-ataxia syndrome, autism spectrum disorder, Rett syndrome, and chorea-acanthocytosis.

Also provided herein is the use of a compound of Formula (I), or a pharmaceutically acceptable salt thereof, a pharmaceutical product comprising a compound of Formula (I), or a pharmaceutically acceptable salt thereof, a pharmaceutical composition comprising a compound of Formula (I), or a pharmaceutically acceptable salt thereof; in the manufacture of a medicament for treating a vesicular monoamine transporter-2 (VMAT2) disease or disorder.

Also provided herein is the use of a compound of Formula (I), or a pharmaceutically acceptable salt thereof, a pharmaceutical product comprising a compound of Formula (I), or a pharmaceutically acceptable salt thereof, a pharmaceutical composition comprising a compound of Formula (I), or a pharmaceutically acceptable salt thereof, in the manufacture of a medicament for treating a neurological or psychiatric disease or disorder.

Also provided herein is the use of a compound of Formula (I), or a pharmaceutically acceptable salt thereof, in the manufacture of a medicament for treating a neurological or psychiatric disease or disorder.

Also provided herein is the use of a compound of Formula (I), or a pharmaceutically acceptable salt thereof, for treating a neurological or psychiatric disease or disorder, wherein the neurological or psychiatric disease or disorder is selected from the group consisting of: hyperkinetic movement disorder, schizophrenia, schizoaffective disorder, a mood disorder, treatment-refractory obsessive-compulsive disorder, neurological dysfunction associated with Lesch-Nyhan syndrome, agitation associated with Alzheimer's disease, Fragile X syndrome or Fragile X-associated tremor-ataxia syndrome, autism spectrum disorder, Rett syndrome, and chorea-acanthocytosis.

Also provided herein is a compound of Formula (I), or a pharmaceutically acceptable salt thereof, a pharmaceutical product comprising a compound of Formula (I), or a pharmaceutically acceptable salt thereof, a pharmaceutical composition comprising a compound of Formula (I), or a pharmaceutically acceptable salt thereof, for use in a method of treatment of the human or animal body by therapy.

Also provided herein is a compound of Formula (I), or a pharmaceutically acceptable salt thereof, for use in a method of treatment of the human or animal body by therapy.

Also provided herein is a compound of Formula (I), or a pharmaceutically acceptable salt thereof, a pharmaceutical product comprising a compound of Formula (I), or a pharmaceutically acceptable salt thereof, a pharmaceutical composition comprising a compound of Formula (I), or a pharmaceutically acceptable salt thereof, for use in a method for treating a vesicular monoamine transporter-2 (VMAT2) disease or disorder.

Also provided herein is a compound of Formula (I), or a pharmaceutically acceptable salt thereof, a pharmaceutical product comprising a compound of Formula (I), or a pharmaceutically acceptable salt thereof, a pharmaceutical composition comprising a compound of Formula (I), or a pharmaceutically acceptable salt thereof; for use in a method for treating a neurological or psychiatric disease or disorder.

Also provided herein is a compound of Formula (I), or a pharmaceutically acceptable salt thereof, for treating a neurological or psychiatric disease or disorder.

In some embodiments, the neurological or psychiatric disease or disorder is selected from the group consisting of: hyperkinetic movement disorder, schizophrenia, schizoaffective disorder, a mood disorder, treatment-refractory obsessive-compulsive disorder, neurological dysfunction associated with Lesch-Nyhan syndrome, agitation associated with Alzheimer's disease, Fragile X syndrome or Fragile X-associated tremor-ataxia syndrome, autism spectrum disorder, Rett syndrome, and chorea-acanthocytosis.

In some embodiments, the vesicular monoamine transporter-2 (VMAT2) disease or disorder is selected from: an ataxias or spinal muscular atrophy; a chorea; a congenital malformation, deformation, or abnormality; a dementia; an oral cavity, salivary gland, or jaw disease; a dyskinesia; a dystonia; an endocrine, nutritional, or metabolic disease; an epilepsy; a habit or impulse disorder; a Huntington's disease or related disorder; a mood or psychotic disorder; a neurotic, stress-related, and somatoform disorder; a degenerative disease of the basal ganglia; an extrapyramidal and movement disorder; a neurological or psychiatric disease or disorder; a nervous system or motor function disorder; a Parkinson's/parkinsonism disorder; a pediatric-onset behavioral and emotional disorder; a pervasive developmental disorder; and a substance abuse or dependence disorder.

BRIEF DESCRIPTION OF THE DRAWINGS

As shown in FIG. 6, intermediates, Compound 1-B, Compound 1-C, and Compound 1-D (including the corresponding stereoisomers thereof), are novel and useful in the preparation of Compounds of Formula (I), and pharmaceutical salts thereof, as described herein.

FIG. 15 shows the VMAT2 Ki values (nM) between compounds provided herein (i.e., Compound 4-1, Compound 4-13, and Compound 4-14) and comparator compounds (i.e., Compound 4-1C, Compound 4-13C, and Compound 4-14C).

FIG. 16 shows the VMAT2 $K_i$ values (nM) between compounds provided herein (i.e., Compound 4-15, Compound 4-17, and Compound 4-18) and comparator compounds (i.e., Compound 4-15C, Compound 4-17C, and Compound 4-18C).

FIG. 18 shows the VMAT2 $K_i$ values (nM) between compounds provided herein (i.e., Compound 4-30, Compound 4-32, and Compound 4-38) and comparator compounds (i.e., Compound 4-30C, Compound 4-32C, and Compound 4-38C).

FIG. 20 shows the VMAT2 Ki values (nM) between compounds provided herein (i.e., Compound 4-27, Compound 4-88, and Compound 4-119) and comparator compounds (i.e., Compound 4-27C, Compound 4-88C, and Compound 4-119C).

FIG. 21 shows the VMAT2 Ki values (nM) between compounds provided herein (i.e., Compound 4-120 and Compound 4-121) and comparator compounds (i.e., Compound 4-120C and Compound 4-121C).

DETAILED DESCRIPTION

Definitions

Figure 1A:
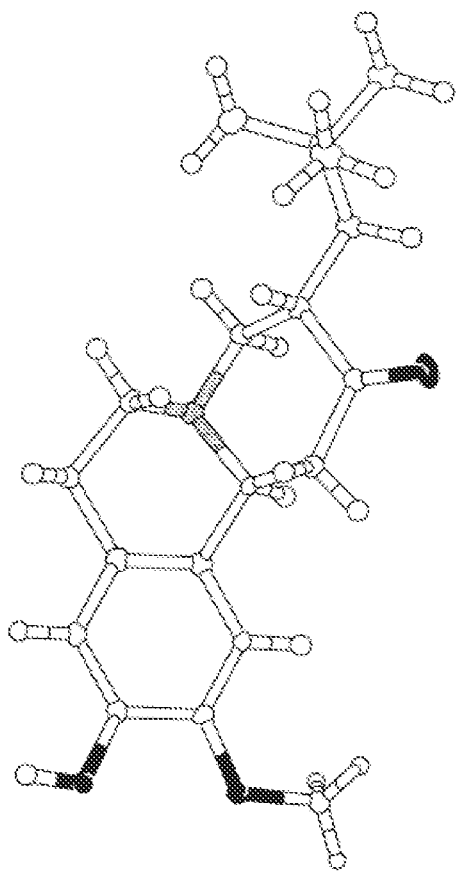
FIG. 1A shows a representation of the single crystal structure of (3S,11bS)-3-(2,2-dimethylpropyl)-9-hydroxy-10-methoxy-1H,2H,3H,4H,6H,7H,11bH-pyrido[2,1-a]isoquinolin-2-one (Compound 2-B (3S,11bS)).
Figure 1A:
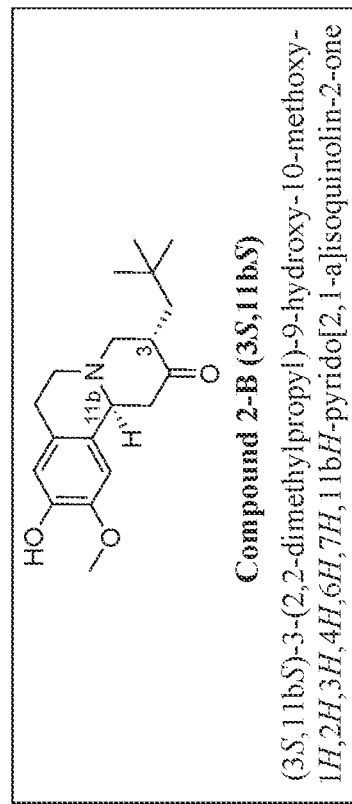

For clarity and consistency, the following definitions will be used throughout this patent document.

As used herein, "about" means ±20% of the stated value, and includes more specifically values of ±10%, ±5%, ±2%, and ±1% of the stated value.

As used herein, "administering" refers to providing a compound described herein or other therapy to a subject in a form that can be introduced into that subject's body in a therapeutically useful form and therapeutically useful amount, including, but not limited to: oral dosage forms, such as, tablets, capsules, syrups, suspensions, and the like; injectable dosage forms, such as, IV, IM, IP, and the like; transdermal dosage forms, including creams, jellies, powders, and patches; buccal dosage forms; inhalation powders, sprays, suspensions, and the like; and rectal suppositories.

A health care practitioner can directly provide a compound described herein to a subject in the form of a sample or can indirectly provide a compound to a subject by providing an oral or written prescription for the compound. Also, for example, a subject can obtain a compound by themselves without the involvement of a health care practitioner. When the compound is administered to the subject, the body is transformed by the compound in some way. When a compound described herein is provided in combination with one or more other agents, "administration" is understood to include the compound and other agents are administered at the same time or at different times. When the agents of a combination are administered at the same time, they can be administered together in a single composition, or they can be administered separately. The preferred method of administration can vary depending on various factors, e.g., the components of the pharmaceutical formulation, the site of the disease, and the severity of the disease.

The term "composition" refers to a compound or crystalline form thereof, including but not limited to, salts, solvates, and hydrates of a compound described herein, in combination with at least one additional component, such as, a composition obtained/prepared during synthesis, preformulation, in-process testing (e.g., TLC, HPLC, NMR samples), and the like.

The term, "compound" as used herein is meant to include all stereoisomers, geometric isomers, tautomers, and isotopic variants of the structures depicted. The term is also meant to refer to compounds described herein, regardless of how they are prepared, e.g., synthetically, through biological process (e.g., metabolism or enzyme conversion), or a combination thereof. All compounds, and pharmaceutically acceptable salts thereof, can be found together with other substances, such as, water and solvents (e.g., hydrates and solvates) or can be isolated. When in the solid state, the compounds described herein and salts thereof can occur in various forms and can, e.g., take the form of co-crystals or solvates, including hydrates. The compounds can be in any solid-state form, such as, a polymorph or solvate, so unless clearly indicated otherwise, reference in the specification to compounds and salts thereof should be understood as encompassing any solid-state form of the compound. In some embodiments, the compounds described herein, or salts thereof, are substantially isolated. By "substantially isolated" is meant that the compound is at least partially or substantially separated from the environment in which it was formed or detected. Partial separation can include, e.g., a composition enriched in the compounds described herein. Substantial separation can include compositions containing at least about 50%, at least about 60%, at least about 70%, at least about 80%, at least about 90%, at least about 95%, at least about 97%, or at least about 99% by weight of the compounds described herein, or salts thereof.

The term "solvate" as used herein refers to a solid-state form of a compound described herein, or a pharmaceutically acceptable salt thereof which includes a stoichiometric or non-stoichiometric amount of a solvent bound by non-covalent intermolecular forces. When the solvent is water, the solvate is a hydrate.

The term "hydrate" as used herein refers to a compound described herein or a salt thereof that further includes a stoichiometric or non-stoichiometric amount of water bound by non-covalent intermolecular forces.

The term "in need of treatment" and the term "in need thereof" when referring to treatment are used interchangeably to mean a judgment made by a caregiver (e.g. physician, nurse, nurse practitioner, etc. in the case of humans; veterinarian in the case of animals, including non-human mammals) that a subject or animal requires or will benefit from treatment. This judgment is made based on a variety of factors that are in the realm of a caregiver's expertise, but that includes the knowledge that the subject or animal is ill, or will become ill, as the result of a disease, condition or disorder that is treatable by the compound described herein. Accordingly, the compound described herein can be used in a protective or preventive manner; or compound described herein can be used to alleviate, inhibit, or ameliorate the disease, condition, or disorder.

The term "subject" refers to any animal, including mammals, such as, mice, rats, other rodents, rabbits, dogs, cats, swine, cattle, sheep, horses, primates, and humans. In the context of a clinical trial or screening or activity experiment the subject can be a healthy volunteer or healthy participant without an underlying VMAT2 mediated disorder or condition or a volunteer or participant that has received a diagnosis for a disorder or condition in need of medical treatment as determined by a health care professional. In the context outside of a clinical trial a subject under the care of a health care professional who has received a diagnosis for a disorder or condition is typically described as a subject.

The term "pediatric subject" refers to a subject under the age of 21 years at the time of diagnosis or treatment. The term "pediatric" can be further divided into various subpopulations including: neonates (from birth through the first month of life); infants (1 month up to two years of age); children (two years of age up to 12 years of age); and adolescents (12 years of age through 21 years of age (up to, but not including, the twenty-second birthday)) see e.g., Berhman et al., Textbook of Pediatrics, 15th Ed. Philadelphia: W.B. Saunders Company, 1996; Rudolph et al., Rudolph's Pediatrics, 21st Ed. New York: McGraw-Hill, 2002; and Avery et al., Pediatric Medicine, 2nd Ed. Baltimore: Williams & Wilkins; 1994.

The phrase "pharmaceutically acceptable" refers to compounds (and salts thereof), compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutical composition" refers to a specific composition comprising at least one active ingredient; including but not limited to, salts, solvates, and hydrates of compounds described herein, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The terms "prevent", "preventing", and "prevention" refer to the elimination or reduction of the occurrence or onset of one or more symptoms associated with a particular disorder. For example, the terms "prevent", "preventing", and "prevention" can refer to the administration of therapy on a prophylactic or preventative basis to a subject who may ultimately manifest at least one symptom of a disorder but who has not yet done so. Such subjects can be identified on the basis of risk factors that are known to correlate with the subsequent occurrence of the disease, such as, the presence of a biomarker. Alternatively, prevention therapy can be administered as a prophylactic measure without prior identification of a risk factor. Delaying the onset of the at least one episode and/or symptom of a disorder can also be considered prevention or prophylaxis. In some embodiments, the subject can be a pediatric subject.

The terms "treat", "treating", and "treatment" refer to medical management of a disease, disorder, or condition of a subject (e.g., subject) (see, e.g., Stedman's Medical Dictionary). In general, an appropriate dose and treatment regimen provide the VMAT2 inhibitor in an amount sufficient to provide therapeutic benefit. Therapeutic benefit for subjects to whom the VMAT2 inhibitor compound(s) described herein are administered, includes, for example, an improved clinical outcome, wherein the object is to prevent or slow or retard (lessen) an undesired physiological change associated with the disease, or to prevent or slow or retard (lessen) the expansion or severity of such disease. The effectiveness of one or more VMAT2 inhibitors can include beneficial or desired clinical results that comprise, but are not limited to, abatement, lessening, or alleviation of symptoms that result from or are associated with the disease to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival. In some embodiments, the subject can be a pediatric subject.

The term "therapeutically effective amount" refers to the amount of the compound described herein, or a pharmaceutically acceptable salt thereof, or an amount of a pharmaceutical composition comprising the compound described herein or a pharmaceutically acceptable salt thereof, that elicits the biological or medicinal response in a tissue, system, animal, or human that is being sought by a subject, researcher, veterinarian, medical doctor, or other clinician or caregiver, which can include one or more of the following:

(1) preventing the disorder, for example, preventing a disease, condition, or disorder in a subject who can be predisposed to the disease, condition, or disorder but does not yet experience or display the relevant pathology or symptomatology;

(2) inhibiting the disorder, for example, inhibiting a disease, condition, or disorder in a subject who is experiencing or displaying the relevant pathology or symptomatology (i.e., arresting further development of the pathology and/or symptomatology); and (3) ameliorating the disorder, for example, ameliorating a disease, condition, or disorder in a subject who is experiencing or displaying the relevant pathology or symptomatology (i.e., reversing the pathology and/or symptomatology).

As used herein, the term "contacting" refers to the bringing together of indicated moieties in an in vitro system or an in vivo system. For example, "contacting" the VMAT2 protein with a compound provided herein includes the administration of a compound provided herein (or a pharmaceutically acceptable salt thereof) to a subject, such as, a human, having a VMAT2 protein, as well as, for example, introducing a compound provided herein into a sample containing a cellular or purified preparation containing the VMAT2 protein.

Chemical Groups

Unless defined otherwise, all technical and scientific terms used herein have the same meaning as is commonly understood by one of ordinary skill in the art to which this disclosure belongs. All patents, applications, published applications, and other publications are incorporated by reference in their entirety.

In the event that there is a plurality of definitions for a term herein, those in this section prevail unless stated otherwise.

The term "n-membered" where n is an integer typically describes the number of ring-forming atoms in a moiety where the number of ring-forming atoms is n. For example, piperidinyl is an example of a 6-membered heterocyclyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of Formula (I), and pharmaceutically acceptable salts thereof, in which a variable appears more than once, each variable can be a different moiety independently selected from the group defining the variable. For example, where a structure is described having, for example, two R groups that are simultaneously present on the same compound, the two R groups can represent different moieties independently selected from the group defined for R, or the two R groups can be the same.

Whenever a group is described as being "substituted" that group can be substituted with one or more of the indicated substituents. Likewise, when a group is described as being "unsubstituted or substituted" if substituted, the substituent(s) can be selected from one or more of the indicated substituents. It is to be understood that substitution at a given atom is limited by valency.

As used herein, "$C_a$-$C_b$" in which "a" and "b" are integers refer to the number of carbon atoms in, for example, an alkyl, alkenyl, or alkynyl group, or the number of carbon atoms in the ring of a cycloalkyl, cycloalkenyl, or aryl group. That is, these groups can contain from "a" to "b", inclusive, carbon atoms. Thus, for example, a "$C_1$-$C_4$alkyl" group refers to all alkyl groups having from 1 to 4 carbons, that is, methyl ($CH_3$—), ethyl ($CH_3CH_2$—), n-propyl ($CH_3CH_2CH_2$—), iso-propyl (($CH_3$)$_2$CH—), n-butyl ($CH_3CH_2CH_2CH_2$—), iso-butyl (($CH_3$)$_2$CHCH$_2$—), sec-butyl ($CH_3CH_2CH(CH_3)$—), and tert-butyl (($CH_3$)$_3$C—). If no "a" and "b" are designated with regard to an alkyl, alkenyl, alkynyl, cycloalkyl, cycloalkenyl, or aryl group, the broadest range described in these definitions is to be assumed.

In addition to the foregoing, as used in the specification and appended claims, unless specified to the contrary, the following terms have the meaning indicated:

The term "alkenyl" refers to an alkyl group that contains in the straight or branched hydrocarbon chain one or more double bonds. Examples of alkenyl groups include allenyl, vinylmethyl, and ethenyl. Examples of alkenyl groups include: vinyl ($CH_2$=CH—), prop-1-en-2-yl ($CH_2$=C(Me)-), prop-1-en-1-yl (MeCH=CH—), allyl ($CH_2$=CHCH$_2$—), but-2-en-2-yl ($CH_3$CH=C(Me)-), but-1-en-1-yl (MeCH$_2$CH=CH—), but-1-en-2-yl ($CH_2$=C(Et)-), 2-methylprop-1-en-1-yl (Me$_2$C=CH—), but-3-en-2-yl ($CH_2$=CHCH(Me)-), 2-methylallyl ($CH_2$=C(Me)CH$_2$—), but-2-en-1-yl (MeCH=CHCH$_2$—), but-3-en-1-yl ($CH_2$=CHCH$_2$CH$_2$—), and buta-1,3-dien-1-yl ($CH_2$=CHCH=CH—). In some embodiments, an alkenyl group can be unsubstituted or substituted. In some embodiments, the alkenyl group can have 2 to 6 carbon atoms. In some embodiments, the alkenyl group can have 2 to 4 carbon atoms. The alkenyl group of the compounds can be designated as "$C_2$-$C_6$alkenyl", "$C_2$-$C_4$alkenyl", or similar designations.

The term "alkoxy" refers to the formula —OR wherein R is an alkyl defined herein. A non-limiting list of alkoxys are methoxy, ethoxy, n-propoxy, 1-methylethoxy (iso-propoxy), n-butoxy, iso-butoxy, sec-butoxy, and tert-butoxy. The alkoxy group can be "$C_1$-$C_6$alkoxy", "$C_1$-$C_4$alkoxy", or similar designations. In some embodiments, an alkoxy can be substituted or unsubstituted.

The term "alkyl" refers to a fully saturated straight or branched hydrocarbon radical. The alkyl group can have 1 to 20 carbon atoms (whenever it appears herein, a numerical range, such as, "1 to 20" refers to each integer in the given range; e.g., "1 to 20 carbon atoms" means that the alkyl group can consist of 1 carbon atom, 2 carbon atoms, 3 carbon atoms, etc., up to and including 20 carbon atoms. In some embodiments, the alkyl group can have 1 to 6 carbons (i.e., "$C_1$-$C_6$alkyl"). Some embodiments are 1 to 5 carbons (i.e., $C_1$-$C_5$alkyl), some embodiments are 1 to 4 carbons (i.e., $C_1$-$C_4$alkyl), some embodiments are 1 to 3 carbons (i.e., $C_1$-$C_3$alkyl), and some embodiments are 1 or 2 carbons. By way of example only, "$C_1$-$C_4$alkyl" indicates that there are one to four carbon atoms in the alkyl chain, i.e., the alkyl chain is selected from methyl, ethyl, n-propyl, iso-propyl, n-butyl, iso-butyl, sec-butyl, and tert-butyl. Examples of an alkyl group include: methyl, ethyl, n-propyl, iso-propyl, n-butyl, sec-butyl, iso-butyl, tert-butyl, pentyl, iso-pentyl, tert-pentyl, neo-pentyl, 1-methylbutyl [i.e., —CH(CH$_3$)CH$_2$CH$_2$CH$_3$], 2-methylbutyl [i.e., —CH$_2$CH(CH$_3$)CH$_2$CH$_3$], n-hexyl and the like. When one or more substituents are present on the alkyl group, the substituent(s) can be bonded at any available carbon atom. In some embodiments, an alkyl group can be substituted or unsubstituted.

The term "alkylamino" refers to an amino group (—NH$_2$) where the nitrogen atom is substituted with one alkyl group. The term "alkyl" has the same definition as described herein. The "alkylamino" group can have 1 to 4 carbon atoms (i.e., C$_1$-C$_4$alkylamino). Examples for an alkylamino group include, —NH(CH$_3$), —NH(CH$_2$CH$_3$), —NH(CH$_2$CH$_2$CH$_3$), and the like.

The term "alkynyl" refers to an alkyl group that contains in the straight or branched hydrocarbon chain one or more triple bonds. Examples of alkynyls include ethynyl and propynyl. An alkynyl group can be unsubstituted or substituted. In some embodiments, an alkynyl group can be unsubstituted or substituted. In some embodiments, the alkynyl group can have 2 to 6 carbon atoms. The alkenyl group of the compounds can be designated as "C$_2$-C$_6$alkynyl" or similar designations.

The term "alkylsulfonyl" refers to a radical consisting of an alkyl radical bonded to the sulfur of a sulfone radical of the formula: —S(=O)$_2$— wherein alkyl has the same definition as described herein. The "alkylsulfonyl" group can have 1 to 4 carbon atoms (i.e., C$_1$-C$_4$alkylsulfonyl). Examples include methylsulfonyl, ethylsulfonyl, n-propylsulfonyl, iso-propylsulfonyl, n-butylsulfonyl, sec-butylsulfonyl, iso-butylsulfonyl, t-butylsulfonyl, and the like.

The term "alkylsulfonyloxy" refers to a radical consisting of an alkyl radical bonded to the sulfur of a sulfonyloxy radical of the formula: —S(=O)$_2$O— wherein alkyl has the same definition as described herein. The "alkylsulfonyloxy" group can have 1 to 4 carbon atoms (i.e., C$_1$-C$_4$alkylsulfonyloxy). Examples include methylsulfonyloxy (CH$_3$S(=O)$_2$O—), ethylsulfonyloxy, n-propylsulfonyloxy, iso-propylsulfonyloxy, n-butylsulfonyloxy, sec-butylsulfonyloxy, iso-butylsulfonyloxy, t-butylsulfonyloxy, and the like.

The term "amino" refers to the group —NH$_2$.

The term "aryl" refers to an aromatic ring system containing 6, 10, or 14 carbon atoms that can contain a single ring, two fused rings or three fused rings, such as, phenyl, naphthalenyl, and phenanthrenyl. In some embodiments, the aryl group can have 6 or 10 carbon atoms (i.e., C$_6$ or C$_{10}$ aryl). In some embodiments, the aryl group is phenyl. When one or more substituents are present on the "aryl" ring, the substituent(s) can be bonded at any available ring carbon. In some embodiments, an aryl group can be substituted or unsubstituted.

The "C-amido" group refers to a "—C(=O)N(R$^A$R$^B$)" group that is connected to the rest of the molecule via a carbon atom, and in which R$^A$ and R$^B$ can be independently hydrogen, C$_1$-C$_6$alkyl, C$_2$-C$_6$alkenyl, C$_2$-C$_6$alkynyl, C$_3$-C$_7$cycloalkyl, C$_5$-C$_8$cycloalkenyl, C$_6$ or C$_{10}$ aryl, heteroaryl, or heterocyclyl.

The term "carbonyl" refers to the group —C(=O)—.

The term "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (i.e., an aromatic system), otherwise the group would be "aryl," as defined herein. When composed of two or more rings, the rings can be connected together in a fused, bridged, or spiro fashion. A cycloalkenyl can contain 3 to 12 atoms in the ring(s) or 3 to 8 atoms in the ring(s). In some embodiments, a cycloalkenyl group can be unsubstituted or substituted. In some embodiments, the cycloalkenyl group can have 4 to 8 carbon atoms (i.e., "C$_4$-C$_8$cycloalkenyl"). An example is cyclohexenyl.

The term "cycloalkyl" refers to a fully saturated all carbon mono- or multi-cyclic ring system. In some embodiments, the cycloalkyl is a monocyclic ring containing 3 to 8 carbon atoms (i.e., "C$_3$-C$_8$cycloalkyl"). In some embodiments, the cycloalkyl is a monocyclic ring containing 3 to 7 carbon atoms (i.e., "C$_3$-C$_7$cycloalkyl"). In some embodiments, the cycloalkyl is a monocyclic or bicyclic ring containing 3 to 7 carbon atoms (i.e., "C$_3$-C$_7$cycloalkyl"). Some embodiments contain 3 to 6 carbons (i.e., "C$_3$-C$_6$cycloalkyl"). Some embodiments contain 3 to 5 carbons. Some embodiments contain 5 to 7 carbons. Some embodiments contain 3 to 4 carbons. Examples include cyclopropyl, cyclobutyl, cyclopentyl, and cyclohexyl. Examples include cyclopropyl, cyclobutyl, cyclopentyl, bicyclo[1.1.1]pentane, and cyclohexyl. When one or more substituents are present on the cycloalkyl group, the substituent(s) can be bonded at any available carbon atom. In some embodiments, a cycloalkyl group can be substituted or unsubstituted.

The term "dialkylamino" refers to an amino group (—NH$_2$) where the nitrogen is substituted with two alkyl groups. The two alkyl groups can be the same or different. The term "alkyl" has the same definition as described herein. The "dialkylamino" group can have 1 to 4 carbon atoms (i.e., C$_2$-C$_4$dialkylamino) provided that the two alkyl groups do not exceed a total of 4 carbon atoms between the two groups. Examples include, —N(CH$_3$)$_2$, —N(CH$_3$)(CH$_2$CH$_3$), —N(CH$_3$)(CH$_2$CH$_2$CH$_3$), and the like.

The term "dialkylsulfamoyl" refers to a sulfonamide group (—S(=O)$_2$NH$_2$) where the nitrogen is substituted with two alkyl groups, the alkyl groups can be the same or different. The term "alkyl" has the same definition as described herein. The "dialkylsulfamoyl" group can have 1 to 4 carbon atoms (i.e., C$_2$-C$_4$dialkylsulfamoyl) provided that two alkyl groups do not exceed a total of 4 carbon atoms between the two alkyl groups. Examples include, —SO$_2$N(CH$_3$)$_2$, —SO$_2$N(CH$_3$)(CH$_2$CH$_3$), —SO$_2$N(CH$_3$)(CH$_2$CH$_2$CH$_3$), —SO$_2$N(CH$_2$CH$_3$)$_2$, —SO$_2$N(CH$_2$CH$_3$)(CH$_2$CH$_2$CH$_3$), and the like.

The term "haloalkoxy" refers to an alkoxy group in which one or more of the hydrogen atoms are replaced by a halogen (e.g., mono-haloalkoxy, di-haloalkoxy, and tri-haloalkoxy). Such groups include but are not limited to, chloromethoxy, fluoromethoxy, difluoromethoxy, trifluoromethoxy, 1-chloro-2-fluoromethoxy, and 2-fluoroisobutoxy. In some embodiments, the haloalkoxy group can have 1 to 6 carbon atoms. The haloalkoxy group of the compounds can be designated as "haloC$_1$-C$_6$alkoxy", "haloC$_1$-C$_4$alkoxy", or similar designations.

The term "haloalkyl" refers to an alkyl group, as defined herein, wherein one or more hydrogen atoms of the alkyl group have been replaced by a halogen atom (e.g., mono-haloalkyl, di-haloalkyl, and tri-haloalkyl). In some embodiments, the haloalkyl group can have 1 to 6 carbons (i.e., "haloC$_1$-C$_6$alkyl"). The haloC$_1$-C$_6$alkyl can be fully substituted in which case it can be represented by the formula C$_n$L$_{2n+1}$, wherein L is a halogen and "n" is 1, 2, 3, 4, 5, or 6. When more than one halogen is present then they can be the same or different and selected from: fluorine, chlorine, bromine, and iodine. In some embodiments, haloalkyl contains 1 to 5 carbons (i.e., haloC$_1$-C$_5$alkyl). In some embodiments, haloalkyl contains 1 to 4 carbons (i.e., haloC$_1$-C$_4$alkyl). In some embodiments, haloalkyl contains 1 to 3 carbons (i.e., haloC$_1$-C$_3$alkyl). In some embodiments, haloalkyl contains 1 or 2 carbons. Examples of haloalkyl groups include fluoromethyl, difluoromethyl, trifluoromethyl, chlorodifluoromethyl, 1-fluoroethyl, 2,2,2-trifluoroethyl, pentafluoroethyl, 4,4,4-trifluorobutyl, and the like.

The term "haloalkylsulfonyl" refers to a radical consisting of a haloalkyl radical bonded to the sulfur of a sulfone radical of the formula: —S(═O)$_2$—, wherein haloalkyl has the same definition as described herein. The "haloalkylsulfonyl" group can have 1 to 4 carbon atoms (i.e., haloC$_1$-C$_4$alkylsulfonyl). Examples include fluoromethylsulfonyl, difluoromethylsulfonyl, trifluoromethylsulfonyl, chlorodifluoromethylsulfonyl, 1-fluoroethylsulfonyl, 2,2,2-trifluoroethylsulfonyl, pentafluoroethylsulfonyl, 4,4,4-trifluorobutylsulfonyl, and the like.

The term "halodialkylamino" refers to an amino group (—NH$_2$) where the nitrogen is substituted with either one alkyl group and one haloalkyl group, or two haloalkyl groups. When the nitrogen is substituted with two haloalkyl groups the groups can be the same or different. The terms "alkyl" and "haloalkyl" has the same definitions as described herein. The "halodialkylamino" group can have 1 to 4 carbon atoms (i.e., haloC$_2$-C$_4$dialkylamino) provided that the two groups do not exceed a total of 4 carbon atoms between the two groups. Examples include, —N(CH$_3$)(CF$_3$), —N(CH$_3$)(CF$_3$), —N(CF$_3$)$_2$, —N(CH$_3$)(CH$_2$CF$_3$), —N(CH$_2$CF$_3$)$_2$, and the like.

The term "halogen" or "halo" refers to fluoro, chloro, bromo, or iodo group. In some embodiments, halogen or halo is fluoro, chloro, or bromo. In some embodiments, halogen or halo is fluoro or chloro. In some embodiments, halogen or halo is fluoro.

The term "heteroaryl" refers to a monocyclic or fused multicyclic aromatic ring system and having at least one heteroatom in the ring system, that is, an element other than carbon, including but not limited to, nitrogen, oxygen, and sulfur. Some embodiments are "5-6 membered heteroaryl" and refers to an aromatic ring containing 5 to 6 ring atoms in a single ring and having at least one heteroatom in the ring system. Examples of heteroaryl rings include, but are not limited to, pyridyl, pyrimidinyl, pyrazinyl, pyridazinyl, triazinyl, furyl, quinolyl, isoquinolyl, thienyl, imidazolyl, thiazolyl, indolyl, isoindolyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, dibenzo[b,d]furan, dibenzo[b,d]thiophene, phenanthridinyl, benzimidazolyl, pyrrolyl, quinolinyl, isoquinolinyl, benzisoxazolyl, imidazo[1,2-b]thiazolyl, and the like. A heteroaryl group can be substituted or unsubstituted. In some embodiments, the heteroaryl group has 5 to 10 ring members or 5 to 7 ring members. The heteroaryl group can be designated as "5-7 membered heteroaryl," "5-10 membered heteroaryl," or similar designations. In some embodiments, the heteroaryl can be a substituted or unsubstituted C$_1$-C$_{13}$ five-, six-, seven, eight-, nine-, ten-, up to 14-membered monocyclic, bicyclic, or tricyclic ring system including 1 to 5 heteroatoms selected from nitrogen, oxygen, and sulfur. In some embodiments, the heteroaryl can be a substituted or unsubstituted C$_1$-C$_5$ five- or six-membered monocyclic ring including 1 to 5 heteroatoms selected from nitrogen, oxygen, and sulfur. In some embodiments, the heteroaryl can be a substituted or unsubstituted C$_5$-C$_9$ 8-, 9-, or 10-membered bicyclic ring system including 1 to 5 heteroatoms selected from nitrogen, oxygen, and sulfur. In some embodiments, the heteroaryl is a substituted or unsubstituted C$_5$-C$_9$ 8-, 9- or 10-membered heteroaryl. In some embodiments, the C$_5$-C$_9$ 8-, 9-, or 10-membered bicyclic heteroaryl is imidazo[2,1-b]thiazolyl, 1H-indolyl, isoindolyl, benzofuranyl, benzothienyl, benzimidazolyl, benzisoxazolyl, indazolyl, purinyl, quinolinyl, isoquinolinyl, quinoxalinyl, pyrido[3,4-b]pyrazinyl or pyrido[4,3-d]pyrimidinyl. In some embodiments, the heteroaryl is a substituted or unsubstituted C$_5$-C$_{13}$ 13- or 14-membered tricyclic ring system including 1 to 5 heteroatoms selected from nitrogen, oxygen, and sulfur. In some embodiments, the heteroaryl can be an azolyl, such as, imidazolyl, pyrazolyl, 1,2,3-triazolyl, 1,2,4-triazolyl, tetrazolyl, 1,2,4-thiadiazolyl, thiazolyl, isothiazolyl, oxazolyl, or isoxazolyl, each of which can be substituted or unsubstituted. In some embodiments, the heteroaryl is a C$_1$-C$_4$ 5-membered heteroaryl. In some embodiments, the C$_1$-C$_4$ 5-membered heteroaryl is furanyl, thienyl, 1,2,4-thiadiazolyl, 1,2,3-thiadiazolyl, isothiazolyl, thiazolyl, imidazolyl, pyrazolyl, isoxazolyl, oxazolyl, pyrrolyl, triazolyl, tetrazolyl. In some embodiments, the heteroaryl is a C$_3$-C$_5$ 6-membered heteroaryl. In some embodiments, the C$_3$-C$_5$ 6-membered heteroaryl is pyridinyl, pyrimidinyl, pyrazinyl, pyridazinyl, or triazinyl. In some embodiments, "5-10 membered heteroaryl" refers to: furanyl, thienyl, pyrrolyl, imidazolyl, oxazolyl, thiazolyl, isoxazolyl, pyrazolyl, isothiazolyl, oxadiazolyl, triazolyl, tetrazolyl, thiadiazolyl, pyridinyl, pyrazinyl, pyrimidinyl, pyridazinyl, quinoxalinyl, triazinyl, benzofuranyl, 1H-indolyl, benzo[b]thiophenyl, and the like. In some embodiments, "5-10 membered heteroaryl" refers to: pyrazinyl, pyridazinyl, pyridinyl, pyrimidinyl, 1H-indolyl, quinoxalinyl, thiadiazolyl, and the like. In some embodiments, "5-10 membered heteroaryl" refers to: pyrazinyl, pyridazinyl, pyridinyl, pyrimidinyl, 1H-indolyl, quinoxalinyl, thiadiazolyl, imidazo[4,5-c]pyridinyl, and the like. In some embodiments, a heteroaryl group can be substituted or unsubstituted.

The term "heterocyclyl" refers to a 3-, 4-, 5-, 6-, 7-, 8-, 9-, 10-, up to 18-membered monocyclic, bicyclic, and tricyclic ring system wherein carbon atoms together with from 1 to 5 heteroatoms constitute said ring system and optionally containing one or more unsaturated bonds situated in such a way, however, that a fully delocalized pi-electron system (aromatic system) does not occur in the monocyclic ring or in at least one ring of the bicyclic or tricyclic ring system. The heteroatom(s) is an element other than carbon including, but not limited to, oxygen, sulfur, and nitrogen. When composed of two or more rings, the rings can be joined together in a fused, bridged, or spiro fashion where the heteroatom(s) can be present in either a non-aromatic or aromatic ring in the ring system. In some embodiments, "4-7 membered heterocyclyl" refers to a saturated non-aromatic ring system containing 4 to 7 ring atoms, where at least one ring atom is a heteroatom. In some embodiments, "3-6 membered heterocyclyl" refers to a saturated non-aromatic ring radical containing 3 to 6 ring atoms, where at least one ring atom is a heteroatom. In some embodiments, "4-6 membered heterocyclyl" refers to a saturated non-aromatic ring radical containing 4 to 6 ring atoms, where at least one ring atom is a heteroatom. In some embodiments, the one or two heteroatoms in the ring system are selected independently from: O (oxygen) and N (nitrogen). In some embodiments, a heterocyclyl can include a carbonyl (C═O) group adjacent to a hetero atom, that is, be substituted with an oxo on a carbon adjacent to a hetero atom, where the substituted ring system is a lactam, lactone, cyclic imide, cyclic thioimide, or cyclic carbamate. Examples of unsubstituted or oxo substituted "heterocyclyl" groups include but are not limited to, aziridinyl, azetidinyl, tetrahydrofuranyl, 1,3-dioxinyl, 1,3-dioxanyl, 1,4-dioxanyl, 1,2-dioxolanyl, 1,3-dioxolanyl, 1,4-dioxolanyl, 1,3-oxathianyl, 1,4-oxathiinyl, 1,3-oxathiolanyl, 1,3-dithiolyl, 1,3-dithiolanyl, 1,4-oxathianyl, tetrahydro-1,4-thiazinyl, 2H-1,2-oxazinyl, maleimidyl, succinimidyl, dioxopiperazinyl, hydantoinyl, imidazolinyl, imidazolidinyl, isoxazolinyl, isoxazolidinyl, isoindolinyl, indolinyl, oxazolinyl, oxazolidinyl, oxazolidinonyl, thiazolinyl, thiazolidinyl, morpholinyl, oxiranyl, piperidinyl N-oxide, piperidinyl, piperazinyl, pyrrolidinyl, pyrrolidonyl, pyrrolidionyl, 4-piperidonyl, pyrazolinyl, pyrazolidinyl, 2-oxopyrrolidinyl, tetrahydropyranyl, 4H-pyranyl, tetrahydrothiopyranyl, 1,4-diazabicyclo[2.2.2]octane, 1,4-diazabicyclo[3.1.1]heptane, 2-azaspiro[3,3]heptane, 2,6-diazaspiro[3,3]heptane, 2-oxa-6-azaspiro[3,3]heptane, and their benzo-fused analogs (e.g., benzimidazolidinonyl, tetrahydroquinolinyl, and 3,4-methylenedioxyphenyl). The heterocyclyl group can be designated as "3-10 membered heterocyclyl" or similar designations. In some embodiments, the heterocyclyl can be a $C_2$-$C_{12}$ 3-, 4-, 5-, 6-, 7-, 8-, 9-, 10-, up to 13-membered monocyclic, bicyclic, or tricyclic ring system including 1 to 5 heteroatoms selected from nitrogen, oxygen, and sulfur. In some embodiments, the heterocyclyl can be a substituted or unsubstituted $C_2$-$C_6$ 3-, 4-, 5-, 6-, or 7-membered monocyclic ring including 1 to 5 heteroatoms selected from nitrogen, oxygen, and sulfur. In some embodiments, the heterocyclyl can be a substituted or unsubstituted $C_2$-$C_{10}$ 4-, 5-, 6-, 7-, 8-, 9-, 10-, or 11-membered bicyclic ring system including 1 to 5 heteroatoms selected from nitrogen, oxygen, and sulfur. In some embodiments, the heterocyclyl can be a substituted or unsubstituted $C_7$-$C_{12}$ 12- or 13-membered tricyclic ring system including 1 to 5 heteroatoms selected from nitrogen, oxygen, and sulfur. In some embodiments, the heteroatom(s) of six membered monocyclic heterocyclyls are selected from one up to three of O (oxygen), N (nitrogen), or S (sulfur), and the heteroatom(s) of five membered monocyclic heterocyclyls are selected from one or two heteroatoms selected from O (oxygen), N (nitrogen), or S (sulfur). In some embodiments, the heterocyclyl can be aziridinyl, azetidinyl, tetrahydrofuranyl, 1,3-dioxinyl, 1,3-dioxanyl, 1,4-dioxanyl, 1,2-dioxolanyl, 1,3-dioxolanyl, 1,3-oxathianyl, 1,4-oxathianyl, 1,3-oxathiolanyl, 1,3-dithiolyl, 1,3-dithiolanyl, 1,4-oxathianyl, tetrahydro-1,4-thiazinyl, imidazolinyl, imidazolidinyl, isoxazolinyl, isoxazolidinyl, isoindolinyl, indolinyl, oxazolinyl, oxazolidinyl, thiazolinyl, thiazolidinyl, morpholinyl, oxiranyl, piperidinyl, piperazinyl, pyrrolidinyl, pyrazolinyl, pyrazolidinyl, tetrahydropyranyl, tetrahydrothiopyranyl, 1,4-diazabicyclo[2.2.2]octane, 1,4-diazabicyclo[3.1.1]heptane, 2-azaspiro[3,3]heptane, 2,6-diazaspiro[3,3]heptane, tetrahydroquinolinyl, 1,2,3,4-tetrahydroisoquinolinyl, 1,2,3,4-tetrahydro-2,6-naphthyridinyl, 1,2,3,4-tetrahydro-2,7-naphthyridinyl, 1,2,3,4-tetrahydro-1,7-naphthyridinyl, 1,2,3,4-tetrahydro-1,6-naphthyridinyl, 5,6,7,8-tetrahydropyrido[2,3-d]pyrimidinyl, 5,6,7,8-tetrahydropyrido[3,4-d]pyrimidinyl, [1,3]dioxolo[4,5-c]pyridinyl, [1,3]dioxolo[4,5-b]pyridinyl, [1,3]dioxolo[4,5-d]pyrimidinyl, or 3,4-methylenedioxyphenyl. In some embodiments, the unsubstituted or substituted heterocyclyl can be selected from aziridinyl, azetidinyl, piperidinyl, morpholinyl, oxetanyl, piperazinyl, pyrrolidinyl, thiomorpholinyl, 2-piperidone, 1,1-dioxidothiomorpholinyl, oxolanyl (tetrahydrofuranyl), and oxanyl (tetrahydropyranyl). When one or more substituents are present on the heterocyclyl group, the substituent(s) can be bonded at any available carbon atom and/or heteroatom. In some embodiments, a heterocyclyl group can be substituted or unsubstituted.

The term "oxo" refers to the =O substituent.

The term "nitro" refers to a —NO$_2$ group.

The term "sulfamoyl" refers to the group —S(=O)$_2$NH$_2$.

As used herein, an "excipient" refers to a substance that is added to a composition to provide, without limitation, bulk, consistency, stability, binding ability, lubrication, disintegrating ability, etc., to the composition. A "diluent" is a type of excipient and refers to an ingredient in a pharmaceutical composition that lacks pharmacological activity but can be pharmaceutically necessary or desirable. For example, a diluent can be used to increase the bulk of a potent drug whose mass is too small for manufacture and/or administration. It can also be a liquid for the dissolution of a drug to be administered by injection, ingestion, or inhalation. A pharmaceutically acceptable excipient is a physiologically and pharmaceutically suitable non-toxic and inactive material or ingredient that does not interfere with the activity of the drug substance. Pharmaceutically acceptable excipients are well known in the pharmaceutical art and described, for example, in Rowe et al., Handbook of Pharmaceutical Excipients: A Comprehensive Guide to Uses, Properties, and Safety, 5th Ed., 2006, and in Remington: The Science and Practice of Pharmacy (Gennaro, 21st Ed. Mack Pub. Co., Easton, Pa. (2005)). Preservatives, stabilizers, dyes, buffers, and the like can be provided in the pharmaceutical composition. One skilled in this art can further formulate a compound as disclosed and described herein in an appropriate manner, and in accordance with accepted practices, such as, those disclosed in Remington, supra.

As used herein, a "dose" or "dosage" refers to the measured quantity of drug substance to be taken at one time by a subject. In certain embodiments, wherein the drug substance is not a free base or free acid, the quantity is the molar equivalent to the corresponding amount of free base or free acid.

As used herein, a "pharmaceutically acceptable salt" refers to salts of a compound having an acidic or basic moiety which are not biologically or otherwise undesirable for use in a pharmaceutical. In many cases, the compounds disclosed herein are capable of forming acid and/or base salts by virtue of the presence of an acidic or basic moiety (e.g. amino and/or carboxyl groups or groups similar thereto). Pharmaceutically acceptable acid addition salts can be formed by combining a compound having a basic moiety with inorganic acids and organic acids. Pharmaceutically acceptable base addition salts can be formed by combining a compound having an acidic moiety with inorganic and organic bases.

The compounds described herein can have one or more stereocenters. All stereoisomers, such as, enantiomers and diastereomers, are intended unless otherwise indicated. It is understood that, in any compound described herein having one or more chiral centers, if an absolute stereochemistry is not expressly indicated, then each center can independently be the (R)-configuration, or the (S)-configuration, or a mixture thereof. Thus, the compounds provided herein can be enantiomerically pure, enantiomerically enriched, a racemic mixture, diastereomerically pure, diastereomerically enriched, or a stereoisomeric mixture. Preparation of enantiomerically pure or enantiomerically enriched forms can be accomplished by resolution of racemic mixtures or by using enantiomerically pure or enriched starting materials or by stereoselective or stereospecific synthesis. Stereochemical definitions are available in E. L. Eliel, S. H. Wilen & L. N. Mander, Stereochemistry of Organic Compounds, John Wiley & Sons, Inc., New York, N.Y., 1994 which is incorporated herein by reference in its entirety. In some embodiments, where the compound described herein is chiral or otherwise includes one or more stereocenters, the compound can be prepared with an enantiomeric excess or diastereomeric excess of greater than about 75%, greater than about 80%, greater than about 85%, greater than about 90%, greater than about 95%, greater than about 99%, greater than about 99.5%, or greater than about 99.9%.

Resolution of racemic mixtures of compounds can be carried out by any of numerous methods known in the art. An example method includes fractional recrystallization using a chiral resolving organic acid with a racemic compound containing a basic group. Other chiral resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like. Similarly, fractional recrystallization using a chiral resolving base can be utilized with a racemic compound containing a basic group.

Resolution of racemic mixtures can also be carried out by elution on a chiral column. A suitable elution solvent composition can be determined by one skilled in the art.

In some embodiments, a compound described herein can be prepared having at least about 5%, at least about 10%, at least about 20%, at least about 30%, at least about 40%, at least about 50%, at least about 60%, at least about 70%, at least about 80%, at least about 90%, at least about 95%, at least about 99%, at least about 99.5%, or at least about 99.9% enantiomeric excess, or an enantiomeric excess within a range defined by any of the preceding numbers. In some embodiments, a compound described herein can be prepared having at least 5%, at least 10%, at least 20%, at least 30%, at least 40%, at least 50%, at least 60%, at least 70%, at least 80%, at least 90%, at least 95%, at least 99%, at least 99.5%, or at least 99.9% enantiomeric excess, or an enantiomeric excess within a range defined by any of the preceding numbers.

In some embodiments, a compound described herein can be prepared having at least about 5%, at least about 10%, at least about 20%, at least about 30%, at least about 40%, at least about 50%, at least about 60%, at least about 70%, at least about 80%, at least about 90%, at least about 95%, at least about 99%, at least about 99.5%, or at least about 99.9% diastereomeric excess, or a diastereomeric excess within a range defined by any of the preceding numbers. In some embodiments, a compound described herein can be prepared having at least 5%, at least 10%, at least 20%, at least 30%, at least 40%, at least 50%, at least 60%, at least 70%, at least 80%, at least 90%, at least 95%, at least 99%, at least 99.5%, or at least 99.9% diastereomeric excess, or a diastereomeric excess within a range defined by any of the preceding numbers.

In addition, it is understood that, when a compound described herein contain one or more double bond(s) (e.g., C=C, C=N, and the like) or other centers of geometric asymmetry, and unless specified otherwise, it is understood that the compound includes both E and Z geometric isomers (e.g., cis or trans). Cis and trans geometric isomers of the compounds described herein can be isolated as a mixture of isomers or as separated isomeric form.

The compounds described herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H-, and 4H-1,2,4-triazole, 1H- and 2H-isoindole, and 1H- and 2H-pyrazole. Tautomeric forms can be in equilibrium or sterically locked into one form by appropriate substitution.

The compounds described herein, and their pharmaceutically acceptable salts, can be found together with other substances, such as, water and solvents, for example, in the form of hydrates or solvates. When in the solid-state, the compounds described herein and salts thereof can occur in various forms and can, e.g., take the form of solvates, including hydrates. The compounds can be in any solid-state form, such as, a crystalline form, amorphous form, solvated form, etc. and unless clearly indicated otherwise, reference in the specification to compounds and salts thereof should be understood as reading on any solid-state form of the compound.

The compounds described herein can be used in a neutral form, such as, a free acid or free base form. Alternatively, the compounds can be used in the form of pharmaceutically acceptable salts, such as, pharmaceutically acceptable addition salts of acids or bases.

In some embodiments, the compounds described herein, or salts thereof, are substantially isolated. The phrase "substantially isolated" refers to the compound that is at least partially or substantially separated from the environment in which it was formed or detected. Partial separation can include, for example, a composition enriched in the compound described herein. Substantial separation can include compositions containing at least about 50%, at least about 60%, at least about 65%, at least about 70%, at least about 75%, at least about 80%, at least about 85%, at least about 90%, at least about 95%, at least about 97%, or at least about 99% by weight of the compound described herein, or salt thereof.

Isotopes

The compounds disclosed and described herein allow and embrace atoms at each position of the compound independently to have: 1) an isotopic distribution for a chemical element in proportional amounts to those usually found in nature or 2) an isotopic distribution in proportional amounts different to those usually found in nature unless the context clearly dictates otherwise. A particular chemical element has an atomic number defined by the number of protons within the atom's nucleus. Each atomic number identifies a specific chemical element, but not the isotope; an atom of a given element can have a wide range in its number of neutrons. The number of both protons and neutrons in the nucleus is the atom's mass number, and each isotope of a given element has a different mass number. Compounds wherein one or more atoms have an isotopic distribution for a chemical element in proportional amounts different to those usually found in nature is commonly referred to as being isotopically-labeled. Each chemical element as represented in a compound structure can include any isotopic distribution of said element. For example, in a compound structure a hydrogen atom can be explicitly disclosed or understood to be present in the compound. At any position of the compound that a hydrogen atom can be present, the hydrogen atom can be an isotopic distribution of hydrogen, including but not limited to protium ($^1$H) and deuterium ($^2$H) in proportional amounts to those usually found in nature and in proportional amounts different to those usually found in nature. Thus, reference herein to a compound encompasses all potential isotopic distributions for each atom unless the context clearly dictates otherwise. Examples of isotopes include isotopes of hydrogen, carbon, nitrogen, oxygen, phosphorous, sulfur, fluorine, chlorine, bromine, and iodine. As one of skill in the art would appreciate, any of the compounds as disclosed and described herein can include radioactive isotopes. Accordingly, also contemplated is use of compounds as disclosed and described herein, wherein one or more atoms have an isotopic distribution different to those usually found in nature, such as, having $^2$H or $^3$H in greater proportion, or $^{11}$C, $^{13}$C, or $^{14}$C in greater proportion than found in nature. By way of general example, and without limitation, isotopes of hydrogen include protium ($^1$H), deuterium ($^2$H), and tritium ($^3$H). Isotopes of carbon include carbon-11 ($^{11}$C), carbon-12 ($^{12}$C), carbon-13 ($^{13}$C), and carbon-14 ($^{14}$C). Isotopes of nitrogen include nitrogen-13 ($^{13}$N), nitrogen-14 ($^{14}$N), and nitrogen-15 ($^{15}$N). Isotopes of oxygen include oxygen-14 ($^{14}$O), oxygen-15 ($^{15}$O), oxygen-16 ($^{16}$O), oxygen-17 ($^{17}$O), and oxygen-18 ($^{18}$O). Isotope of fluorine include fluorine-17 ($^{17}$F), fluorine-18 ($^{18}$F), and fluorine-19 ($^{19}$F). Isotopes of phosphorous include phosphorus-31 ($^{31}$P), phosphorus-32 ($^{32}$P), phosphorus-33 ($^{33}$P), phosphorus-34 ($^{34}$P), phosphorus-35 ($^{35}$P), and phosphorus-36 ($^{36}$P). Isotopes of sulfur include sulfur-32 ($^{32}$S), sulfur-33 ($^{33}$S), sulfur-34 ($^{34}$S), sulfur-35 ($^{35}$S), sulfur-36 ($^{36}$S), and sulfur-38 ($^{38}$S). Isotopes of chlorine include chlorine-35 ($^{35}$Cl), chlorine-36 ($^{36}$Cl), and chlorine-37 ($^{37}$Cl). Isotopes of bromine include bromine-75 ($^{75}$Br), bromine-76 ($^{76}$Br), bromine-77 ($^{77}$Br), bromine-79 ($^{79}$Br), bromine-81 ($^{81}$Br), and bromine-82 ($^{82}$Br). Isotopes of iodine include iodine-123 ($^{123}$I), iodine-124 ($^{124}$I), iodine-125 ($^{125}$I) iodine-131 ($^{131}$I), and iodine-135 ($^{135}$I). In some embodiments, atoms at every position of the compound have an isotopic distribution for each chemical element in proportional amounts to those usually found in nature. In some embodiments, an atom in one position of the compound has an isotopic distribution for a chemical element in proportional amounts different to those usually found in nature (remainder atoms having an isotopic distribution for a chemical element in proportional amounts to those usually found in nature). In some embodiments, atoms in at least two positions of the compound independently have an isotopic distribution for a chemical element in proportional amounts different to those usually found in nature (remainder atoms having an isotopic distribution for a chemical element in proportional amounts to those usually found in nature). In some embodiments, atoms in at least three positions of the compound independently have an isotopic distribution for a chemical element in proportional amounts different to those usually found in nature (remainder atoms having an isotopic distribution for a chemical element in proportional amounts to those usually found in nature). In some embodiments, atoms in at least four positions of the compound independently have an isotopic distribution for a chemical element in proportional amounts different to those usually found in nature (remainder atoms having an isotopic distribution for a chemical element in proportional amounts to those usually found in nature). In some embodiments, atoms in at least five positions of the compound independently have an isotopic distribution for a chemical element in proportional amounts different to those usually found in nature (remainder atoms having an isotopic distribution for a chemical element in proportional amounts to those usually found in nature). In some embodiments, atoms in at least six positions of the compound independently have an isotopic distribution for a chemical element in proportional amounts different to those usually found in nature (remainder atoms having an isotopic distribution for a chemical element in proportional amounts to those usually found in nature).

Certain compounds, for example those having incorporated radioactive isotopes, such as, $^3$H and 4C, are also useful in drug or substrate tissue distribution assays. Tritium ($^3$H) and carbon-14 ($^{14}$C) isotopes are particularly preferred for their ease of preparation and detectability. Compounds with isotopes, such as, deuterium ($^2$H), in proportional amounts greater than usually found in nature can afford certain therapeutic advantages resulting from greater metabolic stability, such as, for example, increased in vivo half-life or reduced dosage requirements. Isotopically-labeled compounds can generally be prepared by performing procedures routinely practiced in the chemical art. Methods are readily available to measure such isotope perturbations or enrichments, such as, mass spectrometry, and for isotopes that are radio-isotopes additional methods are available, such as, radio-detectors used in connection with HPLC or GC.

As used herein, "isotopic variant" means a compound that contains an unnatural proportion of an isotope at one or more of the atoms that constitute such a compound. In certain embodiments, an "isotopic variant" of a compound contains unnatural proportions of one or more isotopes, including, but not limited to, protium ($^1$H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I), iodine-125 ($^{125}$I), iodine-127 ($^{127}$I), iodine-129 ($^{129}$I), and iodine-131 ($^{131}$I) In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^1$H), deuterium ($^2$H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), and oxygen-18 ($^{18}$O). In certain embodiments, an "isotopic variant" of a compound is in an unstable form, that is, radioactive. In certain embodiments, an "isotopic variant" of a compound described herein contains unnatural proportions of one or more isotopes, including, but not limited to, tritium (H), carbon-11 ($^{11}$C), carbon-14 ($^{14}$C), nitrogen-13 ($^{13}$N), oxygen-14 ($^{14}$O), and oxygen-15 ($^{15}$O). It will be understood that, in a compound as provided herein, any hydrogen can include $^2$H as the major isotopic form, as example, or any carbon include be $^{13}$C as the major isotopic form, as example, or any nitrogen can include $^{15}$N as the major isotopic form, as example, and any oxygen can include $^{18}$O as the major isotopic form, as example. In certain embodiments, an "isotopic variant" of a compound contains an unnatural proportion of deuterium ($^2$H).

With regard to the compounds provided herein, when a particular atomic position is designated as having deuterium or "D" or "d", it is understood that the abundance of deuterium at that position is substantially greater than the natural abundance of deuterium, which is about 0.015%. A position designated as having deuterium typically has a minimum isotopic enrichment factor of, in certain embodiments, at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation) at each designated deuterium position. Similarly, with regard to the compounds provided herein when any atomic position is designated as a specific isotope, it is understood that the abundance of the specific isotope at that position is substantially greater than the natural abundance of that isotope. A position designated as having a specific isotope typically has a minimum isotopic enrichment factor of, in certain embodiments, at least 52.5%, at least 60%, at least 67.5%, at least 75%, at least 82.5%, at least 90%, at least 95%, at least 97%, at least 99%, or at least 99.5% incorporation of the isotope at each designated position.

Synthetic methods for incorporating radio-isotopes into organic compounds are applicable to compound described herein and are well known in the art. These synthetic methods, for example, incorporating activity levels of tritium into target molecules, are as follows:

A. Catalytic Reduction with Tritium Gas: This procedure normally yields high specific activity products and requires halogenated or unsaturated precursors.

B. Reduction with Sodium Borohydride [$^3$H]: This procedure is rather inexpensive and requires precursors containing reducible functional groups, such as, aldehydes, ketones, lactones, esters, and the like.

C. Reduction with Lithium Aluminum Hydride [$^3$H]: This procedure offers products at almost theoretical specific activities. It also requires precursors containing reducible functional groups, such as, aldehydes, ketones, lactones, esters, and the like.

D. Tritium Gas Exposure Labeling: This procedure involves exposing precursors containing exchangeable protons to tritium gas in the presence of a suitable catalyst.

E. N-Methylation using Methyl Iodide [$^3$H]: This procedure is usually employed to prepare O-methyl or N-methyl ($^3$H) products by treating appropriate precursors with high specific activity methyl iodide ($^3$H). This method in general allows for higher specific activity, such as, for example, about 70-90 Ci/mmol.

Synthetic methods for incorporating activity levels of $^{125}$I into target molecules include:

A. Sandmeyer and like reactions: This procedure transforms an aryl amine or a heteroaryl amine into a diazonium salt, such as, a diazonium tetrafluoroborate salt and subsequently to $^{125}$I labeled compound using Na$^{125}$I. A representative procedure was reported by Zhu, G-D. and co-workers in J. Org. Chem., 2002, 67, 943-948.

B. Ortho $^{125}$Iodination of phenols: This procedure allows for the incorporation of $^{125}$I at the ortho position of a phenol as reported by Collier, T. L. and co-workers in J. Labelled Compd. Radiopharm., 1999, 42, S264-S266.

C. Aryl and heteroaryl bromide exchange with $^{125}$I: This method is generally a two-step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A representative procedure was reported by Le Bas, M.-D. and co-workers in J. Labelled Compd. Radiopharm., 2001, 44, S280-S282.

A radiolabeled form of a compound described herein can be used in a screening assay to identify/evaluate compounds. In general terms, a newly synthesized or identified compound (i.e., test compound) can be evaluated for its ability to reduce binding of a radiolabeled form of a compound disclosed herein to VMAT2. The ability of a test compound to compete with a radiolabeled form of a compound described herein for the binding to VMAT2 correlates to its binding affinity.

Compounds

Some embodiments provide a compound of Formula (I):

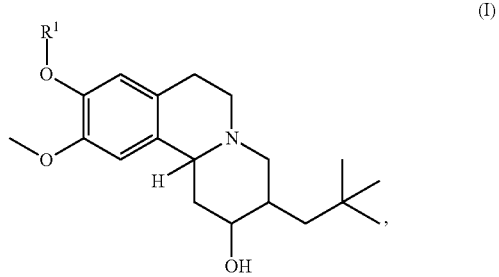

or a pharmaceutically acceptable salt thereof, wherein:

$R^1$ is $R^{2A}$, —(CH$_2$)$_m$—$R^{2B}$, or —(CH$_2$)$_n$—OR$^{2C}$;

$R^{2A}$ is C$_2$-C$_4$alkenyl, C$_1$-C$_6$alkyl, C$_3$-C$_8$cycloalkyl, or 4-7 membered heterocyclyl, each unsubstituted or substituted with one or more $R^A$;

each $R^A$ is independently selected from the group consisting of: C$_1$-C$_4$alkoxy, C$_1$-C$_4$alkyl, C$_1$-C$_4$alkylamino, C$_1$-C$_4$alkylsulfonyl, C$_2$-C$_4$dialkylamino, C$_2$-C$_4$dialkyl- sulfamoyl, halogen, haloC$_1$-C$_4$alkoxy, haloC$_1$-C$_4$alkyl, haloC$_2$-C$_4$dialkylamino, 4-7 membered heterocyclyl, —CN, —OH, and oxo;

$R^{2B}$ is aryl, C$_3$-C$_8$cycloalkyl, 5-10 membered heteroaryl, or 4-7 membered heterocyclyl, each unsubstituted or substituted with one or more $R^B$;

each $R^B$ is independently selected from the group consisting of: C$_1$-C$_4$alkyl, C$_1$-C$_4$alkylsulfonyl, C$_1$-C$_4$alkylsulfonyloxy, —CN, —CH$_2$CN, halogen, haloC$_1$-C$_4$alkyl, haloC$_1$-C$_4$alkylsulfonyl, oxo, and —OH;

$R^{2C}$ is C$_1$-C$_4$alkyl, C$_3$-C$_8$cycloalkyl, or 4-7 membered heterocyclyl, each unsubstituted or substituted with one or more $R^C$;

each $R^C$ is independently —CN or C$_3$-C$_6$cycloalkyl;

m is 0, 1, 2, 3, or 4; and n is 1,2, or 3.

Some embodiments provide a compound of Formula (I):

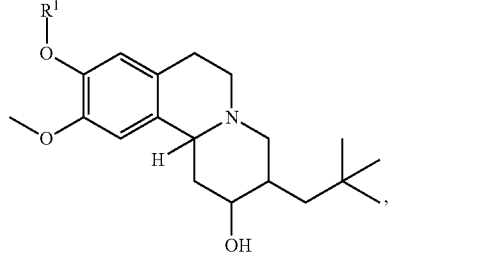

or a pharmaceutically acceptable salt thereof, wherein:

$R^1$ is $R^{2A}$, —(CH$_2$)$_m$—$R^{2B}$, or —(CH$_2$)$_n$—OR$^{2C}$;

$R^{2A}$ is C$_1$-C$_4$alkyl, unsubstituted or substituted with one or more $R^A$;

each $R^A$ is independently selected from the group consisting of: fluoro and —OH;

$R^{2B}$ is $C_3$-$C_8$cycloalkyl or 4-6 membered heterocyclyl, each unsubstituted or substituted with one or more $R^B$;

each $R^B$ is independently selected from the group consisting of: fluoro, —CN, —CH$_2$CN, and —OH;

$R^{2C}$ is $C_1$-$C_4$alkyl or $C_3$-$C_8$cycloalkyl, each unsubstituted or substituted with one or more $R^C$;

each $R^C$ is independently —CN or $C_3$-$C_6$cycloalkyl;

m is 0, 1, 2, or 3; and n is 1, 2, or 3.

In some embodiments, the compound of Formula (I) is a compound of Formula (Ia):

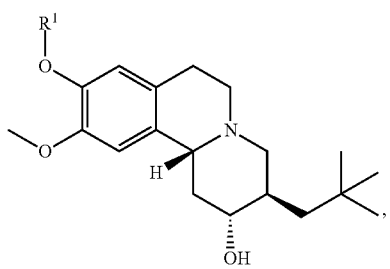

(Ia)

or a pharmaceutically acceptable salt thereof. The stereochemistry for a compound of Formula (Ia) is 2R,3R,11bR.

In some embodiments, the compound of Formula (I) is a compound of Formula (Ic):

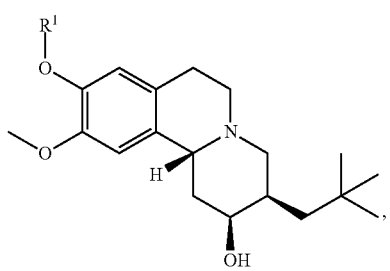

(Ic)

or a pharmaceutically acceptable salt thereof. The stereochemistry for a compound of Formula (Ic) is 2S,3R,11bR.

In some embodiments, the compound of Formula (I) is a compound of Formula (Ie):

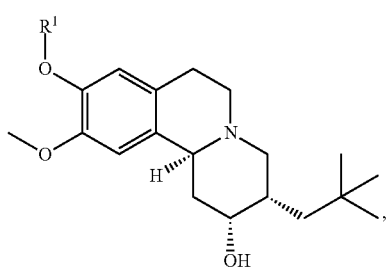

(Ie)

or a pharmaceutically acceptable salt thereof. The stereochemistry for a compound of Formula (Ie) is 2R,3S,11bS.

In some embodiments, the compound of Formula (I) is a compound of Formula (Ig):

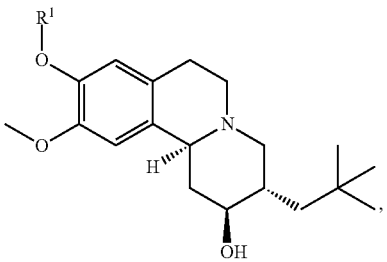

(Ig)

or a pharmaceutically acceptable salt thereof. The stereochemistry for a compound of Formula (Ig) is 2S,3S,11bS.

In some embodiments, $R^1$ is $R^{2A}$.

In some embodiments, $R^{2A}$ is $C_2$-$C_4$alkenyl, $C_1$-$C_6$alkyl, $C_3$-$C_8$cycloalkyl, or 4-7 membered heterocyclyl, each unsubstituted or substituted with one or more $R^A$, wherein $R^A$ is as described herein supra, and infra. In some embodiments, $R^{2A}$ is $C_2$-$C_4$alkenyl, $C_1$-$C_6$alkyl, $C_3$-$C_8$cycloalkyl, or 4-7 membered heterocyclyl, each unsubstituted or substituted with one or more $R^A$, each $R^A$ is independently selected from the group consisting of: $C_1$-$C_4$alkoxy, $C_1$-$C_4$alkyl, $C_1$-$C_4$alkylamino, $C_1$-$C_4$alkylsulfonyl, $C_2$-$C_4$dialkylamino, $C_2$-$C_4$dialkylsulfamoyl, halogen, halo$C_1$-$C_4$alkoxy, halo$C_1$-$C_4$alkyl, halo$C_2$-$C_4$dialkylamino, 4-7 membered heterocyclyl, —CN, —OH, and oxo. It is understood that when more than one $R^A$ is present, they may be the same or different. In some embodiments, when more than one $R^A$ is present, they are the same. In some embodiments, when more than one $R^A$ is present, they are different.

In some embodiments, $R^{2A}$ is $C_2$-$C_4$alkenyl, $C_1$-$C_6$alkyl, $C_3$-$C_8$cycloalkyl, or 4-7 membered heterocyclyl, each unsubstituted or substituted with one, two, three, or four $R^A$. In some embodiments, $R^{2A}$ is $C_2$-$C_4$alkenyl, $C_1$-$C_6$alkyl, $C_3$-$C_8$cycloalkyl, or 4-7 membered heterocyclyl, each unsubstituted or substituted with one $R^A$. In some embodiments, $R^{2A}$ is $C_2$-$C_4$alkenyl, $C_1$-$C_6$alkyl, $C_3$-$C_8$cycloalkyl, or 4-7 membered heterocyclyl, each unsubstituted or substituted with two $R^A$. In some embodiments, $R^{2A}$ is $C_2$-$C_4$alkenyl, $C_1$-$C_6$alkyl, $C_3$-$C_8$cycloalkyl, or 4-7 membered heterocyclyl, each unsubstituted or substituted with three $R^A$.

In some embodiments, $R^{2A}$ is $C_2$-$C_4$alkenyl, unsubstituted or substituted with one or more $R^A$, wherein $R^A$ is as described herein supra, and infra.

In some embodiments, $R^{2A}$ is methylallyl, unsubstituted or substituted with one or more $R^A$.

In some embodiments, $R^{2A}$ is prop-2-en-1-yl, unsubstituted or substituted with one or more methyl. In some embodiments, $R^{2A}$ is methylallyl.

In some embodiments, $R^{2A}$ is $C_1$-$C_6$alkyl, unsubstituted or substituted with one or more $R^A$, wherein $R^A$ is as described herein supra, and infra.

In some embodiments, $R^{2A}$ is $C_1$-$C_6$alkyl, unsubstituted or substituted with one or more $R^A$.

In some embodiments, $R^{2A}$ is n-butyl, ethyl, 2-ethylbutyl, n-propyl, propan-2-yl, 2-methylpropyl, methyl, or n-pentyl, each unsubstituted or substituted with one or more $R^A$.

In some embodiments, each $R^A$ is independently selected from the group consisting of: $C_1$-$C_4$alkoxy, $C_1$-$C_4$alkylamino, $C_1$-$C_4$alkylsulfonyl, $C_2$-$C_4$dialkylamino, $C_2$-$C_4$dialkylsulfamoyl, halogen, halo$C_1$-$C_4$alkoxy, halo$C_2$-$C_4$dialkylamino, 4-7 membered heterocyclyl, —CN, —OH, and oxo. In some embodiments, each $R^A$ is independently selected from the group consisting of: methoxy, methylamino, methylsulfonyl, dimethylamino, N,N-dimethylsulfamoyl, chloro, fluoro, trifluoromethoxy, methyl(2,2,2-trifluoroethyl)amino, methyl(trifluoromethyl)amino, morpholino, —CN, —OH, and oxo.

In some embodiments, $R^{2A}$ is n-butyl, ethyl, 2-ethylbutyl, n-propyl, propan-2-yl, 2-methylpropyl, methyl, or n-pentyl, each unsubstituted or substituted with one or more $R^A$ independently selected from the group consisting of: $C_1$-$C_4$alkoxy, $C_1$-$C_4$alkylamino, $C_1$-$C_4$alkylsulfonyl, $C_2$-$C_4$dialkylamino, $C_2$-$C_4$dialkylsulfamoyl, halogen, halo$C_1$-$C_4$alkoxy, halo$C_2$-$C_4$dialkylamino, 4-7 membered heterocyclyl, —CN, —OH, and oxo.

In some embodiments, $R^{2A}$ is 2,2,2-trifluoroethyl, 2,2-difluoroethyl, 2,2-difluoropropyl, 3,3,3-trifluoropropyl, ethyl, 2-fluoroethyl, 3-fluoropropyl, propan-2-yl, 1,1,1-trifluoropropan-2-yl, 2-hydroxy-2-methylpropyl, 3,3,3-trifluoro-2-hydroxypropyl, 3,3-difluoro-2-hydroxypropyl, methyl, 2-hydroxypropyl, 2-hydroxybutyl, 4,4,4-trifluoro-2-hydroxybutyl, 3,3,3-trifluoro-2-hydroxy-2-methylpropyl, 2,3-dihydroxypropyl, 3-hydroxypropyl, 2-hydroxyethyl, cyanomethyl, 2-(dimethylamino)-2-oxoethyl, 2-(methylamino)-2-oxoethyl, 2-hydroxy-3-methoxypropyl, 2-chloro-2,2-difluoroethyl, 2-hydroxy-3-(2,2,2-trifluoroethoxy)propyl, 2-(methyl(2,2,2-trifluoroethyl)amino)-2-oxoethyl, 3-(methylsulfonyl)propyl, (N,N-dimethylsulfamoyl)methyl, 2-methoxypropyl, 2-ethyl-2-hydroxybutyl, 3-chloro-3,3-difluoropropyl, 2-hydroxy-3-morpholinopropyl, 5,5,5-trifluoropentyl, or 4,4,4-trifluorobutyl.

In some embodiments, $R^{2A}$ is $C_1$-$C_4$alkyl, unsubstituted or substituted with one two, three, or four $R^A$; and each $R^A$ is independently selected from the group consisting of: fluoro and —OH. In some embodiments, $R^{2A}$ is $C_1$-$C_4$alkyl, unsubstituted or substituted with one, two, or three $R^A$; and each $R^A$ is independently selected from the group consisting of: fluoro and —OH. In some embodiments, $R^{2A}$ is $C_2$-$C_4$alkyl. In some embodiments, $R^{2A}$ is —CH$_2$CH$_3$, —CH$_2$CH$_2$CH$_3$, or —CH(CH$_3$)$_2$. In some embodiments, $R^{2A}$ is $C_1$-$C_4$alkyl substituted with one, two, or three fluoro. In some embodiments, $R^{2A}$ is $C_1$-$C_4$alkyl substituted with one, two, or three groups each independently selected from fluoro and a C-amido group.

In some embodiments, $R^{2A}$ is $C_1$-$C_4$alkyl substituted with one, two, or three fluoro. In some embodiments, $R^{2A}$ is —CH$_2$CH$_2$F, —CH$_2$CHF$_2$, —CH$_2$CF$_3$, —CH$_2$CH$_2$CHF$_2$, or —CH$_2$CH$_2$CF$_3$. In some embodiments, $R^{2A}$ is —CH$_2$CH$_2$CHF$_2$ or —CH$_2$CH$_2$CF$_3$.

In some embodiments, $R^{2A}$ is $C_3$-$C_8$cycloalkyl, unsubstituted or substituted with one or more $R^A$, wherein $R^A$ is as described herein supra, and infra.

In some embodiments, $R^{2A}$ is $C_3$-$C_8$cycloalkyl, unsubstituted or substituted with one or more $R^A$.

In some embodiments, $R^{2A}$ is cyclobutyl, cyclopropyl, cyclopentyl, or cyclohexyl, each unsubstituted or substituted with one or more $R^A$.

In some embodiments, each $R^A$ is independently selected from the group consisting of: halogen and halo$C_1$-$C_4$alkyl. In some embodiments, each $R^A$ is independently selected from the group consisting of: fluoro and trifluoromethyl.

In some embodiments, $R^{2A}$ is cyclobutyl, cyclopropyl, cyclopentyl, or cyclohexyl, each unsubstituted or substituted with one or more $R^A$ independently selected from the group consisting of: fluoro and trifluoromethyl. In some embodiments, $R^{2A}$ is cyclopropyl, cyclobutyl, 4-(trifluoromethyl)cyclohexyl, 2-fluorocyclopentyl, or 3,3-difluorocyclopentyl.

In some embodiments, $R^{2A}$ is 4-7 membered heterocyclyl, unsubstituted or substituted with one or more $R^A$, wherein $R^A$ is as described herein supra, and infra.

In some embodiments, $R^{2A}$ is azetidin-3-yl, oxetan-3-yl, or pyrrolidin-3-yl, each unsubstituted or substituted with one or more $R^A$.

In some embodiments, each $R^A$ is independently selected from the group consisting of: $C_1$-$C_6$alkyl, halo$C_1$-$C_4$alkyl, and oxo. In some embodiments, each $R^A$ is independently selected from the group consisting of: methyl, 2,2,2-trifluoroethyl, and oxo.

In some embodiments, $R^{2A}$ is azetidin-3-yl, oxetan-3-yl, or pyrrolidin-3-yl, each unsubstituted or substituted with one or more $R^A$ independently selected from the group consisting of: methyl, 2,2,2-trifluoroethyl, and oxo. In some embodiments, $R^{2A}$ is oxetan-3-yl, oxolan-3-yl (tetrahydrofuran-3-yl), 2-oxo-1-(2,2,2-trifluoroethyl)pyrrolidin-3-yl, or 1-methylazetidin-3-yl.

In some embodiments, $R^{2A}$ is methylallyl, n-butyl, ethyl, 2-ethylbutyl, n-propyl, propan-2-yl, 2-methylpropyl (isobutyl), methyl, n-pentyl, cyclobutyl, cyclopropyl, cyclopentyl, cyclohexyl, azetidin-3-yl, oxetan-3-yl, or pyrrolidin-3-yl; each unsubstituted or substituted with one or more $R^A$ independently selected from the group consisting of: methoxy, methylamino, methylsulfonyl, dimethylamino, N,N-dimethylsulfamoyl, chloro, fluoro, trifluoromethoxy, methyl(2,2,2-trifluoroethyl)amino, methyl(trifluoromethyl) amino, morpholino, —CN, —OH, trifluoromethyl, methyl, 2,2,2-trifluoroethyl, and oxo.

In some embodiments, $R^{2A}$ is methylallyl, 2,2,2-trifluoroethyl, 2,2-difluoroethyl, 2,2-difluoropropyl, 3,3,3-trifluoropropyl, ethyl, 2-fluoroethyl, 3-fluoropropyl, propan-2-yl, 1,1,1-trifluoropropan-2-yl, 2-hydroxy-2-methylpropyl, 3,3,3-trifluoro-2-hydroxypropyl, 3,3-difluoro-2-hydroxypropyl, methyl, 2-hydroxypropyl, 2-hydroxybutyl, 4,4,4-trifluoro-2-hydroxybutyl, 3,3,3-trifluoro-2-hydroxy-2-methylpropyl, 2,3-dihydroxypropyl, 3-hydroxypropyl, 2-hydroxyethyl, cyanomethyl, 2-(dimethylamino)-2-oxoethyl, 2-(methylamino)-2-oxoethyl, 2-hydroxy-3-methoxypropyl, 2-chloro-2,2-difluoroethyl, 2-hydroxy-3-(2,2,2-trifluoroethoxy)propyl, 2-(methyl(2,2,2-trifluoroethyl)amino)-2-oxoethyl, 3-(methylsulfonyl)propyl, (N,N-dimethylsulfamoyl)methyl, 2-methoxypropyl, 2-ethyl-2-hydroxybutyl, 3-chloro-3,3-difluoropropyl, 2-hydroxy-3-morpholinopropyl, cyclopropyl, cyclobutyl, 4-(trifluoromethyl)cyclohexyl, 2-fluorocyclopentyl, 3,3-difluorocyclopentyl, oxetan-3-yl, oxolan-3-yl (tetrahydrofuran-3-yl), 2-oxo-1-(2,2,2-trifluoroethyl)pyrrolidin-3-yl, 1-methylazetidin-3-yl, 5,5,5-trifluoropentyl, or 4,4,4-trifluorobutyl.

In some embodiments, $R^{2A}$ is methylallyl. In some embodiments, $R^{2A}$ is 2,2,2-trifluoroethyl. In some embodiments, $R^{2A}$ is 2,2-difluoroethyl. In some embodiments, $R^{2A}$ is 2,2-difluoropropyl. In some embodiments, $R^{2A}$ is 3,3,3-trifluoropropyl. In some embodiments, $R^{2A}$ is ethyl. In some embodiments, $R^{2A}$ is 2-fluoroethyl. In some embodiments, $R^{2A}$ is 3-fluoropropyl. In some embodiments, $R^{2A}$ is propan-2-yl. In some embodiments, $R^{2A}$ is 1,1,1-trifluoropropan-2-yl. In some embodiments, $R^{2A}$ is 2-hydroxy-2-methylpropyl. In some embodiments, $R^{2A}$ is 3,3,3-trifluoro-2-hydroxypropyl. In some embodiments, $R^{2A}$ is 3,3-difluoro-2-hydroxypropyl. In some embodiments, $R^{2A}$ is methyl. In some embodiments, $R^{2A}$ is 2-hydroxypropyl. In some embodiments, $R^{2A}$ is 2-hydroxybutyl. In some embodiments, $R^{2A}$ is 4,4,4-trifluoro-2-hydroxybutyl. In some embodiments, $R^{2A}$ is 3,3,3-trifluoro-2-hydroxy-2-methylpropyl. In some embodiments, $R^{2A}$ is 2,3-dihydroxypropyl. In some embodiments, $R^{2A}$ is 3-hydroxypropyl. In some embodiments, $R^{2A}$ is 2-hydroxyethyl. In some embodiments, $R^{2A}$ is cyanomethyl. In some embodiments, $R^{2A}$ is 2-(dimethylamino)-2-oxoethyl. In some embodiments, $R^{2A}$ is 2-(methylamino)-2- oxoethyl. In some embodiments, $R^{2A}$ is 2-hydroxy-3-methoxypropyl. In some embodiments, $R^{2A}$ is 2-chloro-2,2-difluoroethyl. In some embodiments, $R^{2A}$ is 2-hydroxy-3-(2,2,2-trifluoroethoxy)propyl. In some embodiments, $R^{2A}$ is 2-(methyl(2,2,2-trifluoroethyl)amino)-2-oxoethyl. In some embodiments, $R^{2A}$ is 3-(methylsulfonyl)propyl. In some embodiments, $R^{2A}$ is (N,N-dimethylsulfamoyl)methyl. In some embodiments, $R^{2A}$ is 2-methoxypropyl. In some embodiments, $R^{2A}$ is 2-ethyl-2-hydroxybutyl. In some embodiments, $R^{2A}$ is 3-chloro-3,3-difluoropropyl. In some embodiments, $R^{2A}$ is 2-hydroxy-3-morpholinopropyl. In some embodiments, $R^{2A}$ is cyclopropyl. In some embodiments, $R^{2A}$ is cyclobutyl. In some embodiments, $R^{2A}$ is 4-(trifluoromethyl)cyclohexyl. In some embodiments, $R^{2A}$ is 2-fluorocyclopentyl. In some embodiments, $R^{2A}$ is 3,3-difluorocyclopentyl. In some embodiments, $R^{2A}$ is oxetan-3-yl. In some embodiments, $R^{2A}$ is oxolan-3-yl (tetrahydrofuran-3-yl). In some embodiments, $R^{2A}$ is 2-oxo-1-(2,2,2-trifluoroethyl)pyrrolidin-3-yl. In some embodiments, $R^{2A}$ is 1-methylazetidin-3-yl. In some embodiments, $R^{2A}$ is 5,5,5-trifluoropentyl. In some embodiments, $R^{2A}$ is 4,4,4-trifluorobutyl.

In some embodiments, $R^1$ is —$(CH_2)_m$—$R^{2B}$.

In some embodiments, the compound of Formula (I) is a compound of Formula (III):

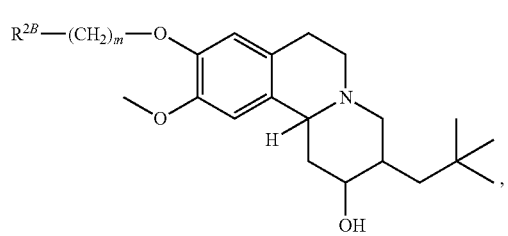

(III)

or a pharmaceutically acceptable salt thereof, wherein: m and $R^{2B}$ have the same definitions as described herein, and each can be selected independently from any of the embodiments as described herein, supra, and infra.

In some embodiments, the compound of Formula (I) is a compound selected from Formula (IIIa), Formula (IIIc), Formula (IIIe), or Formula (IIIg):

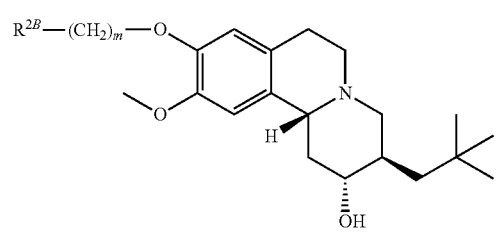

(IIIa)

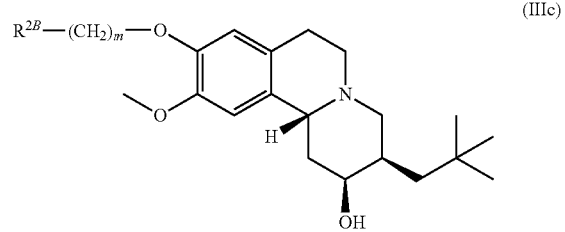

(IIIc)

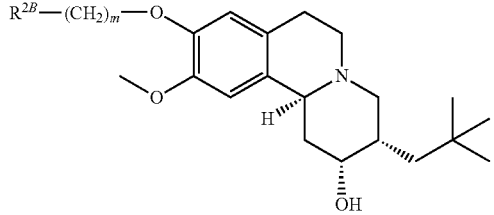

(IIIe)

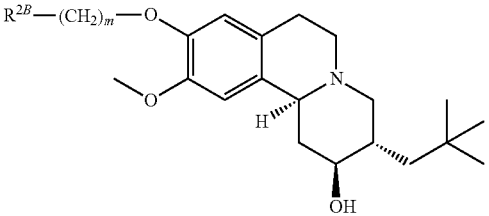

(IIIg)

or a pharmaceutically acceptable salt thereof, wherein: m and $R^{2B}$ have the same definitions as described herein, and each can be selected independently from any of the embodiments as described herein, supra, and infra.

In some embodiments, the compound of Formula (I) is a compound of Formula (IIIa). In some embodiments, the compound of Formula (I) is a compound of Formula (IIIc). In some embodiments, the compound of Formula (I) is a compound of Formula (IIIe). In some embodiments, the compound of Formula (I) is a compound of Formula (IIIg).

In some embodiments, m is 0, 1, 2, 3, or 4.
In some embodiments, m is 0, 1, 2, or 3.
In some embodiments, m is 0, 1, or 2.
In some embodiments, m is 0 or 1.
In some embodiments, m is 0.
In some embodiments, m is 1.
In some embodiments, m is 2.
In some embodiments, m is 3.
In some embodiments, m is 4.

In some embodiments, $R^{2B}$ is aryl, $C_3$-$C_8$cycloalkyl, 5-10 membered heteroaryl, or 4-7 membered heterocyclyl, each unsubstituted or substituted with one or more $R^B$. It is understood that when more than one $R^B$ is present, they may be the same or different. In some embodiments, when more than one $R^B$ is present, they are the same. In some embodiments, when more than one $R^B$ is present, they are different.

In some embodiments, $R^{2B}$ is aryl, $C_3$-$C_8$cycloalkyl, 5-10 membered heteroaryl, or 4-7 membered heterocyclyl, each unsubstituted or substituted with one, two, three, or four $R^B$.

In some embodiments, $R^{2B}$ is aryl, $C_3$-$C_8$cycloalkyl, 5-10 membered heteroaryl, or 4-7 membered heterocyclyl, each unsubstituted or substituted with one $R^B$. In some embodiments, $R^{2B}$ is aryl, $C_3$-$C_8$cycloalkyl, 5-10 membered heteroaryl, or 4-7 membered heterocyclyl, each unsubstituted or substituted with two $R^B$. In some embodiments, $R^{2B}$ is aryl, $C_3$-$C_8$cycloalkyl, 5-10 membered heteroaryl, or 4-7 membered heterocyclyl, each unsubstituted or substituted with three $R^B$. In some embodiments, $R^{2B}$ is aryl, $C_3$-$C_8$cycloalkyl, 5-10 membered heteroaryl, or 4-7 membered heterocyclyl, each unsubstituted or substituted with four $R^B$.

In some embodiments, $R^{2B}$ is aryl, unsubstituted or substituted with one or more $R^B$, wherein $R^B$ is as described herein supra, and infra.

In some embodiments, $R^{2B}$ is phenyl, unsubstituted or substituted with one or more $R^B$ In some embodiments, each $R^B$ is independently selected from the group consisting of: halogen, halo$C_1$-$C_4$alkyl, halo$C_1$-$C_4$alkylsulfonyl, and —CN. In some embodiments, each $R^B$ is independently selected from the group consisting of: fluoro, trifluoromethyl, (difluoromethyl)sulfonyl, and —CN.

In some embodiments, $R^{2B}$ is phenyl, unsubstituted or substituted with one or more $R^B$ independently selected from the group consisting of: fluoro, trifluoromethyl, (difluoromethyl)sulfonyl, and —CN. In some embodiments, $R^{2B}$ is phenyl, 4-fluorophenyl, 3-fluorophenyl, 4-(trifluoromethyl)phenyl, 4-((difluoromethyl)sulfonyl)phenyl, or 3-cyanophenyl.

In some embodiments, $R^{2B}$ is $C_3$-$C_8$cycloalkyl, unsubstituted or substituted with one or more $R^B$ wherein $R^B$ is as described herein supra, and infra.

In some embodiments, $R^{2B}$ is cyclobutyl, cyclopropyl, cyclohexyl, cyclopentyl, or bicyclo[1.1.1]pentan-1-yl, each unsubstituted or substituted with one or more $R^B$.

In some embodiments, each $R^B$ is independently selected from the group consisting of: $C_1$-$C_4$alkyl, $C_1$-$C_4$alkylsulfonyl, $C_1$-$C_4$alkylsulfonyloxy, —CN, —CH$_2$CN, halogen, halo$C_1$-$C_4$alkyl, and —OH.

In some embodiments, each $R^B$ is independently selected from the group consisting of: ethyl, methylsulfonyl, methylsulfonyloxy, —CN, —CH$_2$CN, fluoro, difluoromethyl, trifluoromethyl, and —OH.

In some embodiments, $R^{2B}$ is cyclobutyl, cyclopropyl, cyclohexyl, cyclopentyl, or bicyclo[1.1.1]pentan-1-yl, each unsubstituted or substituted with one or more $R^B$ independently selected from the group consisting of: ethyl, methylsulfonyl, methylsulfonyloxy, —CN, —CH$_2$CN, fluoro, difluoromethyl, trifluoromethyl, and —OH.

In some embodiments, $R^{2B}$ is 1-hydroxycyclobutyl, cyclopropyl, 1-cyanocyclopropyl, 1-fluorocyclopropyl, cyclobutyl, 1-cyanocyclobutyl, 1-(cyanomethyl)cyclopropyl, 4,4-difluoro-1-hydroxycyclohexyl, 2-fluorocyclopentyl, 3,3-difluorocyclopentyl, 3-fluorobicyclo[1.1.1]pentan-1-yl, 1-(difluoromethyl)cyclopropyl, 3-(trifluoromethyl)bicyclo[1.1.1]pentan-1-yl, 3-hydroxy-3-(trifluoromethyl)cyclobutyl, 1-(trifluoromethyl)cyclopentyl, 2-ethylcyclopropyl, 1-((methylsulfonyl)oxy)cyclopropyl, 1-(methylsulfonyl)cyclopropyl, or 2,2-difluorocyclopropyl.

In some embodiments, $R^{2B}$ is $C_3$-$C_6$cycloalkyl, unsubstituted or substituted with one or two $R^B$; and each $R^B$ is independently selected from the group consisting of: fluoro, CN, —CH$_2$CN, and —OH. In some embodiments, $R^{2B}$ is cyclopropyl, cyclobutyl, or cyclopentyl, each unsubstituted or substituted with one or two fluoro.

In some embodiments, $R^{2B}$ is 5-10 membered heteroaryl, unsubstituted or substituted with one or more $R^B$, wherein $R^B$ is as described herein supra, and infra.

In some embodiments, $R^{2B}$ is 1,2,4-oxadiazol-5-yl, 1,3-oxazol-2-yl, 1,3-oxazol-4-yl, 1H-imidazol-2-yl, 1H-pyrazol-5-yl, 1H-tetrazol-5-yl, furan-2-yl, imidazol-1-yl, isoxazol-3-yl, isoxazol-5-yl, pyrazin-2-yl, pyridin-2-yl, pyridin-3-yl, pyrimidin-2-yl, or thiazol-4-yl, each unsubstituted or substituted with one or more $R^B$.

In some embodiments, each $R^B$ is independently selected from the group consisting of $C_1$-$C_4$alkyl and —CN. In some embodiments, each $R^B$ is independently selected from the group consisting of methyl and —CN.

In some embodiments, $R^{2B}$ is 1,2,4-oxadiazol-5-yl, 1,3-oxazol-2-yl, 1,3-oxazol-4-yl, 1H-imidazol-2-yl, 1H-pyrazol-5-yl, 1H-tetrazol-5-yl, furan-2-yl, imidazol-1-yl, isoxazol-3-yl, isoxazol-5-yl, pyrazin-2-yl, pyridin-2-yl, pyridin-3-yl, pyrimidin-2-yl, or thiazol-4-yl, each unsubstituted or substituted with one or more $R^B$ independently selected from the group consisting of methyl and —CN. In some embodiments, $R^{2B}$ is imidazol-1-yl, 5-methyl-1,3-oxazol-2-yl, 5-cyanofuran-2-yl, isoxazol-3-yl, oxazol-4-yl, 6-cyanopyridin-2-yl, 5-cyanopyridin-2-yl, 1,2,4-oxadiazol-5-yl, pyridin-3-yl, pyrimidin-2-yl, isoxazol-5-yl, 1H-imidazol-2-yl, or 1H-tetrazol-5-yl.

In some embodiments, $R^{2B}$ is 4-7 membered heterocyclyl, unsubstituted or substituted with one or more $R^B$, wherein $R^B$ is as described herein supra, and infra.

In some embodiments, $R^{2B}$ is oxetan-3-yl, oxetan-2-yl, oxolan-3-yl (tetrahydrofuran-3-yl), pyrrolidin-1-yl, piperidin-4-yl, tetrahydro-2H-pyran-4-yl, azetidin-3-yl, 1,4-dioxepan-6-yl, or tetrahydro-2H-thiopyran-4-yl, unsubstituted or substituted with one or more $R^B$.

In some embodiments, each $R^B$ is independently selected from the group consisting of $C_1$-$C_4$alkyl, halogen, oxo, and —CN. In some embodiments, each $R^B$ is independently selected from the group consisting of methyl, fluoro, oxo, and —CN.

In some embodiments, $R^{2B}$ is oxetan-3-yl, oxetan-2-yl, oxolan-3-yl (tetrahydrofuran-3-yl), pyrrolidin-1-yl, piperidin-4-yl, tetrahydro-2H-pyran-4-yl, azetidin-3-yl, 1,4-dioxepan-6-yl, or tetrahydro-2H-thiopyran-4-yl, each unsubstituted or substituted with one or more $R^B$ independently selected from the group consisting of methyl, fluoro, oxo, and —CN. In some embodiments, $R^{2B}$ is 3-fluorooxetan-3-yl, oxetan-2-yl, oxetan-3-yl, oxolan-3-yl (tetrahydrofuran-3-yl), 3,3-difluoropyrrolidin-1-yl, 1-cyanopiperidin-4-yl, 1-methylazetidin-3-yl, 6-fluoro-1,4-dioxepan-6-yl, or 1,1-dioxidotetrahydro-2H-thiopyran-4-yl.

In some embodiments, $R^{2B}$ is a 4-5 membered monocyclic heterocyclyl having one ring forming heteroatom selected from oxygen and sulfur, wherein the 4-5 membered monocyclic heterocyclyl is unsubstituted or substituted with one or more $R^B$; and each $R^B$ is independently selected from the group consisting of: fluoro and —OH. In some embodiments, $R^{2B}$ is a $C_3$-$C_4$ 4-5 membered monocyclic heterocyclyl having one ring forming oxygen, wherein the 4-5 membered monocyclic heterocyclyl is unsubstituted or substituted with one or two $R^B$; and each $R^B$ is independently selected from the group consisting of: fluoro and —OH. In some embodiments, $R^{2B}$ is a 4-5 membered monocyclic heterocyclyl having one ring forming oxygen, wherein the 4-5 membered monocyclic heterocyclyl is unsubstituted or substituted with one or two fluoro. In some embodiments, $R^{2B}$ is a $C_3$-$C_4$ 4-5 membered monocyclic heterocyclyl having one ring forming heteroatom selected from oxygen and sulfur, wherein the $C_3$-$C_4$ 4-5 membered monocyclic heterocyclyl is unsubstituted or substituted with one or more $R^B$; and each $R^B$ is independently selected from the group consisting of: fluoro and —OH. In some embodiments, $R^{2B}$ is a 4-5 membered monocyclic heterocyclyl having one ring forming oxygen, wherein the 4-5 membered monocyclic heterocyclyl is unsubstituted or substituted with one or two $R^B$; and each $R^B$ is independently selected from the group consisting of: fluoro and —OH. In some embodiments, $R^{2B}$ is a $C_3$-$C_4$ 4-5 membered monocyclic heterocyclyl having one ring forming oxygen, wherein the $C_3$-$C_4$ 4-5 membered monocyclic heterocyclyl is unsubstituted or substituted with one or two $R^B$; and each $R^B$ is independently selected from the group consisting of: fluoro and —OH. In some embodiments, $R^{2B}$ is a 4-5 membered monocyclic heterocyclyl having one ring forming oxygen, wherein the 4-5 membered monocyclic heterocyclyl is unsubstituted or substituted with one or two fluoro. In some embodiments, $R^{2B}$ is a 4 4-5 membered monocyclic heterocyclyl having one ring forming oxygen, wherein the $C_3$-$C_4$ 4-5 membered monocyclic heterocyclyl is unsubstituted or substituted with one or two fluoro. In some embodiments, $R^{2B}$ is oxetan-3-yl or oxolan-3-yl, each unsubstituted or substituted with one fluoro.

In some embodiments, $R^{2B}$ is heterocyclyl, unsubstituted or substituted with one or more $R^B$; and each $R^B$ is independently selected from the group consisting of: fluoro, chloro, bromo, —CN, —CH$_2$CN, —CH$_2$F, —CHF$_2$, —CF$_3$, —OH, —OCF$_3$, —OCH$_3$, and —OCH$_2$CH$_3$. In some embodiments, $R^{2B}$ is a 3-, 4-, 5-, 6-, 7-, 8-, 9-, 10-, 11-, 12-, or 13-membered monocyclic, bicyclic, or tricyclic heterocyclyl ring system having 1 to 5 ring forming heteroatoms selected from nitrogen, oxygen, and sulfur, wherein the heterocyclyl is unsubstituted or substituted with one or more $R^B$; and each $R^B$ is independently selected from the group consisting of: fluoro, chloro, bromo, —CN, —CH$_2$CN, —CH$_2$F, —CHF$_2$, —CF$_3$, —OH, —OCF$_3$, —OCH$_3$, and —OCH$_2$CH$_3$. In some embodiments, $R^{2B}$ is a 3-, 4-, 5-, 6-, or 7-membered monocyclic heterocyclyl ring having 1 to 5 ring forming heteroatoms selected from nitrogen, oxygen, and sulfur, wherein the heterocyclyl is unsubstituted or substituted with one or more $R^B$; and each $R^B$ is independently selected from the group consisting of: fluoro, chloro, bromo, —CN, —CH$_2$CN, —CH$_2$F, —CHF$_2$, —CF$_3$, —OH, —OCF$_3$, —OCH$_3$, and —OCH$_2$CH$_3$. In some embodiments, $R^{2B}$ is a 4-, 5-, 6-, 7-, 8-, 9-, 10-, or 11-membered bicyclic heterocyclyl ring system having 1 to 5 ring forming heteroatoms selected from nitrogen, oxygen, and sulfur, wherein the heterocyclyl is unsubstituted or substituted with one or more $R^B$; and each $R^B$ is independently selected from the group consisting of: fluoro, chloro, —CN, —CHF$_2$, —CF$_3$, —OH, and —OCH$_3$. In some embodiments, $R^{2B}$ is a 4-5 membered monocyclic heterocyclyl having one ring forming oxygen, wherein the 4-5 membered monocyclic heterocyclyl is unsubstituted or substituted with one or two $R^B$; and each $R^B$ is independently selected from the group consisting of: fluoro and —OH. In some embodiments, $R^{2B}$ is a $C_2$-$C_{12}$ 3-, 4-, 5-, 6-, 7-, 8-, 9-, 10-, up to 13-membered monocyclic, bicyclic, or tricyclic heterocyclyl ring system having 1 to 5 ring forming heteroatoms selected from nitrogen, oxygen, and sulfur, wherein the heterocyclyl is unsubstituted or substituted with one or more $R^B$; and each $R^B$ is independently selected from the group consisting of: fluoro, chloro, bromo, —CN, —CH$_2$CN, —CH$_2$F, —CHF$_2$, —CF$_3$, —OH, —OCF$_3$, —OCH$_3$, and —OCH$_2$CH$_3$. In some embodiments, $R^{2B}$ is a $C_2$-$C_6$ 3-, 4-, 5-, 6-, or 7-membered monocyclic heterocyclyl ring having 1 to 5 ring forming heteroatoms selected from nitrogen, oxygen, and sulfur, wherein the heterocyclyl is unsubstituted or substituted with one or more $R^B$; and each $R^B$ is independently selected from the group consisting of: fluoro, chloro, bromo, —CN, —CH$_2$CN, —CH$_2$F, —CHF$_2$, —CF$_3$, —OH, —OCF$_3$, —OCH$_3$, and —OCH$_2$CH$_3$. In some embodiments, $R^{2B}$ is a $C_2$-$C_{10}$ 4-, 5-, 6-, 7-, 8-, 9-, 10-, or 11-membered bicyclic heterocyclyl ring system having 1 to 5 ring forming heteroatoms selected from nitrogen, oxygen, and sulfur, wherein the heterocyclyl is unsubstituted or substituted with one or more $R^B$; and each $R^B$ is independently selected from the group consisting of: fluoro, chloro, —CN, —CHF$_2$, —CF$_3$, —OH, and —OCH$_3$. In some embodiments, $R^{2B}$ is a $C_3$-$C_4$ 4-5 membered monocyclic heterocyclyl having one ring forming heteroatom selected from oxygen and sulfur, wherein the $C_3$-$C_4$ 4-5 membered monocyclic heterocyclyl is unsubstituted or substituted with one or more $R^B$; and each $R^B$ is independently selected from the group consisting of: fluoro and —OH. In some embodiments, $R^{2B}$ is a $C_3$-$C_4$ 4-5 membered monocyclic heterocyclyl having one ring forming oxygen, wherein the $C_3$-$C_4$ 4-5 membered monocyclic heterocyclyl is unsubstituted or substituted with one or two $R^B$; and each $R^B$ is independently selected from the group consisting of: fluoro and —OH. In some embodiments, $R^{2B}$ is oxetan-3-yl or oxolan-3-yl, each unsubstituted or substituted with one fluoro.

In some embodiments, $R^{2B}$ is: 1,2,4-oxadiazol-5-yl, 1,3-oxazol-2-yl, 1,4-dioxepan-6-yl, 1H-imidazol-2-yl, 1H-pyrazol-5-yl, 1H-tetrazol-5-yl, azetidin-3-yl, bicyclo[1.1.1]pentan-1-yl, cyclobutyl, cyclohexyl, cyclopentyl, cyclopropyl, furan-2-yl, imidazol-1-yl, isoxazol-3-yl, isoxazol-5-yl, oxazol-4-yl, oxetan-2-yl, oxetan-3-yl, oxolan-3-yl (tetrahydrofuran-3-yl), phenyl, piperidin-4-yl, pyrazin-2-yl, pyridin-2-yl, pyridin-3-yl, pyrimidin-2-yl, pyrrolidin-1-yl, tetrahydro-2H-pyran-4-yl, tetrahydro-2H-thiopyran-4-yl, or thiazol-4-yl; each unsubstituted or substituted with one or more groups independently selected from the group consisting of: —CH$_2$CN, —CN, difluoromethyl, ethyl, fluoro, methyl, methylsulfonyl, methylsulfonyloxy, —OH, oxo, phenyl, and trifluoromethyl.

In some embodiments, $R^{2B}$ is 1-((methylsulfonyl)oxy)cyclopropyl, 1-(cyanomethyl)cyclopropyl, 1-(difluoromethyl)cyclopropyl, 1-(methylsulfonyl)cyclopropyl, 1-(trifluoromethyl)cyclopentyl, 1,1-dioxidotetrahydro-2H-thiopyran-4-yl, 1,2,4-oxadiazol-5-yl, 1-cyanocyclobutyl, 1-cyanocyclopropyl, 1-cyanopiperidin-4-yl, 1-fluorocyclobutyl, 1-fluorocyclopropyl, 1H-imidazol-2-yl, 1H-tetrazol-5-yl, 1-hydroxycyclobutyl, 1-methylazetidin-3-yl, 2-ethylcyclopropyl, 2-fluorocyclopentyl, 3-(trifluoromethyl)bicyclo[1.1.1]pentan-1-yl, 3,3-difluorocyclopentyl, 3,3-difluoropyrrolidin-1-yl, 3-fluorobicyclo[1.1.1]pentan-1-yl, 3-fluorooxetan-3-yl, 3-fluorophenyl, 3-hydroxy-3-(trifluoromethyl)cyclobutyl, 4-((difluoromethyl)sulfonyl)phenyl, 4-(trifluoromethyl)phenyl, 4,4-difluoro-1-hydroxycyclohexyl, 4-fluorophenyl, 5-cyanofuran-2-yl, 5-cyanopyridin-2-yl, 5-methyl-1,3-oxazol-2-yl, 6-cyanopyridin-2-yl, 6-fluoro-1,4-dioxepan-6-yl, cyclobutyl, cyclopropyl, imidazol-1-yl, isoxazol-3-yl, isoxazol-5-yl, oxazol-4-yl, oxetan-2-yl, oxetan-3-yl, oxolan-3-yl (tetrahydrofuran-3-yl), phenyl, pyridin-3-yl, pyrimidin-2-yl, 3-cyanophenyl, or 2,2-difluorocyclopropyl.

In some embodiments, $R^{2B}$ is 1-((methylsulfonyl)oxy)cyclopropyl. In some embodiments, $R^{2B}$ is 1-(cyanomethyl)cyclopropyl. In some embodiments, $R^{2B}$ is 1-(difluoromethyl)cyclopropyl. In some embodiments, $R^{2B}$ is 1-(methylsulfonyl)cyclopropyl. In some embodiments, $R^{2B}$ is 1-(trifluoromethyl)cyclopentyl. In some embodiments, $R^{2B}$ is 1,1-dioxidotetrahydro-2H-thiopyran-4-yl. In some embodiments, $R^{2B}$ is 1,2,4-oxadiazol-5-yl. In some embodiments, $R^{2B}$ is 1-cyanocyclobutyl. In some embodiments, $R^{2B}$ is 1-cyanocyclopropyl. In some embodiments, $R^{2B}$ is 1-cyanopiperidin-4-yl. In some embodiments, $R^{2B}$ is 1-fluorocyclobutyl. In some embodiments, $R^{2B}$ is 1-fluorocyclopropyl. In some embodiments, $R^{2B}$ is 1H-imidazol-2-yl. In some embodiments, $R^{2B}$ is 1H-tetrazol-5-yl. In some embodiments, $R^{2B}$ is 1-hydroxycyclobutyl. In some embodiments, $R^{2B}$ is 1-methylazetidin-3-yl. In some embodiments, $R^{2B}$ is 2-ethylcyclopropyl. In some embodiments, $R^{2B}$ is 2-fluorocyclopentyl. In some embodiments, $R^{2B}$ is 2-methylthiazol-4-yl. In some embodiments, $R^{2B}$ is 3-(trifluoromethyl)bicyclo[1.1.1]pentan-1-yl. In some embodiments, $R^{2B}$ is 3,3-difluorocyclopentyl. In some embodiments, $R^{2B}$ is 3,3-difluoropyrrolidin-1-yl. In some embodiments, $R^{2B}$ is 3-fluorobicyclo[1.1.1]pentan-1-yl. In some embodiments, $R^{2B}$ is 3-fluorooxetan-3-yl. In some embodiments, $R^{2B}$ is 3-fluorophenyl. In some embodiments, $R^{2B}$ is 3-hydroxy-3-(trifluoromethyl)cyclobutyl. In some embodiments, $R^{2B}$ is 4-((difluoromethyl)sulfonyl)phenyl. In some embodiments, $R^{2B}$ is 4-(trifluoromethyl)phenyl. In some embodiments, $R^{2B}$ is 4,4-difluoro-_-hydroxycyclohexyl. In some embodiments, $R^{2B}$ is 4-fluorophenyl. In some embodiments, $R^{2B}$ is 5-cyanofuran-2-yl. In some embodiments, $R^{2B}$ is 5-cyanopyridin-2-yl. In some embodiments, $R^{2B}$ is 5-methyl-1,3-oxazol-2-yl. In some embodiments, $R^{2B}$ is 6-cyanopyridin-2-yl. In some embodiments, $R^{2B}$ is 6-fluoro-1,4-dioxepan-6-yl. In some embodiments, $R^{2B}$ is cyclobutyl. In some embodiments, $R^{2B}$ is cyclopropyl. In some embodiments, $R^{2B}$ is imidazol-1-yl. In some embodiments, $R^{2B}$ is isoxazol-3-yl. In some embodiments, $R^{2B}$ is isoxazol-4-yl. In some embodiments, $R^{2B}$ is isoxazol-5-yl. In some embodiments, $R^{2B}$ is oxazol-4-yl. In some embodiments, $R^{2B}$ is oxetan-2-yl. In some embodiments, $R^{2B}$ is oxetan-3-yl. In some embodiments, $R^{2B}$ is oxolan-3-yl (tetrahydrofuran-3-yl). In some embodiments, $R^{2B}$ is phenyl. In some embodiments, $R^{2B}$ is pyridin-3-yl. In some embodiments, $R^{2B}$ is pyrimidin-2-yl. In some embodiments, $R^{2B}$ is 3-cyanophenyl. In some embodiments, $R^{2B}$ is 2,2-difluorocyclopropyl.

In some embodiments, $R^1$ is $-(CH_2)_n-OR^{2C}$.

In some embodiments, the compound is a compound of Formula (V):

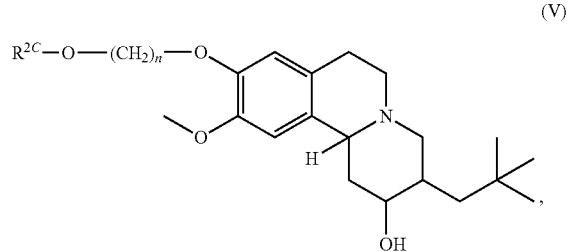

or a pharmaceutically acceptable salt thereof, wherein: n and $R^2c$ have the same definitions as described herein, and each can be selected independently from any of the embodiments as described herein, supra, and infra.

In some embodiments, the compound is a compound selected from Formula (Va), Formula (Vc), Formula (Ve), or Formula (Vg):

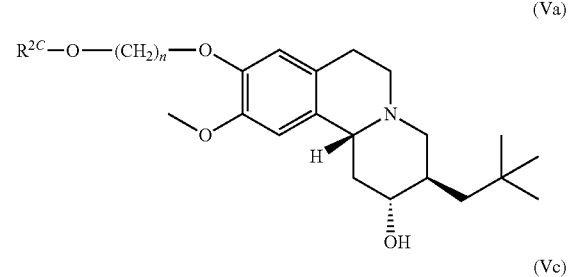

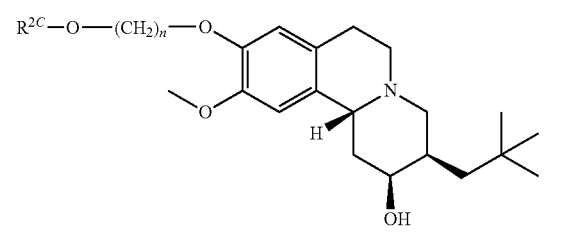

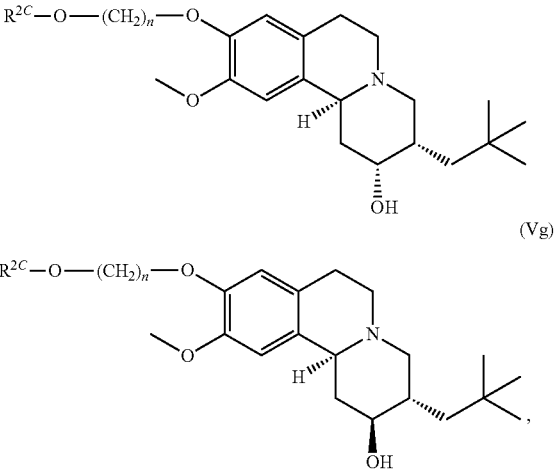

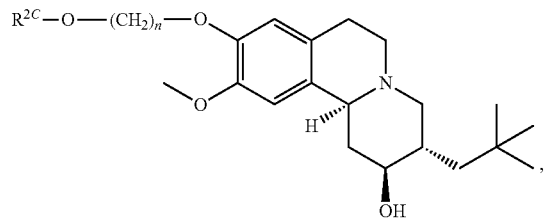

or a pharmaceutically acceptable salt thereof, wherein: n and $R^2c$ have the same definitions as described herein, and each can be selected independently from any of the embodiments as described herein, supra, and infra.

In some embodiments, the compound of Formula (I) is a compound of Formula (Va). In some embodiments, the compound of Formula (I) is a compound of Formula (Vc). In some embodiments, the compound of Formula (I) is a compound of Formula (Ve). In some embodiments, the compound of Formula (I) is a compound of Formula (Vg).

In some embodiments, n is 1, 2, or 3.
In some embodiments, n is 1 or 2.
In some embodiments, n is 1.
In some embodiments, n is 2.
In some embodiments, n is 3.

In some embodiments, $R^2c$ is $C_1$-$C_4$alkyl, $C_3$-$C_8$cycloalkyl, halo$C_1$-$C_4$alkyl, or 4-7 membered heterocyclyl, each unsubstituted or substituted with one or more $R^C$. It is understood that when more than one $R^C$ is present, they may be the same or different. In some embodiments, when more than one $R^C$ is present, they are the same. In some embodiments, when more than one $R^C$ is present, they are different.

In some embodiments, $R^2c$ is $C_1$-$C_4$alkyl, $C_3$-$C_8$cycloalkyl, halo$C_1$-$C_4$alkyl, or 4-7 membered heterocyclyl, each unsubstituted or substituted with one, two, three, or four $R^C$. In some embodiments, $R^{2C}$ is $C_1$-$C_4$alkyl, $C_3$-$C_8$cycloalkyl, halo$C_1$-$C_4$alkyl, or 4-7 membered heterocyclyl, each unsubstituted or substituted with one $R^C$. In some embodiments, $R^2c$ is $C_1$-$C_4$alkyl, $C_3$-$C_8$cycloalkyl, halo$C_1$-$C_4$alkyl, or 4-7 membered heterocyclyl, each unsubstituted or substituted with two $R^C$. In some embodiments, $R^2c$ is $C_1$-$C_4$alkyl, $C_3$-$C_8$cycloalkyl, halo$C_1$-$C_4$alkyl, or 4-7 membered heterocyclyl, each unsubstituted or substituted with three $R^C$. In some embodiments, $R^2c$ is $C_1$-$C_4$alkyl, $C_3$-$C_8$cycloalkyl, halo$C_1$-$C_4$alkyl, or 4-7 membered heterocyclyl, each unsubstituted or substituted with four $R^C$.

In some embodiments, $R^2c$ is $C_1$-$C_4$alkyl, unsubstituted or substituted with one or more $R^C$, wherein $R^C$ is as described herein supra, and infra. In some embodiments, $R^2c$ is ethyl, isopropyl, or methyl, each unsubstituted or substituted with one or more $R^C$.

In some embodiments, each $R^C$ is independently —CN or $C_3$-$C_8$cycloalkyl. In some embodiments, each $R^C$ is independently selected from the group consisting of: cyclopropyl and —CN.

In some embodiments, $R^{2C}$ is ethyl, isopropyl, or methyl, each unsubstituted or substituted with one or more $R^C$ independently selected from the group consisting of: cyclopropyl and —CN. In some embodiments, $R^{2C}$ is methyl, cyano(cyclopropyl)methyl, 2-cyanopropan-2-yl, cyanomethyl, or 1-cyanoethyl.

In some embodiments, $R^{2C}$ is $C_3$-$C_8$cycloalkyl, unsubstituted or substituted with one or more $R^C$, wherein $R^C$ is as described herein supra, and infra.

In some embodiments, $R^{2C}$ is cyclobutyl, unsubstituted or substituted with one or more $R^C$.

In some embodiments, each $R^C$ is —CN.

In some embodiments, $R^{2C}$ is cyclobutyl, unsubstituted or substituted with one or more —CN. In some embodiments, $R^{2C}$ is 1-cyanocyclobutyl.

In some embodiments, $R^{2C}$ is 4-7 membered heterocyclyl, unsubstituted or substituted with one or more $R^C$, wherein $R^C$ is as described herein supra, and infra.

In some embodiments, $R^{2C}$ is oxetan-3-yl or tetrahydro-2H-pyran-4-yl, each unsubstituted or substituted with one or more $R^C$. In some embodiments, $R^C$ is —CN.

In some embodiments, $R^{2C}$ is oxetan-3-yl or tetrahydro-2H-pyran-4-yl, each unsubstituted or substituted with one or more —CN. In some embodiments, $R^{2C}$ is oxetan-3-yl or 4-cyanotetrahydro-2H-pyran-4-yl.

In some embodiments, $R^{2C}$ is $C_1$-$C_4$alkyl or $C_3$-$C_5$cycloalkyl, each substituted with one, two, three, or four $R^C$; and each $R^C$ is independently —CN or $C_3$-$C_6$cycloalkyl. In some embodiments, $R^{2C}$ is $C_1$-$C_4$alkyl or $C_3$-$C_5$cycloalkyl, each substituted with one or more $R^C$; and each $R^C$ is independently —CN or $C_3$-$C_6$cycloalkyl. In some embodiments, $R^{2C}$ is cyclobutyl substituted with one —CN. In some embodiments, $R^{2C}$ is $C_1$-$C_3$alkyl substituted with one —CN and one $C_3$-$C_5$cycloalkyl. In some embodiments, $R^{2C}$ is $C_1$-$C_2$alkyl substituted with one —CN and one $C_3$-$C_4$cycloalkyl. In some embodiments, $R^{2C}$ is $C_1$-$C_2$alkyl substituted with one —CN and one cyclopropyl. In some embodiments, $R^{2C}$ is $C_1$-$C_3$alkyl substituted with one —CN.

In some embodiments, $R^{2C}$ is ethyl, isopropyl, methyl, cyclobutyl, oxetan-3-yl, or tetrahydro-2H-pyran-4-yl, each unsubstituted or substituted with one or more groups independently selected from the group consisting of: cyclopropyl and —CN.

In some embodiments, $R^{2C}$ is methyl, cyano(cyclopropyl)methyl, 2-cyanopropan-2-yl, cyanomethyl, 1-cyanoethyl, 1-cyanocyclobutyl, oxetan-3-yl, or 4-cyanotetrahydro-2H-pyran-4-yl.

In some embodiments, $R^{2C}$ is methyl. In some embodiments, $R^{2C}$ is cyano(cyclopropyl)methyl. In some embodiments, $R^{2C}$ is 2-cyanopropan-2-yl. In some embodiments, $R^{2C}$ is cyanomethyl. In some embodiments, $R^{2C}$ is 1-cyanoethyl. In some embodiments, $R^{2C}$ is 1-cyanocyclobutyl. In some embodiments, $R^{2C}$ is oxetan-3-yl. In some embodiments, $R^{2C}$ is 4-cyanotetrahydro-2H-pyran-4-yl.

$R^1$ Groups

In some embodiments, $R^1$ is methylallyl, 2,2,2-trifluoroethyl, 2,2-difluoroethyl, 2,2-difluoropropyl, 3,3,3-trifluoropropyl, ethyl, 2-fluoroethyl, 3-fluoropropyl, propan-2-yl, 1,1,1-trifluoropropan-2-yl, 2-hydroxy-2-methylpropyl, 3,3,3-trifluoro-2-hydroxypropyl, 3,3-difluoro-2-hydroxypropyl, methyl, 2-hydroxypropyl, 2-hydroxybutyl, 4,4,4-trifluoro-2-hydroxybutyl, 3,3,3-trifluoro-2-hydroxy-2-methylpropyl, 2,3-dihydroxypropyl, 3-hydroxypropyl, 2-hydroxyethyl, cyanomethyl, 2-(dimethylamino)-2-oxoethyl, 2-(methylamino)-2-oxoethyl, 2-hydroxy-3-methoxypropyl, 2-chloro-2,2-difluoroethyl, 2-hydroxy-3-(2,2,2-trifluoroethoxy)propyl, 2-(methyl(2,2,2-trifluoroethyl)amino)-2-oxoethyl, 3-(methylsulfonyl)propyl, (N,N-dimethylsulfamoyl)methyl, 2-methoxypropyl, 2-ethyl-2-hydroxybutyl, 3-chloro-3,3-difluoropropyl, 2-hydroxy-3-morpholinopropyl, cyclopropyl, cyclobutyl, 4-(trifluoromethyl)cyclohexyl, 2-fluorocyclopentyl, 3,3-difluorocyclopentyl, oxetan-3-yl, oxolan-3-yl (tetrahydrofuran-3-yl), 2-oxo-1-(2,2,2-trifluoroethyl)pyrrolidin-3-yl, 1-methylazetidin-3-yl, (1-((methylsulfonyl)oxy)cyclopropyl)methyl, (1-(cyanomethyl)cyclopropyl)methyl, (1-(difluoromethyl)cyclopropyl)methyl, (1-(methylsulfonyl)cyclopropyl)methyl, (1-(trifluoromethyl)cyclopentyl)methyl, (1,1-dioxidotetrahydro-2H-thiopyran-4-yl)methyl, (1,2,4-oxadiazol-5-yl)methyl, (1-cyanocyclobutyl)methyl, (1-cyanocyclopropyl)methyl, (1-cyanopiperidin-4-yl)methyl, (1-fluorocyclobutyl)methyl, (1-fluorocyclopropyl)methyl, (1H-imidazol-2-yl)methyl, (1H-tetrazol-5-yl)methyl, (1-hydroxycyclobutyl)methyl, (1-methylazetidin-3-yl)methyl, (2-ethylcyclopropyl)methyl, (3-(trifluoromethyl)bicyclo[1.1.1]pentan-1-yl)methyl, (3-fluorobicyclo[1.1.1]pentan-1-yl)methyl, (3-fluorooxetan-3-yl)methyl, (3-hydroxy-3-(trifluoromethyl)cyclobutyl)methyl, (4,4-difluoro-1-hydroxycyclohexyl)methyl, (5-cyanofuran-2-yl)methyl, (5-cyanopyridin-2-yl)methyl, (5-methyl-1,3-oxazol-2-yl)methyl, (6-cyanopyridin-2-yl)methyl, (6-fluoro-1,4-dioxepan-6-yl)methyl, (isoxazol-3-yl)methyl, (isoxazol-5-yl)methyl, (oxazol-4-yl)methyl, (oxetan-2-yl)methyl, (oxetan-3-yl)methyl, (pyridin-3-yl)methyl, 2-(1-cyanocyclopropyl)ethyl, 2-(1H-imidazol-1-yl)ethyl, 2-(3,3-difluoropyrrolidin-1-yl)ethyl, 3-fluorobenzyl, 4-((difluoromethyl)sulfonyl)benzyl, 4-(trifluoromethyl)benzyl, 4-(trifluoromethyl)phenethyl, 4-fluorobenzyl, benzyl, cyclopropylmethyl, pyrimidin-2-ylmethyl, (2-cyanopropan-2-yl)oxy)ethyl, 2-((4-cyanotetrahydro-2H-pyran-4-yl)oxy)ethyl, 2-(1-cyanocyclobutoxy)ethyl, 2-(1-cyanoethoxy)ethyl, 2-(cyano(cyclopropyl)methoxy)ethyl, 2-(cyanomethoxy)ethyl, 2-(oxetan-3-yloxy)ethyl, 2-methoxyethyl, 5,5,5-trifluoropentyl, 3-cyanobenzyl, 4-fluorophenethyl, cyclobutylmethyl, 4,4,4-trifluorobutyl, or (2,2-difluorocyclopropyl)methyl.

In some embodiments, $R^1$ is methylallyl, 2,2,2-trifluoroethyl, 2,2-difluoroethyl, 2,2-difluoropropyl, 3,3,3-trifluoropropyl, ethyl, 2-fluoroethyl, 3-fluoropropyl, propan-2-yl, 1,1,1-trifluoropropan-2-yl, 2-hydroxy-2-methylpropyl, 3,3,3-trifluoro-2-hydroxypropyl, 3,3-difluoro-2-hydroxypropyl, methyl, 2-hydroxypropyl, 2-hydroxybutyl, 4,4,4-trifluoro-2-hydroxybutyl, 3,3,3-trifluoro-2-hydroxy-2-methylpropyl, 2,3-dihydroxypropyl, 3-hydroxypropyl, 2-hydroxyethyl, cyanomethyl, 2-(dimethylamino)-2-oxoethyl, 2-(methylamino)-2-oxoethyl, 2-hydroxy-3-methoxypropyl, 2-chloro-2,2-difluoroethyl, 2-hydroxy-3-(2,2,2-trifluoroethoxy)propyl, 2-(methyl(2,2,2-trifluoroethyl)amino)-2-oxoethyl, 3-(methylsulfonyl)propyl, (N,N-dimethylsulfamoyl)methyl, 2-methoxypropyl, 2-ethyl-2-hydroxybutyl, 3-chloro-3,3-difluoropropyl, 2-hydroxy-3-morpholinopropyl, cyclopropyl, cyclobutyl, 4-(trifluoromethyl)cyclohexyl, 2-fluorocyclopentyl, 3,3-difluorocyclopentyl, oxetan-3-yl, oxolan-3-yl (tetrahydrofuran-3-yl), 2-oxo-1-(2,2,2-trifluoroethyl)pyrrolidin-3-yl, 1-methylazetidin-3-yl, 5,5,5-trifluoropentyl, or 4,4,4-trifluorobutyl.

In some embodiments, $R^1$ is (1-((methylsulfonyl)oxy)cyclopropyl)methyl, (1-(cyanomethyl)cyclopropyl)methyl, (1-(difluoromethyl)cyclopropyl)methyl, (1-(methylsulfonyl)cyclopropyl)methyl, (1-(trifluoromethyl)cyclopentyl)methyl, (1,1-dioxidotetrahydro-2H-thiopyran-4-yl)methyl, (1,2,4-oxadiazol-5-yl)methyl, (1-cyanocyclobutyl)methyl, (1-cyanocyclopropyl)methyl, (1-cyanopiperidin-4-yl)methyl, (1-fluorocyclobutyl)methyl, (1-fluorocyclopropyl)methyl, (1H-imidazol-2-yl)methyl, (1H-tetrazol-5-yl)

methyl, (1-hydroxycyclobutyl)methyl, (1-methylazetidin-3-yl)methyl, (2-ethylcyclopropyl)methyl, (3-(trifluoromethyl)bicyclo[1.1.1]pentan-1-yl)methyl, (3-fluorobicyclo[1.1.1]pentan-1-yl)methyl, (3-fluorooxetan-3-yl)methyl, (3-hydroxy-3-(trifluoromethyl)cyclobutyl)methyl, (4,4-difluoro-1-hydroxycyclohexyl)methyl, (5-cyanofuran-2-yl)methyl, (5-cyanopyridin-2-yl)methyl, (5-methyl-1,3-oxazol-2-yl)methyl, (6-cyanopyridin-2-yl)methyl, (6-fluoro-1,4-dioxepan-6-yl)methyl, (isoxazol-3-yl)methyl, (isoxazol-5-yl)methyl, (oxazol-4-yl)methyl, (oxetan-2-yl)methyl, (oxetan-3-yl)methyl, (pyridin-3-yl)methyl, 2-(1-cyanocyclopropyl)ethyl, 2-(1H-imidazol-1-yl)ethyl, 2-(3,3-difluoropyrrolidin-1-yl)ethyl, 2-fluorocyclopentyl, 3,3-difluorocyclopentyl, 3-fluorobenzyl, 4-((difluoromethyl)sulfonyl)benzyl, 4-(trifluoromethyl)benzyl, 4-(trifluoromethyl)phenethyl, 4-fluorobenzyl, benzyl, cyclobutyl, cyclopropyl, cyclopropylmethyl, oxetan-3-yl, oxolan-3-yl (tetrahydrofuran-3-yl), pyrimidin-2-ylmethyl, 3-cyanobenzyl, 4-fluorophenethyl, cyclobutylmethyl, or (2,2-difluorocyclopropyl)methyl.

In some embodiments, $R^1$ is (2-cyanopropan-2-yl)oxy)ethyl, 2-((4-cyanotetrahydro-2H-pyran-4-yl)oxy)ethyl, 2-(1-cyanocyclobutoxy)ethyl, 2-(1-cyanoethoxy)ethyl, 2-(cyano(cyclopropyl)methoxy)ethyl, 2-(cyanomethoxy)ethyl, 2-(oxetan-3-yloxy)ethyl, or 2-methoxyethyl.

In some embodiments, $R^1$ is methylallyl. In some embodiments, $R^1$ is 2,2,2-trifluoroethyl. In some embodiments, $R^1$ is 2,2-difluoroethyl. In some embodiments, $R^1$ is 2,2-difluoropropyl. In some embodiments, $R^1$ is 3,3,3-trifluoropropyl. In some embodiments, $R^1$ is ethyl. In some embodiments, $R^1$ is 2-fluoroethyl. In some embodiments, $R^1$ is 3-fluoropropyl. In some embodiments, $R^1$ is propan-2-yl. In some embodiments, $R^1$ is 1,1,1-trifluoropropan-2-yl. In some embodiments, $R^1$ is 2-hydroxy-2-methylpropyl. In some embodiments, $R^1$ is 3,3,3-trifluoro-2-hydroxypropyl. In some embodiments, $R^1$ is 3,3-difluoro-2-hydroxypropyl. In some embodiments, $R^1$ is methyl. In some embodiments, $R^1$ is 2-hydroxypropyl. In some embodiments, $R^1$ is 2-hydroxybutyl. In some embodiments, $R^1$ is 4,4,4-trifluoro-2-hydroxybutyl. In some embodiments, $R^1$ is 3,3,3-trifluoro-2-hydroxy-2-methylpropyl. In some embodiments, $R^1$ is 2,3-dihydroxypropyl. In some embodiments, $R^1$ is 3-hydroxypropyl. In some embodiments, $R^1$ is 2-hydroxyethyl. In some embodiments, $R^1$ is cyanomethyl. In some embodiments, $R^1$ is 2-(dimethylamino)-2-oxoethyl. In some embodiments, $R^1$ is 2-(methylamino)-2-oxoethyl. In some embodiments, $R^1$ is 2-hydroxy-3-methoxypropyl. In some embodiments, $R^1$ is 2-chloro-2,2-difluoroethyl. In some embodiments, $R^1$ is 2-hydroxy-3-(2,2,2-trifluoroethoxy)propyl. In some embodiments, $R^1$ is 2-(methyl(2,2,2-trifluoroethyl)amino)-2-oxoethyl. In some embodiments, $R^1$ is 3-(methylsulfonyl)propyl. In some embodiments, $R^1$ is (N,N-dimethylsulfamoyl)methyl. In some embodiments, $R^1$ is 2-methoxypropyl. In some embodiments, $R^1$ is 2-ethyl-2-hydroxybutyl. In some embodiments, $R^1$ is 3-chloro-3,3-difluoropropyl. In some embodiments, $R^1$ is 2-hydroxy-3-morpholinopropyl. In some embodiments, $R^1$ is cyclopropyl. In some embodiments, $R^1$ is cyclobutyl. In some embodiments, $R^1$ is 4-(trifluoromethyl)cyclohexyl. In some embodiments, $R^1$ is 2-fluorocyclopentyl. In some embodiments, $R^1$ is 3,3-difluorocyclopentyl. In some embodiments, $R^1$ is oxetan-3-yl. In some embodiments, $R^1$ is oxolan-3-yl (tetrahydrofuran-3-yl). In some embodiments, $R^1$ is 2-oxo-1-(2,2,2-trifluoroethyl)pyrrolidin-3-yl. In some embodiments, $R^1$ is 1-methylazetidin-3-yl. In some embodiments, $R^1$ is (1-((methylsulfonyl)oxy)cyclopropyl)methyl. In some embodiments, $R^1$ is (1-(cyanomethyl)cyclopropyl)methyl. In some embodiments, $R^1$ is (1-(difluoromethyl)cyclopropyl)methyl. In some embodiments, $R^1$ is (1-(methylsulfonyl)cyclopropyl)methyl. In some embodiments, $R^1$ is (1-(trifluoromethyl)cyclopentyl)methyl. In some embodiments, $R^1$ is (1,1-dioxidotetrahydro-2H-thiopyran-4-yl)methyl. In some embodiments, $R^1$ is (1,2,4-oxadiazol-5-yl)methyl. In some embodiments, $R^1$ is (1-cyanocyclobutyl)methyl. In some embodiments, $R^1$ is (1-cyanocyclopropyl)methyl. In some embodiments, $R^1$ is (1-cyanopiperidin-4-yl)methyl. In some embodiments, $R^1$ is (1-fluorocyclobutyl)methyl. In some embodiments, $R^1$ is (1-fluorocyclopropyl)methyl. In some embodiments, $R^1$ is (1H-imidazol-2-yl)methyl. In some embodiments, $R^1$ is (1H-tetrazol-5-yl)methyl. In some embodiments, $R^1$ is (1-hydroxycyclobutyl)methyl. In some embodiments, $R^1$ is (1-methylazetidin-3-yl)methyl. In some embodiments, $R^1$ is (2-ethylcyclopropyl)methyl. In some embodiments, $R^1$ is (3-(trifluoromethyl)bicyclo[1.1.1]pentan-1-yl)methyl. In some embodiments, $R^1$ is (3-fluorobicyclo[1.1.1]pentan-1-yl)methyl. In some embodiments, $R^1$ is (3-fluorooxetan-3-yl)methyl. In some embodiments, $R^1$ is (3-hydroxy-3-(trifluoromethyl)cyclobutyl)methyl. In some embodiments, $R^1$ is (4,4-difluoro-1-hydroxycyclohexyl)methyl. In some embodiments, $R^1$ is (5-cyanofuran-2-yl)methyl. In some embodiments, $R^1$ is (5-cyanopyridin-2-yl)methyl. In some embodiments, $R^1$ is (5-methyl-1,3-oxazol-2-yl)methyl. In some embodiments, $R^1$ is (6-cyanopyridin-2-yl)methyl. In some embodiments, $R^1$ is (6-fluoro-1,4-dioxepan-6-yl)methyl. In some embodiments, $R^1$ is (isoxazol-3-yl)methyl. In some embodiments, $R^1$ is (isoxazol-5-yl)methyl. In some embodiments, $R^1$ is (oxazol-4-yl)methyl. In some embodiments, $R^1$ is (oxetan-2-yl)methyl. In some embodiments, $R^1$ is (oxetan-3-yl)methyl. In some embodiments, $R^1$ is (pyridin-3-yl)methyl. In some embodiments, $R^1$ is 2-(1-cyanocyclopropyl)ethyl. In some embodiments, $R^1$ is 2-(1H-imidazol-1-yl)ethyl. In some embodiments, $R^1$ is 2-(3,3-difluoropyrrolidin-1-yl)ethyl. In some embodiments, $R^1$ is 3-fluorobenzyl. In some embodiments, $R^1$ is 4-((difluoromethyl)sulfonyl)benzyl. In some embodiments, $R^1$ is 4-(trifluoromethyl)benzyl. In some embodiments, $R^1$ is 4-(trifluoromethyl)phenethyl. In some embodiments, $R^1$ is 4-fluorobenzyl. In some embodiments, $R^1$ is benzyl. In some embodiments, $R^1$ is cyclopropylmethyl. In some embodiments, $R^1$ is pyrimidin-2-ylmethyl. In some embodiments, $R^1$ is (2-cyanopropan-2-yl)oxy)ethyl. In some embodiments, $R^1$ is 2-((4-cyanotetrahydro-2H-pyran-4-yl)oxy)ethyl. In some embodiments, $R^1$ is 2-(1-cyanocyclobutoxy)ethyl. In some embodiments, $R^1$ is 2-(1-cyanoethoxy)ethyl. In some embodiments, $R^1$ is 2-(cyano(cyclopropyl)methoxy)ethyl. In some embodiments, $R^1$ is 2-(cyanomethoxy)ethyl. In some embodiments, $R^1$ is 2-(oxetan-3-yloxy)ethyl. In some embodiments, $R^1$ is 2-methoxyethyl. In some embodiments, $R^1$ is 5,5,5-trifluoropentyl. In some embodiments, $R^1$ is 3-cyanobenzyl. In some embodiments, $R^1$ is 4-fluorophenethyl. In some embodiments, $R^1$ is cyclobutylmethyl. In some embodiments, $R^1$ is 4,4,4-trifluorobutyl. In some embodiments, $R^1$ is (2,2-difluorocyclopropyl)methyl. It is understood that when the $R^1$ group has a chiral carbon, the chiral carbon can be (R) or (S). In some embodiments, when the $R^1$ group has a chiral carbon, the chiral carbon is (R). In some embodiments, when the $R^1$ group has a chiral carbon, the chiral carbon is (S). Further, it is understood that when the $R^1$ group has two chiral carbons, the chiral carbons can be independently (R) or (S). In some embodiments, when the $R^1$ group has two chiral carbons, both chiral carbons are (R). In some embodiments, when the $R^1$ group has two chiral carbons, both chiral carbons are (S). In some embodiments, when the $R^1$ group has two chiral carbons, one chiral carbon is (R) and the other chiral carbon is (S).

In some embodiments, $R^1$ is —CH₃. In some embodiments, $R^1$ is —CD₃. In some embodiments, $R^1$ is —CH₂CH₃. In some embodiments, $R^1$ is —CD₂CD₃. In some embodiments, $R^1$ is —CH₂CH₂OCH₃, —CH₂CH(OH)CH₃, —CH₂CH(OH)CF₃, —CH₂CF₃, —CH₂CF₂H, —CH₂CH₂F, —CH₂CH₂CF₃, —CH₂CH₂CHF₂, —CH₂CH₂CH₂F, or —CH(CH₃)(CF₃). In some embodiments, $R^1$ is —CH₂CF₃, —CH₂CF₂H, —CH₂CH₂CF₃, or —CH₂CH₂CHF₂.

In some embodiments, $R^1$ is —CH₂CH₃, —CH(CH₃)₂, —CH₂CN, —CH₂CF₃, —CH(CH₃)(CF₃), —CH₂CF₂H, —CH₂CF₂H, —CH₂CF₂CH₃, —CH₂CH₂CF₃, —CH₂CH₂CH₂H, —CH₂CH₂OCH₃,

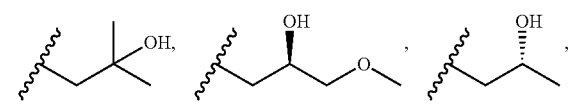
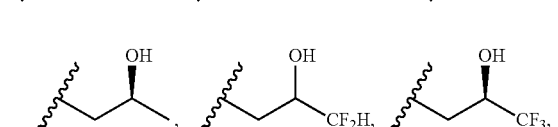
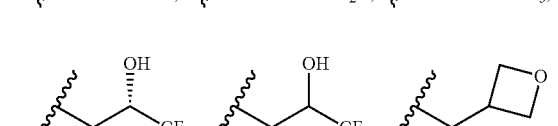
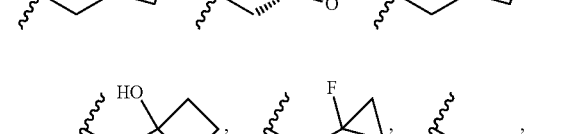
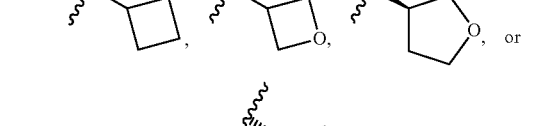

In some embodiments, $R^1$ is —CH₂CH₃, —CH(CH₃)₂, —CH₂CF₃, —CH(CH₃)(CF₃), —CH₂CF₂H, —CH₂CF₂H, —CH₂CF₂CH₃, —CH₂CH₂CF₃, —CH₂CH₂CH₂H, —CH₂CH₂OCH₃,

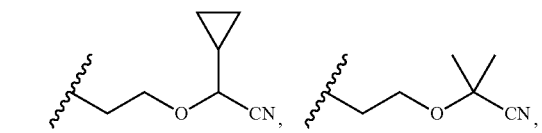
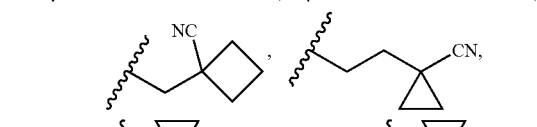

In some embodiments, $R^1$ is —CH₃, —CH₂CH₃, —CH(CH₃)₂, —CH₂CH(CH₃)₂, —CH₂CN,

Some embodiments include every combination of one or more compounds and pharmaceutically acceptable salts thereof selected from the following group shown in Table A. Some embodiments include every combination of one or more compounds selected from the following group shown in Table A.

TABLE A

| Cmpd No. | Chemical Structure | Chemical Name |
|---|---|---|
| 4-1 | 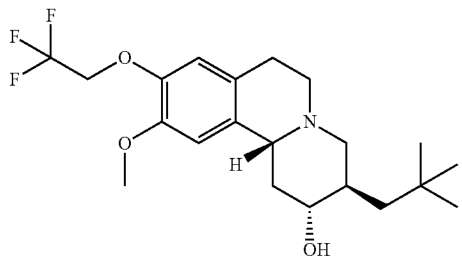 [SMILES: COc1cc2c(cc1OCC(F)(F)F)CCN1C[C@@H](CC(C)(C)C)[C@H](O)C[C@H]21] | (2R,3R,11bR)-3-(2,2-dimethylpropyl)-10-methoxy-9-(2,2,2-trifluoroethoxy)-1H,2H,3H,4H,6H,7H,11bH-pyrido[2,1-a]isoquinolin-2-ol |
| 4-2 | 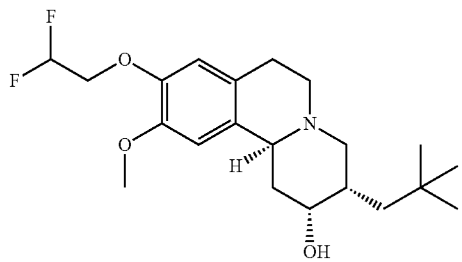 [SMILES: COc1cc2c(cc1OCC(F)F)CCN1C[C@H](CC(C)(C)C)[C@H](O)C[C@@H]21] | (2R,3S,11bS)-9-(2,2-difluoroethoxy)-3-(2,2-dimethylpropyl)-10-methoxy-1H,2H,3H,4H,6H,7H,11bH-pyrido[2,1-a]isoquinolin-2-ol |
| 4-3 | 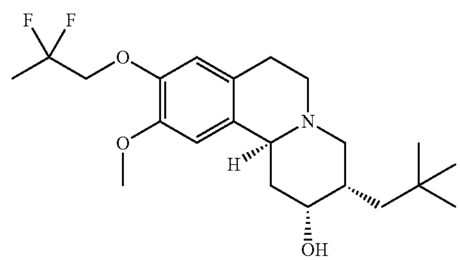 [SMILES: COc1cc2c(cc1OCC(C)(F)F)CCN1C[C@H](CC(C)(C)C)[C@H](O)C[C@@H]21] | (2R,3S,11bS)-9-(2,2-difluoropropoxy)-3-(2,2-dimethylpropyl)-10-methoxy-1H,2H,3H,4H,6H,7H,11bH-pyrido[2,1-a]isoquinolin-2-ol |
| 4-4 | 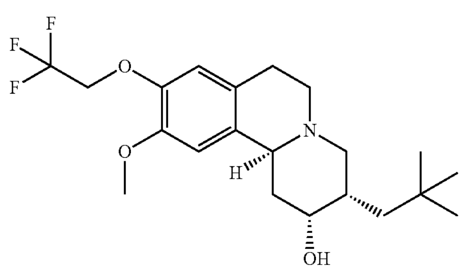 [SMILES: COc1cc2c(cc1OCC(F)(F)F)CCN1C[C@H](CC(C)(C)C)[C@H](O)C[C@@H]21] | (2R,3S,11bS)-3-(2,2-dimethylpropyl)-10-methoxy-9-(2,2,2-trifluoroethoxy)-1H,2H,3H,4H,6H,7H,11bH-pyrido[2,1-a]isoquinolin-2-ol |
| 4-5 | 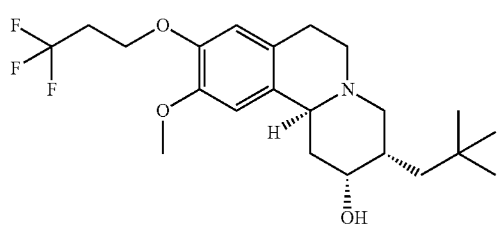 [SMILES: COc1cc2c(cc1OCCC(F)(F)F)CCN1C[C@H](CC(C)(C)C)[C@H](O)C[C@@H]21] | (2R,3S,11bS)-3-(2,2-dimethylpropyl)-10-methoxy-9-(3,3,3-trifluoropropoxy)-1H,2H,3H,4H,6H,7H,11bH-pyrido[2,1-a]isoquinolin-2-ol |
| 4-6 | 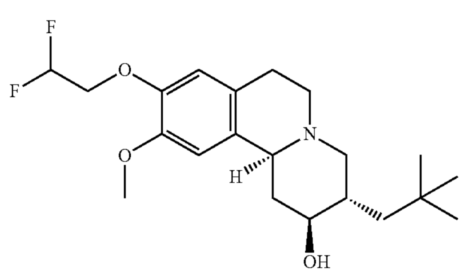 [SMILES: COc1cc2c(cc1OCC(F)F)CCN1C[C@H](CC(C)(C)C)[C@@H](O)C[C@@H]21] | (2S,3S,11bS)-9-(2,2-difluoroethoxy)-3-(2,2-dimethylpropyl)-10-methoxy-1H,2H,3H,4H,6H,7H,11bH-pyrido[2,1-a]isoquinolin-2-ol |

TABLE A-continued

| Cmpd No. | Chemical Structure | Chemical Name |
|---|---|---|
| 4-7 | 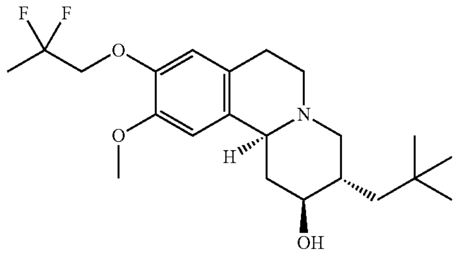 [SMILES: COc1cc2c(cc1OCC(C)(F)F)CCN1C[C@H](CC(C)(C)C)[C@@H](O)C[C@@H]21] | (2S,3S,11bS)-9-(2,2-difluoropropoxy)-3-(2,2-dimethylpropyl)-10-methoxy-1H,2H,3H,4H,6H,7H,11bH-pyrido[2,1-a]isoquinolin-2-ol |
| 4-8 | 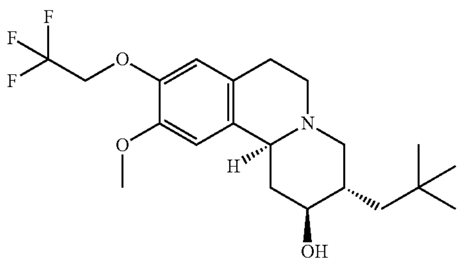 [SMILES: COc1cc2c(cc1OCC(F)(F)F)CCN1C[C@H](CC(C)(C)C)[C@@H](O)C[C@@H]21] | (2S,3S,11bS)-3-(2,2-dimethylpropyl)-10-methoxy-9-(2,2,2-trifluoroethoxy)-1H,2H,3H,4H,6H,7H,11bH-pyrido[2,1-a]isoquinolin-2-ol |
| 4-9 | 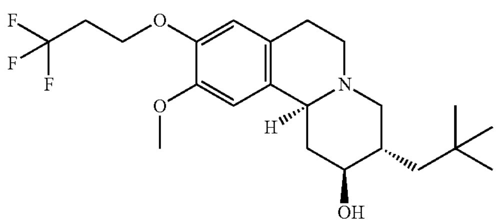 [SMILES: COc1cc2c(cc1OCCC(F)(F)F)CCN1C[C@H](CC(C)(C)C)[C@@H](O)C[C@@H]21] | (2S,3S,11bS)-3-(2,2-dimethylpropyl)-10-methoxy-9-(3,3,3-trifluoropropoxy)-1H,2H,3H,4H,6H,7H,11bH-pyrido[2,1-a]isoquinolin-2-ol |
| 4-10 | 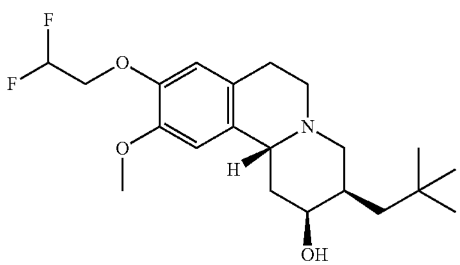 [SMILES: COc1cc2c(cc1OCC(F)F)CCN1C[C@@H](CC(C)(C)C)[C@@H](O)C[C@H]21] | (2S,3R,11bR)-9-(2,2-difluoroethoxy)-3-(2,2-dimethylpropyl)-10-methoxy-1H,2H,3H,4H,6H,7H,11bH-pyrido[2,1-a]isoquinolin-2-ol |
| 4-11 | 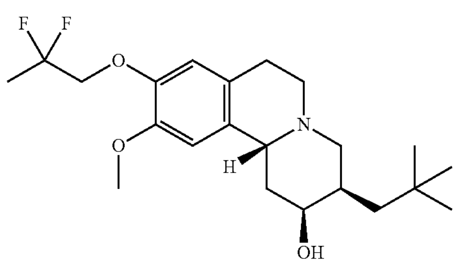 [SMILES: COc1cc2c(cc1OCC(C)(F)F)CCN1C[C@@H](CC(C)(C)C)[C@@H](O)C[C@H]21] | (2S,3R,11bR)-9-(2,2-difluoropropoxy)-3-(2,2-dimethylpropyl)-10-methoxy-1H,2H,3H,4H,6H,7H,11bH-pyrido[2,1-a]isoquinolin-2-ol |
| 4-12 | 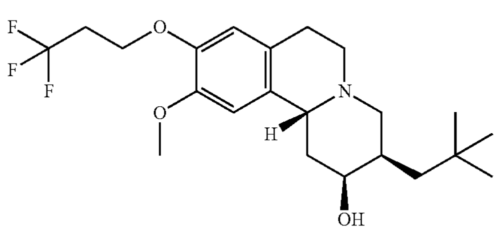 [SMILES: COc1cc2c(cc1OCCC(F)(F)F)CCN1C[C@@H](CC(C)(C)C)[C@@H](O)C[C@H]21] | (2S,3R,11bR)-3-(2,2-dimethylpropyl)-10-methoxy-9-(3,3,3-trifluoropropoxy)-1H,2H,3H,4H,6H,7H,11bH-pyrido[2,1-a]isoquinolin-2-ol |

TABLE A-continued

| Cmpd No. | Chemical Structure | Chemical Name |
|---|---|---|
| 4-13 | 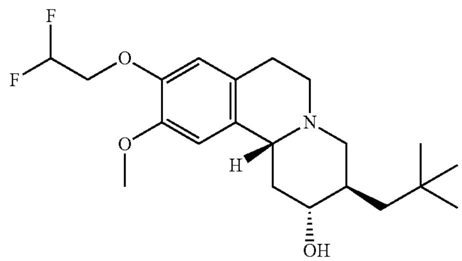 [SMILES: COc1cc2c(cc1OCC(F)F)CCN1C[C@@H](CC(C)(C)C)[C@H](O)C[C@H]21] | (2R,3R,11bR)-9-(2,2-difluoroethoxy)-3-(2,2-dimethylpropyl)-10-methoxy-1H,2H,3H,4H,6H,7H,11bH-pyrido[2,1-a]isoquinolin-2-ol |
| 4-14 | 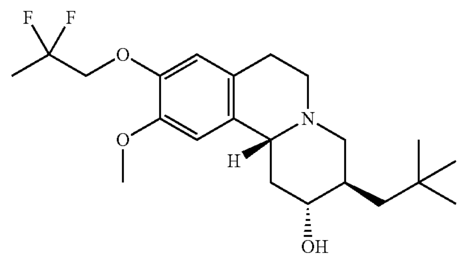 [SMILES: COc1cc2c(cc1OCC(C)(F)F)CCN1C[C@@H](CC(C)(C)C)[C@H](O)C[C@H]21] | (2R,3R,11bR)-9-(2,2-difluoropropoxy)-3-(2,2-dimethylpropyl)-10-methoxy-1H,2H,3H,4H,6H,7H,11bH-pyrido[2,1-a]isoquinolin-2-ol |
| 4-15 | 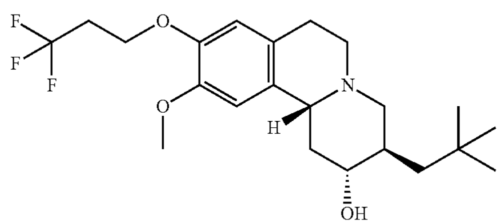 [SMILES: COc1cc2c(cc1OCCC(F)(F)F)CCN1C[C@@H](CC(C)(C)C)[C@H](O)C[C@H]21] | (2R,3R,11bR)-3-(2,2-dimethylpropyl)-10-methoxy-9-(3,3,3-trifluoropropoxy)-1H,2H,3H,4H,6H,7H,11bH-pyrido[2,1-a]isoquinolin-2-ol |
| 4-16 | 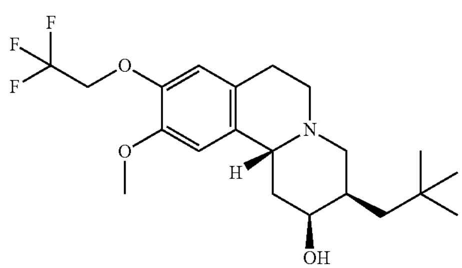 [SMILES: COc1cc2c(cc1OCC(F)(F)F)CCN1C[C@@H](CC(C)(C)C)[C@@H](O)C[C@H]21] | (2S,3R,11bR)-3-(2,2-dimethylpropyl)-10-methoxy-9-(2,2,2-trifluoroethoxy)-1H,2H,3H,4H,6H,7H,11bH-pyrido[2,1-a]isoquinolin-2-ol |
| 4-17 | 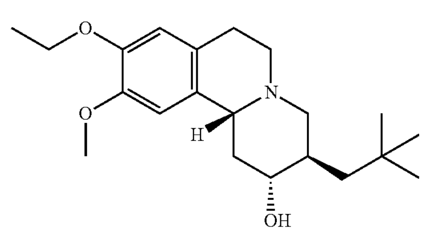 [SMILES: CCOc1cc2c(cc1OC)[C@H]1C[C@@H](O)[C@H](CC(C)(C)C)CN1CC2] | (2R,3R,11bR)-3-(2,2-dimethylpropyl)-9-ethoxy-10-methoxy-1H,2H,3H,4H,6H,7H,11bH-pyrido[2,1-a]isoquinolin-2-ol |
| 4-18 | 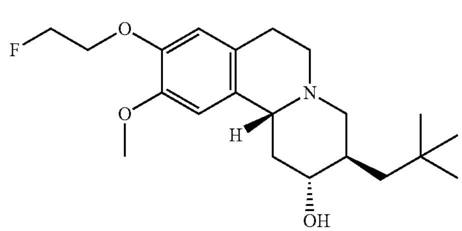 [SMILES: COc1cc2c(cc1OCCF)CCN1C[C@@H](CC(C)(C)C)[C@H](O)C[C@H]21] | (2R,3R,11bR)-3-(2,2-dimethylpropyl)-9-(2-fluoroethoxy)-10-methoxy-1H,2H,3H,4H,6H,7H,11bH-pyrido[2,1-a]isoquinolin-2-ol |

TABLE A-continued

| Cmpd No. | Chemical Structure | Chemical Name |
|---|---|---|
| 4-19 | 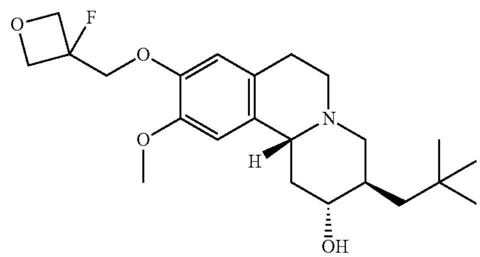 [SMILES: COc1cc2c(cc1OCC1(F)COC1)CCN1C[C@@H](CC(C)(C)C)[C@H](O)C[C@H]21] | (2R,3R,11bR)-3-(2,2-dimethylpropyl)-9-[(3-fluorooxetan-3-yl)methoxy]-10-methoxy-1H,2H,3H,4H,6H,7H,11bH-pyrido[2,1-a]isoquinolin-2-ol |
| 4-20 | 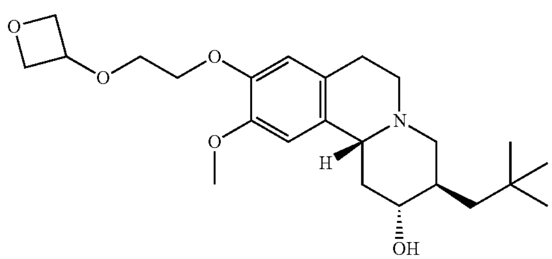 [SMILES: COc1cc2c(cc1OCCOC1COC1)CCN1C[C@@H](CC(C)(C)C)[C@H](O)C[C@H]21] | (2R,3R,11bR)-3-(2,2-dimethylpropyl)-10-methoxy-9-[2-(oxetan-3-yloxy)ethoxy]-1H,2H,3H,4H,6H,7H,11bH-pyrido[2,1-a]isoquinolin-2-ol |
| 4-21 | 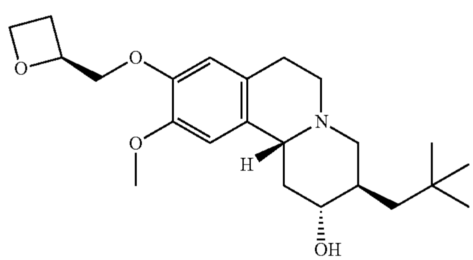 [SMILES: COc1cc2c(cc1OC[C@@H]1CCO1)CCN1C[C@@H](CC(C)(C)C)[C@H](O)C[C@H]21] | (2R,3R,11bR)-3-(2,2-dimethylpropyl)-10-methoxy-9-[(2S)-oxetan-2-ylmethoxy]-1H,2H,3H,4H,6H,7H,11bH-pyrido[2,1-a]isoquinolin-2-ol |
| 4-22 | 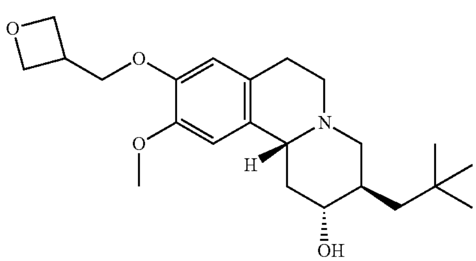 [SMILES: COc1cc2c(cc1OCC1COC1)CCN1C[C@@H](CC(C)(C)C)[C@H](O)C[C@H]21] | (2R,3R,11bR)-3-(2,2-dimethylpropyl)-10-methoxy-9-(oxetan-3-ylmethoxy)-1H,2H,3H,4H,6H,7H,11bH-pyrido[2,1-a]isoquinolin-2-ol |
| 4-23 | 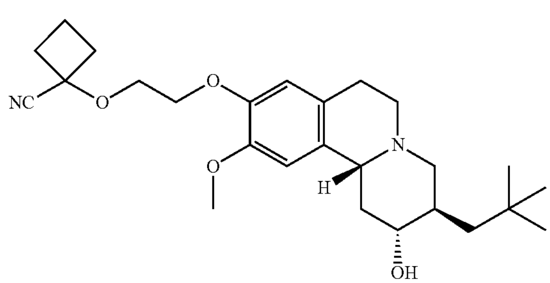 [SMILES: COc1cc2c(cc1OCCOC1(C#N)CCC1)CCN1C[C@@H](CC(C)(C)C)[C@H](O)C[C@H]21] | 1-(2-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}ethoxy)cyclobutane-1-carbonitrile |
| 4-24 | 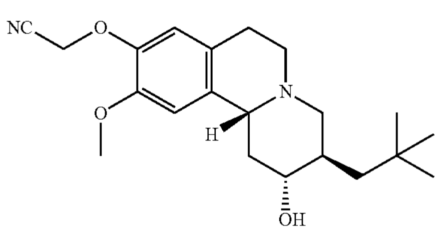 [SMILES: COc1cc2c(cc1OCC#N)CCN1C[C@@H](CC(C)(C)C)[C@H](O)C[C@H]21] | 2-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}acetonitrile |

TABLE A-continued

| Cmpd No. | Chemical Structure | Chemical Name |
|---|---|---|
| 4-25 | 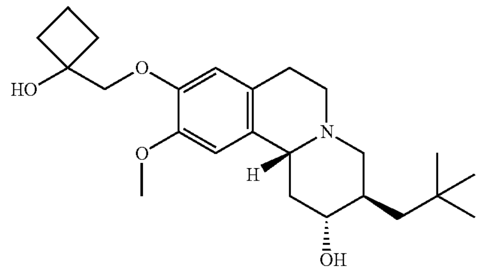 | (2R,3R,11bR)-3-(2,2-dimethylpropyl)-9-[(1-hydroxycyclobutyl)methoxy]-10-methoxy-1H,2H,3H,4H,6H,7H,11bH-pyrido[2,1-a]isoquinolin-2-ol |
| 4-26 | 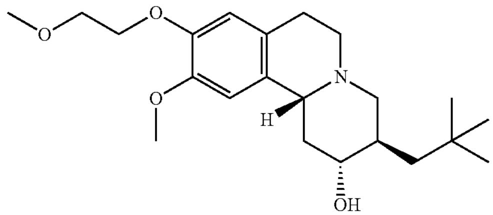 [SMILES: COCCOc1cc2c(cc1OC)[C@H]1C[C@@H](O)[C@H](CC(C)(C)C)CN1CC2] | (2R,3R,11bR)-3-(2,2-dimethylpropyl)-10-methoxy-9-(2-methoxyethoxy)-1H,2H,3H,4H,6H,7H,11bH-pyrido[2,1-a]isoquinolin-2-ol |
| 4-27 | 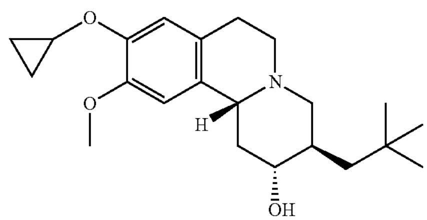 [SMILES: COc1cc2c(cc1OC1CC1)CCN1C[C@@H](CC(C)(C)C)[C@H](O)C[C@H]21] | (2R,3R,11bR)-9-cyclopropoxy-3-(2,2-dimethylpropyl)-10-methoxy-1H,2H,3H,4H,6H,7H,11bH-pyrido[2,1-a]isoquinolin-2-ol |
| 4-28 | 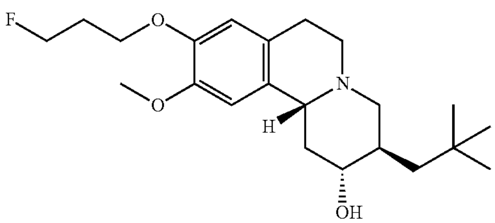 [SMILES: COc1cc2c(cc1OCCCF)CCN1C[C@@H](CC(C)(C)C)[C@H](O)C[C@H]21] | (2R,3R,11bR)-3-(2,2-dimethylpropyl)-9-(3-fluoropropoxy)-10-methoxy-1H,2H,3H,4H,6H,7H,11bH-pyrido[2,1-a]isoquinolin-2-ol |
| 4-29 | 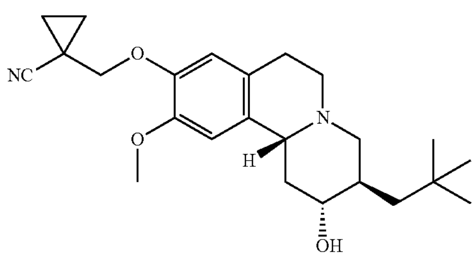 [SMILES: COc1cc2c(cc1OCC1(C#N)CC1)CCN1C[C@@H](CC(C)(C)C)[C@H](O)C[C@H]21] | 1-({[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}methyl)cyclopropane-1-carbonitrile |
| 4-30 | 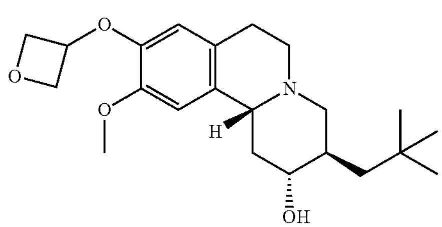 [SMILES: COc1cc2c(cc1OC1COC1)CCN1C[C@@H](CC(C)(C)C)[C@H](O)C[C@H]21] | (2R,3R,11bR)-3-(2,2-dimethylpropyl)-10-methoxy-9-(oxetan-3-yloxy)-1H,2H,3H,4H,6H,7H,11bH-pyrido[2,1-a]isoquinolin-2-ol |

TABLE A-continued

| Cmpd No. | Chemical Structure | Chemical Name |
|---|---|---|
| 4-31 | 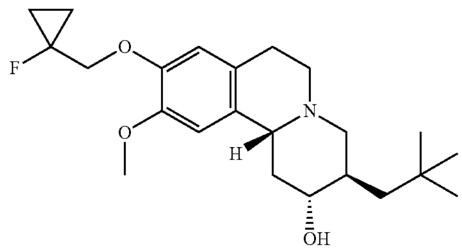 [SMILES: COc1cc2c(cc1OCC1(F)CC1)CCN1C[C@@H](CC(C)(C)C)[C@H](O)C[C@H]21] | (2R,3R,11bR)-3-(2,2-dimethylpropyl)-9-[(1-fluorocyclopropyl)methoxy]-10-methoxy-1H,2H,3H,4H,6H,7H,11bH-pyrido[2,1-a]isoquinolin-2-ol |
| 4-32 | 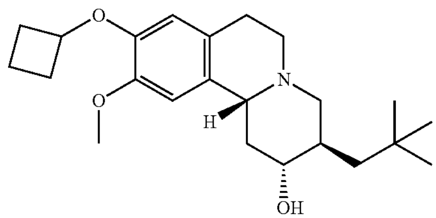 [SMILES: COc1cc2c(cc1OC1CCC1)CCN1C[C@@H](CC(C)(C)C)[C@H](O)C[C@H]21] | (2R,3R,11bR)-9-cyclobutoxy-3-(2,2-dimethylpropyl)-10-methoxy-1H,2H,3H,4H,6H,7H,11bH-pyrido[2,1-a]isoquinolin-2-ol |
| 4-33 | 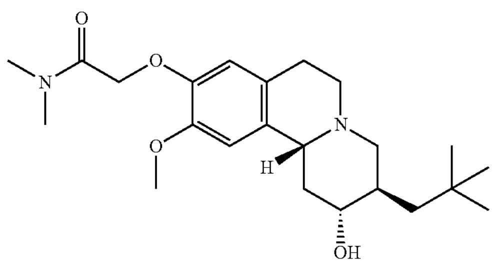 [SMILES: COc1cc2c(cc1OCC(=O)N(C)C)CCN1C[C@@H](CC(C)(C)C)[C@H](O)C[C@H]21] | 2-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}-N,N-dimethylacetamide |
| 4-34 | 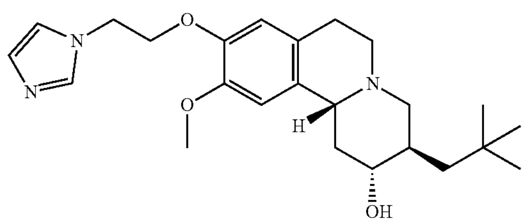 [SMILES: COc1cc2c(cc1OCCn1ccnc1)CCN1C[C@@H](CC(C)(C)C)[C@H](O)C[C@H]21] | (2R,3R,11bR)-3-(2,2-dimethylpropyl)-9-[2-(1H-imidazol-1-yl)ethoxy]-10-methoxy-1H,2H,3H,4H,6H,7H,11bH-pyrido[2,1-a]isoquinolin-2-ol |
| 4-35 | 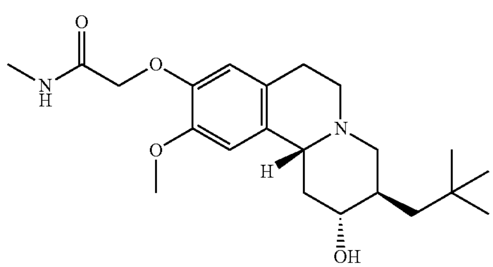 [SMILES: CNC(=O)COc1cc2c(cc1OC)[C@H]1C[C@@H](O)[C@H](CC(C)(C)C)CN1CC2] | 2-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}-N-methylacetamide |
| 4-36 | 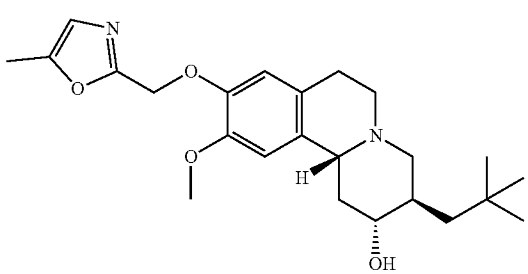 [SMILES: COc1cc2c(cc1OCc1ncc(C)o1)CCN1C[C@@H](CC(C)(C)C)[C@H](O)C[C@H]21] | (2R,3R,11bR)-3-(2,2-dimethylpropyl)-10-methoxy-9-[(5-methyl-1,3-oxazol-2-yl)methoxy]-1H,2H,3H,4H,6H,7H,11bH-pyrido[2,1-a]isoquinolin-2-ol |

TABLE A-continued

| Cmpd No. | Chemical Structure | Chemical Name |
|---|---|---|
| 4-37 | 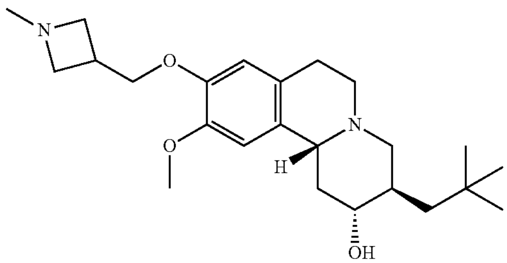 [SMILES: COc1cc2c(cc1OCC1CN(C)C1)CCN1C[C@@H](CC(C)(C)C)[C@H](O)C[C@H]21] | (2R,3R,11bR)-3-(2,2-dimethylpropyl)-10-methoxy-9-[(1-methylazetidin-3-yl)methoxy]-1H,2H,3H,4H,6H,7H,11bH-pyrido[2,1-a]isoquinolin-2-ol |
| 4-38 | 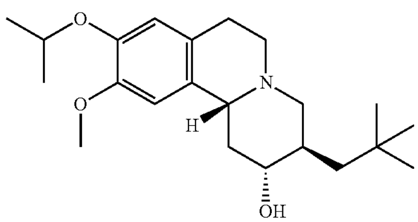 [SMILES: COc1cc2c(cc1OC(C)C)CCN1C[C@@H](CC(C)(C)C)[C@H](O)C[C@H]21] | (2R,3R,11bR)-3-(2,2-dimethylpropyl)-10-methoxy-9-(propan-2-yloxy)-1H,2H,3H,4H,6H,7H,11bH-pyrido[2,1-a]isoquinolin-2-ol |
| 4-39 | 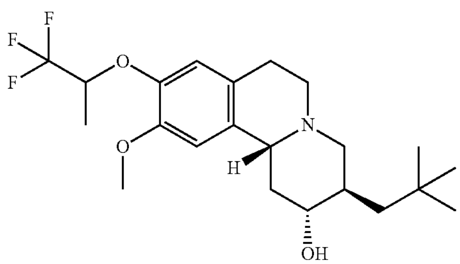 [SMILES: COc1cc2c(cc1OC(C)C(F)(F)F)CCN1C[C@@H](CC(C)(C)C)[C@H](O)C[C@H]21] | (2R,3R,11bR)-3-(2,2-dimethylpropyl)-10-methoxy-9-[(1,1,1-trifluoropropan-2-yl)oxy]-1H,2H,3H,4H,6H,7H,11bH-pyrido[2,1-a]isoquinolin-2-ol |
| 4-40 | 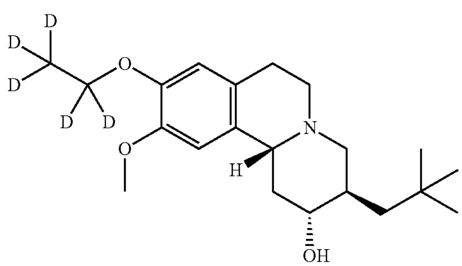 [SMILES: [2H]C([2H])([2H])C([2H])([2H])Oc1cc2c(cc1OC)[C@H]1C[C@@H](O)[C@H](CC(C)(C)C)CN1CC2] | (2R,3R,11bR)-3-(2,2-dimethylpropyl)-9-(ethoxy-$d_5$)-10-methoxy-1H,2H,3H,4H,6H,7H,11bH-pyrido[2,1-a]isoquinolin-2-ol or (2R,3R,11bR)-3-(2,2-dimethylpropyl)-9-($^2H_5$)ethoxy-10-methoxy-1H,2H,3H,4H,6H,7H,11bH-pyrido[2,1-a]isoquinolin-2-ol |
| 4-41 | 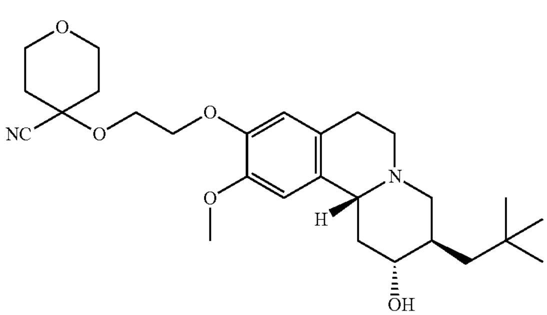 [SMILES: COc1cc2c(cc1OCCOC1(C#N)CCOCC1)CCN1C[C@@H](CC(C)(C)C)[C@H](O)C[C@H]21] | 4-(2-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}ethoxy)oxane-4-carbonitrile |

TABLE A-continued

| Cmpd No. | Chemical Structure | Chemical Name |
|---|---|---|
| 4-42 | 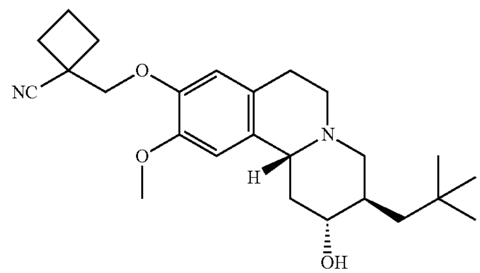 [SMILES: COc1cc2c(cc1OCC1(C#N)CCC1)CCN1C[C@@H](CC(C)(C)C)[C@H](O)C[C@H]21] | 1-({[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}methyl)cyclobutane-1-carbonitrile |
| 4-43 | 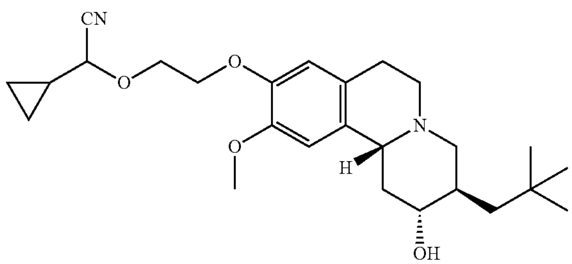 [SMILES: COc1cc2c(cc1OCCOC(C#N)C1CC1)CCN1C[C@@H](CC(C)(C)C)[C@H](O)C[C@H]21] | 2-(2-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}ethoxy)-2-cyclopropylacetonitrile |
| 4-44 | 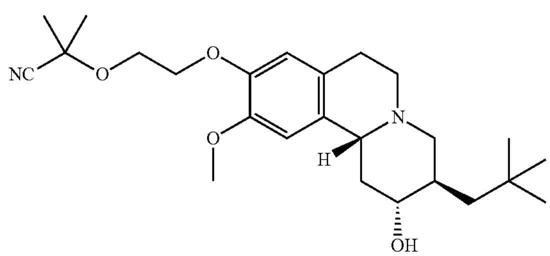 [SMILES: COc1cc2c(cc1OCCOC(C)(C)C#N)CCN1C[C@@H](CC(C)(C)C)[C@H](O)C[C@H]21] | 2-(2-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}ethoxy)-2-methylpropanenitrile |
| 4-45 | 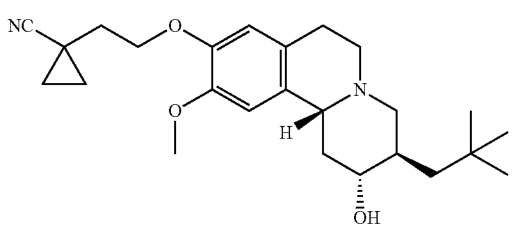 [SMILES: COc1cc2c(cc1OCCC1(C#N)CC1)CCN1C[C@@H](CC(C)(C)C)[C@H](O)C[C@H]21] | 1-(2-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}ethyl)cyclopropane-1-carbonitrile |
| 4-46 | 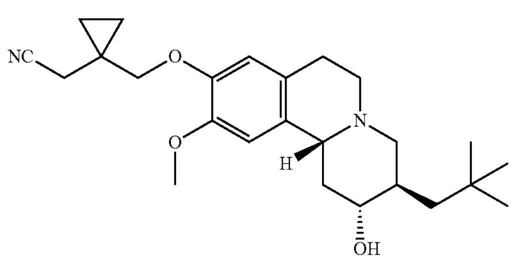 [SMILES: COc1cc2c(cc1OCC1(CC#N)CC1)CCN1C[C@@H](CC(C)(C)C)[C@H](O)C[C@H]21] | 2-[1-({[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}methyl)cyclopropyl]acetonitrile |
| 4-47 | 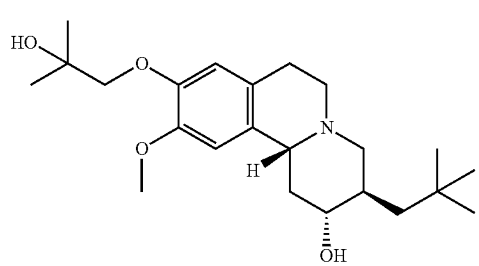 [SMILES: COc1cc2c(cc1OCC(C)(C)O)CCN1C[C@@H](CC(C)(C)C)[C@H](O)C[C@H]21] | (2R,3R,11bR)-3-(2,2-dimethylpropyl)-9-(2-hydroxy-2-methylpropoxy)-10-methoxy-1H,2H,3H,4H,6H,7H,11bH-pyrido[2,1-a]isoquinolin-2-ol |

TABLE A-continued

| Cmpd No. | Chemical Structure | Chemical Name |
|---|---|---|
| 4-48 | 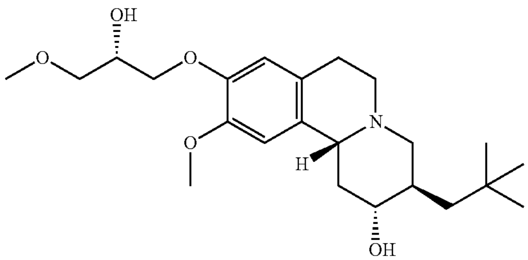 [SMILES: COC[C@H](O)COc1cc2c(cc1OC)[C@H]1C[C@@H](O)[C@H](CC(C)(C)C)CN1CC2] | (2R,3R,11bR)-3-(2,2-dimethylpropyl)-9-[(2S)-2-hydroxy-3-methoxypropoxy]-10-methoxy-1H,2H,3H,4H,6H,7H,11bH-pyrido[2,1-a]isoquinolin-2-ol |
| 4-49 | 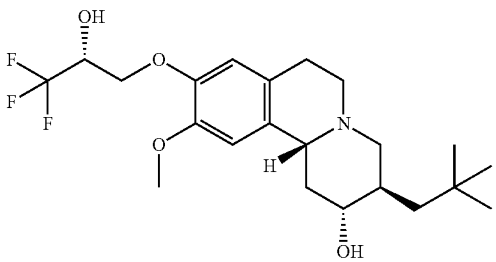 [SMILES: COc1cc2c(cc1OC[C@@H](O)C(F)(F)F)CCN1C[C@@H](CC(C)(C)C)[C@H](O)C[C@H]21] | (2R,3R,11bR)-3-(2,2-dimethylpropyl)-10-methoxy-9-[(2R)-3,3,3-trifluoro-2-hydroxypropoxy]-1H,2H,3H,4H,6H,7H,11bH-pyrido[2,1-a]isoquinolin-2-ol |
| 4-50 | 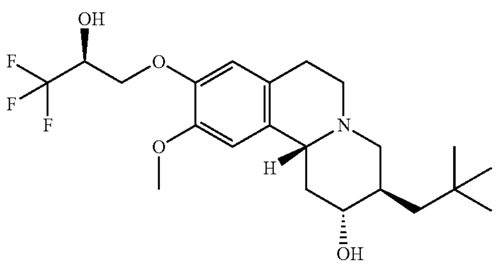 [SMILES: COc1cc2c(cc1OC[C@H](O)C(F)(F)F)CCN1C[C@@H](CC(C)(C)C)[C@H](O)C[C@H]21] | (2R,3R,11bR)-3-(2,2-dimethylpropyl)-10-methoxy-9-[(2S)-3,3,3-trifluoro-2-hydroxypropoxy]-1H,2H,3H,4H,6H,7H,11bH-pyrido[2,1-a]isoquinolin-2-ol |
| 4-51 | 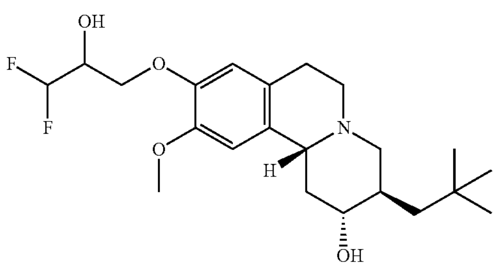 [SMILES: COc1cc2c(cc1OCC(O)C(F)F)CCN1C[C@@H](CC(C)(C)C)[C@H](O)C[C@H]21] | (2R,3R,11bR)-9-(3,3-difluoro-2-hydroxypropoxy)-3-(2,2-dimethylpropyl)-10-methoxy-1H,2H,3H,4H,6H,7H,11bH-pyrido[2,1-a]isoquinolin-2-ol |
| 4-52 | 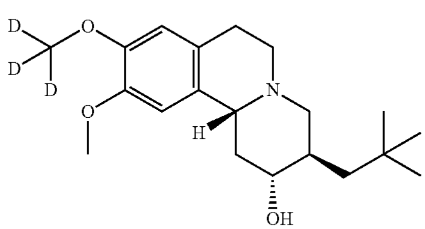 [SMILES: [2H]C([2H])([2H])Oc1cc2c(cc1OC)[C@H]1C[C@@H](O)[C@H](CC(C)(C)C)CN1CC2] | (2R,3R,11bR)-3-(2,2-dimethylpropyl)-9-(methoxy-d$_3$)-10-methoxy-1H,2H,3H,4H,6H,7H,11bH-pyrido[2,1-a]isoquinolin-2-ol or (2R,3R,11bR)-3-(2,2-dimethylpropyl)-9-($^2$H3)methoxy-10-methoxy-1H,2H,3H,4H,6H,7H,11bH-pyrido[2,1-a]isoquinolin-2-ol |
| 4-53 | 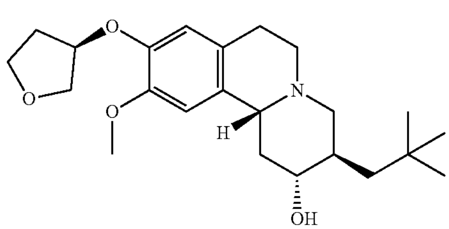 [SMILES: COc1cc2c(cc1O[C@@H]1CCOC1)CCN1C[C@@H](CC(C)(C)C)[C@H](O)C[C@H]21] | (2R,3R1bR)-3-(2,2-dimethylpropyl)-10-methoxy-9-[(3R)-oxolan-3-yloxy]-1H,2H,3H,4H,6H,7H,11bH-pyrido[2,1-a]isoquinolin-2-ol |

TABLE A-continued

| Cmpd No. | Chemical Structure | Chemical Name |
|---|---|---|
| 4-54 | 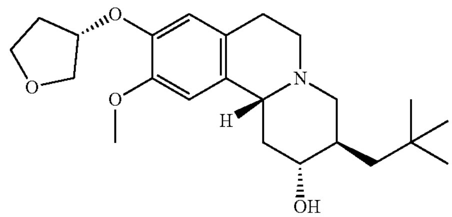 [SMILES: COc1cc2c(cc1O[C@H]1CCOC1)CCN1C[C@@H](CC(C)(C)C)[C@H](O)C[C@H]21] | (2R,3R,11bR)-3-(2,2-dimethylpropyl)-10-methoxy-9-[(3S)-oxolan-3-yloxy]-1H,2H,3H,4H,6H,7H,11bH-pyrido[2,1-a]isoquinolin-2-ol |
| 4-55 | 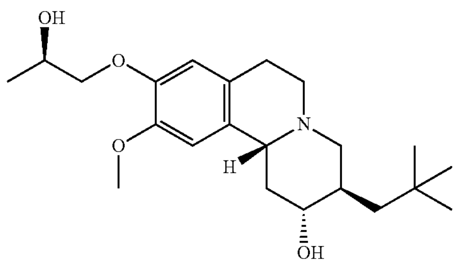 [SMILES: COc1cc2c(cc1OC[C@@H](C)O)CCN1C[C@@H](CC(C)(C)C)[C@H](O)C[C@H]21] | (2R,3R,11bR)-3-(2,2-dimethylpropyl)-9-[(2R)-2-hydroxypropoxy]-10-methoxy-1H,2H,3H,4H,6H,7H,11bH-pyrido[2,1-a]isoquinolin-2-ol |
| 4-56 | 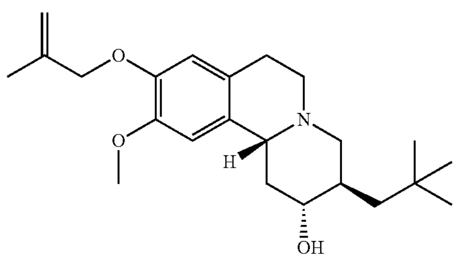 [SMILES: C=C(C)COc1cc2c(cc1OC)[C@H]1C[C@@H](O)[C@H](CC(C)(C)C)CN1CC2] | (2R,3R,11bR)-3-(2,2-dimethylpropyl)-10-methoxy-9-[(2-methylprop-2-en-1-yl)oxy]-1H,2H,3H,4H,6H,7H,11bH-pyrido[2,1-a]isoquinolin-2-ol |
| 4-57 | 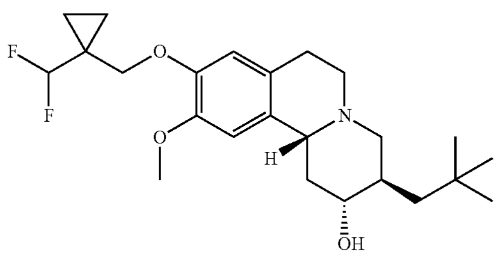 [SMILES: COc1cc2c(cc1OCC1(C(F)F)CC1)CCN1C[C@@H](CC(C)(C)C)[C@H](O)C[C@H]21] | (2R,3R,11bR)-9-{[1-(difluoromethyl)cyclopropyl]methoxy}-3-(2,2-dimethylpropyl)-10-methoxy-1H,2H,3H,4H,6H,7H,11bH-pyrido[2,1-a]isoquinolin-2-ol |
| 4-58 | 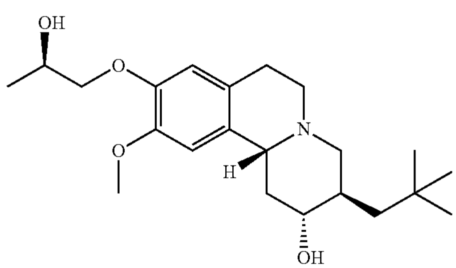 [SMILES: COc1cc2c(cc1OC[C@@H](C)O)CCN1C[C@@H](CC(C)(C)C)[C@H](O)C[C@H]21] | (2R,3R,11bR)-3-(2,2-dimethylpropyl)-9-[(2R)-2-hydroxybutoxy]-10-methoxy-1H,2H,3H,4H,6H,7H,11bH-pyrido[2,1-a]isoquinolin-2-ol |
| 4-59 | 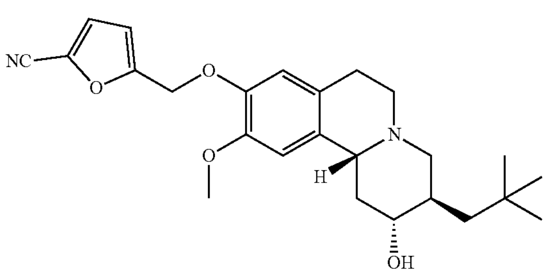 [SMILES: COc1cc2c(cc1OCc1ccc(C#N)o1)CCN1C[C@@H](CC(C)(C)C)[C@H](O)C[C@H]21] | 5-({[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}methyl)furan-2-carbonitrile |

TABLE A-continued

| Cmpd No. | Chemical Structure | Chemical Name |
|---|---|---|
| 4-60 | 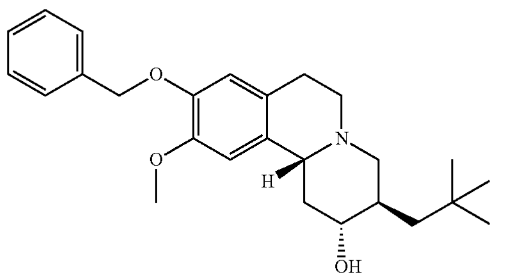 [SMILES: COc1cc2c(cc1OCc1ccccc1)CCN1C[C@@H](CC(C)(C)C)[C@H](O)C[C@H]21] | (2R,3R,11bR)-9-(benzyloxy)-3-(2,2-dimethylpropyl)-10-methoxy-1H,2H,3H,4H,6H,7H,11bH-pyrido[2,1-a]isoquinolin-2-ol |
| 4-61 | 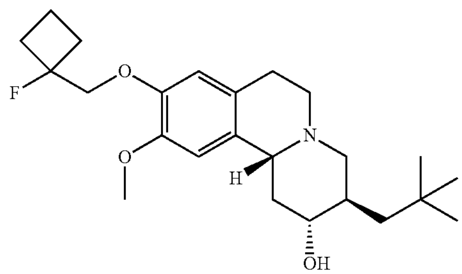 [SMILES: COc1cc2c(cc1OCC1(F)CCC1)CCN1C[C@@H](CC(C)(C)C)[C@H](O)C[C@H]21] | (2R,3R,11bR)-3-(2,2-dimethylpropyl)-9-[(1-fluorocyclobutyl)methoxy]-10-methoxy-1H,2H,3H,4H,6H,7H,11bH-pyrido[2,1-a]isoquinolin-2-ol |
| 4-62 | 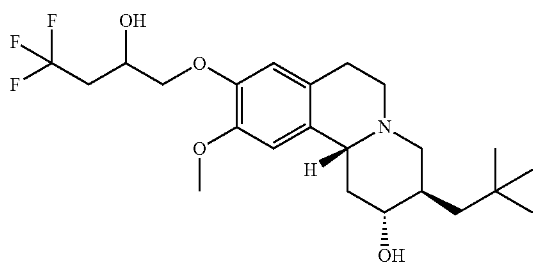 [SMILES: COc1cc2c(cc1OCC(O)CC(F)(F)F)CCN1C[C@@H](CC(C)(C)C)[C@H](O)C[C@H]21] | (2R,3R,11bR)-3-(2,2-dimethylpropyl)-10-methoxy-9-(4,4,4-trifluoro-2-hydroxybutoxy)-1H,2H,3H,4H,6H,7H,11bH-pyrido[2,1-a]isoquinolin-2-ol |
| 4-63 | 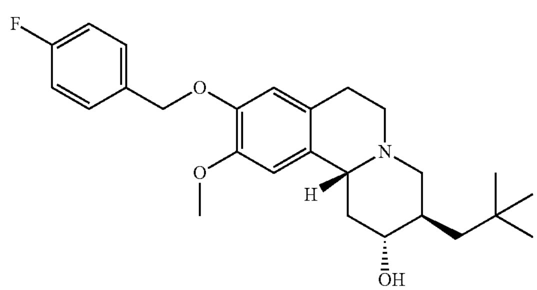 [SMILES: COc1cc2c(cc1OCc1ccc(F)cc1)CCN1C[C@@H](CC(C)(C)C)[C@H](O)C[C@H]21] | (2R,3R,11bR)-3-(2,2-dimethylpropyl)-9-[(4-fluorophenyl)methoxy]-10-methoxy-1H,2H,3H,4H,6H,7H,11bH-pyrido[2,1-a]isoquinolin-2-ol |
| 4-64 | 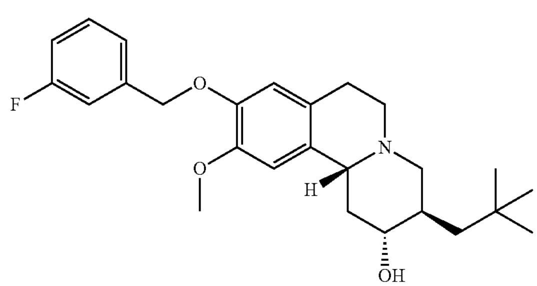 [SMILES: COc1cc2c(cc1OCc1cccc(F)c1)CCN1C[C@@H](CC(C)(C)C)[C@H](O)C[C@H]21] | (2R,3R,11bR)-3-(2,2-dimethylpropyl)-9-[(3-fluorophenyl)methoxy]-10-methoxy-1H,2H,3H,4H,6H,7H,11bH-pyrido[2,1-a]isoquinolin-2-ol |

TABLE A-continued

| Cmpd No. | Chemical Structure | Chemical Name |
|---|---|---|
| 4-65 | 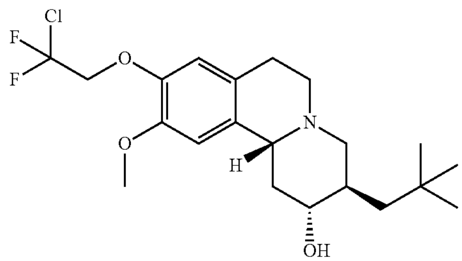 | (2R,3R,11bR)-9-(2-chloro-2,2-difluoroethoxy)-3-(2,2-dimethylpropyl)-10-methoxy-1H,2H,3H,4H,6H,7H,11bH-pyrido[2,1-a]isoquinolin-2-ol |
| 4-66 | 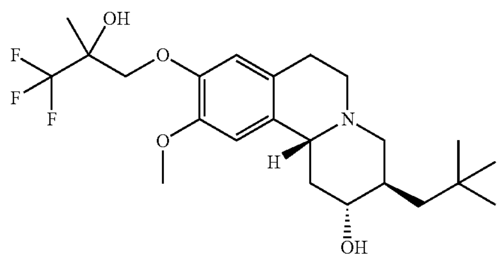 [SMILES: COc1cc2c(cc1OCC(C)(O)C(F)(F)F)CCN1C[C@@H](CC(C)(C)C)[C@H](O)C[C@H]21] | (2R,3R,11bR)-3-(2,2-dimethylpropyl)-10-methoxy-9-(3,3,3-trifluoro-2-hydroxy-2-methylpropoxy)-1H,2H,3H,4H,6H,7H,11bH-pyrido[2,1-a]isoquinolin-2-ol |
| 4-67 | 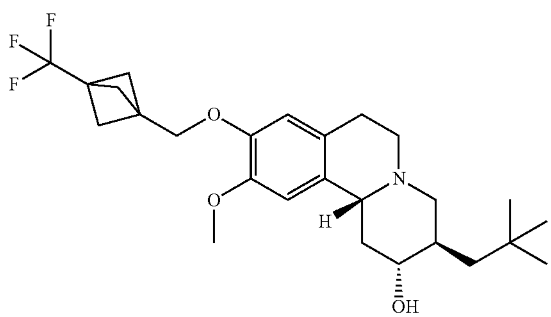 [SMILES: COc1cc2c(cc1OCC13CC(C(F)(F)F)(C1)C3)CCN1C[C@@H](CC(C)(C)C)[C@H](O)C[C@H]21] | (2R,3R,11bR)-3-(2,2-dimethylpropyl)-10-methoxy-9-{[3-(trifluoromethyl)bicyclo[1.1.1]pentan-1-yl]methoxy}-1H,2H,3H,4H,6H,7H,11bH-pyrido[2,1-a]isoquinolin-2-ol |
| 4-68 | 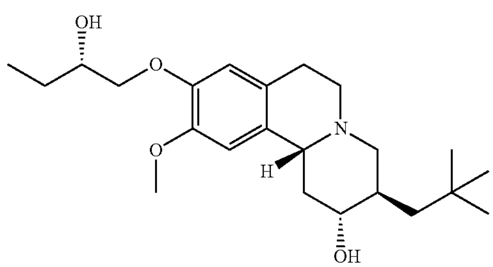 [SMILES: CC[C@H](O)COc1cc2c(cc1OC)[C@H]1C[C@@H](O)[C@H](CC(C)(C)C)CN1CC2] | (2R,3R,11bR)-3-(2,2-dimethylpropyl)-9-[(2S)-2-hydroxybutoxy]-10-methoxy-1H,2H,3H,4H,6H,7H,11bH-pyrido[2,1-a]isoquinolin-2-ol |
| 4-69 | 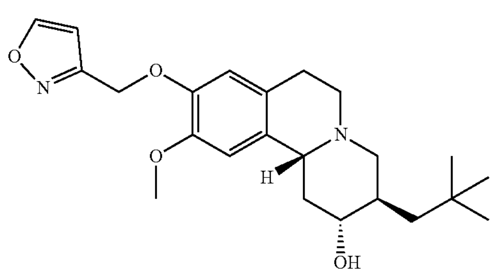 [SMILES: COc1cc2c(cc1OCc1ccon1)CCN1C[C@@H](CC(C)(C)C)[C@H](O)C[C@H]21] | (2R,3R,11bR)-3-(2,2-dimethylpropyl)-10-methoxy-9-(1,2-oxazol-3-ylmethoxy)-1H,2H,3H,4H,6H,7H,11bH-pyrido[2,1-a]isoquinolin-2-ol |

TABLE A-continued

| Cmpd No. | Chemical Structure | Chemical Name |
|---|---|---|
| 4-70 | 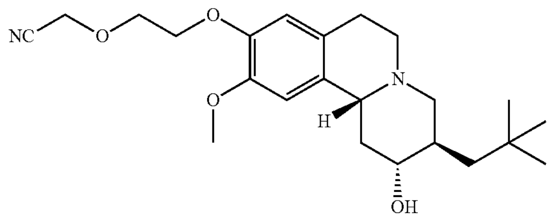 [SMILES: COc1cc2c(cc1OCCOCC#N)CCN1C[C@@H](CC(C)(C)C)[C@H](O)C[C@H]21] | 2-(2-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}ethoxy)acetonitrile |
| 4-71 | 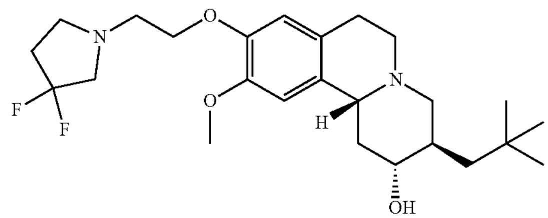 [SMILES: COc1cc2c(cc1OCCN1CCC(F)(F)C1)CCN1C[C@@H](CC(C)(C)C)[C@H](O)C[C@H]21] | (2R,3R,11bR)-9-[2-(3,3-difluoropyrrolidin-1-yl)ethoxy]-3-(2,2-dimethylpropyl)-10-methoxy-1H,2H,3H,4H,6H,7H,11bH-pyrido[2,1-a]isoquinolin-2-ol |
| 4-72 | 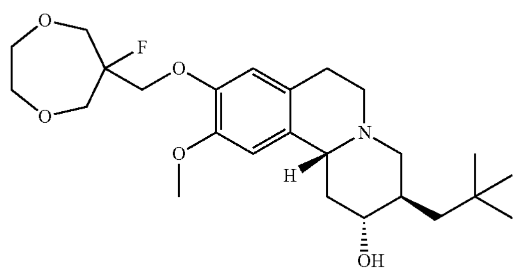 [SMILES: COc1cc2c(cc1OCC1(F)COCCOC1)CCN1C[C@@H](CC(C)(C)C)[C@H](O)C[C@H]21] | (2R,3R,11bR)-3-(2,2-dimethylpropyl)-9-[(6-fluoro-1,4-dioxepan-6-yl)methoxy]-10-methoxy-1H,2H,3H,4H,6H,7H,11bH-pyrido[2,1-a]isoquinolin-2-ol |
| 4-73 | 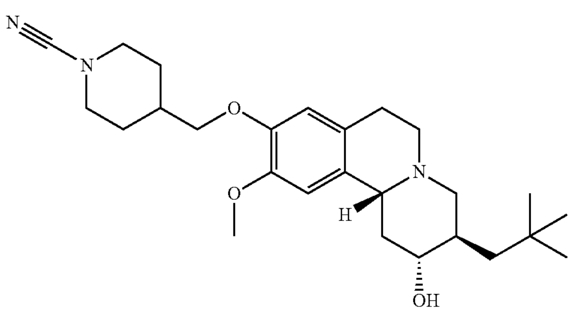 [SMILES: COc1cc2c(cc1OCC1CCN(C#N)CC1)CCN1C[C@@H](CC(C)(C)C)[C@H](O)C[C@H]21] | 4-({[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}ethyl)piperidine-1-carbonitrile |
| 4-74 | 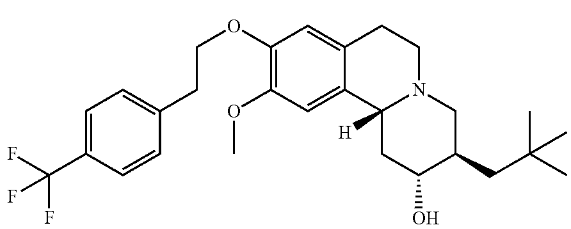 [SMILES: COc1cc2c(cc1OCCc1ccc(C(F)(F)F)cc1)CCN1C[C@@H](CC(C)(C)C)[C@H](O)C[C@H]21] | (2R,3R,11bR)-3-(2,2-dimethylpropyl)-10-methoxy-9-{2-[4-(trifluoromethyl)phenyl]ethoxy}-1H,2H,3H,4H,6H,7H,11bH-pyrido[2,1-a]isoquinolin-2-ol |
| 4-75 | 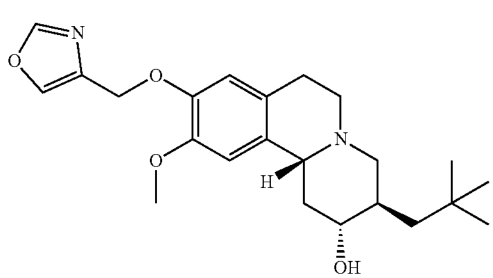 [SMILES: COc1cc2c(cc1OCc1cocn1)CCN1C[C@@H](CC(C)(C)C)[C@H](O)C[C@H]21] | (2R,3R,11bR)-3-(2,2-dimethylpropyl)-10-methoxy-9-(1,3-oxazol-4-ylmethoxy)-1H,2H,3H,4H,6H,7H,11bH-pyrido[2,1-a]isoquinolin-2-ol |

TABLE A-continued

| Cmpd No. | Chemical Structure | Chemical Name |
|---|---|---|
| 4-76 | 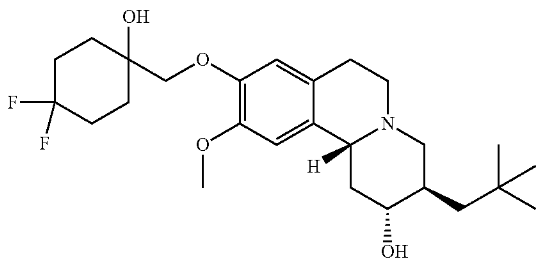 [SMILES: COc1cc2c(cc1OCC1(O)CCC(F)(F)CC1)CCN1C[C@@H](CC(C)(C)C)[C@H](O)C[C@H]21] | (2R,3R,11bR)-9-[(4,4-difluoro-1-hydroxycyclohexyl)methoxy]-3-(2,2-dimethylpropyl)-10-methoxy-1H,2H,3H,4H,6H,7H,11bH-pyrido[2,1-a]isoquinolin-2-ol |
| 4-77 | 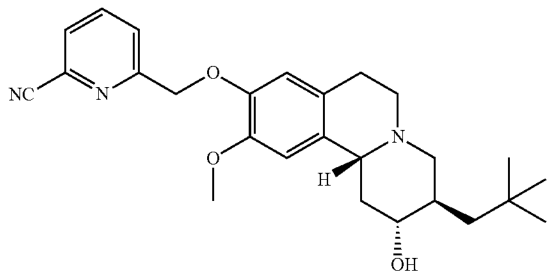 [SMILES: COc1cc2c(cc1OCc1cccc(C#N)n1)CCN1C[C@@H](CC(C)(C)C)[C@H](O)C[C@H]21] | 6-({[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}methyl)pyridine-2-carbonitrile |
| 4-78 | 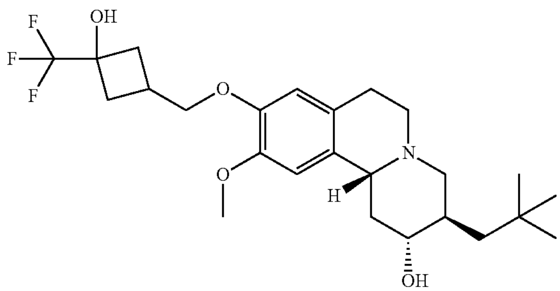 [SMILES: COc1cc2c(cc1OCC1CC(O)(C(F)(F)F)C1)CCN1C[C@@H](CC(C)(C)C)[C@H](O)C[C@H]21] | (2R,3R,11bR)-3-(2,2-dimethylpropyl)-9-{[3-hydroxy-3-(trifluoromethyl)cyclobutyl]methoxy}-10-methoxy-1H,2H,3H,4H,6H,7H,11bH-pyrido[2,1-a]isoquinolin-2-ol |
| 4-79 | 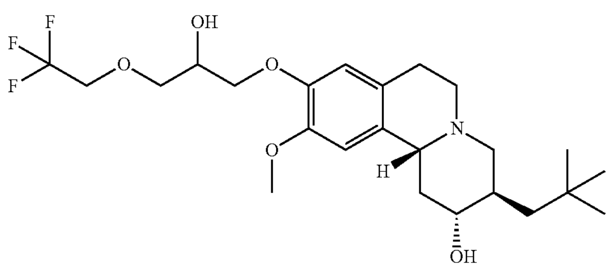 [SMILES: COc1cc2c(cc1OCC(O)COCC(F)(F)F)CCN1C[C@@H](CC(C)(C)C)[C@H](O)C[C@H]21] | ((2R,3R,11bR)-3-(2,2-dimethylpropyl)-9-[2-hydroxy-3-(2,2,2-trifluoroethoxy)propoxy]-10-methoxy-1H,2H,3H,4H,6H,7H,11bH-pyrido[2,1-a]isoquinolin-2-ol |
| 4-80 | 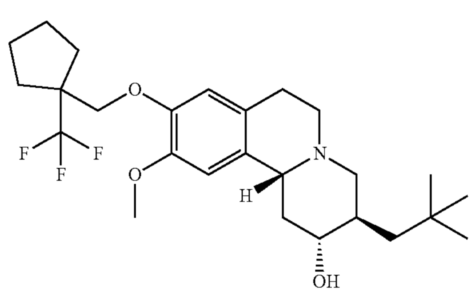 [SMILES: COc1cc2c(cc1OCC1(C(F)(F)F)CCCC1)CCN1C[C@@H](CC(C)(C)C)[C@H](O)C[C@H]21] | (2R,3R,11bR)-3-(2,2-dimethylpropyl)-10-methoxy-9-{[1-(trifluoromethyl)cyclopentyl]methoxy}-1H,2H,3H,4H,6H,7H,11bH-pyrido[2,1-a]isoquinolin-2-ol |

TABLE A-continued

| Cmpd No. | Chemical Structure | Chemical Name |
|---|---|---|
| 4-81 | 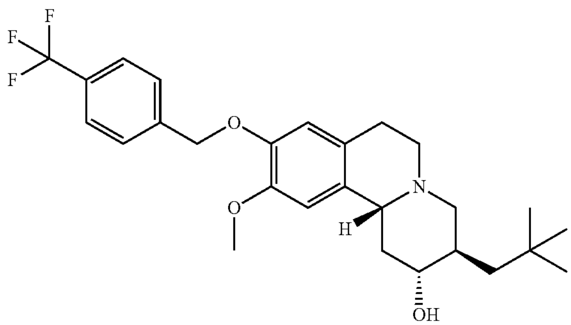 [SMILES: COc1cc2c(cc1OCc1ccc(C(F)(F)F)cc1)CCN1C[C@@H](CC(C)(C)C)[C@H](O)C[C@H]21] | (2R,3R,11bR)-3-(2,2-dimethylpropyl)-10-methoxy-9-{[4-(trifluoromethyl)phenyl]methoxy}-1H,2H,3H,4H,6H,7H,11bH-pyrido[2,1-a]isoquinolin-2-ol |
| 4-82 | 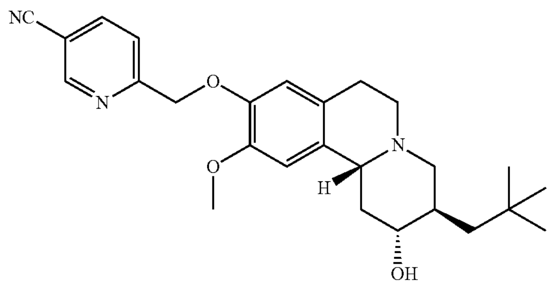 [SMILES: COc1cc2c(cc1OCc1ccc(C#N)cn1)CCN1C[C@@H](CC(C)(C)C)[C@H](O)C[C@H]21] | 6-({[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}methyl)pyridine-3-carbonitrile |
| 4-83 | 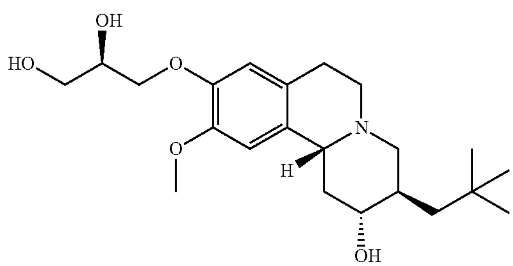 [SMILES: COc1cc2c(cc1OC[C@H](O)CO)CCN1C[C@@H](CC(C)(C)C)[C@H](O)C[C@H]21] | (2R)-3-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}propane-1,2-diol |
| 4-84 | 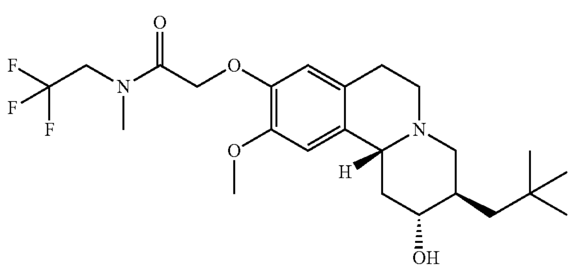 [SMILES: COc1cc2c(cc1OCC(=O)N(C)CC(F)(F)F)CCN1C[C@@H](CC(C)(C)C)[C@H](O)C[C@H]21] | 2-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}-N-methyl-N-(2,2,2-trifluoroethyl)acetamide |
| 4-85 | 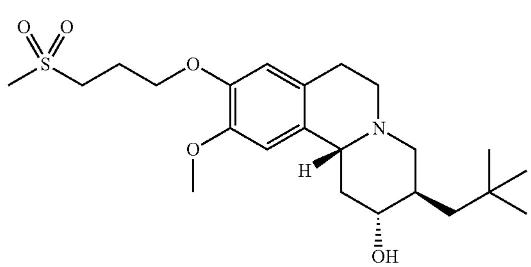 [SMILES: COc1cc2c(cc1OCCCS(C)(=O)=O)CCN1C[C@@H](CC(C)(C)C)[C@H](O)C[C@H]21] | (2R,3R,11bR)-3-(2,2-dimethylpropyl)-9-(3-methanesulfonylpropoxy)-10-methoxy-1H,2H,3H,4H,6H,7H,11bH-pyrido[2,1-a]isoquinolin-2-ol |

TABLE A-continued

| Cmpd No. | Chemical Structure | Chemical Name |
|---|---|---|
| 4-86 | 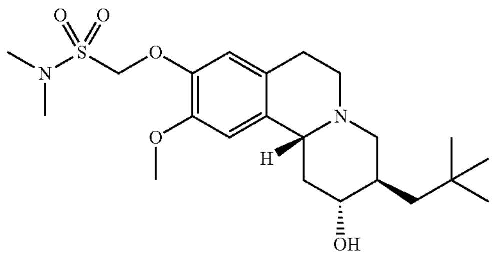 [SMILES: COc1cc2c(cc1OCS(=O)(=O)N(C)C)CCN1C[C@@H](CC(C)(C)C)[C@H](O)C[C@H]21] | 1-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}-N,N-dimethylmethanesulfonamide |
| 4-87 | 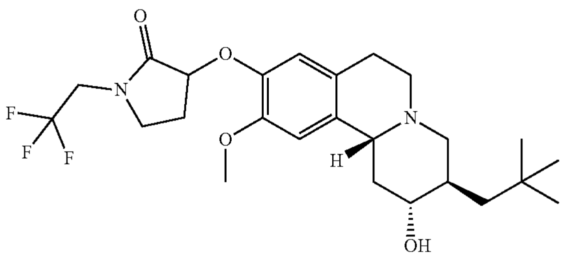 [SMILES: COc1cc2c(cc1OC1CCN(CC(F)(F)F)C1=O)CCN1C[C@@H](CC(C)(C)C)[C@H](O)C[C@H]21] | 3-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}-1-(2,2,2-trifluoroethyl)pyrrolidin-2-one |
| 4-88 | 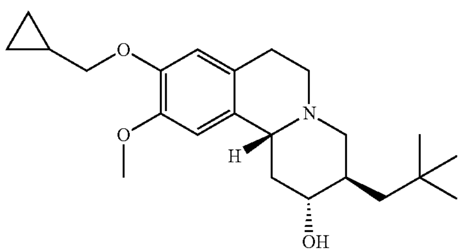 [SMILES: COc1cc2c(cc1OCC1CC1)CCN1C[C@@H](CC(C)(C)C)[C@H](O)C[C@H]21] | (2R,3R,11bR)-9-(cyclopropylmethoxy)-3-(2,2-dimethylpropyl)-10-methoxy-1H,2H,3H,4H,6H,7H,11bH-pyrido[2,1-a]isoquinolin-2-ol |
| 4-89 | 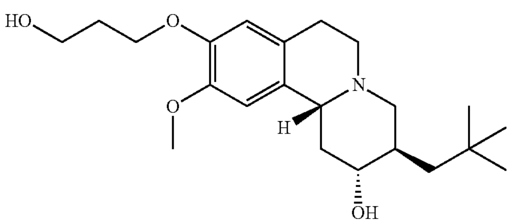 [SMILES: COc1cc2c(cc1OCCCO)CCN1C[C@@H](CC(C)(C)C)[C@H](O)C[C@H]21] | (2R,3R,11bR)-3-(2,2-dimethylpropyl)-9-(3-hydroxypropoxy)-10-methoxy-1H,2H,3H,4H,6H,7H,11bH-pyrido[2,1-a]isoquinolin-2-ol |
| 4-90 | 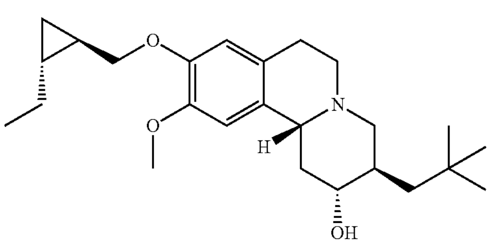 [SMILES: CC[C@@H]1C[C@H]1COc1cc2c(cc1OC)[C@H]1C[C@@H](O)[C@H](CC(C)(C)C)CN1CC2] | (2R,3R,11bR)-3-(2,2-dimethylpropyl)-9-{[(1R,2R)-2-ethylcyclopropyl]methoxy}-10-methoxy-1H,2H,3H,4H,6H,7H,11bH-pyrido[2,1-a]isoquinolin-2-ol |
| 4-91 | 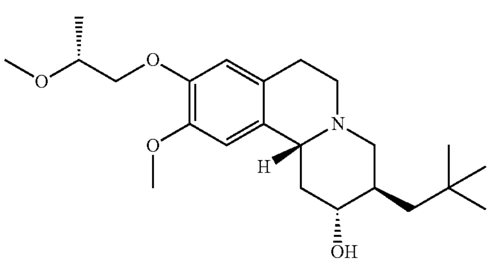 [SMILES: COc1cc2c(cc1OC[C@@H](C)OC)CCN1C[C@@H](CC(C)(C)C)[C@H](O)C[C@H]21] | (2R,3R,11bR)-3-(2,2-dimethylpropyl)-10-methoxy-9-[(2R)-2-methoxypropoxy]-1H,2H,3H,4H,6H,7H,11bH-pyrido[2,1-a]isoquinolin-2-ol |

TABLE A-continued

| Cmpd No. | Chemical Structure | Chemical Name |
|---|---|---|
| 4-92 | 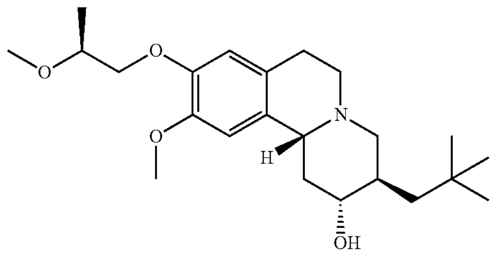 [SMILES: COc1cc2c(cc1OC[C@H](C)OC)CCN1C[C@@H](CC(C)(C)C)[C@H](O)C[C@H]21] | (2R,3R,11bR)-3-(2,2-dimethylpropyl)-10-methoxy-9-[(2S)-2-methoxypropoxy]-1H,2H,3H,4H,6H,7H,11bH-pyrido[2,1-a]isoquinolin-2-ol |
| 4-93 | 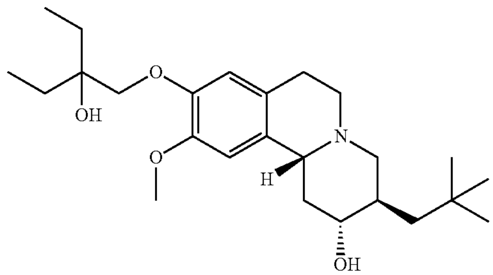 [SMILES: CCC(O)(CC)COc1cc2c(cc1OC)[C@H]1C[C@@H](O)[C@H](CC(C)(C)C)CN1CC2] | (2R,3R,11bR)-3-(2,2-dimethylpropyl)-9-(2-ethyl-2-hydroxybutoxy)-10-methoxy-1H,2H,3H,4H,6H,7H,11bH-pyrido[2,1-a]isoquinolin-2-ol |
| 4-94 | 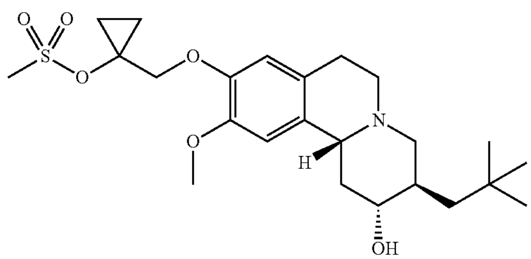 [SMILES: COc1cc2c(cc1OCC1(OS(C)(=O)=O)CC1)CCN1C[C@@H](CC(C)(C)C)[C@H](O)C[C@H]21] | 1-({[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}methyl)cyclopropyl methanesulfonate |
| 4-95 | 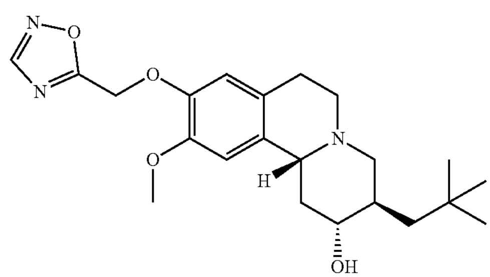 [SMILES: COc1cc2c(cc1OCc1ncno1)CCN1C[C@@H](CC(C)(C)C)[C@H](O)C[C@H]21] | (2R,3R,11bR)-3-(2,2-dimethylpropyl)-10-methoxy-9-(1,2,4-oxadiazol-5-ylmethoxy)-1H,2H,3H,4H,6H,7H,11bH-pyrido[2,1-a]isoquinolin-2-ol |
| 4-96 | 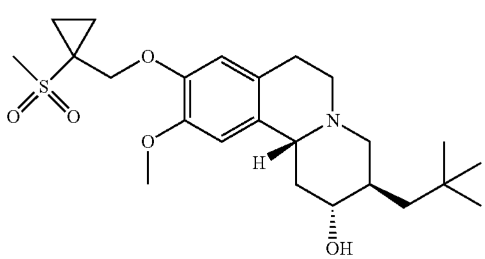 [SMILES: COc1cc2c(cc1OCC1(S(C)(=O)=O)CC1)CCN1C[C@@H](CC(C)(C)C)[C@H](O)C[C@H]21] | (2R,3R,11bR)-3-(2,2-dimethylpropyl)-9-[(1-methanesulfonylcyclopropyl)methoxy]-10-methoxy-1H,2H,3H,4H,6H,7H,11bH-pyrido[2,1-a]isoquinolin-2-ol |

TABLE A-continued

| Cmpd No. | Chemical Structure | Chemical Name |
| --- | --- | --- |
| 4-97 | 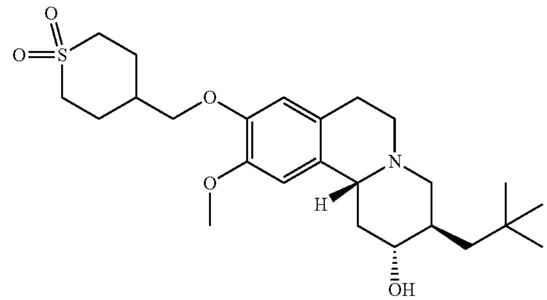 [SMILES: COc1cc2c(cc1OCC1CCS(=O)(=O)CC1)CCN1C[C@@H](CC(C)(C)C)[C@H](O)C[C@H]21] | 4-({[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}methyl)-1λ⁶-thiane-1,1-dione |
| 4-98 | 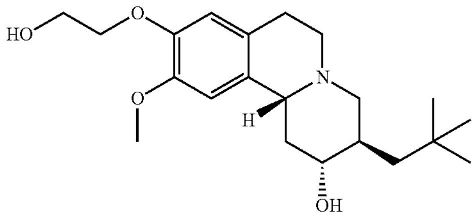 [SMILES: COc1cc2c(cc1OCCO)CCN1C[C@@H](CC(C)(C)C)[C@H](O)C[C@H]21] | (2R,3R,11bR)-3-(2,2-dimethylpropyl)-9-(2-hydroxyethoxy)-10-methoxy-1H,2H,3H,4H,6H,7H,11bH-pyrido[2,1-a]isoquinolin-2-ol |
| 4-99 | 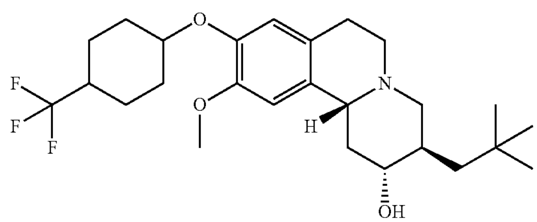 [SMILES: COc1cc2c(cc1OC1CCC(C(F)(F)F)CC1)CCN1C[C@@H](CC(C)(C)C)[C@H](O)C[C@H]21] | (2R,3R,11bR)-3-(2,2-dimethylpropyl)-10-methoxy-9-{[4-(trifluoromethyl)cyclohexyl]oxy}-1H,2H,3H,4H,6H,7H,11bH-pyrido[2,1-a]isoquinolin-2-ol |
| 4-100 | 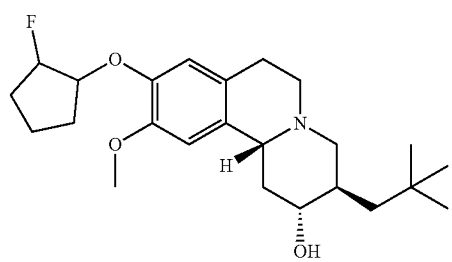 [SMILES: COc1cc2c(cc1OC1CCCC1F)CCN1C[C@@H](CC(C)(C)C)[C@H](O)C[C@H]21] | (2R,3R,11bR)-3-(2,2-dimethylpropyl)-9-[(2-fluorocyclopentyl)oxy]-10-methoxy-1H,2H,3H,4H,6H,7H,11bH-pyrido[2,1-a]isoquinolin-2-ol |
| 4-101 | 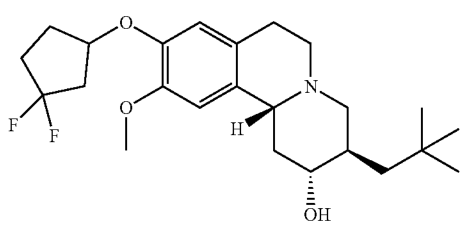 [SMILES: COc1cc2c(cc1OC1CCC(F)(F)C1)CCN1C[C@@H](CC(C)(C)C)[C@H](O)C[C@H]21] | (2R,3R,11bR)-9-[(3,3-difluorocyclopentyl)oxy]-3-(2,2-dimethylpropyl)-10-methoxy-1H,2H,3H,4H,6H,7H,11bH-pyrido[2,1-a]isoquinolin-2-ol |
| 4-102 | 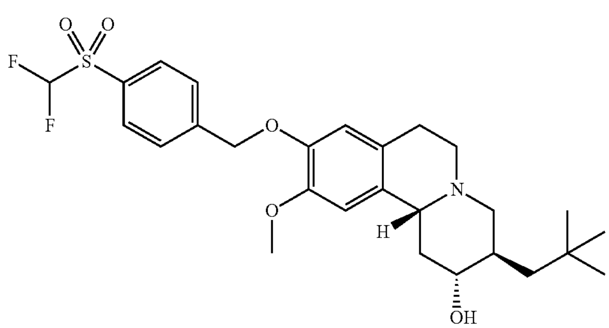 [SMILES: COc1cc2c(cc1OCc1ccc(S(=O)(=O)C(F)F)cc1)CCN1C[C@@H](CC(C)(C)C)[C@H](O)C[C@H]21] | (2R,3R,11bR)-9-[(4-difluoromethanesulfonylphenyl)methoxy]-3-(2,2-dimethylpropyl)-10-methoxy-1H,2H,3H,4H,6H,7H,11bH-pyrido[2,1-a]isoquinolin-2-ol |

TABLE A-continued

| Cmpd No. | Chemical Structure | Chemical Name |
|---|---|---|
| 4-103 | 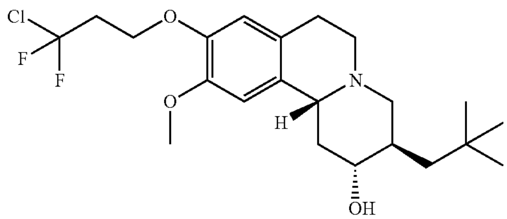 [SMILES: COc1cc2c(cc1OCCC(F)(F)Cl)CCN1C[C@@H](CC(C)(C)C)[C@H](O)C[C@H]21] | (2R,3R,11bR)-9-(3-chloro-3,3-difluoropropoxy)-3-(2,2-dimethylpropyl)-10-methoxy-1H,2H,3H,4H,6H,7H,11bH-pyrido[2,1-a]isoquinolin-2-ol |
| 4-104 | 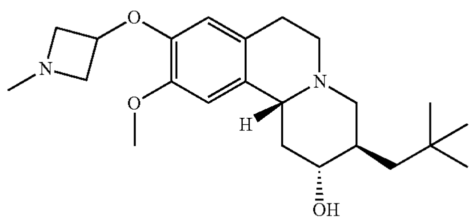 [SMILES: COc1cc2c(cc1OC1CN(C)C1)CCN1C[C@@H](CC(C)(C)C)[C@H](O)C[C@H]21] | (2R,3R,11bR)-3-(2,2-dimethylpropyl)-10-methoxy-9-[(1-methylazetidin-3-yl)oxy]-1H,2H,3H,4H,6H,7H,11bH-pyrido[2,1-a]isoquinolin-2-ol |
| 4-105 | 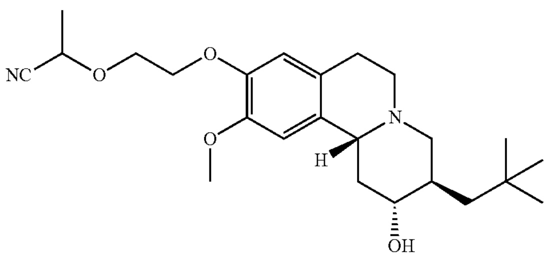 [SMILES: COc1cc2c(cc1OCCOC(C)C#N)CCN1C[C@@H](CC(C)(C)C)[C@H](O)C[C@H]21] | 2-(2-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}ethoxy)propanenitrile |
| 4-106 | 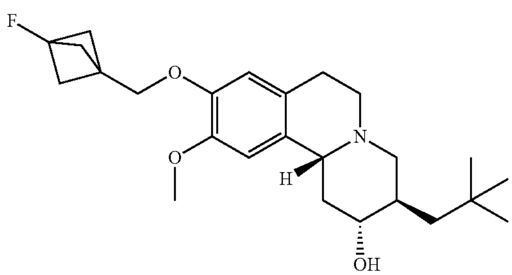 [SMILES: COc1cc2c(cc1OCC13CC(F)(C1)C3)CCN1C[C@@H](CC(C)(C)C)[C@H](O)C[C@H]21] | (2R,3R,11R)-3-(2,2-dimethylpropyl)-9-({3-fluorobicyclo[1.1.1]pentan-1-yl}methoxy)-10-methoxy-1H,2H,3H,4H,6H,7H,11bH-pyrido[2,1-a]isoquinolin-2-ol |
| 4-107 | 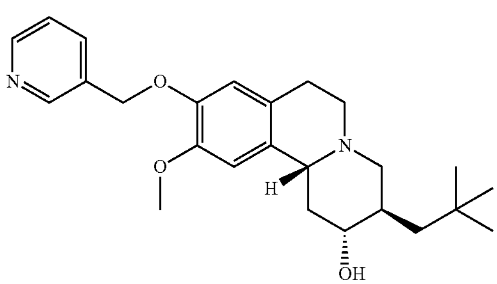 [SMILES: COc1cc2c(cc1OCc1cccnc1)CCN1C[C@@H](CC(C)(C)C)[C@H](O)C[C@H]21] | (2R,3R,11bR)-3-(2,2-dimethylpropyl)-10-methoxy-9-(pyridin-3-ylmethoxy)-1H,2H,3H,4H,6H,7H,11bH-pyrido[2,1-a]isoquinolin-2-ol |
| 4-108 | 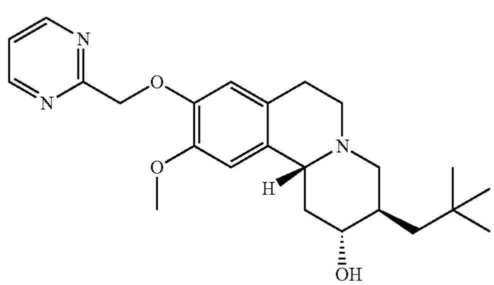 [SMILES: COc1cc2c(cc1OCc1ncccn1)CCN1C[C@@H](CC(C)(C)C)[C@H](O)C[C@H]21] | (2R,3R,11bR)-3-(2,2-dimethylpropyl)-10-methoxy-9-(pyrimidin-2-ylmethoxy)-1H,2H,3H,4H,6H,7H,11bH-pyrido[2,1-a]isoquinolin-2-ol |

TABLE A-continued

| Cmpd No. | Chemical Structure | Chemical Name |
| --- | --- | --- |
| 4-109 | 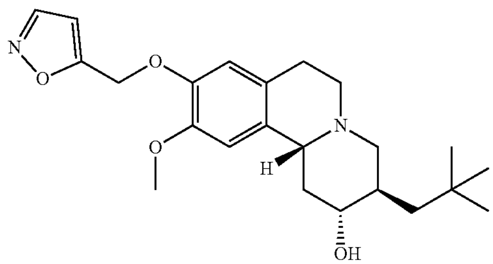 [SMILES: COc1cc2c(cc1OCc1ccno1)CCN1C[C@@H](CC(C)(C)C)[C@H](O)C[C@H]21] | (2R,3R,11bR)-3-(2,2-dimethylpropyl)-10-methoxy-9-(1,2-oxazol-5-ylmethoxy)-1H,2H,3H,4H,6H,7H,11bH-pyrido[2,1-a]isoquinolin-2-ol |
| 4-110 | 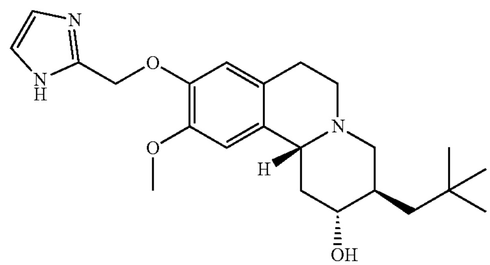 [SMILES: COc1cc2c(cc1OCc1ncc[nH]1)CCN1C[C@@H](CC(C)(C)C)[C@H](O)C[C@H]21] | (2R,3R,11bR)-3-(2,2-dimethylpropyl)-9-(1H-imidazol-2-ylmethoxy)-10-methoxy-1H,2H,3H,4H,6H,7H,11bH-pyrido[2,1-a]isoquinolin-2-ol |
| 4-111 | 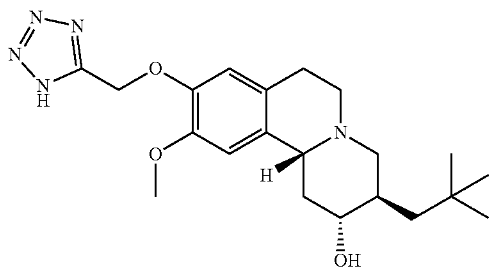 [SMILES: COc1cc2c(cc1OCc1nnn[nH]1)CCN1C[C@@H](CC(C)(C)C)[C@H](O)C[C@H]21] | (2R,3R,11bR)-3-(2,2-dimethylpropyl)-10-methoxy-9-(1H-1,2,3,4-tetrazol-5-ylmethoxy)-1H,2H,3H,4H,6H,7H,11bH-pyrido[2,1-a]isoquinolin-2-ol |
| 4-112 | 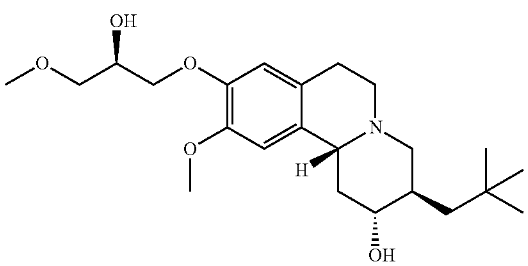 [SMILES: COC[C@@H](O)COc1cc2c(cc1OC)[C@H]1C[C@@H](O)[C@H](CC(C)(C)C)CN1CC2] | (2R,3R,11bR)-3-(2,2-dimethylpropyl)-9-[(2R)-2-hydroxy-3-methoxypropoxy]-10-methoxy-1H,2H,3H,4H,6H,7H,11bH-pyrido[2,1-a]isoquinolin-2-ol |
| 4-113 | 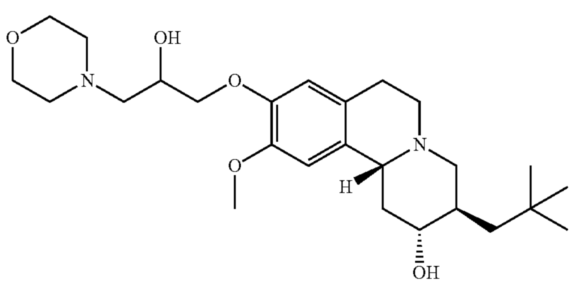 [SMILES: COc1cc2c(cc1OCC(O)CN1CCOCC1)CCN1C[C@@H](CC(C)(C)C)[C@H](O)C[C@H]21] | (2R,3R,11bR)-3-(2,2-dimethylpropyl)-9-[2-hydroxy-3-(morpholin-4-yl)propoxy]-10-methoxy-1H,2H,3H,4H,6H,7H,11bH-pyrido[2,1-a]isoquinolin-2-ol |

TABLE A-continued

| Cmpd No. | Chemical Structure | Chemical Name |
| --- | --- | --- |
| 4-114 | 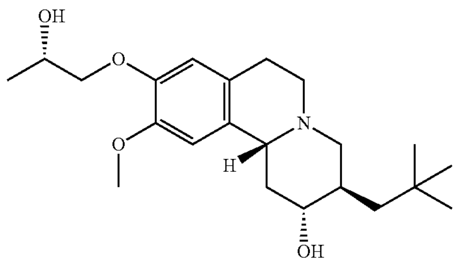 [SMILES: COc1cc2c(cc1OC[C@H](C)O)CCN1C[C@@H](CC(C)(C)C)[C@H](O)C[C@H]21] | (2R,3R,11bR)-3-(2,2-dimethylpropyl)-9-[(2S)-2-hydroxypropoxy]-10-methoxy-1H,2H,3H,4H,6H,7H,11bH-pyrido[2,1-a]isoquinolin-2-ol |
| 4-115 | 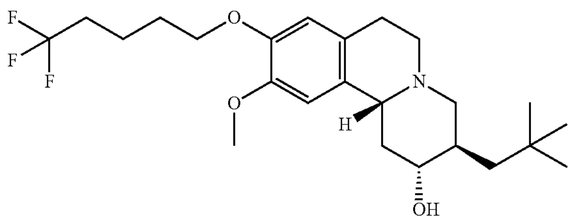 [SMILES: COc1cc2c(cc1OCCCCC(F)(F)F)CCN1C[C@@H](CC(C)(C)C)[C@H](O)C[C@H]21] | (2R,3R,11bR)-3-(2,2-dimethylpropyl)-10-methoxy-9-[(5,5,5-trifluoropentyl)oxy]-1H,2H,3H,4H,6H,7H,11bH-pyrido[2,1-a]isoquinolin-2-ol |
| 4-116 | 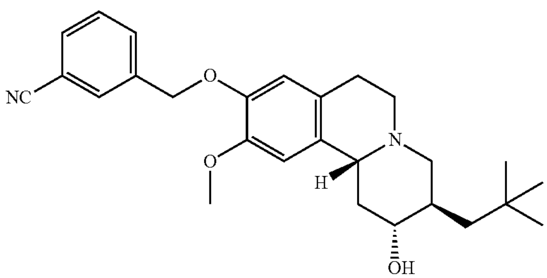 [SMILES: COc1cc2c(cc1OCc1cccc(C#N)c1)CCN1C[C@@H](CC(C)(C)C)[C@H](O)C[C@H]21] | 3-({[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}methyl)benzonitrile |
| 4-117 | 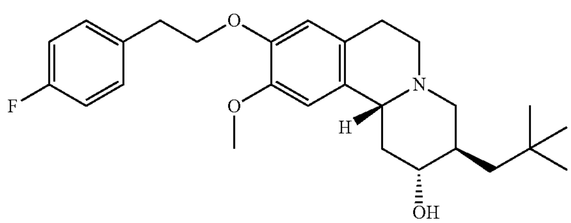 [SMILES: COc1cc2c(cc1OCCc1ccc(F)cc1)CCN1C[C@@H](CC(C)(C)C)[C@H](O)C[C@H]21] | (2R,3R,11bR)-3-(2,2-dimethylpropyl)-9-[2-(4-fluorophenyl)ethoxy]-10-methoxy-1H,2H,3H,4H,6H,7H,11bH-pyrido[2,1-a]isoquinolin-2-ol |
| 4-118 | 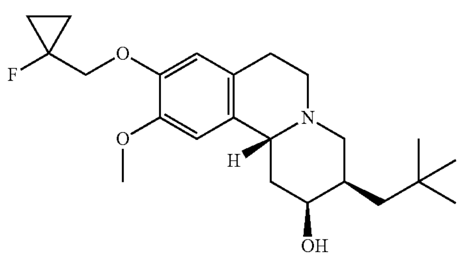 [SMILES: COc1cc2c(cc1OCC1(F)CC1)CCN1C[C@@H](CC(C)(C)C)[C@@H](O)C[C@H]21] | (2S,3R,11bR)-3-(2,2-dimethylpropyl)-9-[(1-fluorocyclopropyl)methoxy]-10-methoxy-1H,2H,3H,4H,6H,7H,11bH-pyrido[2,1-a]isoquinolin-2-ol |
| 4-119 | 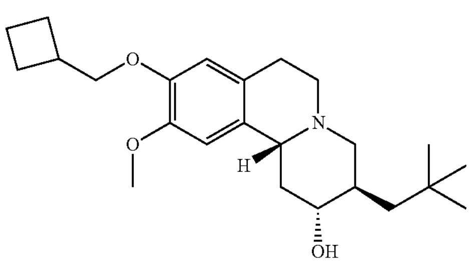 [SMILES: COc1cc2c(cc1OCC1CCC1)CCN1C[C@@H](CC(C)(C)C)[C@H](O)C[C@H]21] | (2R,3R,11bR)-9-(cyclobutylmethoxy)-3-(2,2-dimethylpropyl)-10-methoxy-1H,2H,3H,4H,6H,7H,11bH-pyrido[2,1-a]isoquinolin-2-ol |

TABLE A-continued

| Cmpd No. | Chemical Structure | Chemical Name |
|---|---|---|
| 4-120 | 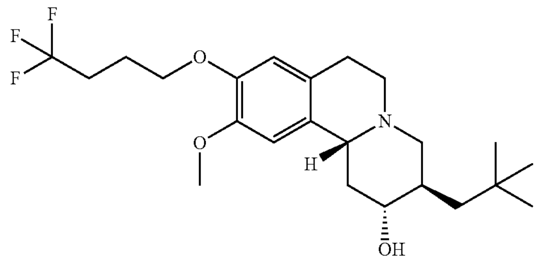 [SMILES: COc1cc2c(cc1OCCCC(F)(F)F)CCN1C[C@@H](CC(C)(C)C)[C@H](O)C[C@H]21] | (2R,3R,11bR)-3-(2,2-dimethylpropyl)-10-methoxy-9-(4,4,4-trifluorobutoxy)-1H,2H,3H,4H,6H,7H,11bH-pyrido[2,1-a]isoquinolin-2-ol |
| 4-121 | 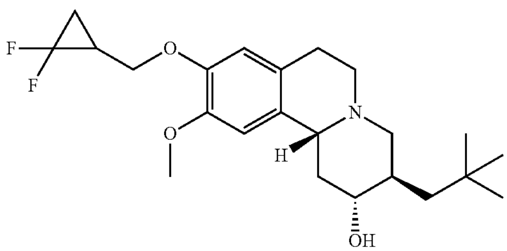 [SMILES: COc1cc2c(cc1OCC1CC1(F)F)CCN1C[C@@H](CC(C)(C)C)[C@H](O)C[C@H]21] | (2R,3R,11bR)-9-[(2,2-difluorocyclopropyl)methoxy]-3-(2,2-dimethylpropyl)-10-methoxy-1H,2H,3H,4H,6H,7H,11bH-pyrido[2,1-a]isoquinolin-2-ol |
| 5-1 | 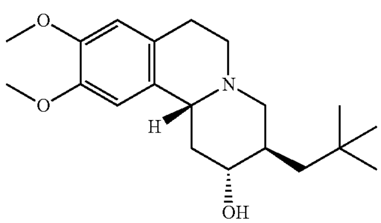 [SMILES: COc1cc2c(cc1OC)[C@H]1C[C@@H](O)[C@H](CC(C)(C)C)CN1CC2] | (2R,3R,11bR)-3-(2,2-dimethylpropyl)-9,10-dimethoxy-1H,2H,3H,4H,6H,7H,11bH-pyrido[2,1-a]isoquinolin-2-ol |
| 5-2 | 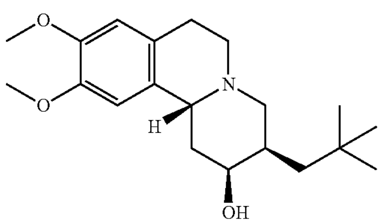 [SMILES: COc1cc2c(cc1OC)[C@H]1C[C@H](O)[C@H](CC(C)(C)C)CN1CC2] | (2S,3R,11bR)-3-(2,2-dimethylpropyl)-9,10-dimethoxy-1H,2H,3H,4H,6H,7H,11bH-pyrido[2,1-a]isoquinolin-2-ol |
| 5-3 | 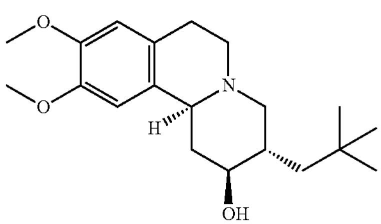 [SMILES: COc1cc2c(cc1OC)[C@@H]1C[C@H](O)[C@@H](CC(C)(C)C)CN1CC2] | (2S,3S,11bS)-3-(2,2-dimethylpropyl)-9,10-dimethoxy-1H,2H,3H,4H,6H,7H,11bH-pyrido[2,1-a]isoquinolin-2-ol |
| 5-4 | 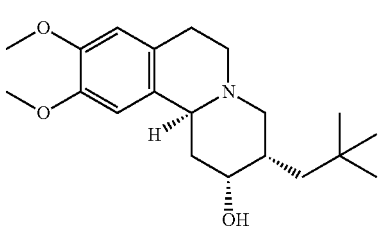 [SMILES: COc1cc2c(cc1OC)[C@@H]1C[C@@H](O)[C@@H](CC(C)(C)C)CN1CC2] | (2R,3S,11bS)-3-(2,2-dimethylpropyl)-9,10-dimethoxy-1H,2H,3H,4H,6H,7H,11bH-pyrido[2,1-a]isoquinolin-2-ol |

Each and every compound of Formula (I), method, composition, or use described herein also optionally includes the limitation that the compound of Formula (I) is not one or more compounds selected from the group consisting of: Compound 4-33, Compound 4-34, Compound 4-35, Compound 4-37, Compound 4-95, Compound 4-96, Compound 4-97, Compound 4-100, Compound 4-101, Compound 4-102, Compound 4-103, Compound 4-104, Compound 4-105, Compound 4-106, Compound 4-107, Compound 4-108, Compound 4-109, Compound 4-110, Compound 4-111, Compound 4-112, Compound 4-113, and Compound 5-4.

Some embodiments provide a compound of Table 10A and/or Table 10B, or a pharmaceutically acceptable salt thereof. Some embodiments provide a compound having the structure:

Compound 4-1

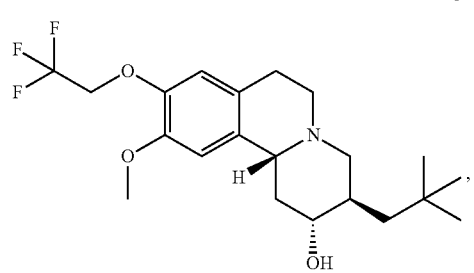

Compound 4-13

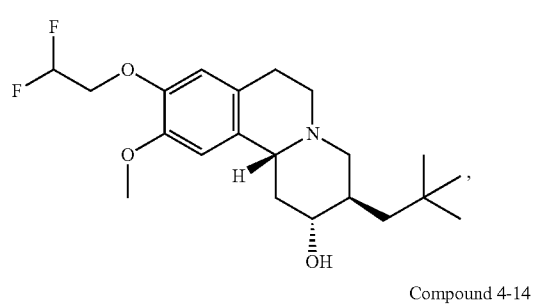

Compound 4-14

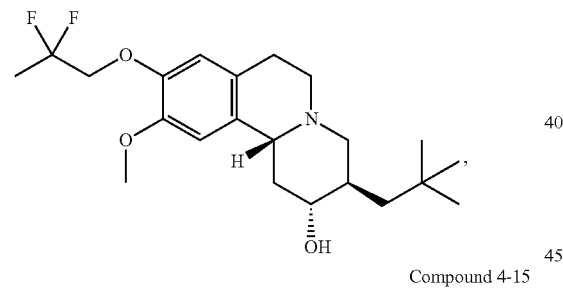

Compound 4-15

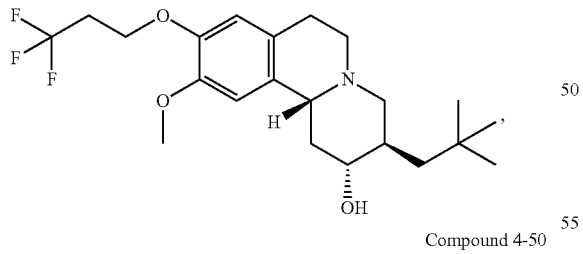

Compound 4-50

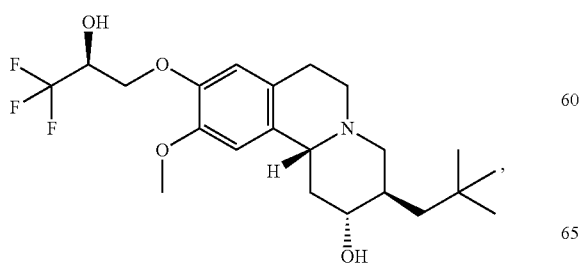

-continued

Compound 4-49

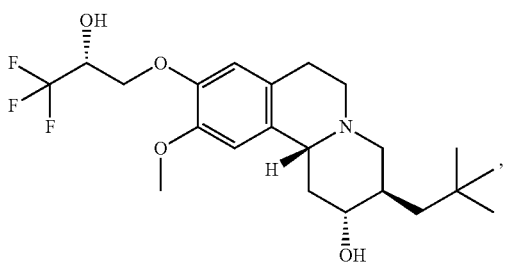

Compound 4-51

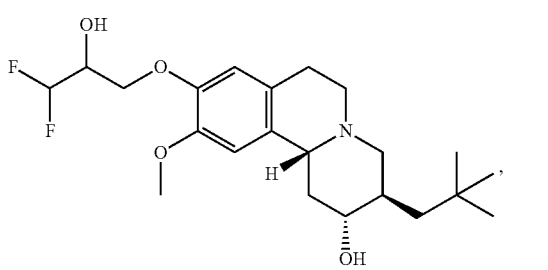

Compound 4-55

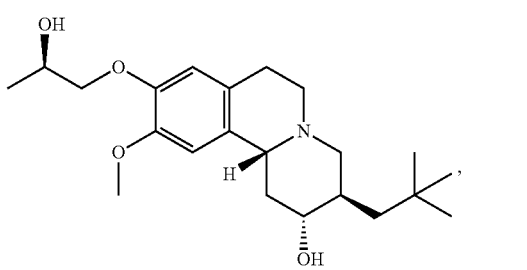

Compound 4-18

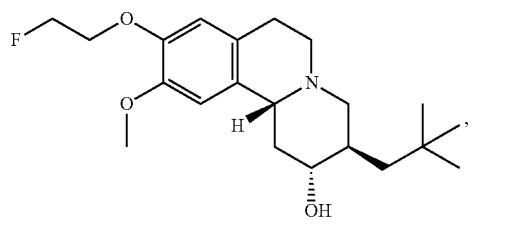

Compound 4-28

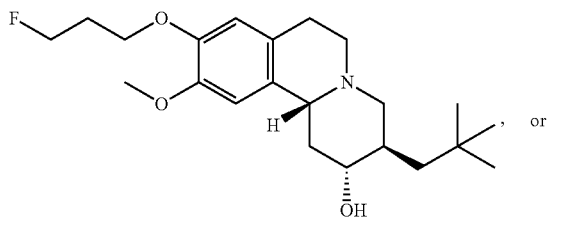

Compound 4-39

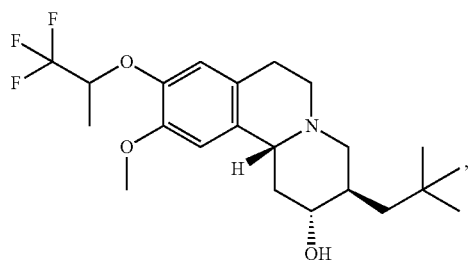

or a pharmaceutically acceptable salt thereof.

Some embodiments provide a compound having the structure:

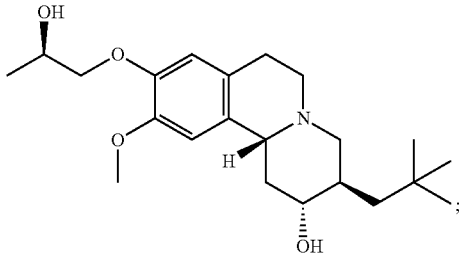 [SMILES: COc1cc2c(cc1OC[C@@H](C)O)CCN1C[C@@H](CC(C)(C)C)[C@H](O)C[C@H]21]

or a pharmaceutically acceptable salt thereof.

Some embodiments provide a compound having the structure:

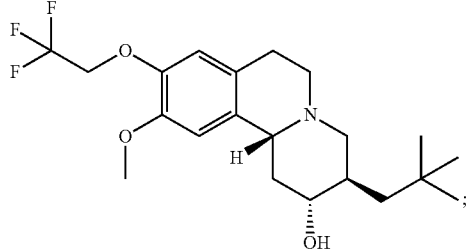 [SMILES: COc1cc2c(cc1OCC(F)(F)F)CCN1C[C@@H](CC(C)(C)C)[C@H](O)C[C@H]21]

or a pharmaceutically acceptable salt thereof.

Some embodiments provide a compound having the structure:

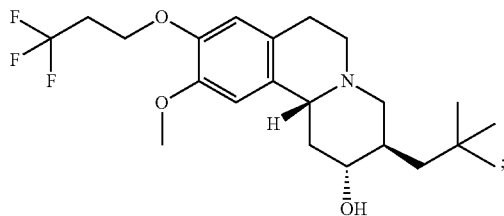 [SMILES: COc1cc2c(cc1OCCC(F)(F)F)CCN1C[C@@H](CC(C)(C)C)[C@H](O)C[C@H]21]

or a pharmaceutically acceptable salt thereof.

Some embodiments provide a compound having the structure:

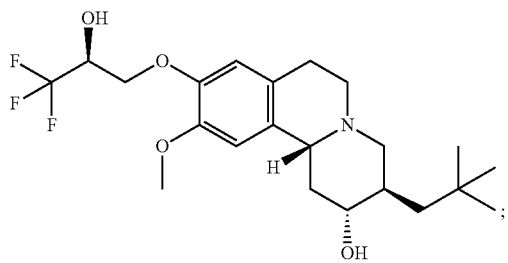 [SMILES: COc1cc2c(cc1OC[C@H](O)C(F)(F)F)CCN1C[C@@H](CC(C)(C)C)[C@H](O)C[C@H]21]

or a pharmaceutically acceptable salt thereof.

Some embodiments provide a compound having the structure:

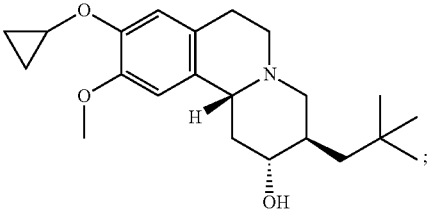 [SMILES: COc1cc2c(cc1OC1CC1)CCN1C[C@@H](CC(C)(C)C)[C@H](O)C[C@H]21]

or a pharmaceutically acceptable salt thereof.

Some embodiments provide a compound having the structure:

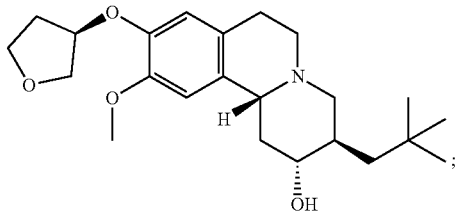 [SMILES: COc1cc2c(cc1O[C@@H]1CCOC1)CCN1C[C@@H](CC(C)(C)C)[C@H](O)C[C@H]21]

or a pharmaceutically acceptable salt thereof.

Some embodiments provide a compound having the structure:

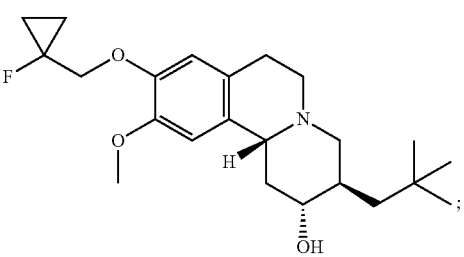 [SMILES: COc1cc2c(cc1OCC1(F)CC1)CCN1C[C@@H](CC(C)(C)C)[C@H](O)C[C@H]21]

or a pharmaceutically acceptable salt thereof.

Some embodiments provide a compound having the structure:

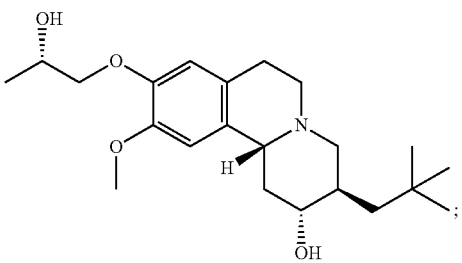 [SMILES: COc1cc2c(cc1OC[C@H](C)O)CCN1C[C@@H](CC(C)(C)C)[C@H](O)C[C@H]21]

or a pharmaceutically acceptable salt thereof.

Some embodiments provide a compound having the structure:

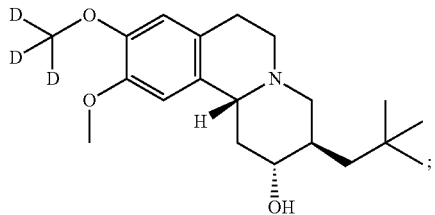 [SMILES: [2H]C([2H])([2H])Oc1cc2c(cc1OC)[C@H]1C[C@@H](O)[C@H](CC(C)(C)C)CN1CC2]

or a pharmaceutically acceptable salt thereof.

Intermediates Useful in Preparing Compounds of Formula (I)

Certain intermediates as described herein, supra, and infra, are novel and useful in the preparation of compounds of Formula (I).

In some embodiments, a compound is selected from the group consisting of: 9-(benzyloxy)-10-methoxy-3-neopentyl-1,3,4,6,7,11b-hexahydro-2H-pyrido[2,1-a]isoquinolin-2-one (Compound 1-B); 9-(benzyloxy)-10-methoxy-3-neopentyl-1,3,4,6,7,11b-hexahydro-2H-pyrido[2,1-a]isoquinolin-2-ol (Compound 1-C); 10-methoxy-3-neopentyl-1,3,4,6,7,11b-hexahydro-2H-pyrido[2,1-a]isoquinoline-2,9-diol (Compound 1-D); and 9-hydroxy-10-methoxy-3-neopentyl-1,3,4,6,7,11b-hexahydro-2H-pyrido[2,1-a]isoquinolin-2-one (Compound 2-B), or a salt thereof.

In some embodiments, a compound is: 9-(benzyloxy)-10-methoxy-3-neopentyl-1,3,4,6,7,11b-hexahydro-2H-pyrido[2,1-a]isoquinolin-2-one (Compound 1-B), or a salt thereof. In some embodiments, a compound is selected from the group consisting of: (3R,11bR)-9-(benzyloxy)-10-methoxy-3-neopentyl-1,3,4,6,7,11b-hexahydro-2H-pyrido[2,1-a]isoquinolin-2-one (Compound 1-B (3R,11bR)); and (3S,11bS)-9-(benzyloxy)-10-methoxy-3-neopentyl-1,3,4,6,7,11b-hexahydro-2H-pyrido[2,1-a]isoquinolin-2-one (Compound 1-B (3S,11bS)), or a salt thereof. In some embodiments, a compound is: (3R,11 bR)-9-(benzyloxy)-10-methoxy-3-neopentyl-1,3,4,6,7,11b-hexahydro-2H-pyrido[2,1-a]isoquinolin-2-one (Compound 1-B (3R,11bR)), or a salt thereof. In some embodiments, a compound is:

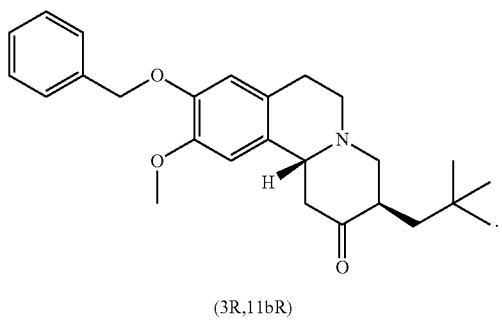

1-B (3R,11bR)

In some embodiments, a compound is: 9-(benzyloxy)-10-methoxy-3-neopentyl-1,3,4,6,7,11b-hexahydro-2H-pyrido[2,1-a]isoquinolin-2-ol (Compound 1-C), or a salt thereof. In some embodiments, the salt is DPTTA. In some embodiments, a compound is: (2R,3R,11bR)-9-(benzyloxy)-10-methoxy-3-neopentyl-1,3,4,6,7,11b-hexahydro-2H-pyrido[2,1-a]isoquinolin-2-ol (Compound 1-C(2R,3R,11bR)), or a salt thereof. In some embodiments, the salt is DPTTA. In some embodiments, a compound is:

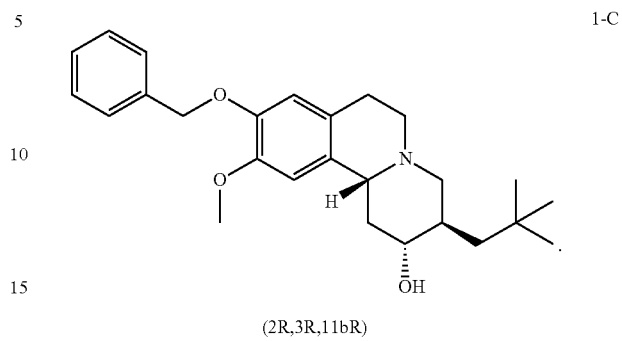

1-C (2R,3R,11bR)

In some embodiments, a compound is: 10-methoxy-3-neopentyl-1,3,4,6,7,11b-hexahydro-2H-pyrido[2,1-a]isoquinoline-2,9-diol (Compound 1-D), or a salt thereof. In some embodiments, a compound is selected from the group consisting of: (2R,3R,11bR)-3-(2,2-dimethylpropyl)-10-methoxy-1H,2H,3H,4H,6H,7H,11bH-pyrido[2,1-a]isoquinoline-2,9-diol (Compound 1-D (2R,3R,11bR)); (2S,3S,11bS)-10-methoxy-3-neopentyl-1,3,4,6,7,11b-hexahydro-2H-pyrido[2,1-a]isoquinoline-2,9-diol (Compound 1-D (2S,3S,11bS)); (2S,3R,11 bR)-10-methoxy-3-neopentyl-1,3,4,6,7,11b-hexahydro-2H-pyrido[2,1-a]isoquinoline-2,9-diol (Compound 1-D (2S,3R,11bR)); and (2R,3S,11bS)-10-methoxy-3-neopentyl-1,3,4,6,7,11b-hexahydro-2H-pyrido[2,1-a]isoquinoline-2,9-diol (Compound 1-D (2R,3S,11bS)), or a salt thereof. In some embodiments, a compound is: (2R,3R,11bR)-3-(2,2-dimethylpropyl)-10-methoxy-1H,2H,3H,4H,6H,7H,11bH-pyrido[2,1-a]isoquinoline-2,9-diol (Compound 1-D (2R,3R,11bR)), or a salt thereof. In some embodiments, a compound is:

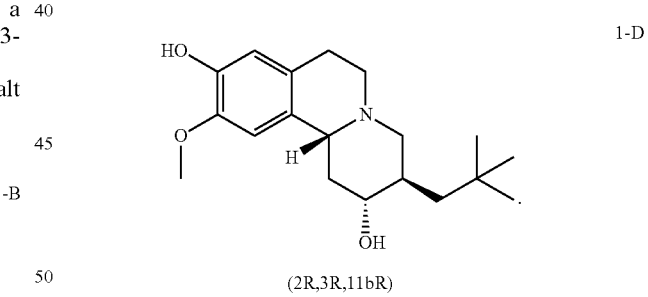

1-D (2R,3R,11bR)

In some embodiments, a compound is: 9-hydroxy-10-methoxy-3-neopentyl-1,3,4,6,7,11b-hexahydro-2H-pyrido[2,1-a]isoquinolin-2-one (Compound 2-B), or a salt thereof. In some embodiments, a compound is selected from the group consisting of: (3R,11bR)-3-(2,2-dimethylpropyl)-9-hydroxy-10-methoxy-1H,2H,3H,4H,6H,7H,11bH-pyrido[2,1-a]isoquinolin-2-one (Compound 2-B (3R,11bR)); and (3S,11bS)-3-(2,2-dimethylpropyl)-9-hydroxy-10-methoxy-1H,2H,3H,4H,6H,7H,11bH-pyrido[2,1-a]isoquinolin-2-one (Compound 2-B (3S,11bS)), or a salt thereof. In some embodiments, a compound is: (3R,11bR)-3-(2,2-dimethylpropyl)-9-hydroxy-10-methoxy-1H,2H,3H,4H,6H,7H,11bH-pyrido[2,1-a]isoquinolin-2-one (Compound 2-B (3R,11bR)), or a salt thereof. In some embodiments, a compound is:

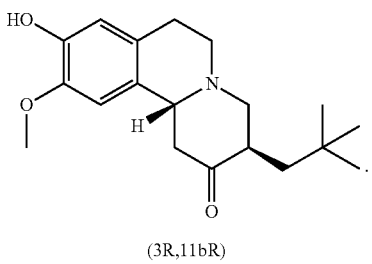

2-B (3R,11bR)

It is further appreciated that certain features, which are, for clarity, described in the context of separate embodiments, can also be provided in combination in a single embodiment. Conversely, various features which are, for brevity, described in the context of a single embodiment, can also be provided separately or in any suitable subcombination.

Pharmaceutical Compositions, Formulation, and Dosage Forms

The present disclosure further provides for pharmaceutical products, such as, pharmaceutical compositions, formulations, unit dosage forms, and kits; each comprising a compound of Formula (I), or a pharmaceutically acceptable salt thereof.

The present disclosure further provides for pharmaceutical compositions comprising any one of the VMAT2 inhibitor compounds described herein (e.g., a compound of Formula (I), including specific compounds described herein) and at least one pharmaceutically acceptable excipient for use in the methods described here, such as, for treating hyperkinetic movement disorders. A pharmaceutically acceptable excipient is a physiologically and pharmaceutically suitable non-toxic and inactive material or ingredient that does not interfere with the activity of the drug substance; an excipient also can be called a carrier. The formulation methods and excipients described herein are exemplary and are in no way limiting. Pharmaceutically acceptable excipients are well known in the pharmaceutical art and described, for example, in Rowe et al., Handbook of Pharmaceutical Excipients: A Comprehensive Guide to Uses, Properties, and Safety, 5$^{th}$ Ed., 2006, and in Remington: The Science and Practice of Pharmacy (Gennaro, 21$^{st}$ Ed. Mack Pub. Co., Easton, Pa. (2005)).

The compositions can also be formulated as pills, capsules, granules, or tablets which contain, in addition to an VMAT2 inhibitor, diluents, dispersing and surface active agents, binders, and lubricants. One skilled in this art can further formulate the VMAT2 inhibitor in an appropriate manner, and in accordance with accepted practices, such as, those disclosed in Remington, supra.

Methods of administration include systemic administration of a VMAT2 inhibitor described herein, preferably in the form of a pharmaceutical composition as discussed above. As used herein, systemic administration includes oral and parenteral methods of administration. For oral administration, suitable pharmaceutical compositions include powders, granules, pills, tablets, and capsules as well as liquids, syrups, suspensions, and emulsions.

Pharmaceutical preparations for oral administration can be obtained by any suitable method, typically by uniformly mixing the compound(s) with liquids or finely divided solid carriers, or both, in the required proportions and then, if necessary, processing the mixture, after adding suitable auxiliaries, if desired, forming the resulting mixture into a desired shape to obtain tablets or dragee cores.

Conventional excipients, such as, binding agents, fillers, adjuvant, carrier, acceptable wetting agents, tableting lubricants, and disintegrants can be used in tablets and capsules for oral administration. Liquid preparations for oral administration can be in the form of solutions, emulsions, aqueous or oily suspensions, and syrups. Alternatively, the oral preparations can be in the form of dry powder that can be reconstituted with water or another suitable liquid vehicle before use. Parenteral dosage forms can be prepared by dissolving the compound in a suitable liquid vehicle and filter sterilizing the solution before lyophilization, or simply filling and sealing an appropriate vial or ampule.

Some embodiments provide methods for preparing a pharmaceutical composition comprising the step of admixing a compound of Formula (I), or a pharmaceutically acceptable salt thereof, and a pharmaceutically acceptable carrier.

Formulations suitable for vaginal administration can be presented as pessaries, tampons, creams, gels, pastes, foams, or sprays containing in addition to the drug substance such carriers as are known in the art to be appropriate.

In making pharmaceutical compositions, the drug substance is typically mixed (i.e., admixed) with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, catrer, or medium for the drug substance. Thus, the compositions can be in the form of tablets, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

For preparing solid form pharmaceutical compositions, such as, powders, tablets, capsules, cachets, suppositories, and dispersible granules an excipient can be one or more substances which may also act as diluents, flavoring agents, solubilizers, lubricants, suspending agents, binders, preservatives, tablet disintegrating agents, or an encapsulating material. Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

For preparing suppositories, a low melting wax, such as, an admixture of fatty acid glycerides or cocoa butter, is first melted and the active component is dispersed homogeneously therein, as by stirring. The molten homogenous mixture is then poured into convenient sized molds, allowed to cool and thereby to solidify.

Liquid form preparations include solutions, suspensions, and emulsions, for example, water or water-propylene glycol solutions. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent.

The pharmaceutical compositions can take such forms as suspensions, solutions, or emulsions in oily or aqueous vehicles and can contain formulatory agents, such as, suspending, stabilizing and/or dispersing agents. Alternatively, the pharmaceutical compositions can be in powder form, obtained by aseptic isolation of sterile solid or by lyophilization from solution, for constitution with a suitable vehicle, e.g. sterile, pyrogen-free water, before use.

The pharmaceutical compositions can be formulated as an aqueous solution, an aqua-alcoholic solution, a solid suspension, an emulsion, a liposomal suspension, or a freeze-dried powder for reconstitution. Such pharmaceutical compositions can be administered directly or as an admixture for further dilution/reconstitution. Route of administration includes intravenous bolus, intravenous infusion, irrigation, and instillation.

Aqueous formulations suitable for oral use can be prepared by dissolving or suspending the active component in water and adding suitable colorants, flavors, stabilizing, and thickening agents, as desired.

Aqueous suspensions suitable for oral use can be made by dispersing the finely divided drug substance in water with viscous material.

For topical administration to the epidermis the compounds described herein, or pharmaceutically acceptable salts thereof can be formulated as gels, ointments, creams, or lotions, or as a transdermal patch. Also, formulations suitable for topical administration in the mouth include lozenges comprising drug substance in a flavored base.

Solutions or suspensions can be applied directly to the nasal cavity by conventional means, for example with a dropper, pipette, or spray. The formulations can be provided in single or multi-dose form. In the latter case of a dropper or pipette, this can be achieved by the patient administering an appropriate, predetermined volume of the solution or suspension. In the case of a spray, this can be achieved for example by means of a metering atomizing spray pump.

Administration to the respiratory tract can also be achieved by means of an aerosol formulation provided in a pressurized pack with a suitable propellant. If the compounds described herein, or pharmaceutically acceptable salts thereof or pharmaceutical compositions comprising them are administered as aerosols, for example as nasal aerosols or by inhalation, this can be carried out, for example, using a spray, a nebulizer, a pump nebulizer, an inhalation apparatus, a metered inhaler, or a dry powder inhaler.

Alternatively, the pharmaceutical composition can be provided in the form of a dry powder, for example, a powder mix of the compound in a suitable, powder base, such as, lactose, starch, starch derivatives. Conveniently the powder carrier will form a gel in the nasal cavity. The powder composition may be presented in unit dose form for example in capsules or cartridges of, e.g., gelatin, or blister packs from which the powder may be administered by means of an inhaler.

The compounds Formula (I), or pharmaceutically acceptable salts thereof can also be administered via a rapid dissolving or a slow-release composition, wherein the composition includes a biodegradable rapid dissolving or slow-release carrier.

The pharmaceutical preparations are preferably in unit dosage forms. In such form, the preparation is subdivided into unit doses containing appropriate quantities of the drug substance. The unit dosage form can be a packaged preparation, the package containing discrete quantities of preparation, such as, packeted tablets, capsules, and powders in vials or ampoules. Also, the unit dosage form can be a capsule, tablet, cachet, or lozenge itself, or it can be the appropriate number of any of these in packaged form. In some embodiments, the pharmaceutical preparation is a tablet or capsule for oral administration. In some embodiments, the pharmaceutical preparation is a liquid formulated for intravenous administration.

The compositions can be formulated in a unit dosage form, each dosage containing the drug substance or equivalent mass of the drug substance. The term "unit dosage forms" refers to physically discrete units of a formulation suitable as unitary dosages for human subjects and other mammals, each unit containing a predetermined quantity of active material calculated to produce the desired therapeutic effect, in association with a suitable excipient, as described herein.

The liquid forms including the drug substance can be incorporated for administration orally or by injection include aqueous solutions, suitably flavored syrups, aqueous or oil suspensions, and flavored emulsions with edible oils.

The pharmaceutical compositions described herein can be sterilized by conventional sterilization techniques, or can be sterile filtered. Aqueous solutions can be packaged for use as is, or lyophilized, the lyophilized preparation being combined with a sterile aqueous carrier prior to administration.

Compositions for inhalation or insufflation include solutions and suspensions in pharmaceutically acceptable, aqueous or organic solvents, or mixtures thereof, and powders. The liquid or solid compositions may contain suitable excipients as described herein. In some embodiments, the compositions are administered by the oral or nasal respiratory route for local or systemic effect. Compositions can be nebulized by use of inert gases. Nebulized solutions may be breathed directly from the nebulizing device, or the nebulizing device can be attached to a face masks tent, or intermittent positive pressure breathing machine. Solution, suspension, or powder compositions can be administered orally or nasally from devices which deliver the formulation in an appropriate manner.

The compositions may, if desired, be presented in a pack or dispenser device which may contain one or more-unit dosage forms containing the drug substance. The pack may for example comprise metal or plastic foil, such as, a blister pack. The pack or dispenser device can be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

For preparing solid compositions, such as, tablets, the drug substance can be mixed with an excipient to form a solid preformulation composition containing a homogeneous mixture of components. When referring to these preformulation compositions as homogeneous, the drug substance is typically dispersed evenly throughout the composition so that the composition can be readily subdivided into equally effective unit dosage forms, such as, tablets and capsules.

Kits with unit doses of one or more of the compounds described herein, or a pharmaceutically acceptable salt thereof, usually in oral or injectable doses, are provided. Such kits can include a container containing the unit dose, an informational package insert describing the use and attendant benefits of the drugs in treating pathological condition of interest, and optionally an appliance or device for delivery of the composition.

The compounds described herein, or a pharmaceutically acceptable salt thereof, can be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

The amount of compound or composition administered to a subject will also vary depending upon what is being administered, the purpose of the administration, such as, prophylaxis or therapy, the state of the subject, the manner of administration, and the like. In therapeutic applications, compositions can be administered to a subject already suffering from a disease in an amount sufficient to cure or at least partially arrest the symptomology and/or pathology of the disease and its complications. Therapeutically effective doses will depend on the disease condition being treated as well as by the judgment of the attending clinician depending upon factors, such as, the severity of the disease, the age, weight, and general condition of the subject, and the like.

The desired dose may conveniently be presented in a single dose or presented as divided doses administered at appropriate intervals, for example, as two, three, four, or more sub-doses per day. The sub-dose itself can be further divided, e.g., into a number of discrete loosely spaced administrations. The daily dose can be divided, especially when relatively large amounts are administered as deemed appropriate, into several, for example two, three, or four-part administrations. If appropriate, depending on individual behavior, it can be necessary to deviate upward or downward from the daily dose indicated.

It will be apparent to those skilled in the art that the dosage forms described herein can comprise a compound described herein or pharmaceutically acceptable salt thereof.

Preparations

As used herein, a "preparation" is the product of a process used to make or isolate a compound as disclosed and described herein, wherein the preparation contains at least one other component in addition to the compound. In some embodiments, the preparation comprises a chemical entity.

As used herein, a "chemical entity" defined in the context of a "preparation," refers to a compound as disclosed and described herein and at least one other component in addition to the compound. For example, a chemical entity can be a co-crystal or salt of a compound as disclosed and described herein.

Some embodiments provide a preparation comprising a compound as disclosed and described herein. In some embodiments, the compound is a component of a chemical entity. In some embodiments, the chemical entity is a salt of a compound as disclosed and described herein. In some embodiments, the chemical entity is a (2S,3S)-2,3-bis(4-methylbenzoyloxy)butanedioic acid (DPTTA) salt of a compound as disclosed and described herein.

In some embodiments, the compound of the preparation is in at least 5%, 10%, 20%, 30%, 40%, 50%, 60%, 70%, 80%, 90%, 95%, 99%, 99.5%, or 99.9% enantiomeric excess, or an enantiomeric excess within a range defined by any of the preceding numbers. In some embodiments, the compound of the preparation is in at least 90%, 91%, 92%, 93%, 94%, 95%, 96%, 97%, 98%, 99%, 99.5%, or 99.9% enantiomeric excess, or an enantiomeric excess within a range defined by any of the preceding numbers.

In some embodiments, the compound of the preparation is in at least 5%, 10%, 20%, 30%, 40%, 50%, 60%, 70%, 80%, 90%, 95%, 99%, or 99.9% diastereomeric excess, or a diastereomeric excess within a range defined by any of the preceding numbers. In some embodiments, the compound of the preparation is in at least 90%, 91%, 92%, 93%, 94%, 95%, 96%, 97%, 98%, 99%, 99.5%, or 99.9% diastereomeric excess, or a diastereomeric excess within a range defined by any of the preceding numbers.

In some embodiments, the preparation comprises at least 5%, 10%, 20%, 30%, 40%, 50%, 60%, 70%, 80%, 90%, or 93% by weight of the compound, or a % by weight within a range defined by any of the preceding numbers. In some embodiments, the preparation comprises at least 50%, 60%, 70%, 80%, 90%, or 93% by weight of the compound, or a % by weight within a range defined by any of the preceding numbers. In some embodiments, the preparation comprises at most 50%, 60%, 70%, 80%, 90%, 93%, or 95% by weight of the compound, or a % by weight within a range defined by any of the preceding numbers.

In some embodiments, the preparation comprises at least 50% by weight of the compound. In some embodiments, the preparation is in the form of a solid, i.e., a solid preparation. In some embodiments, the preparation is used to prepare a pharmaceutical composition.

Methods of Use

The compounds of Formula (I) as disclosed and described herein are inhibitors of VMAT2. Accordingly, the present disclosure includes a method of inhibiting VMAT2 (i.e., decreasing at least one function of VMAT2 or decreasing expression of VMAT2) by contacting the VMAT2 with a compound as disclosed and described herein, or a pharmaceutically acceptable salt thereof. In some embodiments, the contacting can occur in vitro, such as, where the VMAT2 is located in a purified preparation or in a cell outside of a living organism (e.g., in a tissue sample or a cellular preparation). In some embodiments, the contacting can occur in vivo, such as, where the VMAT2 is located in a living organism.

The VMAT2 inhibitors described herein can reduce the level of monoamines in the central nervous system. Accordingly, the present disclosure includes a method of reducing the level of monoamines in the central nervous system of a subject comprising administering to the subject an amount of a compound of Formula (I), or a pharmaceutically acceptable salt thereof, sufficient to lower the level of monoamines relative to the level prior to administration.

The VMAT2 inhibitors as disclosed and described herein are believed to have utility over a wide range of therapeutic applications, and may be used to treat or prevent a variety of disorders which are caused by or linked to inhibition of the human vesicular monoamine transporter isoform 2. These disorders include neurological and psychiatric disorders, for example, hyperkinetic movement disorders, schizophrenia, and mood disorders. A compound of Formula (I), or a pharmaceutically acceptable salt thereof, can be used in any of the therapeutic methods disclosed and described herein. Also, (3R,11bR)-3-(2,2-dimethylpropyl)-9,10-dimethoxy-1H,2H,3H,4H,6H,7H,11bH-pyrido[2,1-a]isoquinolin-2-one (Compound 5-A (3R,11bR)), or a pharmaceutically acceptable salt thereof, or (3S,11bS)-3-(2,2-dimethylpropyl)-9,10-dimethoxy-1H,2H,3H,4H,6H,7H,11bH-pyrido[2,1-a]isoquinolin-2-one (Compound 5-A (3S,11bS)) or a pharmaceutically acceptable salt thereof, or an isotopic variant of a Compound 5-A (3R,11bR) or Compound 5-A (3S,11bS) can be used in any of the therapeutic methods disclosed and described herein. In some embodiments, the isotopic variant of a Compound 5-A (3R,11bR) or Compound 5-A (3S,11bS) can have a deuterium in three or more positions in an isotopic distribution in proportional amounts different to those usually found in nature. In some embodiments, a Compound 5-A (3R,11bR) or Compound 5-A (3S,11bS) can have at least 95%, 97%, 99%, 99.5%, or 99.9% deuterium incorporation in three or more positions, or deuterium incorporation in three or more positions within a range defined by any of the preceding numbers.

Accordingly, in various embodiments as disclosed herein, methods are provided for treating or preventing a neurological and/or psychiatric disease or disorder in a subject in need thereof by administering to the subject a pharmaceutically effective amount of a VMAT2 inhibitor as described herein, or a pharmaceutically acceptable salt thereof. The neurological and/or psychiatric disease or disorder can be, for example, a hyperkinetic movement disorder, schizophrenia, schizoaffective disorder, a mood disorder, treatment-refractory obsessive-compulsive disorder, neurological dysfunction associated with Lesch-Nyhan syndrome, agitation associated with Alzheimer's disease, Fragile X syndrome or Fragile X-associated tremor-ataxia syndrome, autism spectrum disorder (e.g., restricted and repetitive behaviors associated with Autism spectrum disorder (ASD)), Rett syndrome, or chorea-acanthocytosis.

In various other embodiments as disclosed herein, methods are provided for treating or preventing a vesicular monoamine transporter-2 (VMAT2) disease or disorder in a subject in need thereof by administering to the subject a pharmaceutically effective amount of a VMAT2 inhibitor as described herein, or a pharmaceutically acceptable salt thereof. The VMAT2 disease or disorder can be, for example, an ataxias or spinal muscular atrophy; a chorea; a congenital malformation, deformation, or abnormality; a dementia; an oral cavity, salivary gland, or jaw disease; a dyskinesia; a dystonia; an endocrine, nutritional, or metabolic disease; an epilepsy; a habit or impulse disorder; a Huntington's disease or related disorder; a mood or psychotic disorder; a neurotic, stress-related, and somatoform disorder; a degenerative disease of the basal ganglia; an extrapyramidal and movement disorder; a neurological or psychiatric disease or disorder; a nervous system or motor function disorder; a Parkinson's/parkinsonism disorder; a pediatric-onset behavioral and emotional disorder; a pervasive developmental disorder; and a substance abuse or dependence disorder.

Accordingly, in various embodiments as disclosed herein, methods are provided for treating or preventing a hyperkinetic movement disorder in a subject in need thereof by administering to the subject in need thereof a pharmaceutically effective amount of a VMAT2 inhibitor described herein, or a pharmaceutically acceptable salt thereof. In some embodiments, the hyperkinetic movement disorder is tardive dyskinesia, Tourette's syndrome, Huntington's disease, chorea associated with Huntington's disease, or tics. In other embodiments, the hyperkinetic movement disorder is ataxia, chorea, dystonia, hemifacial spasm, myoclonus, restless leg syndrome, or tremors.

In some embodiments, methods are provided for treating or preventing a mood disorder in a subject in need thereof by administering to the subject in need thereof a pharmaceutically effective amount of a VMAT2 inhibitor described herein, or a pharmaceutically acceptable salt thereof. In some embodiments, the mood disorder is bipolar disorder, major depressive disorder, mania in a mood disorder, or depression in a mood disorder.

In some embodiments as disclosed herein, methods are provided for treating or preventing schizophrenia or schizoaffective disorder in a subject in need thereof by administering to the subject in need thereof a pharmaceutically effective amount of a VMAT2 inhibitor described herein, or a pharmaceutically acceptable salt thereof.

In some embodiments, the neurological or psychiatric disease or disorder is a hyperkinetic movement disorder.

In some embodiments, the hyperkinetic movement disorder is tardive dyskinesia.

In some embodiments, the hyperkinetic movement disorder is Tourette's syndrome.

In some embodiments, the hyperkinetic movement disorder is Huntington's disease.

In some embodiments, the hyperkinetic movement disorder is tics.

In some embodiments, the hyperkinetic movement disorder is chorea associated with Huntington's disease.

In some embodiments, the hyperkinetic movement disorder is ataxia, chorea, dystonia, hemifacial spasm, Huntington's disease, myoclonus, restless leg syndrome, or tremors.

In some embodiments, the neurological or psychiatric disease or disorder is restricted and repetitive behaviors associated with Autism spectrum disorder (ASD).

In some embodiments, the neurological or psychiatric disease or disorder is obsessions and compulsions in partial and non-responders (or completely refractory) with obsessive-compulsive disorder (OCD). In some embodiments, the neurological or psychiatric disease or disorder is obsessions and compulsions in partial and non-responders (or completely refractory) with obsessive-compulsive disorder (OCD) and the compounds described herein are administered as adjunctive therapy. In some embodiments, the compounds described here are administered as adjunctive therapy with the primary therapy being treatment with antidepressants.

In some embodiments, the neurological or psychiatric disease or disorder is Bipolar I Disorder. In some embodiments, the compound described herein is administered as monotherapy for the treatment of Bipolar I Disorder. In some embodiments, the compound described herein is administered as maintenance therapy for the treatment of Bipolar I Disorder. In some embodiments, the compound described herein is administered as monotherapy maintenance therapy for the treatment of Bipolar I Disorder. In some embodiments, the VMAT2-inhibiting compound of Formula (I), or a pharmaceutically acceptable salt thereof, is administered to the patient to treat or prevent a disease or disorder selected from:

ataxias or spinal muscular atrophies, such as, spinocerebellar ataxia type 17 (SCA17)/HDL4, ataxia, spinal muscular atrophy, amyotrophic lateral sclerosis, familial amyotrophic lateral sclerosis, bulbospinal muscular atrophy congenital, dentatorubral-pallidoluysian atrophy, hereditary motor neuron disease, and hereditary spastic paraplegia;

chorea, such as, benign hereditary chorea, chorea, chorea associated with mitochondrial disease/causes, chorea associated with Wilson's disease, chorea gravidarum, chorea-acanthocytosis, drug-induced chorea, hemiballism, rheumatic/Sydenham's chorea, and thyrotoxic chorea/hyperthyroid chorea;

congenital malformations, deformations, or abnormalities, such as, Angelman syndrome, congenital neurological disorder, Aicardi's syndrome, neurofibromatosis, congenital facial nerve hypoplasia, Moebius II syndrome, Cockayne's syndrome, Sjogren-Larsson syndrome, Laurence-Moon-Bardet-Biedl syndrome, Fragile X syndrome, and Prader-Willi syndrome;

dementia, such as, AIDS-related dementia, Alzheimer's disease, congenital neurological degeneration, Lewy body dementia, micro-infarct dementia, pre-senile dementia, senile dementia, and vascular dementia;

diseases of oral cavity, salivary glands, and jaws, such as, glossodynia/burning mouth syndrome and temporomandibular joint disorder;

dyskinesia, such as, pharyngeal dyskinesia, dyskinesia, dyskinesia (neonatal), dyskinesia (oesophageal), levodopa-induced dyskinesia, paroxysmal kinesigenic dyskinesias, paroxysmal nonkinesigneic dyskinesias, and respiratory dyskinesia;

dystonia, such as, blepharospasm, buccoglossal syndrome, drug-induced acute dystonia, dystonia, early onset primary dystonia, genetic torsion dystonia, hand dystonia/writer's cramp, idiopathic nonfamilial dystonia, idiopathic orofacial dystonia/Meige's disease, laryngeal dystonia, oromandibular dystonia, and spasmodic torticollis/cervical dystonia;

endocrine, nutritional, and metabolic diseases, such as, Wilson's Disease, diabetes mellitus, obesity, syndrome X, and Lesch-Nyhan syndromes;

epilepsy, such as, Baltic myoclonic epilepsy, benign familial neonatal convulsions, epilepsy, epilepsy congenital, Lafora's myoclonic epilepsy, severe myoclonic epilepsy of infancy, and convulsions;

habit and impulse disorders, such as, binge eating disorder, kleptomania, impulse control disorders, trichotillomania, intermittent explosive disorder, pathological gambling, and pyromania;

Huntington's disease or related disorders, such as, Huntington's disease, Huntington's disease-like syndromes 1-3, Huntington's chorea, and X-linked McLeod Neuroacanthocytosis syndrome;

mood or psychotic disorders, such as, schizophrenia, psychosis, mania, bipolar disorder, depression, and mood disorders;

other diseases or disorders, such as, fumbling, hypokinesia, hypokinesia (neonatal), movement disorder, rabbit syndrome, spasticity, up and down phenomenon, asthma, cancer, congenital nystagmus, familial hemiplegic migraine, fetal movement disorder, and rheumatoid arthritis;

neurotic, stress-related, and somatoform disorders, such as, social anxiety disorder, panic disorder, generalized anxiety disorder, obsessive-compulsive disorder, post-traumatic stress disorder, and psychogenic movement disorder;

other degenerative diseases of basal ganglia, such as, pantothenate kinase-associated neurodegeneration, progressive supranuclear palsy, multiple system atrophy, dyslexia, basal ganglion degeneration, and neuroferritinopathy;

other extrapyramidal and movement disorders, such as, hemiballismus, extrapyramidal disorder, essential tremor, geniospasm, hyperexplexia, akathisia, ballismus/hemiballism, myoclonus, and restless legs syndrome/Willis-Ekbom's syndrome;

other nervous system or motor function, such as, sleep-related bruxism, abnormal involuntary movement disorders, alien limb syndrome, Alzheimer's disease (agitation), clumsiness, clonic hemifacial spasm, olfactory nerve agenesis, congenital cranial nerve paralysis, exercise ataxia syndrome, familial periodic paralysis, congenital hemiparesis, fine motor delay, fine motor skill dysfunction, gross motor delay, multiple sclerosis, congenital flaccid paralysis, congenital Homer's syndrome, alternating hemiplegia of childhood, motor developmental delay, cerebral palsy, athetoid cerebral palsy, posturing, pseudoparalysis, psychomotor hyperactivity, bradykinesia, synkinesis, akinesia, Riley-Day syndrome, and athetosis;

Parkinson's/parkinsonism, such as, parkinsonism, drug-induced parkinsonism, micrographia, and Parkinson's disease;

pediatric-onset behavioral and emotional disorders, such as, attention deficit hyperactivity disorder, attention deficit disorder, hyperkinesia, hyperkinesia (neonatal), oppositional defiant disorder, provisional tic disorder, persistent (chronic) motor or vocal tic disorder, stereotypic movement disorder, stereotypy, and Tourette's syndrome;

pervasive developmental disorders, such as, autism spectrum disorders, Rett's syndrome, Asperger's syndrome, pervasive developmental disorder NOS, and dyslexia; and substance abuse or dependence, such as, addiction disorders, alcoholism, cocaine dependence, illegal drug abuse, methamphetamine abuse, methamphetamine addiction/dependence, methamphetamine use disorder, morphine abuse, morphine-analogue abuse, nicotine dependence, polysubstance abuse, and prescription drug abuse.

In some embodiments, the patient which is treated has been determined to have 22q11.2 deletion syndrome. In some embodiments, the patient is predisposed to developing a psychiatric disorder due to the patient having 22q11.2 deletion syndrome. In some embodiments, the patient has been determined to have COMT haploinsufficiency. In some embodiments, the patient is predisposed to developing a psychiatric disorder due to the patient having COMT haploinsufficiency.

In another embodiment, the VMAT2 inhibitors described herein may be hydrolyzed in the body of a mammal to compounds that may inhibit the human vesicular monoamine transporter isoform 2. As such, these VMAT2 inhibitors may have additional utility in altering the in vivo properties of the metabolite in a mammal, such as, the maximum concentration or duration of action.

Characterizing any of the VMAT2 inhibitors described herein may be determined using methods described herein, and those in the art. For example, dopamine depletion may be determined using the locomotor activity (LMA) assay. Another in vivo animal model includes the conditioned avoidance response (CAR) test, which has been shown to be an effective and reliable preclinical model for assessing the antipsychotic activity of compounds.

Combination Therapy

The compounds of the present disclosure, or their pharmaceutically acceptable salts, can be used as monotherapy, or in combination with one or more other pharmaceutical agents. In some embodiments, a compound of Formula (I), or its pharmaceutically acceptable salt, is administered together with (simultaneously or sequentially) one or more pharmaceutical agents selected from antidepressants, antipsychotics (typical or atypical), antiepileptics, antimicrobials, antiarrhythmics, mood stabilizers, and gastrointestinal drugs. In some embodiments, a compound of Formula (I), or a pharmaceutically acceptable salt thereof, is used in adjunctive therapy which refers to a treatment that is used in conjunction with a primary treatment and its purpose is to assist the primary treatment. Adjunctive therapies are typically co-administered therapies. As an example of adjunctive therapy, if obsessive-compulsive disorder is being treated, the primary therapy may be, e.g., an antidepressant, and the co-administration of a compound described herein would be considered an adjunctive therapy.

Compound Synthesis

Detailed compound synthesis methods are described herein in the Examples. In general, starting components are commercially available chemicals and may be obtained from commercial sources or may be made according to organic synthesis techniques known to those skilled in this art, starting from commercially available chemicals and/or from compounds described in the chemical literature.

In general, the compounds used in the reactions described herein may be made according to organic synthesis techniques known to those skilled in this art, starting from commercially available chemicals and/or from compounds described in the chemical literature. Methods known to one of ordinary skill in the art may be identified through various reference books and databases. Suitable reference books and treatise that detail the synthesis of reactants useful in the preparation of compounds of the present disclosure, or provide references to articles that describe the preparation, include for example, "Synthetic Organic Chemistry," John Wiley & Sons, Inc., New York; S. R. Sandler et al., "Organic Functional Group Preparations," 2nd Ed., Academic Press, New York, 1983; H. O. House, "Modem Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure," 4th Ed., Wiley-Interscience, New York, 1992.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses according to known methods, where many of the standard chemical supply houses (e.g., those listed above) provide custom synthesis services.

The term "reducing agent" refers to a compound that contributes a hydride to an electrophilic position of a reactant compound, such as, an unsaturated carbon (e.g. carbon of a carbonyl moiety), such as, converting a ketone containing reactant compound to an alcohol product compound or converting an ester containing reactant compound to an alcohol product compound. The reducing agent can be a hydride reducing agent. Example hydride reducing agents include, but are not limited to, diborane, borane (e.g. borane tetrahydrofuran complex), 9-borabicyclo[3.3.1]nonane, lithium aluminum hydride, diisobutylaluminum hydride, lithium diisobutyl-tert-butoxyaluminum hydride, lithium tri-tert-butoxyaluminum hydride, lithium tris[(3-ethyl-3-pentyl)oxy]aluminohydride, sodium bis(2-methoxyethoxy)aluminum dihydride, sodium aluminum hydride, calcium borohydride, lithium borohydride, magnesium borohydride, potassium borohydride, tetrabutylammonium borohydride, tetraethylammonium borohydride, tetramethylammonium borohydride, bis(triphenylphosphine)copper(I) borohydride, lithium 9-borabicyclo[3.3.1]nonane hydride, sodium triacetoxyborohydride, potassium tri-sec-butylborohydride, sodium tri-sec-butylborohydride, potassium trisiamylborohydride, lithium triethylborohydride, potassium triethylborohydride, sodium triethylborohydride, potassium triphenylborohydride, lithium dimethylaminoborohydride, lithium pyrrolidinoborohydride, sodium cyanoborohydride, sodium trimethoxyborohydride, sodium borohydride, and the like.

The term "halogenating agent" refers to a compound that contributes a halogen atom to a reactant compound, such as, converting an alcohol reactant compound to an alkyl halide product compound. Examples of halogenating agents include, but not limited to, thionyl chloride, oxalyl chloride, phosphorus oxychloride, phosphorus pentachloride, phosphorus trichloride, methanesulfonyl chloride and NaI, p-toluenesulfonyl chloride and NaI, phosphorus tribromide, triphenylphosphine dibromide, phosphorus pentabromide, or thionyl bromide, and the like.

The term "base" refers to a compound that is an electron pair donor in an acid-base reaction.

The base can be an inorganic base or an organic base.

The term "organic base" refers to a base including at least one C—H bond (e.g. an amine base). In some embodiments, the amine base can be a primary, secondary, or tertiary amine.

The term "inorganic base" refers to a base that does not include at least one C—H bond and includes at least one alkali metal or alkaline earth metal.

The term "acid" refers to a compound that is an electron pair acceptor in an acid-base reaction.

The acid can be an inorganic acid or organic acid.

The term "inorganic acid" refers to an acid that does not include a carbon bond. Inorganic acids can be a strong acid or a weak acid.

The term "organic acid" refers to an acid including at least one C—H bond, C—F bond, or C—C bond.

Certain Abbreviations

The specification includes numerous abbreviations, whose definitions are listed in the following table:

| Abbreviation | Definition |
| --- | --- |
| ACN | Acetonitrile |
| aq. | Aqueous |
| EtOAc | Ethyl acetate |
| DCM | Dichloromethane or methylene chloride |
| d | Day |
| de | Diastereomeric excess |
| DPTTA | (2S,3S)-2,3-bis(4-methylbenzoyloxy)butanedioic acid |
| ee | Enantiomeric excess |
| EtOH | Ethyl alcohol |
| h | Hour |
| HPLC | High-performance liquid chromatography |
| i-PrOH | Isopropyl alcohol |
| min. | Minute(s) |
| MeOH | Methyl alcohol |
| MTBE | Methyl tert-butyl ether |
| RT | Room temperature |
| TFA | Trifluoroacetic acid |
| THF | Tetrahydrofuran |

EXAMPLES

The following examples are included to demonstrate embodiments of the disclosure. However, those of skill in the art should, in light of the present disclosure, appreciate that many changes can be made in the specific embodiments which are disclosed and still obtain a like or similar result without departing from the spirit and scope of the disclosure.

Analytical HPLC analyses were performed on an LC-MS system with a UV Detector (Dionex™ UVD 170u UV/VIS Detector), Corona array detector (Thermo™ Veo™ RS), and mass spectrometer (Dionex MSQ Plus™). Reverse-phase preparative HPLC purifications were performed on a liquid chromatography-mass spectrometry (LCMS) system C18 Kinetix 5 100 A 150×21.2 mm column by Phenomenex using ACN/water gradient containing 0.05% TFA run at 1.1 mL/min and 50° C. Supercritical fluid chromatography purification (SFC) was performed using a Waters™ Prep 100q™ system, equipped with a UV Detector (Waters™ 2998 Photodiode Array Detector™) and mass spectrometer (Waters™ Acquity QDa Detector™). A Waters™ Viridis™ BEH 2-Ethylpyridine 130 Å 5 μm, 30 mm×100 mm column was used with a $CO_2$ and 0.3% $NH_4OH$ in MeOH gradient, run at 100 mL/min, 40° C., and 105 bar back pressure regulator. All final compounds were analyzed by analytical HPLC-MS, and peaks were monitored at 220, 212, 270, and 254 nm in the UV, by mass spectrometer, and through the charged aerosol detector for purity. $^1H$ was recorded in an appropriate NMR solvent, such as, dimethylsulfoxide-$d_6$ (DMSO-$d_6$), on a Bruker 400 MHz spectrometer equipped with a Broad Band NMR probe, or on a Bruker 500 MHz spectrometer equipped with a 5 mm QNP probe with Z gradient. The $^1H$ chemical signals are given in parts per million (ppm) with the residual solvent signal used as reference. The chemical shifts are expressed in ppm (δ) and coupling constants (J) are reported in hertz (Hz). Reactions were performed under an atmosphere of dry nitrogen unless otherwise stated.

Figure 6:
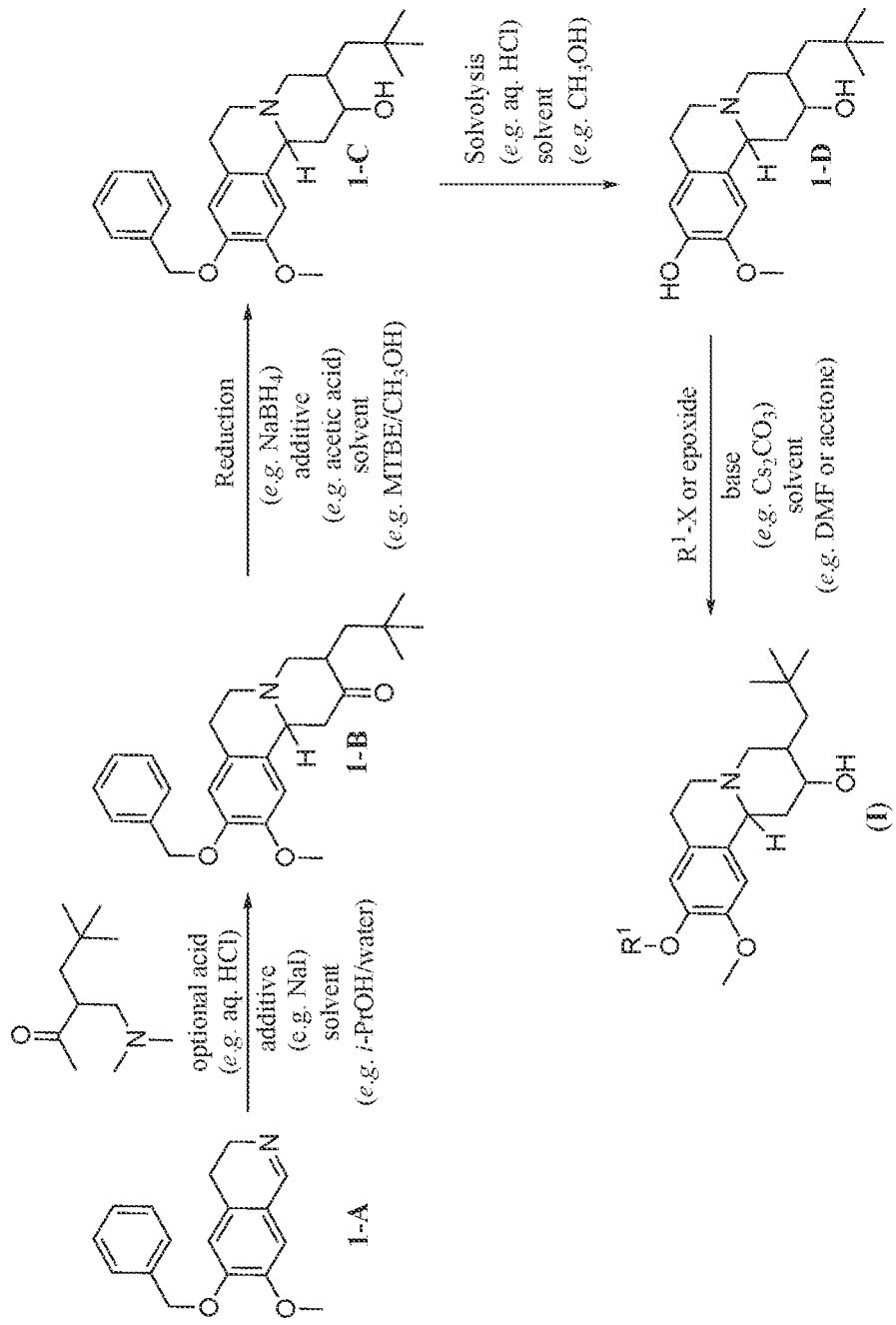
FIG. 6 shows a general synthetic scheme for the preparation of Compounds of Formula (I) and intermediates related thereto, wherein $R^1$ has the same meaning as described herein and X is a leaving group, such as, halo (e.g. I, Cl, and Br), or $OS(O)_2R^z$ (e.g. mesylate (-OMs), triflate (-OTf), and tosylate (-OTs), wherein $R^z$ has the same meaning as described herein).

I. The general synthetic scheme for the preparation of compounds of Formula (I) is shown in FIG. 6, wherein X is halo (e.g. I, Cl, or Br), $OS(O)_2OR^1$, or $OS(O)_2R^z$ wherein $R^z$ is $C_1$-$C_6$alkyl, halo$C_1$-$C_6$alkyl, or phenyl, said phenyl unsubstituted or substituted with one or more halo, nitro, $C_1$-$C_6$alkyl, halo$C_1$-$C_6$alkyl, $C_1$-$C_6$alkoxy, or halo$C_1$-$C_6$alkoxy. Alternatively, $R^1$—X, where X is I, Cl, or Br can be prepared by reacting commercially available HO—$R^1$ with a halogenating agent.

According to FIG. 6, compounds of general Formula (I), as described herein, can be synthesized in several steps from Compound 1-A. In one instance, a sequence for the formation of compounds of general Formula (I) includes condensation of Compound 1-A with 3-[(dimethylamino)methyl]-5,5-dimethylhexan-2-one, optionally in the presence of an acid and an additive, such as, NaI, in a solvent or a solvent mixture, such as, i-PrOH/water and the like to afford Compound 1-B. Reduction of Compound 1-B in the presence of a reducing agent, such as, sodium aluminum hydride, calcium borohydride, lithium borohydride, magnesium borohydride, potassium borohydride, tetrabutylammonium borohydride, tetraethylammonium borohydride, tetramethylammonium borohydride, bis(triphenylphosphine)copper(I) borohydride, lithium 9-borabicyclo[3.3.1]nonane hydride, sodium triacetoxyborohydride, lithium tri-sec-butylborohydride, potassium tri-sec-butylborohydride, sodium tri-sec-butylborohydride, potassium trisiamylborohydride, lithium triethylborohydride, potassium triethylborohydride, sodium triethylborohydride, potassium triphenylborohydride, lithium dimethylaminoborohydride, lithium pyrrolidinoborohydride, sodium cyanoborohydride, sodium trimethoxyborohydride, sodium borohydride, and the like, in a solvent or a solvent mixture, such as, methanol, MTBE, and the like, optionally in the presence of an additive, such as, acetic acid, affords Compound 1-C. Preparation of Compound 1-D can be accomplished by hydrogenolysis or solvolysis, for example, treating Compound 1-C with an acid in a solvent, such as, methanol, and the like. Finally, Compound 1-D can be treated with $R^1$—X, wherein X is a leaving group, such as, I, Br, Cl, triflate, and the like; or an epoxide, in the presence of a base in a solvent, such as, DMF, acetone, and the like, to afford compounds of general Formula (I).

Figure 7:
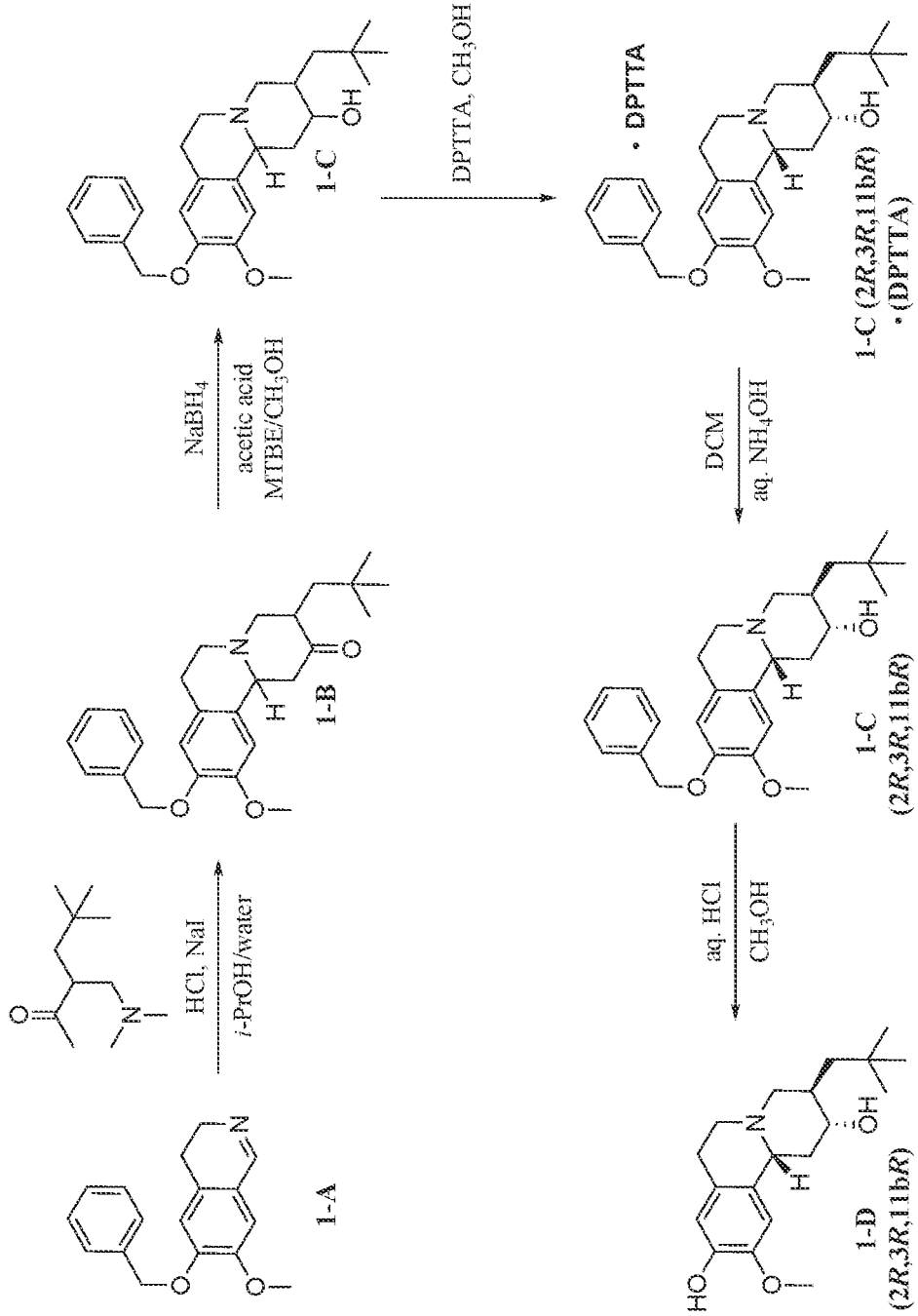
FIG. 7 shows a general synthetic scheme for the preparation of (2R,3R,11bR)-3-(2,2-dimethylpropyl)-10-methoxy-1H,2H,3H,4H,6H,7H,11bH-pyrido[2,1-a]isoquinoline-2,9-diol (Compound 1-D (2R,3R,11bR)) utilizing a resolution step of 9-(benzyloxy)-3-(2,2-dimethylpropyl)-10-methoxy-1H,2H,3H,4H,6H,7H,11bH-pyrido[2,1-a]isoquinolin-2-ol (Compound 1-C) with (2S,3S)-2,3-bis(4-methylbenzoyloxy)butanedioic acid (DPTTA) to provide (2R,3R,11bR)-9-(benzyloxy)-3-(2,2-dimethylpropyl)-10-methoxy-1H,2H,3H,4H,6H,7H,11bH-pyrido[2,1-a]isoquinolin-2-ol (Compound 1-C (2R,3R,11bR)) that is subsequently deprotected to provide Compound 1-D (2R,3R,11bR).

Example 1A: Preparation of (2R,3R,11bR)-3-(2,2-dimethylpropyl)-10-methoxy-1H,2H,3H,4H,6H,7H,11bH-pyrido[2,1-a]isoquinoline-2,9-diol (Compound 1-D (2R,3R,11bR)), See FIG. 7

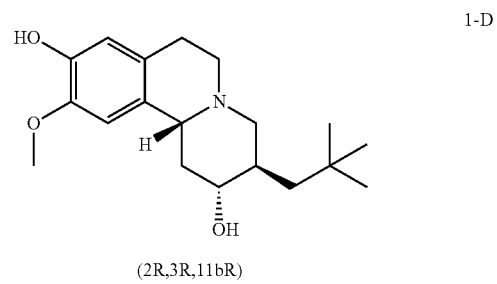 [SMILES: COc1cc2c(cc1O)CCN1C[C@@H](CC(C)(C)C)[C@H](O)C[C@H]21]

(2R,3R,11bR)

Step 1: Synthesis of 9-(benzyloxy)-3-(2,2-dimethylpropyl)-10-methoxy-1H,2H,3H,4H,6H,7H,11bH-pyrido[2,1-a]isoquinolin-2-one (Compound 1-B)

A suspension of 6-(benzyloxy)-7-methoxy-3,4-dihydroisoquinoline (Compound 1-A, 25 g, 93.5 mmol, 1.2 eq) in water (63 mL) was prepared and cooled to 0° C. Then, aq. HCl (6.7 mL, 12.1N, 1.05 eq) followed by sodium iodide (5.83 g, 38.9 mmol, 0.5 eq) were added and the resulting mixture was warmed to RT. Lastly, a solution of 3-[(dimethylamino)methyl]-5,5-dimethylhexan-2-one (14.4 g, 77.9 mmol, 1.0 eq) in i-PrOH (22 mL) was added and the reaction mixture was stirred vigorously at 45° C. for 3 d. The resulting suspension was cooled, the precipitate collected, and the filtrate extracted into DCM. The collected precipitate was dissolved in DCM and added to the combined organic layers, dried over $MgSO_4$, filtered to remove solid and concentrated in vacuo. Silica gel columns (220 g×2, 120 g×1) were loaded using DCM and run with an increasing gradient of EtOAc (0-40% over 20 minutes) in hexanes to afford 9-(benzyloxy)-3-(2,2-dimethylpropyl)-10-methoxy-1H,2H,3H,4H,6H,7H,11bH-pyrido[2,1-a]isoquinolin-2-one (Compound 1-B, 22.6 g, 55.5 mmol, 71%).

Step 2: Synthesis of 9-(benzyloxy)-3-(2,2-dimethylpropyl)-10-methoxy-1H,2H,3H,4H,6H,7H,11bH-pyrido[2,1-a]isoquinolin-2-ol (Compound 1-C)

To a solution of 9-(benzyloxy)-3-(2,2-dimethylpropyl)-10-methoxy-1H,2H,3H,4H,6H,7H,11bH-pyrido[2,1-a]isoquinolin-2-one (Compound 1-B, 22.6 g, 55.5 mmol, 1.0 eq) in MTBE:MeOH (4:1, 113 mL) and acetic acid (3.2 mL, 55.5 mmol, 1.0 eq) was carefully added solid sodium borohydride (2.3 g, 61.0 mmol, 1.1 eq) portionwise. Reaction progression was monitored hourly by LC/MS. Subsequently, 4:1 MTBE:MeOH (56 mL), 0.5 eq of acetic acid and an additional 2.0 eq of sodium borohydride were added to the stirring mixture. After stirring overnight at RT, 1N NaOH (180 mL) was added, and the resulting mixture heated to 50° C. for 3 h. The mixture was cooled to RT and allowed to stand for 1 h. The resulting precipitate was collected by vacuum filtration, rinsed with excess water (~600 mL) until pH<10 and lastly washed with MTBE. The filter cake was dried to provide 9-(benzyloxy)-3-(2,2-dimethylpropyl)-10-methoxy-1H,2H,3H,4H,6H,7H,11bH-pyrido[2,1-a]isoquinolin-2-ol (Compound 1-C, 18.7 g, 42.1 mmol, 76%).

Step 3: Synthesis of (2R,3R,11bR)-9-(benzyloxy)-3-(2,2-dimethylpropyl)-10-methoxy-1H,2H,3H,4H,6H,7H,11bH-pyrido[2,1-a]isoquinolin-2-ol (Compound 1-C(2R,3R,11bR) Also Referred to as Compound 4-60 in Table A)

To a suspension of 9-(benzyloxy)-3-(2,2-dimethylpropyl)-10-methoxy-1H,2H,3H,4H,6H,7H,11bH-pyrido[2,1-a]isoquinolin-2-ol (Compound 1-C, 18.7 g, 42.1 mmol, 1.0 eq) in MeOH (150 mL) was added (2S,3S)-2,3-bis(4-methylbenzoyloxy)butanedioic acid (DPTTA, 17.9 g, 46.3 mmol, 1.1 eq) portion wise. Additional MeOH (100 mL) and heat (65° C.) were required to dissolve solids. The resulting solution was cooled to 60° C., seeded with previously prepared Compound 1-C (2R,3R,11bR)-(DPTTA) (138 mg, for example see EXAMPLE 1B) and stirred at 60° C. for 30 min. Then, the mixture was cooled to RT at a rate of 4° C./h then stirred overnight at RT. The resulting precipitate was collected by vacuum filtration and dried to provide Compound 1-C-(2R,3R,11bR) (DPTTA) (14.7 g, 18.5 mmol, 44%) as a white solid. An optical purity of 100% ee as a single diastereomer was determined by chiral supercritical fluid chromatography (SFC) analysis. Chiral purity analysis was performed using a Waters™ Ultra-Performance Convergence Chromatography (UPC2)™ supercritical fluid chromatography (SFC) system, equipped with a UV Detector (Waters™ Acquity UPC2 PDA Detector™) and mass spectrometer (Waters™ Acquity QDa Detector™). A Chiral Technologies Inc™ ChiralPak™ IC/SFC 1.6 µm, 2.1 mm×50 mm column was used with an isocratic gradient at 85% CO₂ and 15% 0.5% DMEA in MeOH, at 1.5 mL/min, 55° C., and 1500 psi back pressure regulator. An extracted wavelength of 285 nm was used for % ee quantification and analysis.

The chiral salt pair was suspended in DCM and water was added. The mixture was basified with saturated aq. NH₄OH until pH~10. The mixture was extracted three times with DCM. The organic extracts were dried over MgSO₄, filtered, and concentrated in vacuo to give (2R,3R,11bR)-9-(benzyloxy)-3-(2,2-dimethylpropyl)-10-methoxy-1H,2H,3H,4H,6H,7H,11bH-pyrido[2,1-a]isoquinolin-2-ol (Compound 1-C (2R,3R,11bR), 7.41 g, 18.1 mmol, 43%).

Step 4: Synthesis of (2R,3R,11bR)-3-(2,2-dimethylpropyl)-10-methoxy-1H,2H,3H,4H,6H,7H,11bH-pyrido[2,1-a]isoquinoline-2,9-diol (Compound 1-D (2R,3R,11bR))

To a solution of (2R,3R,11bR)-9-(benzyloxy)-3-(2,2-dimethylpropyl)-10-methoxy-1H,2H,3H,4H,6H,7H,11bH-pyrido[2,1-a]isoquinolin-2-ol (Compound 1-C(2R,3R,11bR), 6.9 g, 16.8 mmol, 1.0 eq) in MeOH (68 mL) cooled to 0° C. was added 37% aq. HCl (34 mL) dropwise over 30 min. The resulting mixture was stirred at 0° C. for 30 min, warmed to RT and stirred for 30 min and finally stirred at 80° C. overnight. The mixture was transferred to a 2 L flask, diluted with water (60 mL) and DCM (100 mL) and cooled to 0° C. Then, saturated aq. NaHCO₃ was added dropwise until reaching a pH of ~8, adding additional DCM as needed to aid stirring. The resulting precipitate was collected by vacuum filtration, rinsed with water and MTBE, dried and set aside. The filtrate was extracted with 5:1 DCM:i-PrOH. The combined organic layers were dried over MgSO₄, filtered to remove solid and concentrated in vacuo. The resulting solid was combined with the filter cake to provide (2R,3R,11bR)-3-(2,2-dimethylpropyl)-10-methoxy-1H,2H, 3H,4H,6H,7H,11bH-pyrido[2,1-a]isoquinoline-2,9-diol (Compound 1-D (2R,3R,11bR), 5.5 g, 17.2 mmol) in near quantitative yield.

Figure 8:
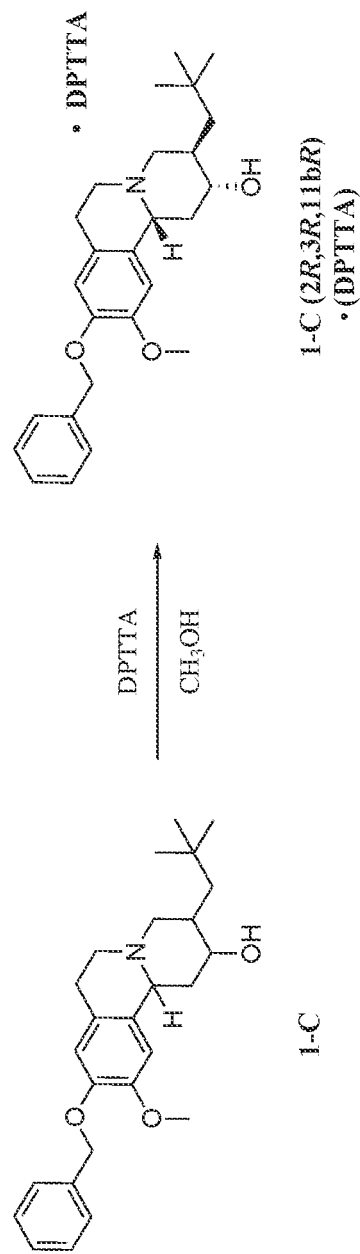
FIG. 8 shows a representative reaction for the preparation of the salt of (2R,3R,11bR)-9-(benzyloxy)-3-(2,2-dimethylpropyl)-10-methoxy-1H,2H,3H,4H,6H,7H,11bH-pyrido[2,1-a]isoquinolin-2-ol (Compound 1-C(2R,3R,11bR)) and (2S,3S)-2,3-bis(4-methylbenzoyloxy)butanedioic acid (DPTTA), see Example 1B.

Example 1B: Preparation of the Salt of (2R,3R,11bR)-9-(benzyloxy)-10-methoxy-3-neopentyl-1,3,4,6,7,11b-hexahydro-2H-pyrido[2,1-a]isoquinolin-2-ol and (2S,3S)-2,3-bis(4-methylbenzoyloxy)butanedioic Acid (Compound 1-C-(2R,3R,11bR) (DPTTA)), See FIG. 8

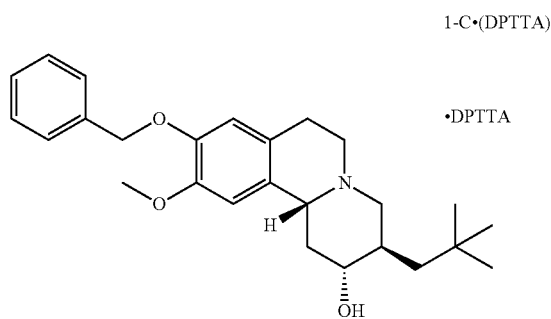 [SMILES: COc1cc2c(cc1OCc1ccccc1)CCN1C[C@@H](CC(C)(C)C)[C@H](O)C[C@H]21]

To a suspension of 9-(benzyloxy)-3-(2,2-dimethylpropyl)-10-methoxy-1H,2H,3H,4H,6H,7H,11bH-pyrido[2,1-a]isoquinolin-2-ol (Compound 1-C, 506 mg, 1.24 mmol, 1.0 eq) in MeOH (7 mL) was added (2S,3S)-2,3-bis(4-methylbenzoyloxy)butanedioic acid (DPTTA, 494 mg, 1.24 mmol, 1.0 eq) portion wise. The resulting mixture was heated to reflux with stirring to achieve a clear solution. The mixture was cooled to RT without stirring and let stand 16 h at RT. The resulting precipitate was collected by vacuum filtration, rinsed with methanol (1 mL) and dried to provide Compound 1-C-(2R,3R,11bR) (DPTTA) (365 mg, 37%) as a white solid. An optical purity of 90% ee was determined by chiral SFC analysis. Chiral purity analysis was performed using a Waters™ Ultra-Performance Convergence Chromatography (UPC2)™ supercritical fluid chromatography (SFC) system, equipped with a UV Detector (Waters™ Acquity UPC2 PDA Detector™) and mass spectrometer (Waters™ Acquity QDa Detector™). A Chiral Technologies Inc™ ChiralPak™ IC/SFC 1.6 µm, 2.1 mm×50 mm column was used with an isocratic gradient at 85% CO₂ and 15% 0.5% DMEA in MeOH, at 1.5 mL/min, 55° C., and 1500 psi back pressure regulator. An extracted wavelength of 285 nm was used for % ee quantification and analysis. A 20 mg sample of the solid was set aside for further recrystallizations and the mother liquors and remaining white solids were recombined and concentrated in vacuo. This mixture was suspended in MeOH (5 mL) and heated to reflux to achieve a clear solution. Stirring was stopped and the mixture cooled to 60° C. and seeded with 2 mg of the prior 90% ee Compound 1-C-(2R,3R,11bR) (DPTTA) solid. The mixture was allowed to stand for 1 h at 60° C. then reduced the temperature by 5° C. each hour until at RT, then let stand for 16 h. The resulting precipitate was collected by vacuum filtration, rinsed with methanol (1 mL), and dried to provide Compound 1-C-(2R,3R,11bR) (DPTTA) (200 mg, 20%). An optical purity of 100% ee as a single diastereomer was determined by chiral SFC analysis.

Figure 9:
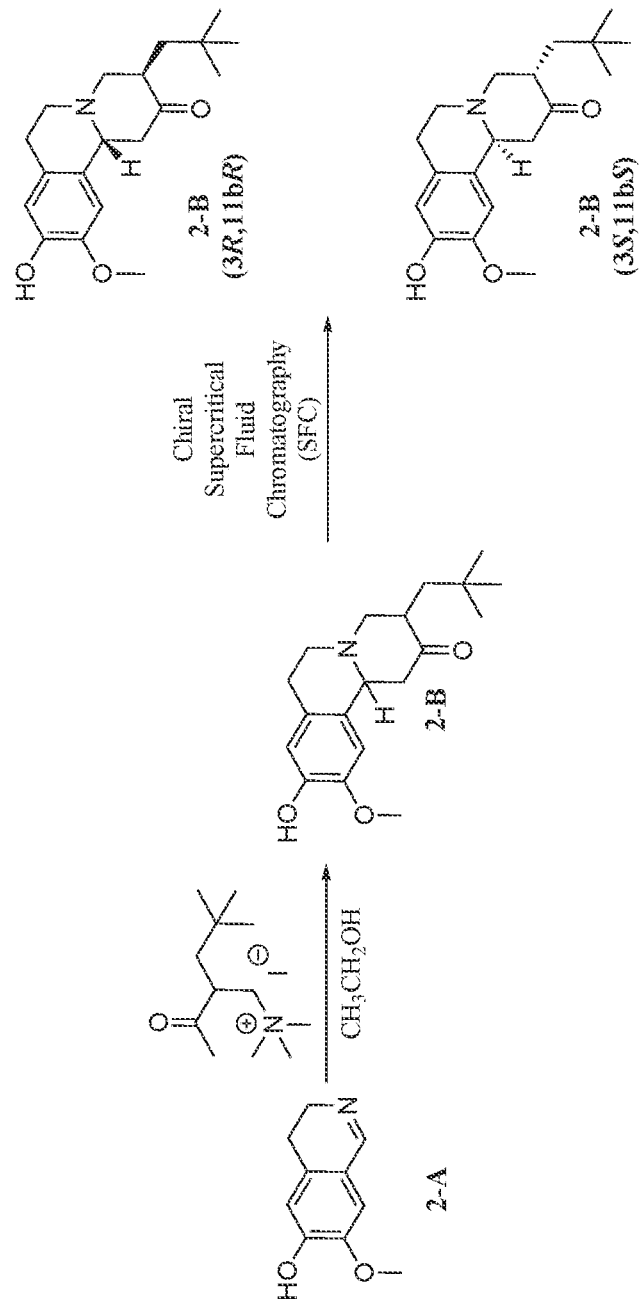
FIG. 9 shows a general synthetic scheme for the preparation of (3R,11bR)-3-(2,2-dimethylpropyl)-9-hydroxy-10-methoxy-1H,2H,3H,4H,6H,7H,11bH-pyrido[2,1-a]isoquinolin-2-one (Compound 2-B (3R,11bR)) and (3S,11bS)-3-(2,2-dimethylpropyl)-9-hydroxy-10-methoxy-1H,2H,3H,4H,6H,7H,11bH-pyrido[2,1-a]isoquinolin-2-one (Compound 2-B (3S,11bS)) using chiral supercritical fluid chromatography (SFC), see Example 2.

Example 2: Preparation of (3R,11bR)-3-(2,2-dimethylpropyl)-9-hydroxy-10-methoxy-1H,2H,3H,4H,6H,7H,11bH-pyrido[2,1-a]isoquinolin-2-one (Compound 2-B (3R,11bR)) and (3S,11bS)-3-(2,2-dimethylpropyl)-9-hydroxy-10-methoxy-1H,2H,3H,4H,6H,7H,11bH-pyrido[2,1-a]isoquinolin-2-one (Compound 2-B (3S,11bS)), See FIG. 9

Step 1: Synthesis of 3-(2,2-dimethylpropyl)-9-hydroxy-10-methoxy-1H,2H,3H,4H,6H,7H,11bH-pyrido[2,1-a]isoquinolin-2-one (Compound 2-B)

To a solution of 7-methoxy-3,4-dihydroisoquinolin-6-ol (Compound 2-A, 7.2 g, 40.7 mmol, 1.2 eq) in EtOH (66 mL) was added [2-(2,2-dimethylpropyl)-3-oxobutyl]trimethylazanium iodide (11.1 g, 33.9 mmol, 1.0 eq) and the resulting mixture was stirred at reflux for 3 d. The mixture was cooled, diluted with aq. NaHCO$_3$, and extracted with DCM. The combined organic layers were dried over MgSO$_4$, filtered, and concentrated in vacuo. The crude material was dry loaded on celite and chromatographed on a silica gel column (220 g) with an increasing gradient of EtOAc (0-60% over 20 minutes) in hexanes. Due to a co-eluting impurity, the material was dry loaded on celite and re-chromatographed on a silica gel column (80 g) using a shallower gradient of EtOAc (0-45% over 20 minutes) in hexanes to provide 3-(2,2-dimethylpropyl)-9-hydroxy-10-methoxy-1H,2H,3H,4H,6H,7H,11bH-pyrido[2,1-a]isoquinolin-2-one (Compound 2-B, 4.2 g, 13.3 mmol, 39%) as a 7:1 mixture of racemic diastereomers.

Step 2: Isolation of (3R,11bR)-3-(2,2-dimethylpropyl)-9-hydroxy-10-methoxy-1H,2H,3H,4H,6H,7H,11bH-pyrido[2,1-a]isoquinolin-2-one (Compound 2-B (3R,11bR)) and (3S,11bS)-3-(2,2-dimethylpropyl)-9-hydroxy-10-methoxy-1H,2H,3H,4H,6H,7H,11bH-pyrido[2,1-a]isoquinolin-2-one (Compound 2-B (3S,11bS))

Separation of the 3-(2,2-dimethylpropyl)-9-hydroxy-10-methoxy-1H,2H,3H,4H,6H,7H,11bH-pyrido[2,1-a]isoquinolin-2-one (Compound 2-B) enantiomers was achieved by preparing a solution in a minimal volume of MeOH and subjecting to preparative chiral SFC. Chiral compound separation was performed using a Pic Solution™ SFC-PICLAB-Prep 200™ supercritical fluid chromatography (SFC) system, equipped with a UV Detector and an Advion™ mass spectrometer. A Chiral Technologies Inc™ ChiralPak™ IG/SFC 5 µm, 20 mm×250 mm column was used with an isocratic gradient at 80% CO$_2$ and 20% 0.5% DMEA in MeOH, at 150 mL/min, 55° C., and 100 bar back pressure regulator. Following purification, 1.6 g each of (3R,11bR)-3-(2,2-dimethylpropyl)-9-hydroxy-10-methoxy-1H,2H,3H,4H,6H,7H,11bH-pyrido[2,1-a]isoquinolin-2-one (Compound 2-B (3R,11bR)) (99% ee) and (3S,11bS)-3-(2,2-dimethylpropyl)-9-hydroxy-10-methoxy-1H,2H,3H,4H,6H,7H,11bH-pyrido[2,1-a]isoquinolin-2-one (Compound 2-B (3S,11bS)) (100% ee) were isolated.

Suitable crystals were generated by slow evaporation of a solution of Compound 2-B (3S,11bS) in acetone. Absolute stereochemistry was confirmed by obtaining a small molecule crystal structure of Compound 2-B (3S,11bS).

Single Crystal X-Ray Structure of Compound 2-B (3S,11bS).

The single crystal structure of (3S,11bS)-3-(2,2-dimethylpropyl)-9-hydroxy-10-methoxy-1H,2H,3H,4H,6H,7H,11bH-pyrido[2,1-a]isoquinolin-2-one (Compound 2-B (3S,11bS)) was determined. The absolute configuration parameter (Flack parameter) is near zero when the configuration assignment is correct, and near +1 when the configuration is wrong. For this data set, the Flack parameter is 0.06(3) for the assignment shown in FIG. 1A. Crystallographic information is shown in Table 1.

TABLE 1

| Crystal Data for Compound 2-B (3S,11bS) | |
|---|---|
| Molecular Formula | C$_{19}$H$_{27}$NO$_3$ |
| Formula weight (g/mol) | 317.41 |
| Wavelength | 1.54178 Å |
| Radiation (Å) | Cu Kα (λ = 1.54178 Å) |
| Instrument | Bruker Microstar APEX II CCD |
| Crystal system | Monoclinic |
| space group | P 1 2$_1$ 1 |
| Temperature (K) | 100.0 |
| Unit cell dimensions | a = 6.8023(2) Å    α = 90° |
| | b = 8.9511(3) Å    β = 94.837(3)° |
| | c = 13.9008(5) Å   γ = 90° |
| Volume | 843.38(5) Å$^3$ |
| Z,Z' | 2 |
| Density (calculated) | 1.250 Mg/m$^3$ |
| F(000) | 344 |
| Crystal size | 0.18 × 0.12 × 0.02 mm$^3$ |

Figure 10:
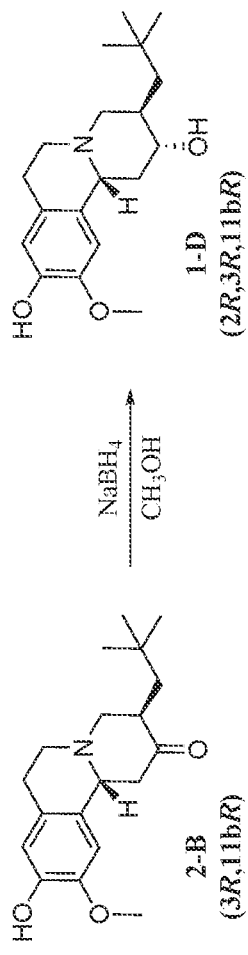
FIG. 10 shows a representative reduction step as described in Example 3 for the preparation of (2R,3R,11bR)-3-(2,2-dimethylpropyl)-10-methoxy-1H,2H,3H,4H,6H,7H,11bH-pyrido[2,1-a]isoquinoline-2,9-diol (Compound 1-D (2R,3R,11bR)) from (3R,11bR)-3-(2,2-dimethylpropyl)-9-hydroxy-10-methoxy-1H,2H,3H,4H,6H,7H,11bH-pyrido[2,1-a]isoquinolin-2-one (Compound 2-B (3R,11bR)); and a representative reduction step for the preparation of (2S,3S,11bS)-3-(2,2-dimethylpropyl)-10-methoxy-1H,2H,3H,4H,6H,7H,11bH-pyrido[2,1-a]isoquinoline-2,9-diol (Compound 1-D (2S,3S,11bS)) from (3S,11bS)-3-(2,2-dimethylpropyl)-9-hydroxy-10-methoxy-1H,2H,3H,4H,6H,7H,11bH-pyrido[2,1-a]isoquinolin-2-one (Compound 2-B (3S,11bS)).
Figure 10:
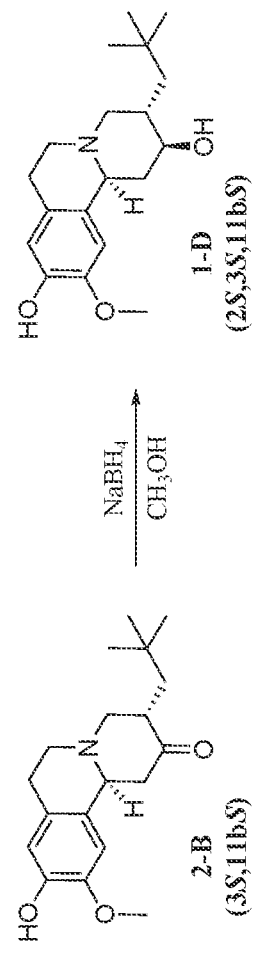

Example 3: Alternative Preparation of (2R,3R,11bR)-3-(2,2-dimethylpropyl)-10-methoxy-1H,2H,3H,4H,6H,7H,11bH-pyrido[2,1-a]isoquinoline-2,9-diol (Compound 1-D (2R,3R,11bR)) and Preparation of (2S,3S,11bS)-3-(2,2-dimethylpropyl)-10-methoxy-1H,2H,3H,4H,6H,7H,11bH-pyrido[2,1-a]isoquinoline-2,9-diol (Compound 1-D (2S,3S,11bS)), See FIG. 10

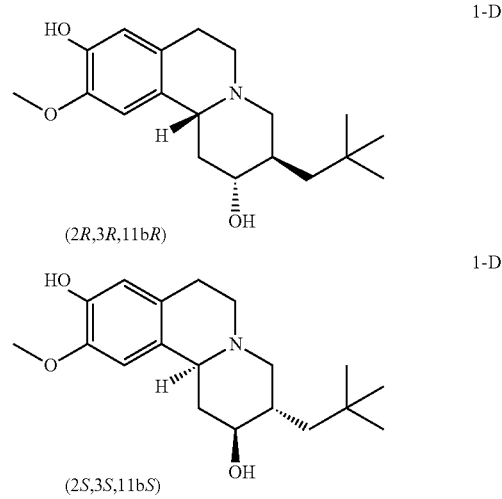

Synthesis of (2R,3R,11bR)-3-(2,2-dimethylpropyl)-10-methoxy-1H,2H,3H,4H,6H,7H,11bH-pyrido[2,1-a]isoquinoline-2,9-diol (Compound 1-D (2R,3R,11bR))

To a solution of (3R,11bR)-3-(2,2-dimethylpropyl)-9-hydroxy-10-methoxy-1H,2H,3H,4H,6H,7H,11bH-pyrido[2,1-a]isoquinolin-2-one (Compound 2-B (3R,11bR), 733 mg, 2.31 mmol, 1.0 eq) in MeOH (5 mL) was added sodium borohydride (131 mg, 3.46 mmol, 1.5 eq). The resulting mixture was stirred 16 h at RT at which point additional sodium borohydride was added (44 mg, 1.16 mmol, 0.5 eq). The mixture was stirred an additional 3 h at RT. The excess reagent was quenched with water, and the resulting mixture extracted three times with 5:1 DCM:i-PrOH. The combined organic layers were dried over MgSO$_4$, filtered to remove solid and concentrated in vacuo. The resultant solid was suspended in MTBE (5.9 mL) and MeOH (1.5 mL) and the resulting mixture was heated to 50° C. for 1 h with stirring. The suspension was cooled to RT and the solids collected by filtration. The filter cake was rinsed with MTBE (2.2 mL) and the solids were collected to give (2R,3R,11bR)-3-(2,2-dimethylpropyl)-10-methoxy-1H,2H,3H,4H,6H,7H,11bH-pyrido[2,1-a]isoquinoline-2,9-diol (Compound 1-D (2R,3R,11bR), 567 mg, 1.77 mmol, 35:1 dr, 77%).

Single Crystal X-Ray Structure of Compound 1-D (2R, 3R,11bR).

Crystals of Compound 1-D (2R,3R,11bR) were grown using a CrystalBreeder system. Approximately 5 mg of Compound 1-D (2R,3R,11bR) in 0.25 mL of DMF (~20 mg/mL) was slow thermo-cycled several times from 5° C. to 80° C. Multiple vials were utilized. After the thermo-cycling, large needles formed on the sides of the vials. The solvent was decanted, and the crystals were analyzed. A suitable crystal was selected for single crystal X-ray structure determination. A similar preparation using ACN also provided crystals, but the crystals grown from DMF provided better crystals that were more suitable for further analysis.

Figure 1B:
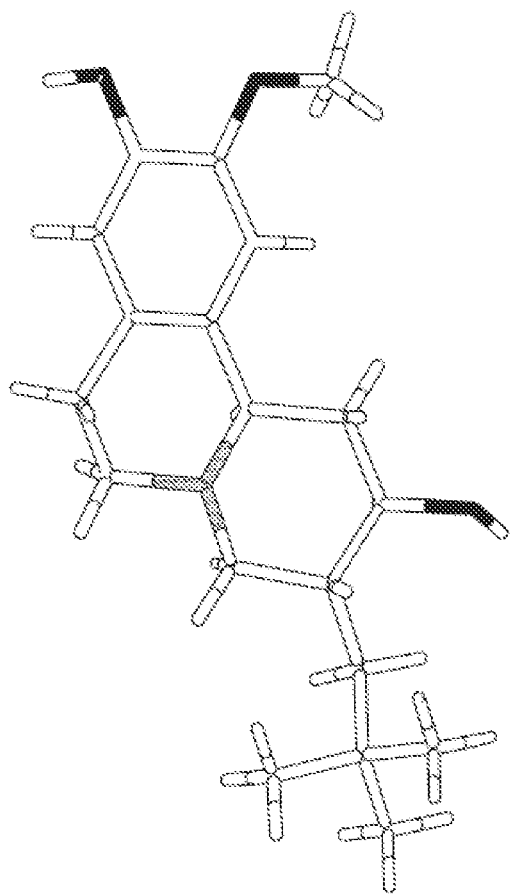
FIG. 1B shows a representation of the single crystal structure of (2R,3R,11bR)-3-(2,2-dimethylpropyl)-10-methoxy-1H,2H,3H,4H,6H,7H,11bH-pyrido[2,1-a]isoquinoline-2,9-diol (Compound 1-D (2R,3R,11bR)).
Figure 1B:
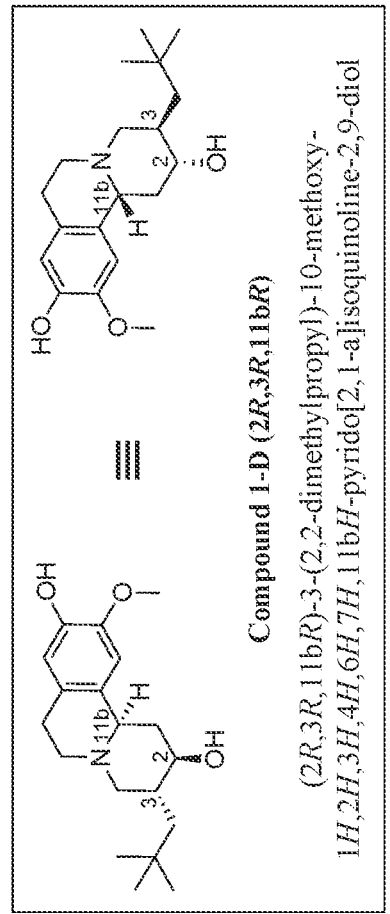

The crystal structure of Compound 1-D (2R,3R,11bR) was solved. The structure was determined to be anhydrous and unsolvated; the three chiral centers at C2, C3, and C11b were all determined to have the R configuration. See FIG. 1B for the asymmetric unit for the crystal structure. The crystal data, unit system and space group for Compound 1-D (2R,3R,11bR) are shown in Table 2. Data collection and refinement parameters for Compound 1-D (2R,3R,11bR) are shown in Table 3.

TABLE 2

Crystal Data for Compound 1-D (2R,3R,11bR)

| | |
|---|---|
| Chemical formula | C$_{19}$H$_{29}$NO$_3$ |
| Mr | 319.43 |
| Crystal system, Space group | Orthorhombic, P2$_1$2$_1$2$_1$ |
| Data collection temperature (K) | 150 |
| a (Å) | 9.1345 (3) |
| b (Å) | 12.3990 (4) |
| c (Å) | 14.9842 (6) |
| volume (Å3) | 1697.09 (10) |
| Z | 4 |
| Radiation type | Cu Kα |
| Crystal shape | Plate |
| Color | Colorless |
| Crystal size (mm) | 0.13 × 0.11 × 0.04 |

TABLE 3

Data collection and Refinement Parameters for Compound 1-D (2R,3R,11bR)

| | |
|---|---|
| Diffractometer | Bruker AXS D8 Quest diffractometer with PhotonIII_C14 charge-integrating and photon counting pixel array detector |
| Radiation source | I-mu-S microsource X-ray tube |
| Absolute structure parameter | 0.03 (10) |

Synthesis of (2S,3S,11bS)-3-(2,2-dimethylpropyl)-10-methoxy-1H,2H,3H,4H,6H,7H,11bH-pyrido[2,1-a]isoquinoline-2,9-diol (Compound 1-D (2S,3S, 11bS))

(2S,3S,11bS)-3-(2,2-Dimethylpropyl)-10-methoxy-1H, 2H,3H,4H,6H,7H,11bH-pyrido[2,1-a]isoquinoline-2,9-diol (Compound 1-D (2S,3S,11bS)) was made in an analogous manner to prepare Compound 1-D (2R,3R,11bR) using (3S,11bS)-3-(2,2-dimethylpropyl)-9-hydroxy-10-methoxy-1H,2H,3H,4H,6H,7H,11bH-pyrido[2,1-a]isoquinolin-2-one (Compound 2-B (3S,11bS)) as the starting material and sodium borohydride as the reducing agent.

Figure 11:
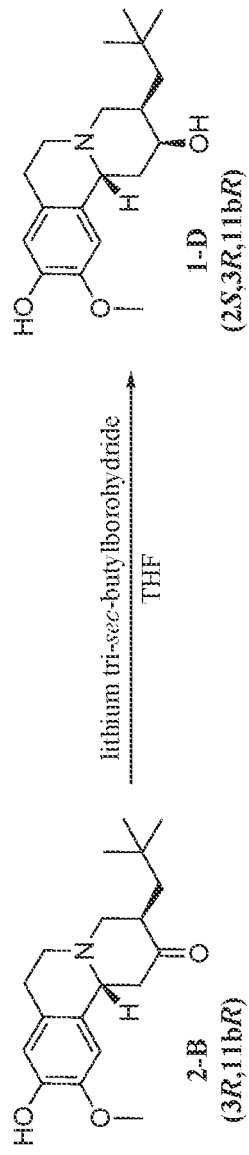
FIG. 11 shows a representative reduction step as described in Example 4 for the preparation of (2S,3R,11bR)-3-(2,2-dimethylpropyl)-10-methoxy-1H,2H,3H,4H,6H,7H,11bH-pyrido[2,1-a]isoquinoline-2,9-diol (Compound 1-D (2S,3R,11bR)) from (3R,11bR)-3-(2,2-dimethylpropyl)-9-hydroxy-10-methoxy-1H,2H,3H,4H,6H,7H,11bH-pyrido[2,1-a]isoquinolin-2-one (Compound 2-B (3R,11bR)); and a representative reduction step for the preparation of (2R,3S,11bS)-3-(2,2-dimethylpropyl)-10-methoxy-1H,2H,3H,4H,6H,7H,11bH-pyrido[2,1-a]isoquinoline-2,9-diol (Compound 1-D (2R,3S,11bS)) from (3S,11bS)-3-(2,2-dimethylpropyl)-9-hydroxy-10-methoxy-1H,2H,3H,4H,6H,7H,11bH-pyrido[2,1-a]isoquinolin-2-one (Compound 2-B (3S,11bS)).
Figure 11:
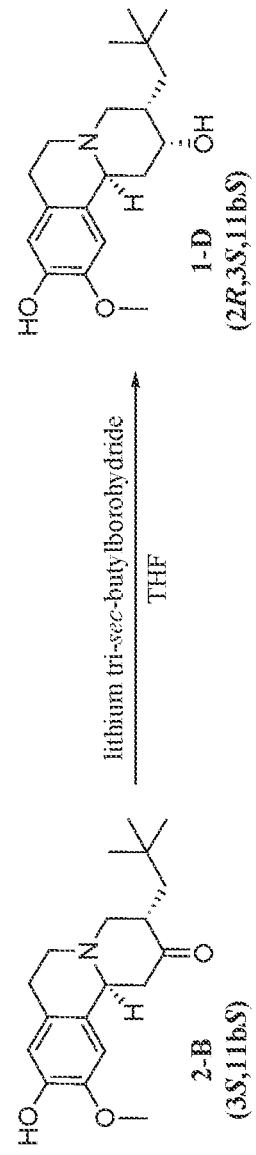

Example 4: Preparation of (2S,3R,11bR)-3-(2,2-dimethylpropyl)-10-methoxy-1H,2H,3H,4H,6H,7H, 11bH-pyrido[2,1-a]isoquinoline-2,9-diol (Compound 1-D (2S,3R,11bR)) and (2R,3S,11bS)-3-(2,2-dimethylpropyl)-10-methoxy-1H,2H,3H,4H,6H,7H, 11bH-pyrido[2,1-a]isoquinoline-2,9-diol (Compound 1-D (2R,3S,11bS)), See FIG. 11

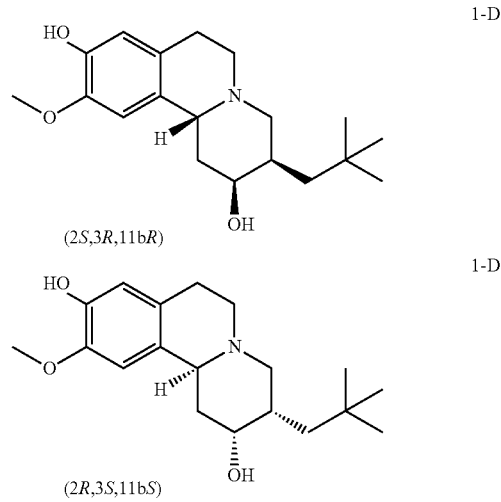

Synthesis of (2S,3R,11bR)-3-(2,2-dimethylpropyl)-10-methoxy-1H,2H,3H,4H,6H,7H,11bH-pyrido[2,1-a]isoquinoline-2,9-diol (Compound 1-D (2S,3R, 11bR))

A solution of (3R,11bR)-3-(2,2-dimethylpropyl)-9-hydroxy-10-methoxy-1H,2H,3H,4H,6H,7H,11bH-pyrido[2,1-a]isoquinolin-2-one (Compound 2-B (3R,11bR), 48 mg, 0.15 mmol, 1.0 eq) in THF (0.75 mL) was cooled to 0° C. Then, a solution of lithium tri-sec-butylborohydride (1M THF, 0.30 mL, 0.30 mmol, 2.0 eq) was added dropwise. The resulting mixture was stirred at 0° C. for 30 min, warmed to RT and stirred for 3 h. The mixture was concentrated in vacuo, diluted with water, and extracted with DCM. The combined organic layers were dried over MgSO$_4$, filtered to remove solids, and concentrated in vacuo. Silica gel column (4 g) was loaded using DCM and run with an increasing gradient of EtOAc (0-60% over 30 minutes) in hexanes. Fractions were split between pure product (Compound 1-D (2S,3R,11bR), 16 mg) and product with the minor diastereomer (28 mg, 10:1 diastereomeric ratio between Compound 1-D (2S,3R,11bR): Compound 1-D (2R,3R,11bR)). Taken together, (2S,3R,11bR)-3-(2,2-dimethylpropyl)-10-methoxy-1H,2H,3H,4H,6H,7H,11bH-pyrido[2,1-a]isoquinoline-2,9-diol was isolated in a combined yield (Compound 1-D (2S,3R,11bR), 44 mg) of 91%.

Synthesis of (2R,3S,11bS)-3-(2,2-dimethylpropyl)-10-methoxy-1H,2H,3H,4H,6H,7H,11bH-pyrido[2,1-a]isoquinoline-2,9-diol (Compound 1-D (2R,3S,11bS))

(2R,3S,11bS)-3-(2,2-Dimethylpropyl)-10-methoxy-1H,2H,3H,4H,6H,7H,11bH-pyrido[2,1-a]isoquinoline-2,9-diol (Compound 1-D (2R,3S,11bS)) was made in an analogous manner to prepare Compound 1-D (2S,3R,11bR) using (3S,11bS)-3-(2,2-dimethylpropyl)-9-hydroxy-10-methoxy-1H,2H,3H,4H,6H,7H,11bH-pyrido[2,1-a]isoquinolin-2-one (Compound 2-B (3S,11bS)) as the starting material and lithium tri-sec-butylborohydride as the reducing agent.

Figure 12:
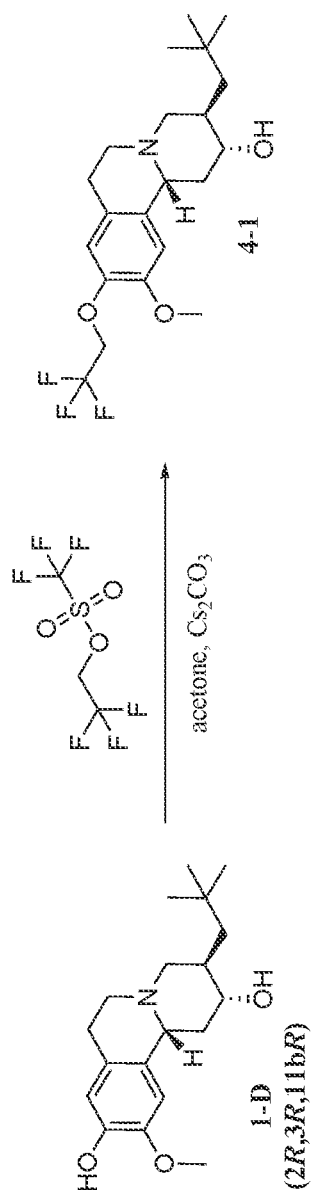
FIG. 12 shows a representative reaction used in the preparation of (2R,3R,11bR)-3-(2,2-dimethylpropyl)-10-methoxy-9-(2,2,2-trifluoroethoxy)-1H,2H,3H,4H,6H,7H,11bH-pyrido[2,1-a]isoquinolin-2-ol (Compound 4-1) using (2R,3R,11bR)-3-(2,2-dimethylpropyl)-10-methoxy-1H,2H,3H,4H,6H,7H,11bH-pyrido[2,1-a]isoquinoline-2,9-diol (Compound 1-D (2R,3R,11bR)) and 2,2,2-trifluoroethyl trifluoromethanesulfonate ($CF_3CH_2OTf$) in the presence of cesium carbonate and acetone, see Example 5A. Also shown in FIG. 12 is a representative reaction used in the preparation of (2R,3R,11bR)-3-(2,2-dimethylpropyl)-9-[(2R)-2-hydroxypropoxy]-10-methoxy-1H,2H,3H,4H,6H,7H,11bH-pyrido[2,1-a]isoquinolin-2-ol (Compound 4-55) using (2R,3R,11bR)-3-(2,2-dimethylpropyl)-10-methoxy-1H,2H,3H,4H,6H,7H,11bH-pyrido[2,1-a]isoquinoline-2,9-diol (Compound 1-D (2R,3R,11bR)) and (R)-2-methyloxirane in the presence of cesium carbonate and DMF, see Example 5F.
Figure 12:
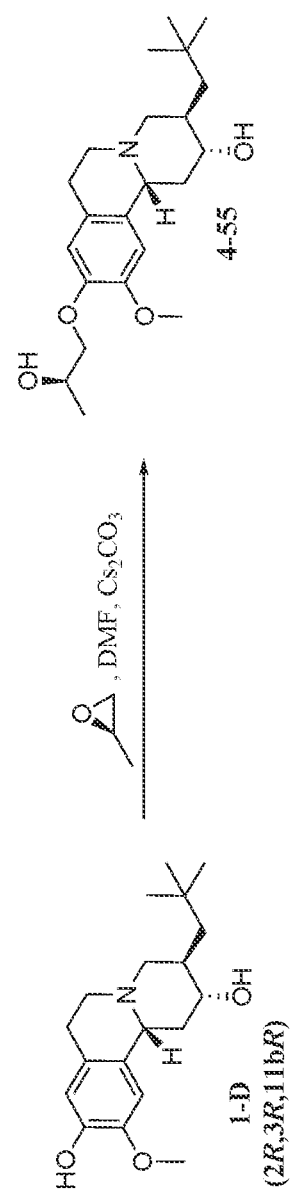

Example 5A: Preparation of (2R,3R,11bR)-3-(2,2-dimethylpropyl)-10-methoxy-9-(2,2,2-trifluoroethoxy)-1H,2H,3H,4H,6H,7H,11bH-pyrido[2,1-a]isoquinolin-2-ol (Compound 4-1), See FIG. 12

4-1

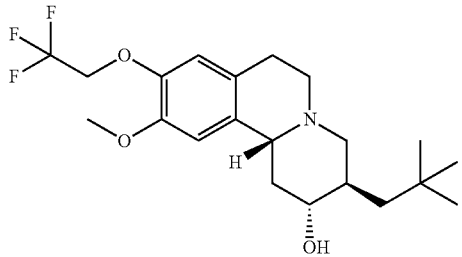

To a solution of (2R,3R,11bR)-3-(2,2-dimethylpropyl)-10-methoxy-1H,2H,3H,4H,6H,7H,11bH-pyrido[2,1-a]isoquinoline-2,9-diol (Compound 1-D (2R,3R,11bR), 0.20 g, 0.63 mmol, 1.0 eq) in acetone (6.3 mL) was added cesium carbonate (0.61 g, 1.9 mmol, 3.0 eq) and the resulting mixture stirred at RT for 10 min. Then, 2,2,2-trifluoroethyl trifluoromethanesulfonate (0.19 g, 0.82 mmol, 1.3 eq) was added and the mixture stirred at RT overnight. The mixture was diluted with water and extracted with 5:1 DCM:i-PrOH. The combined organic layers were dried over MgSO$_4$, filtered to remove solids, and concentrated in vacuo. Silica gel column (40 g) was loaded using DCM and run with an increasing gradient of EtOAc (0-50% over 25 min) in hexanes to afford (2R,3R,11bR)-3-(2,2-dimethylpropyl)-10-methoxy-9-(2,2,2-trifluoroethoxy)-1H,2H,3H,4H,6H,7H,11bH-pyrido[2,1-a]isoquinolin-2-ol (Compound 4-1, 0.19 g, 0.47 mmol, 75%) as a white solid. $^1$H NMR (400 MHz, DMSO-d$_6$): δ (ppm) 6.81 (s, 1H), 6.79 (s, 1H), 4.63 (q, J=8.9 Hz, 2H), 4.56 (d, J=6.4 Hz, 1H), 3.76 (s, 3H), 3.13-3.00 (m, 2H), 2.99-2.83 (m, 3H), 2.57-2.44 (m, 2H), 2.32-2.26 (m, 1H), 1.94 (t, J=11.2 Hz, 1H), 1.70 (d, J=13.6 Hz, 1H), 1.48-1.40 (m, 1H), 1.27 (q, J=11.5 Hz, 1H), 0.91 (s, 9H), 0.81 (dd, J=14.0, 7.6 Hz, 1H).

Example 5B: Preparation of (2R,3R,11bR)-9-cyclopropoxy-3-(2,2-dimethylpropyl)-10-methoxy-1H,2H,3H,4H,6H,7H,11bH-pyrido[2,1-a]isoquinolin-2-ol (Compound 4-27)

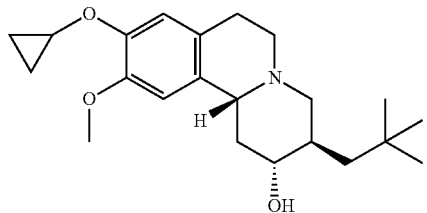 [SMILES: COc1cc2c(cc1OC1CC1)CCN1C[C@@H](CC(C)(C)C)[C@H](O)C[C@H]21]

To a solution of (2R,3R,11bR)-3-(2,2-dimethylpropyl)-10-methoxy-1H,2H,3H,4H,6H,7H,11bH-pyrido[2,1-a]isoquinoline-2,9-diol (Compound 1-D (2R,3R,11bR), 0.80 g, 2.50 mmol, 1.0 eq) in DMF (40 mL) was added cesium carbonate (2.44 g, 7.50 mmol, 3.0 eq) at 50° C. A solution of cyclopropyl trifluoromethanesulfonate (0.60 g, 3.13 mmol, 1.25 eq) in DMF (3 mL) was added via syringe pump over 6 h. The resulting mixture was stirred at 50° C. an additional 10 h. The mixture was diluted with water and extracted three times with EtOAc. The combined organic extracts were washed five times with water, dried over MgSO$_4$, filtered, and concentrated in vacuo. A silica gel column (24 g) was loaded using DCM and run with an increasing gradient of EtOAc (0-100% over 25 min) in hexanes to afford impure (2R,3R,11bR)-9-cyclopropoxy-3-(2,2-dimethylpropyl)-10-methoxy-1H,2H,3H,4H,6H,7H,11bH-pyrido[2,1-a]isoquinolin-2-ol (Compound 4-27, 0.83 g, 2.31 mmol) as an off white solid. To remove trace impurities, crude Compound 4-27 (0.83 g, 2.31 mmol, 1.0 eq) was dissolved in anhydrous THF (14 mL) under an atmosphere of nitrogen at 0° C. with stirring. A 2M solution of lithium aluminum hydride in THF (2.3 mL, 4.62 mmol, 2.0 eq) was added dropwise over 10 min. The temperature was increased to 60° C. and stirred 16 h. The mixture was cooled to 0° C. then sodium sulfate dodecahydrate (0.65 g, 2.02 mmol, 0.9 eq) was added over the course of 10 min then allowed to stir 20 min. The mixture was filtered over celite, and the filter cake was rinsed with acetone, MeOH, and DCM. The filtrate was concentrated in vacuo then redissolved in 1:1 DCM/EtOAc and washed three times with 1M aq. NaOH. The organic layer was dried with MgSO$_4$, filtered, and concentrated in vacuo. The crude material was submitted to three chromatographic separations: a silica gel column (12 g) loaded using DCM run with an increasing gradient of EtOAc (0-75% over 25 min) in hexanes, a basic alumina column (24 g) run with an increasing gradient of EtOAc (0-75% over 25 min) in hexanes and a reversed-phase C18 column (30 g) loaded using DMSO run with an increasing gradient of MeCN (10-70% over 20 min) in water to afford (2R,3R,11bR)-9-cyclopropoxy-3-(2,2-dimethylpropyl)-10-methoxy-1H,2H,3H,4H,6H,7H,11bH-pyrido[2,1-a]isoquinolin-2-ol (Compound 4-27, 0.40 g, 1.11 mmol, 44% over two steps) as a white solid. $^1$H NMR (500 MHz, DMSO-d$_6$): δ (ppm) 6.89 (s, 1H), 6.71 (s, 1H), 4.55 (d, J=6.3 Hz, 1H), 3.75 (tt, J=6.0, 3.0 Hz, 1H), 3.69 (s, 3H), 3.11-3.04 (m, 1H), 3.00 (br d, J=11.2 Hz, 1H), 2.94 (dd, J=11.8, 4.4 Hz, 1H), 2.92-2.86 (m, 2H), 2.55 (dd, J=14.3, 3.8 Hz, 1H), 2.48-2.42 (m, 1H), 2.33-2.25 (m, 1H), 1.92 (t, J=11.5 Hz, 1H), 1.69 (d, J=12.9 Hz, 1H), 1.48-1.39 (m, 1H), 1.25 (q, J=11.5 Hz, 1H), 0.90 (s, 9H), 0.80 (dd, J=13.8, 7.5 Hz, 1H), 0.75-0.70 (m, 2H), 0.64-0.60 (m, 2H).

Example 5C: Preparation of (2R,3R,11bR)-3-(2,2-dimethylpropyl)-10-methoxy-9-(oxetan-3-yloxy)-1H,2H,3H,4H,6H,7H,11bH-pyrido[2,1-a]isoquinolin-2-ol (Compound 4-30)

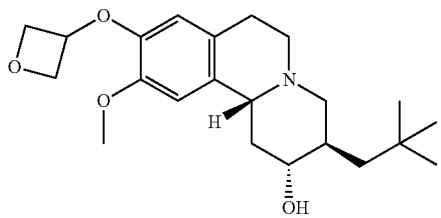 [SMILES: COc1cc2c(cc1OC1COC1)CCN1C[C@@H](CC(C)(C)C)[C@H](O)C[C@H]21]

To a solution of (2R,3R,11bR)-3-(2,2-dimethylpropyl)-10-methoxy-1H,2H,3H,4H,6H,7H,11bH-pyrido[2,1-a]isoquinoline-2,9-diol (Compound 1-D (2R,3R,11bR), 0.20 g, 0.63 mmol, 1.0 eq) in DMF (6 mL) was added cesium carbonate (0.61 g, 1.88 mmol, 3.0 eq) and the resulting mixture stirred at RT for 10 min. Then, 3-bromooxetane (0.12 mL, 1.56 mmol, 2.5 eq) was added and the mixture stirred at 60° C. for 6 h. The mixture was cooled to RT, diluted with water, and extracted three times with EtOAc. The combined organic extracts were washed five times with water, dried over MgSO$_4$, filtered, and concentrated in vacuo. The crude material was submitted to two chromatographic separations: a silica gel column (4 g) loaded using DCM run with an increasing gradient of EtOAc (0-100% over 30 min) in hexanes and a reversed-phase C18 column (16 g) loaded using DMSO run with an increasing gradient of MeCN (10-100% over 25 min) in water to afford (2R,3R,11bR)-3-(2,2-dimethylpropyl)-10-methoxy-9-(oxetan-3-yloxy)-1H,2H,3H,4H,6H,7H,11bH-pyrido[2,1-a]isoquinolin-2-ol (Compound 4-30, 0.15 g, 0.41 mmol, 65%) as a white solid. $^1$H NMR (400 MHz, DMSO-d$_6$): δ (ppm) 6.77 (s, 1H), 6.31 (s, 1H), 5.15 (quin, J=5.5 Hz, 1H), 4.88 (t, J=6.7 Hz, 2H), 4.57-4.51 (m, 3H), 3.75 (s, 3H), 3.12-3.04 (m, 1H), 3.04-2.91 (m, 2H), 2.90-2.79 (m, 2H), 2.46-2.42 (m, 1H), 2.31-2.23 (m, 1H), 1.92 (brt, J=11.3 Hz, 1H), 1.70 (d, J=13.6 Hz, 1H), 1.47-1.38 (m, 1H), 1.25 (q, J=1.0 Hz, 1H), 0.90 (s, 9H), 0.81 (dd, J=13.8, 7.5 Hz, 1H).

Example 5D: Preparation of (2R,3R,11bR)-3-(2,2-dimethylpropyl)-10-methoxy-9-[(2S)-3,3,3-trifluoro-2-hydroxypropoxy]-1H,2H,3H,4H,6H,7H,11bH-pyrido[2,1-a]isoquinolin-2-ol (Compound 4-50)

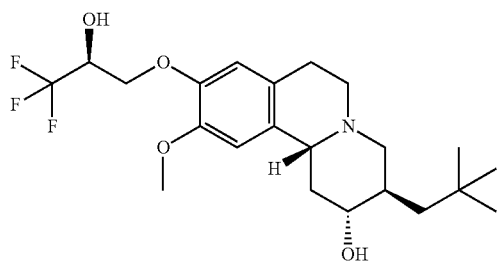 [SMILES: COc1cc2c(cc1OC[C@H](O)C(F)(F)F)CCN1C[C@@H](CC(C)(C)C)[C@H](O)C[C@H]21]

To a solution of (2R,3R,11bR)-3-(2,2-dimethylpropyl)-10-methoxy-1H,2H,3H,4H,6H,7H,11bH-pyrido[2,1-a]isoquinoline-2,9-diol (Compound 1-D (2R,3R,11bR), 0.20 g, 0.63 mmol, 1.0 eq) in DMF (6 mL) was added cesium carbonate (0.61 g, 1.88 mmol, 3.0 eq) and the resulting mixture stirred at RT for 10 min. Then, (2S)-2-(trifluoromethyl)oxirane (72 µL, 0.94 mmol, 1.5 eq) was added and the mixture stirred at RT for 6 h. An additional portion of (2S)-2-(trifluoromethyl)oxirane (24 µL, 0.31 mmol, 0.5 eq) was added and the mixture stirred at RT for an additional hour. The mixture was diluted with water and extracted three times with EtOAc. The combined organic extracts were washed five times with water, dried over MgSO$_4$, filtered, and concentrated in vacuo. The crude material was submitted to two chromatographic separations: a silica gel column (12 g) loaded using DCM run with an increasing gradient of EtOAc (0-65% over 20 min) in hexanes and a reversed-phase C18 column (16 g) loaded using DMSO run with an increasing gradient of MeCN (10-40% over 25 min, then 40%-90% over 15 min) in water to afford (2R,3R,11bR)-3-(2,2-dimethylpropyl)-10-methoxy-9-[(2S)-3,3,3-trifluoro-2-hydroxypropoxy]-1H,2H,3H,4H,6H,7H,11bH-pyrido[2,1-a]isoquinolin-2-ol (Compound 4-50, 0.13 g, 0.31 mmol, 50%) as a white solid. $^1$H NMR (400 MHz, DMSO-d$_6$): δ (ppm) 6.76 (s, 1H), 6.72 (s, 1H), 6.60 (d, J=6.2 Hz, 1H), 4.55 (d, J=6.5 Hz, 1H), 4.41-4.30 (m, 1H), 4.12 (dd, J=10.5, 4.0 Hz, 1H), 3.98 (dd, J=10.3, 6.7 Hz, 1H), 3.74 (s, 3H), 3.12-2.83 (m, 5H), 2.59-2.54 (m, 1H), 2.46-2.43 (m, 1H), 2.32-2.23 (m, 1H), 1.93 (brt, J=11.2 Hz, 1H), 1.70 (bd, J=14.1 Hz, 1H), 1.48-1.38 (m, 1H), 1.26 (q, J=11.5 Hz, 1H), 0.91 (s, 9H), 0.81 (br dd, J=13.8, 7.5 Hz, 1H).

Example 5E: Preparation of (2R,3R,11bR)-3-(2,2-dimethylpropyl)-10-methoxy-9-[(3R)-oxolan-3-yloxy]-1H,2H,3H,4H,6H,7H,11bH-pyrido[2,1-a]isoquinolin-2-ol (Compound 4-53)

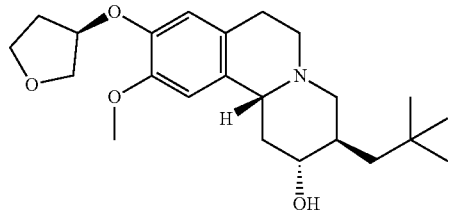 [SMILES: COc1cc2c(cc1O[C@@H]1CCOC1)CCN1C[C@@H](CC(C)(C)C)[C@H](O)C[C@H]21]

To a solution of (2R,3R,11bR)-3-(2,2-dimethylpropyl)-10-methoxy-1H,2H,3H,4H,6H,7H,11bH-pyrido[2,1-a]isoquinoline-2,9-diol (Compound 1-D (2R,3R,11bR), 0.30 g, 0.94 mmol, 1.0 eq) in DMF (3 mL) was added cesium carbonate (0.92 g, 2.82 mmol, 3.0 eq) and the resulting mixture stirred at RT for 10 min. Then, (3S)-3-iodooxolane (0.15 mL, 1.41 mmol, 1.5 eq) was added and the mixture stirred at RT overnight. The mixture was diluted with water and extracted three times with EtOAc. The combined organic extracts were washed five times with water, dried over MgSO$_4$, filtered, and concentrated in vacuo. The crude material was submitted to four chromatographic separations: a dry loaded (celite) basic alumina column (24 g) run with an increasing gradient of MeOH (0-5% over 10 min, then 100% for 10 min) in DCM, a dry loaded (celite) silica column (4 g) run with an increasing gradient of EtOAc (0-100% over 20 min) in hexanes, a reversed-phase C18 column (30 g) loaded with DMSO run with an increasing gradient of MeCN (10-50% over 20 min) in water and a dry loaded (celite) silica column (4 g) run with an increasing gradient of EtOAc (0-100% over 20 min) in hexanes to afford (2R,3R,11bR)-3-(2,2-dimethylpropyl)-10-methoxy-9-[(3R)-oxolan-3-yloxy]-1H,2H,3H,4H,6H,7H,11bH-pyrido[2,1-a]isoquinolin-2-ol (Compound 4-53, 0.14 g, 0.35 mmol, 38%) as a white solid. $^1$H NMR (400 MHz, DMSO-d$_6$): δ (ppm) 6.74 (s, 1H), 6.62 (s, 1H), 4.95-4.89 (m, 1H), 4.55 (d, J=6.5 Hz, 1H), 3.86-3.73 (m, 4H), 3.72 (s, 3H), 3.13-3.04 (m, 1H), 3.01 (br d, J=11.5 Hz, 1H), 2.95 (dd, J=11.7, 4.2 Hz, 1H), 2.92-2.82 (m, 2H), 2.58-2.53 (m, 1H), 2.49-2.44 (m, 1H), 2.32-2.24 (m, 1H), 2.19-2.08 (m, 1H), 1.99-1.88 (m, 2H), 1.70 (d, J=13.1 Hz, 1H), 1.48-1.39 (m, 1H), 1.26 (q, J=11.4 Hz, 1H), 0.91 (s, 9H), 0.81 (dd, J=13.9, 7.4 Hz, 1H).

Example 5F: Preparation of (2R,3R,11bR)-3-(2,2-dimethylpropyl)-9-[(2R)-2-hydroxypropoxy]-10-methoxy-1H,2H,3H,4H,6H,7H,11bH-pyrido[2,1-a]isoquinolin-2-ol (Compound 4-55), See FIG. 12

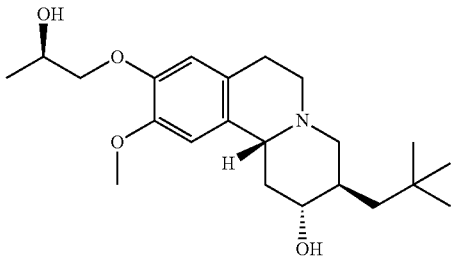 [SMILES: COc1cc2c(cc1OC[C@@H](C)O)CCN1C[C@@H](CC(C)(C)C)[C@H](O)C[C@H]21]

To a solution of (2R,3R,11bR)-3-(2,2-dimethylpropyl)-10-methoxy-1H,2H,3H,4H,6H,7H,11bH-pyrido[2,1-a]isoquinoline-2,9-diol (Compound 1-D (2R,3R,11bR), 1.00 g, 3.13 mmol, 1.0 eq) in DMF (28 mL) was added cesium carbonate (3.06 g, 9.39 mmol, 3.0 eq) and the resulting mixture stirred at RT for 10 min. Then, (R)-2-methyloxirane (0.31 mL, 6.26 mmol, 2 eq) was added and the mixture stirred at 80° C. for 16 h. An additional portion of (R)-2-methyloxirane (0.16 mL, 3.13 mmol, 1 eq) was added and the mixture stirred at 80° C. for an additional 4 h. A third addition of (R)-2-methyloxirane (39 μL, 0.78 mmol, 0.25 eq) was added and the mixture stirred at 80° C. for an additional 3 h. The mixture was cooled to RT, diluted with water, and extracted three times with 5:1 DCM:i-PrOH. The combined organic extracts were washed five times with water, dried over MgSO$_4$, filtered, and concentrated in vacuo. A silica gel column (24 g) was loaded using DCM and run with an increasing gradient of EtOAc (0-100% over 20 min) in hexanes to afford impure (2R,3R,11bR)-3-(2,2-dimethylpropyl)-9-[(2R)-2-hydroxypropoxy]-10-methoxy-1H,2H,3H,4H,6H,7H,11bH-pyrido[2,1-a]isoquinolin-2-ol (Compound 4-55, 0.95 g) as an off white solid. The crude white solid was recrystallized from 1:1 hexanes/EtOAc to afford crude 4-55 (0.70 g) as an off white solid. A reversed-phase C18 column (100 g) was loaded using DMSO and run with an increasing gradient of MeCN (10-70% over 25 min) in water to afford (2R,3R,11bR)-3-(2,2-dimethylpropyl)-9-[(2R)-2-hydroxypropoxy]-10-methoxy-1H,2H,3H,4H,6H, 7H,11bH-pyrido[2,1-a]isoquinolin-2-ol (Compound 4-55, 0.59 g, 1.55 mmol, 50%) as a white solid. $^1$H NMR (500 MHz, DMSO-d$_6$): δ (ppm) 6.71 (s, 1H), 6.63 (s, 1H), 4.77 (d, J=4.4 Hz, 1H), 4.54 (d, J=6.6 Hz, 1H), 3.96-3.87 (m, 1H), 3.77 (dd, J=9.3, 6.3 Hz, 1H), 3.72 (s, 3H), 3.68 (dd, J=9.5, 5.5 Hz, 1H), 3.11-3.05 (m, 1H), 2.99 (br d, J=11.0 Hz, 1H), 2.94 (dd, J=11.8, 4.1 Hz, 1H), 2.90-2.83 (m, 2H), 2.55-2.51 (m, 1H), 2.47-2.42 (m, 1H), 2.30-2.24 (m, 1H), 1.91 (t, J=11.2 Hz, 1H), 1.69 (d, J=12.6 Hz, 1H), 1.47-1.40 (m, 1H), 1.25 (q, J=11.5 Hz, 1H), 1.13 (d, J=6.0 Hz, 3H), 0.90 (s, 9H), 0.80 (dd, J=13.7, 7.7 Hz, 1H).

Representative reagents (i.e., R$^1$—X) used to synthesize compounds in Table 10A and Table 10B, include those shown in Table 8.

TABLE 8

R$^1$—X

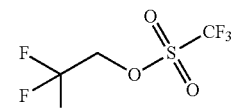

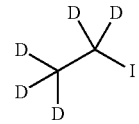

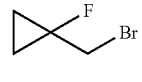

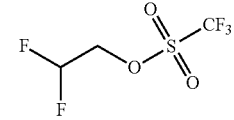

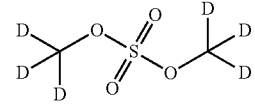 [SMILES: [2H]C([2H])([2H])OS(=O)(=O)OC([2H])([2H])[2H]]

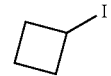

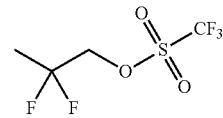

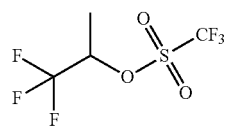

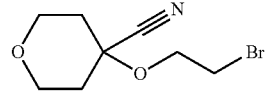 [SMILES: N#CC1(OCCBr)CCOCC1]

TABLE 8-continued

R¹—X (structures of alkylating agents)

Representative epoxide reagents used to synthesize compounds shown in Table 10A and Table 10B, include those shown in Table 9.

TABLE 9

| Epoxide | Epoxide | Epoxide |
| --- | --- | --- |
| (structure) | (structure) | (structure) |
| (structure) | (structure) | (structure) |

Table 10A and Table 10B, shown below, provide the observed (Obs) ion m/z ratio for Compound 4-1, Compound 4-27, Compound 4-30, Compound 4-50, Compound 4-55, and other representative compounds that were made analogously to the procedure described in the above examples. In many cases, a dialkylsulfate, alkyl bromide, alkyl chloride, or alkyl iodide shown in Table 8 was used in place of atriflate. In other cases, an epoxide shown in Table 9 was used in place of atriflate. Also frequently, final compounds were submitted directly to purification by preparative HPLC.

TABLE 10A

| Cmpd. No. | —R¹ | Chemical Name | Obs. Ion (m/z) |
|---|---|---|---|
| 4-1 | 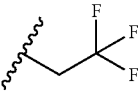 | (2R,3R,11bR)-3-(2,2-dimethylpropyl)-10-methoxy-9-(2,2,2-trifluoroethoxy)-1H,2H,3H,4H,6H,7H,11bH-pyrido[2,1-a]isoquinolin-2-ol | 402.2 |
| 4-2 | 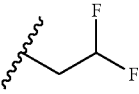 [SMILES: *CC(F)F] | (2R,3S,11bS)-9-(2,2-difluoroethoxy)-3-(2,2-dimethylpropyl)-10-methoxy-1H,2H,3H,4H,6H,7H,11bH-pyrido[2,1-a]isoquinolin-2-ol | 384.2 |
| 4-3 | 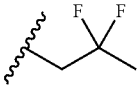 [SMILES: *CC(C)(F)F] | (2R,3S,11bS)-9-(2,2-difluoropropoxy)-3-(2,2-dimethylpropyl)-10-methoxy-1H,2H,3H,4H,6H,7H,11bH-pyrido[2,1-a]isoquinolin-2-ol | 398.3 |
| 4-4 | 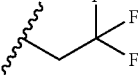 | (2R,3S,11bS)-3-(2,2-dimethylpropyl)-10-methoxy-9-(2,2,2-trifluoroethoxy)-1H,2H,3H,4H,6H,7H,11bH-pyrido[2,1-a]isoquinolin-2-ol | 402.2 |
| 4-5 | 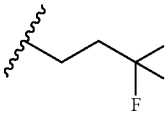 | (2R,3S,11bS)-3-(2,2-dimethylpropyl)-10-methoxy-9-(3,3,3-trifluoropropoxy)-1H,2H,3H,4H,6H,7H,11bH-pyrido[2,1-a]isoquinolin-2-ol | 416.2 |
| 4-6 | 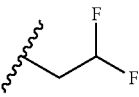 | (2S,3S,11bS)-9-(2,2-difluoroethoxy)-3-(2,2-dimethylpropyl)-10-methoxy-1H,2H,3H,4H,6H,7H,11bH-pyrido[2,1-a]isoquinolin-2-ol | 384.2 |
| 4-7 | 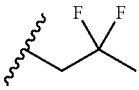 | (2S,3S,11bS)-9-(2,2-difluoropropoxy)-3-(2,2-dimethylpropyl)-10-methoxy-1H,2H,3H,4H,6H,7H,11bH-pyrido[2,1-a]isoquinolin-2-ol | 398.3 |
| 4-8 | 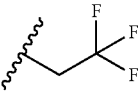 [SMILES: *CC(F)(F)F] | (2S,3S,11bS)-3-(2,2-dimethylpropyl)-10-methoxy-9-(2,2,2-trifluoroethoxy)-1H,2H,3H,4H,6H,7H,11bH-pyrido[2,1-a]isoquinolin-2-ol | 402.2 |
| 4-9 | 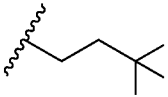 | (2S,3S,11bS)-3-(2,2-dimethylpropyl)-10-methoxy-9-(3,3,3-trifluoropropoxy)-1H,2H,3H,4H,6H,7H,11bH-pyrido[2,1-a]isoquinolin-2-ol | 416.2 |
| 4-10 | 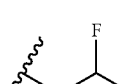 | (2S,3R,11bR)-9-(2,2-difluoroethoxy)-3-(2,2-dimethylpropyl)-10-methoxy-1H,2H,3H,4H,6H,7H,11bH-pyrido[2,1-a]isoquinolin-2-ol | 384.2 |
| 4-11 | 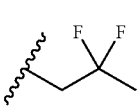 [SMILES: *CC(C)(F)F] | (2S,3R,11bR)-9-(2,2-difluoropropoxy)-3-(2,2-dimethylpropyl)-10-methoxy-1H,2H,3H,4H,6H,7H,11bH-pyrido[2,1-a]isoquinolin-2-ol | 398.3 |
| 4-12 | 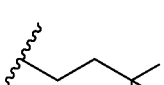 | (2S,3R,11bR)-3-(2,2-dimethylpropyl)-10-methoxy-9-(3,3,3-trifluoropropoxy)-1H,2H,3H,4H,6H,7H,11bH-pyrido[2,1-a]isoquinolin-2-ol | 416.2 |
| 4-13 | 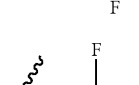 | (2R,3R,11bR)-9-(2,2-difluoroethoxy)-3-(2,2-dimethylpropyl)-10-methoxy-1H,2H,3H,4H,6H,7H,11bH-pyrido[2,1-a]isoquinolin-2-ol | 384.2 |
| 4-14 | 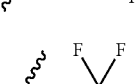 | (2R,3R,11bR)-9-(2,2-difluoropropoxy)-3-(2,2-dimethylpropyl)-10-methoxy-1H,2H,3H,4H,6H,7H,11bH-pyrido[2,1-a]isoquinolin-2-ol | 398.3 |

TABLE 10A-continued

| Cmpd. No. | —R¹ | Chemical Name | Obs. Ion (m/z) |
|---|---|---|---|
| 4-15 | | (2R,3R,11bR)-3-(2,2-dimethylpropyl)-10-methoxy-9-(3,3,3-trifluoropropoxy)-1H,2H,3H,4H,6H,7H,11bH-pyrido[2,1-a]isoquinolin-2-ol | 416.2 |
| 4-16 | | (2S,3R,11bR)-3-(2,2-dimethylpropyl)-10-methoxy-9-(2,2,2-trifluoroethoxy)-1H,2H,3H,4H,6H,7H,11bH-pyrido[2,1-a]isoquinolin-2-ol | 402.2 |
| 4-17 | | (2R,3R,11bR)-3-(2,2-dimethylpropyl)-9-ethoxy-10-methoxy-1H,2H,3H,4H,6H,7H,11bH-pyrido2,1-a]isoquinolin-2-ol | 348.3 |
| 4-18 | | (1R,3R,11bR)-3-(2,2-dimethylpropyl)-9-(2-fluoroethoxy)-10-methoxy-1H,2H,3H,4H,6H,7H,11bH-pyrido[2,1-a]isoquinolin-2-ol | 366.2 |
| 4-19 | | (2R,3R,11bR)-3-(2,2-dimethylpropyl)-9-[(3-fluorooxetan-3-yl)methoxy]-10-methoxy-1H,2H,3H,4H,6H,7H,11bH-pyrido[2,1-a]isoquinolin-2-ol | 408.3 |
| 4-20 | | (2R,3R,11bR)-3-(2,2-dimethylpropyl)-10-methoxy-9-[2-(oxetan-3-yloxy)ethoxy]-1H,2H,3H,4H,6H,7H,11bH-pyrido[2,1-a]isoquinolin-2-ol | 420.3 |
| 4-21 | | (2R,3R,11bR)-3-(2,2-dimethylpropyl)-10-methoxy-9-[(2S)-oxetan-2-ylmethoxy]-1H,2H,3H,4H,6H,7H,11bH-pyrido[2,1-a]isoquinolin-2-ol | 390.3 |
| 4-22 | | (2R,3R,11bR)-3-(2,2-dimethylpropyl)-10-methoxy-9-(oxetan-3-ylmethoxy)-1H,2H,3H,4H,6H,7H,11bH-pyrido[2,1-a]isoquinolin-2-ol | 390.3 |
| 4-23 | | 1-(2-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}ethoxy)cyclobutane-1-carbonitrile | 443.3 |
| 4-24 | | 2-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}acetonitrile | 359.2 |
| 4-25 | | (2R,3R,11bR)-3-(2,2-dimethylpropyl)-9-[(1-hydroxycyclobutyl)methoxy]-10-methoxy-1H,2H,3H,4H,6H,7H,11bH-pyrido[2,1-a]isoquinolin-2-ol | 404.3 |
| 4-26 | | (2R,3R,11bR)-3-(2,2-dimethylpropyl)-10-methoxy-9-(2-methoxyethoxy)-1H,2H,3H,4H,6H,7H,11bH-pyrido[2,1-a]isoquinolin-2-ol | 378.3 |
| 4-27 | | (2R,3R,11bR)-9-cyclopropoxy-3-(2,2-dimethylpropyl)-10-methoxy-1H,2H,3H,4H,6H,7H,11bH-pyrido[2,1-a]isoquinolin-2-ol | 360.3 |
| 4-28 | | (2R,3R,11bR))-3-(2,2-dimethylpropyl)-9-(3-fluoropropoxy)-10-methoxy-1H,2H,3H,4H,6H,7H,11bH-pyrido[2,1-a]isoquinolin-2-ol | 380.3 |

TABLE 10A-continued

| Cmpd. No. | —R¹ | Chemical Name | Obs. Ion (m/z) |
|---|---|---|---|
| 4-29 | cyclopropyl-CN | 1-({[(2R,3R,11bR))-3-(2,2-dimethylpropyl)-2-hydroxy-10-methoxy-1H,2H,3H,4H,6H,7H,11bH-pyrido[2,1-a]isoquinolin-9-yl]oxy}methyl)cyclo-propane-1-carbonitrile | 399.3 |
| 4-30 | oxetan-3-yl | (2R,3R,11bR)-3-(2,2-dimethylpropyl)-10-methoxy-9-(oxetan-3-yloxy)-1H,2H,3H,4H,6H,7H,11bH-pyrido[2,1-a]isoquinolin-2-ol | 376.3 |
| 4-31 | 1-fluorocyclopropyl-CH₂ | (2R,3R,11bR)-3-(2,2-dimethylpropyl)-9-[(1-fluorocyclopropyl)methoxy]-10-methoxy-1H,2H,3H,4H,6H,7H,11bH-pyrido[2,1-a]isoquinolin-2-ol | 392.3 |
| 4-32 | cyclobutyl | (2R,3R,11bR)-9-cyclobutoxy-3-(2,2-dimethylpropyl)-10-methoxy-1H,2H,3H,4H,6H,7H,11bH-pyrido[2,1-a]isoquinolin-2-ol | 374.3 |
| 4-33 | —CH₂C(O)N(CH₃)₂ | 2-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}-N,N-dimethylacetamide | 405.3 |
| 4-34 | —CH₂CH₂-imidazol-1-yl | (2R,3R,11bR)-3-(2,2-dimethylpropyl)-9-[2-(1H-imidazol-1-yl)ethoxy]-10-methoxy-1H,2H,3H,4H,6H,7H,11bH-pyrido[2,1-a]isoquinolin-2-ol | 414.3 |
| 4-35 | —CH₂C(O)NHCH₃ | 2-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}-N-methylacetamide | 391.3 |
| 4-36 | (5-methyl-1,3-oxazol-2-yl)methyl | (2R,3R,11bR)-3-(2,2-dimethylpropyl)-10-methoxy-9-[(5-methyl-1,3-oxazol-2-yl)methoxy]-1H,2H,3H,4H,6H,7H,11bH-pyrido[2,1-a]isoquinolin-2-ol | 415.3 |
| 4-37 | (1-methylazetidin-3-yl)methyl | (2R,3R,11bR)-3-(2,2-dimethylpropyl)-10-methoxy-9-[(1-methylazetidin-3-yl)methoxy]-1H,2H,3H,4H,6H,7H,11bH-pyrido[2,1-a]isoquinolin-2-ol | 403.3 |
| 4-38 | isopropyl | (2R,3R,11bR)-3-(2,2-dimethylpropyl)-10-methoxy-9-(propan-2-yloxy)-1H,2H,3H,4H,6H,7H,11bH-pyrido[2,1-a]isoquinolin-2-ol | 362.3 |
| 4-39 | —CH(CH₃)CF₃ | (2R,3R,11bR)-3-(2,2-dimethylpropyl)-10-methoxy-9-[(1,1,1-trifluoropropan-2-yl)oxy]-1H,2H,3H,4H,6H,7H,11bH-pyrido[2,1-a]isoquinolin-2-ol | 416.2 |
| 4-40 | —CD₂CD₃ (ethyl-d₅) | (2R,3R,11bR)-3-(2,2-dimethylpropyl)-9-(ethoxy-d₅)-10-methoxy-1H,2H,3H,4H,6H,7H,11bH-pyrido[2,1-a]isoquinolin-2-ol or (2R,3R,11bR)-3-(2,2-dimethylpropyl)-9-(²H₅)ethoxy-10-methoxy- | 353.3 |
| 4-41 | —CH₂CH₂O-(4-cyano-oxan-4-yl) | 4-(2-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}ethoxy)oxane-4-carbonitrile | 473.3 |

TABLE 10A-continued

| Cmpd. No. | —R¹ | Chemical Name | Obs. Ion (m/z) |
|---|---|---|---|
| 4-42 | 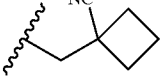 | 1-({[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}methyl)cyclobutane-1-carbonitrile | 413.3 |
| 4-43 | 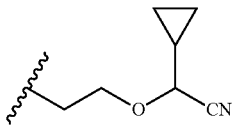 | 2-(2-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}ethoxy)-2-cyclopropylacetonitrile | 443.3 |
| 4-44 | 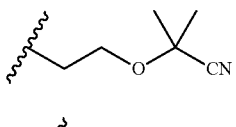 | 2-(2-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}ethoxy)-2-methylpropanenitrile | 431.3 |
| 4-45 | 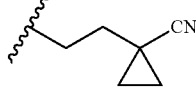 | 1-(2-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}ethyl)cyclopropane-1-carbonitrile | 413.3 |
| 4-46 | 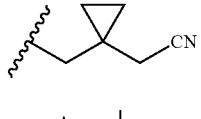 | 2-[1-({[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}methyl)cyclopropyl]acetonitrile | 413.3 |
| 4-47 | 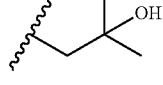 | (2R,3R,11bR)-3-(2,2-dimethylpropyl)-9-(2-hydroxy-2-methylpropoxy)-10-methoxy-1H,2H,3H,4H,6H,7H,11bH-pyrido[2,1-a]isoquinolin-2-ol | 392.3 |
| 4-48 | 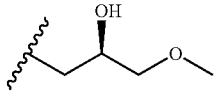 [SMILES: *C[C@@H](O)COC] | (2R,3R,11bR)-3-(2,2-dimethylpropyl)-9-[(2S)-2-hydroxy-3-methoxypropoxy]-10-methoxy-1H,2H,3H,4H,6H,7H,11bH-pyrido[2,1-a]isoquinolin-2-ol | 408.3 |
| 4-49 | 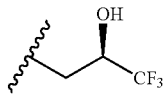 | (2R,3R,11bR)-3-(2,2-dimethylpropyl)-10-methoxy-9-[(2R)-3,3,3-trifluoro-2-hydroxypropoxy]-1H,2H,3H,4H,6H,7H,11bH-pyrido[2,1-a]isoquinolin-2-ol | 432.2 |
| 4-50 | 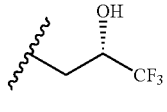 | (2R,3R,11bR)-3-(2,2-dimethylpropyl)-10-methoxy-9-[(2S)-3,3,3-trifluoro-2-hydroxypropoxy]-1H,2H,3H,4H,6H,7H,11bH-pyrido[2,1-a]isoquinolin-2-ol | 432.2 |
| 4-51 | 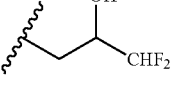 | (2R,3R,11bR)-9-(3,3-difluoro-2-hydroxypropoxy)-3-(2,2-dimethylpropyl)-10-methoxy-1H,2H,3H,4H,6H,7H,11bH-pyrido[2,1-a]isoquinolin-2-ol | 414.5 |
| 4-52 | 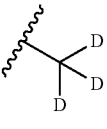 | (2R,3R,11bR)-3-(2,2-dimethylpropyl)-9-(methoxy-d₃)-10-methoxy-1H,2H,3H,4H,6H,7H,11bH-pyrido[2,1-a]isoquinolin-2-ol or (2R,3R,11bR)-3-(2,2-dimethylpropyl)-9-(²H3)methoxy-10-methoxy-1H,2H,3H,4H,6H,7H,11bH-pyrido[2,1-a]isoquinolin-2-ol | 337.3 |
| 4-53 | 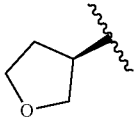 [SMILES: *[C@@H]1CCOC1] | (2R,3R,11bR)-3-(2,2-dimethylpropyl)-10-methoxy-9-[(3R)-oxolan-3-yloxy]-1H,2H,3H,4H,6H,7H,11bH-pyrido[2,1-a]isoquinolin-2-ol | 390.3 |
| 4-54 | 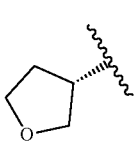 [SMILES: *[C@H]1CCOC1] | (2R,3R,11bR)-3-(2,2-dimethylpropyl)-10-methoxy-9-[(3S)-oxolan-3-yloxy]-1H,2H,3H,4H,6H,7H,11bH-pyrido[2,1-a]isoquinolin-2-ol | 390.3 |

TABLE 10A-continued

| Cmpd. No. | —R¹ | Chemical Name | Obs. Ion (m/z) |
|---|---|---|---|
| 4-55 | (structure: CH₂CH(OH)CH₃ with R stereochem) | (2R,3R,11bR)-3-(2,2-dimethylpropyl)-9-[(2R)-2-hydroxypropoxy]-10-methoxy-1H,2H,3H,4H,6H,7H,11bH-pyrido[2,1-a]isoquinolin-2-ol | 378.3 |

TABLE 10B

| Cmpd. No. | —R¹ | Chemical Name | Obs. Ion (m/z) |
|---|---|---|---|
| 4-56 | (2-methylallyl) | (2R,3R,11bR)-3-(2,2-dimethylpropyl)-10-methoxy-9-[(2-methylprop-2-en-1-yl)oxy]-1H,2H,3H,4H,6H,7H,11bH-pyrido[2,1-a]isoquinolin-2-ol | 374.3 |
| 4-57 | (1-(difluoromethyl)cyclopropyl)methyl | (2R,3R,11bR)-9-{[1-(difluoromethyl)cyclopropyl]methoxy}-3-(2,2-dimethylpropyl)-10-methoxy-1H,2H,3H,4H,6H,7H,11bH-pyrido[2,1-a]isoquinolin-2-ol | 424.3 |
| 4-58 | (2R)-2-hydroxybutyl | (2R,3R,11bR)-3-(2,2-dimethylpropyl)-9-[(2R)-2-hydroxybutoxy]-10-methoxy-1H,2H,3H,4H,6H,7H,11bH-pyrido[2,1-a]isoquinolin-2-ol | 392.3 |
| 4-59 | (5-cyanofuran-2-yl)methyl | 5-({[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}methyl)furan-2-carbonitrile | 425.2 |
| 4-60 | benzyl | (2R,3R,11bR)-9-(benzyloxy)-3-(2,2-dimethylpropyl)-10-methoxy-1H,2H,3H,4H,6H,7H,11bH-pyrido[2,1-a]isoquinolin-2-ol | 410.3 |
| 4-61 | (1-fluorocyclobutyl)methyl | (2R,3R,11bR)-3-(2,2-dimethylpropyl)-9-[(1-fluorocyclobutyl)methoxy]-10-methoxy-1H,2H,3H,4H,6H,7H,11bH-pyrido[2,1-a]isoquinolin-2-ol | 406.3 |
| 4-62 | 4,4,4-trifluoro-2-hydroxybutyl | (2R,3R,11bR)-3-(2,2-dimethylpropyl)-10-methoxy-9-(4,4,4-trifluoro-2-hydroxybutoxy)-1H,2H,3H,4H,6H,7H,11bH-pyrido[2,1-a]isoquinolin-2-ol | 446.3 |
| 4-63 | (4-fluorophenyl)methyl | (2R,3R,11bR)-3-(2,2-dimethylpropyl)-9-[(4-fluorophenyl)methoxy]-10-methoxy-1H,2H,3H,4H,6H,7H,11bH-pyrido[2,1-a]isoquinolin-2-ol | 428.3 |
| 4-64 | (3-fluorophenyl)methyl | (2R,3R,11bR)-3-(2,2-dimethylpropyl)-9-[(3-fluorophenyl)methoxy]-10-methoxy-1H,2H,3H,4H,6H,7H,11bH-pyrido[2,1-a]isoquinolin-2-ol | 428.3 |
| 4-65 | 2-chloro-2,2-difluoroethyl | (2R,3R,11bR)-9-(2-chloro-2,2-difluoroethoxy)-3-(2,2-dimethylpropyl)-10-methoxy-1H,2H,3H,4H,6H,7H,11bH-pyrido[2,1-a]isoquinolin-2-ol | 418.2 |
| 4-66 | 3,3,3-trifluoro-2-hydroxy-2-methylpropyl | (2R,3R,11bR)-3-(2,2-dimethylpropyl)-10-methoxy-9-(3,3,3-trifluoro-2-hydroxy-2-methylpropoxy)-1H,2H,3H,4H,6H,7H,11bH-pyrido[2,1-a]isoquinolin-2-ol | 446.2 |

TABLE 10B-continued

| Cmpd. No. | —R¹ | Chemical Name | Obs. Ion (m/z) |
|---|---|---|---|
| 4-67 | | (2R,3R,11bR)-3-(2,2-dimethylpropyl)-10-methoxy-9-{[3-(trifluoromethyl)bicyclo[1.1.1]pentan-1-yl]methoxy}-1H,2H,3H,4H,6H,7H,11bH-pyrido[2,1-a]isoquinolin-2-ol | 468.2 |
| 4-68 | | (2R,3R,11bR)-3-(2,2-dimethylpropyl)-9-[(2S)-2-hydroxybutoxy]-10-methoxy-1H,2H,3H,4H,6H,7H,11bH-pyrido[2,1-a]isoquinolin-2-ol | 392.3 |
| 4-69 | | (2R,3R,11bR)-3-(2,2-dimethylpropyl)-10-methoxy-9-(1,2-oxazol-3-ylmethoxy)-1H,2H,3H,4H,6H,7H,11bH-pyrido[2,1-a]isoquinolin-2-ol | 401.3 |
| 4-70 | | 2-(2-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}ethoxy)acetonitrile | 403.3 |
| 4-71 | | (2R,3R,11bR)-9-[2-(3,3-difluoropyrrolidin-1-yl)ethoxy]-3-(2,2-dimethylpropyl)-10-methoxy-1H,2H,3H,4H,6H,7H,11bH-pyrido[2,1-a]isoquinolin-2-ol | 453.3 |
| 4-72 | | (2R,3R,11bR)-3-(2,2-dimethylpropyl)-9-[(6-fluoro-1,4-dioxepan-6-yl)methoxy]-10-methoxy-1H,2H,3H,4H,6H,7H,11bH-pyrido[2,1-a]isoquinolin-2-ol | 452.3 |
| 4-73 | | 4-({[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}methyl)piperidine-1-carbonitrile | 442.3 |
| 4-74 | | (2R,3R,11bR)-3-(2,2-dimethylpropyl)-10-methoxy-9-{2-[4-(trifluoromethyl)phenyl]ethoxy}-1H,2H,3H,4H,6H,7H,11bH-pyrido[2,1-a]isoquinolin-2-ol | 492.3 |
| 4-75 | | (2R,3R,11bR)-3-(2,2-dimethylpropyl)-10-methoxy-9-(1,3-oxazol-4-ylmethoxy)-1H,2H,3H,4H,6H,7H,11bH-pyrido[2,1-a]isoquinolin-2-ol | 401.3 |
| 4-76 | | (2R,3R,11bR)-9-[(4,4-difluoro-1-hydroxycyclohexyl)methoxy]-3-(2,2-dimethylpropyl)-10-methoxy-1H,2H,3H,4H,6H,7H,11bH-pyrido[2,1-a]isoquinolin-2-ol | 468.3 |
| 4-77 | | 6-({[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}methyl)pyridine-2-carbonitrile | 436.3 |

TABLE 10B-continued

| Cmpd. No. | —R¹ | Chemical Name | Obs. Ion (m/z) |
|---|---|---|---|
| 4-78 | | (2R,3R,11bR)-3(2,2-dimethylpropyl)-9-{[3-hydroxy-3-(trifluoromethyl)cyclobutyl]methoxy}-10-methoxy-1H,2H,3H,4H,6H,7H,11bH-pyrido[2,1-a]isoquinolin-2-ol | 472.3 |
| 4-79 | | ((2R,3R,11bR)-3-(2,2-dimethylpropyl)-9-[2-hydroxy-3-(2,2,2-trifluoroethoxy)propoxy]-10-methoxy-1H,2H,3H,4H,6H,7H,11bH-pyrido[2,1-a]isoquinolin-2-ol | 476.3 |
| 4-80 | | (2R,3R,11bR)-3-(2,2-dimethylpropyl)-10-methoxy-9-{[1-(trifluoromethyl)cyclopentyl]methoxy}-1H,2H,3H,4H,6H,7H,11bH-pyrido[2,1-a]isoquinolin-2-ol | 470.3 |
| 4-81 | | (2R,3R,11bR)-3-(2,2-dimethylpropyl)-10-methoxy-9-{[4-(trifluoromethyl)phenyl]methoxy}-1H,2H,3H,4H,6H,7H,11bH-pyrido[2,1-a]isoquinolin-2-ol | 478.3 |
| 4-82 | | 6-({[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}methyl)pyridine-3-carbonitrile | 436.3 |
| 4-83 | | (2R)-3-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}propane-1,2-diol | 394.3 |
| 4-84 | | 2-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}-N-methyl-N-(2,2,2-trifluoroethyl)acetamide | 473.2 |
| 4-85 | | (2R,3R,11bR)-3-(2,2-dimethylpropyl)-9-(3-methanesulfonylpropoxy)-10-methoxy-1H,2H,3H,4H,6H,7H,11bH-pyrido[2,1-a]isoquinolin-2-ol | 440.2 |
| 4-86 | | 1-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}-N,N-dimethylmethanesulfonamide | 441.3 |
| 4-87 | | 3-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}-1-(2,2,2-trifluoroethyl)pyrrolidin-2-one | 485.2 |
| 4-88 | | (2R,3R,11bR)-9-(cyclopropylmethoxy)-3-(2,2-dimethylpropyl)-10-methoxy-1H,2H,3H,4H,6H,7H,11bH-pyrido[2,1-a]isoquinolin-2-ol | 374.3 |
| 4-89 | | (2R,3R,11bR)-3-(2,2-dimethylpropyl)-9-(3-hydroxypropoxy)-10-methoxy-1H,2H,3H,4H,6H,7H,11bH-pyrido[2,1-a]isoquinolin-2-ol | 378.3 |

TABLE 10B-continued

| Cmpd. No. | —R¹ | Chemical Name | Obs. Ion (m/z) |
|---|---|---|---|
| 4-90 | 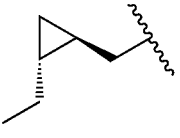 [SMILES: *C[C@@H]1C[C@H]1CC] | (2R,3R,11bR)-3-(2,2-dimethylpropyl)-9-{[(1R,2R)-2-ethylcyclopropyl]methoxy}-10-methoxy-1H,2H,3H,4H,6H,7H,11bH-pyrido[2,1-a]isoquinolin-2-ol | 402.3 |
| 4-91 | 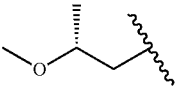 | (2R,3R,11bR)-3-(2,2-dimethylpropyl)-10-methoxy-9-[(2R)-2-methoxypropoxy]-1H,2H,3H,4H,6H,7H,11bH-pyrido[2,1-a]isoquinolin-2-ol | 392.3 |
| 4-92 | 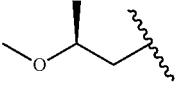 [SMILES: *C[C@H](C)OC] | (2R,3R,11bR)-3-(2,2-dimethylpropyl)-10-methoxy-9-[(2S)-2-methoxypropoxy]-1H,2H,3H,4H,6H,7H,11bH-pyrido[2,1-a]isoquinolin-2-ol | 392.3 |
| 4-93 | 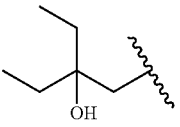 | (2R,3R,11bR)-3-(2,2-dimethylpropyl)-9-(2-ethyl-2-hydroxybutoxy)-10-methoxy-1H,2H,3H,4H,6H,7H,11bH-pyrido[2,1-a]isoquinolin-2-ol | 420.3 |
| 4-94 | 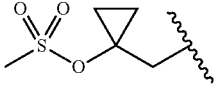 [SMILES: *CC1(OS(C)(=O)=O)CC1] | 1-({[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}methyl)cyclopropylmethanesulfonate | 468.3 |
| 4-95 | 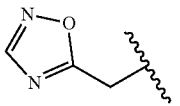 [SMILES: *Cc1ncno1] | (2R,3R,11bR)-3-(2,2-dimethylpropyl)-10-methoxy-9-(1,2,4-oxadiazol-5-ylmethoxy)-1H,2H,3H,4H,6H,7H,11bH-pyrido[2,1-a]isoquinolin-2-ol | 402.3 |
| 4-96 | 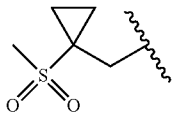 [SMILES: *CC1(S(C)(=O)=O)CC1] | (2R,3R,11bR)-3-(2,2-dimethylpropyl)-9-[(1-methanesulfonylcyclopropyl)methoxy]-10-methoxy-1H,2H,3H,4H,6H,7H,11bH-pyrido[2,1-a]isoquinolin-2-ol | 452.3 |
| 4-97 | 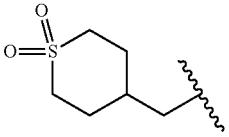 [SMILES: *CC1CCS(=O)(=O)CC1] | 4-({[(2R,3R,11bR)-3-(2,2-dimethylpropyl)-2-hydroxy-10-methoxy-1H,2H,3H,4H,6H,1H,11bH-pyrido[2,1-a]isoquinolin-9-yl]oxy}methyl)-1$\lambda^6$-thiane-1,1-dione | 466.3 |
| 4-98 | 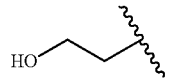 | (2R,3R,11bR)-3-(2,2-dimethylpropyl)-9-(2-hydroxyethoxy)-10-methoxy-1H,2H,3H,4H,6H,7H,11bH-pyrido[2,1-a]isoquinolin-2-ol | 364.3 |
| 4-99 | 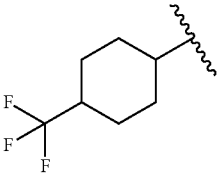 [SMILES: *C1CCC(C(F)(F)F)CC1] | (2R,3R,11bR)-3-(2,2-dimethylpropyl)-10-methoxy-9-{[4-(trifluoromethyl)cyclohexyl]oxy}-1H,2H,3H,4H,6H,7H,11bH-pyrido[2,1-a]isoquinolin-2-ol | 470.3 |
| 4-100 | 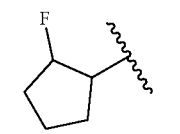 [SMILES: *C1CCCC1F] | (2R,3R,11bR)-3-(2,2-dimethylpropyl)-9-[(2-fluorocyclopentyl)oxy]-10-methoxy-1H,2H,3H,4H,6H,7H,11bH-pyrido[2,1-a]isoquinolin-2-ol | 405.3 |
| 4-101 | 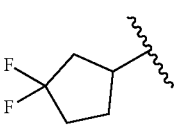 [SMILES: *C1CCC(F)(F)C1] | (2R,3R,11bR)-9-[(3,3-difluorocyclopentyl)oxy]-3-(2,2-dimethylpropyl)-10-methoxy-1H,2H,3H,4H,6H,7H,11bH-pyrido[2,1-a]isoquinolin-2-ol | 424.3 |

TABLE 10B-continued

| Cmpd. No. | —R¹ | Chemical Name | Obs. Ion (m/z) |
|---|---|---|---|
| 4-102 | 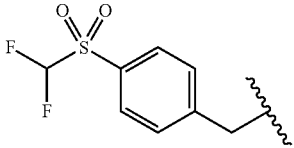 [SMILES: *Cc1ccc(S(=O)(=O)C(F)F)cc1] | (2R,3R,11bR)-9-[(4-difluoromethanesulfonylphenyl)methoxy]-3-(2,2-dimethylpropyl)-10-methoxy-1H,2H,3H,4H,6H,7H,11bH-pyrido[2,1-a]isoquinolin-2-ol | 524.2 |
| 4-103 | 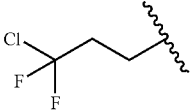 [SMILES: *CCC(F)(F)Cl] | (2R,3R,11bR)-9-(3-chloro-3,3-difluoropropoxy)-3-(2,2-dimethylpropyl)-10-methoxy-1H,2H,3H,4H,6H,7H,11bH-pyrido[2,1-a]isoquinolin-2-ol | 431.2 |
| 4-104 | 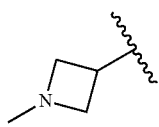 [SMILES: *C1CN(C)C1] | (2R,3R,11bR)-3-(2,2-dimethylpropyl)-10-methoxy-9-[(1-methylazetidin-3-yl)oxy]-1H,2H,3H,4H,6H,7H,11bH-pyrido[2,1-a]isoquinolin-2-ol | 389.3 |
| 4-105 | 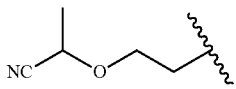 [SMILES: *CCOC(C)C#N] | 2-(2-{[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}ethoxy)propanenitrile | 417.3 |
| 4-106 | 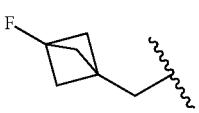 | (2R,3R,11bR)-3-(2,2-dimethylpropyl)-9-({3-fluorobicyclo[1.1.1]pentan-1-yl}methoxy)-10-methoxy-1H,2H,3H,4H,6H,7H,11bH-pyrido2,1-a]isoquinolin-2-ol | 418.3 |
| 4-107 | 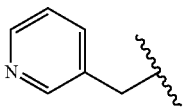 [SMILES: *Cc1cccnc1] | (2R,3R,11bR)-3-(2,2-dimethylpropyl)-10-methoxy-9-(pyridin-3-ylmethoxy)-1H,2H,3H,4H,6H,7H,11bH-pyrido[2,1-a]isoquinolin-2-ol | 411.3 |
| 4-108 | 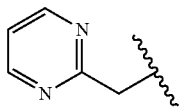 [SMILES: *Cc1ncccn1] | (2R,3R,11bR)-3-(2,2-dimethylpropyl)-10-methoxy-9-(pyrimidin-2-ylmethoxy)-1H,2H,3H,4H,6H,7H,11bH-pyrido[2,1-a]isoquinolin-2-ol | 412.3 |
| 4-109 | 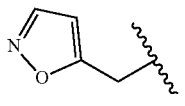 [SMILES: *Cc1ccno1] | (2R,3R,11bR)-3-(2,2-dimethylpropyl)-10-methoxy-9-(1,2-oxazol-5-ylmethoxy)-1H,2H,3H,4H,6H,7H,11bH-pyrido[2,1-a]isoquinolin-2-ol | 401.3 |
| 4-110 | 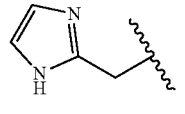 | (2R,3R,11bR)-3-(2,2-dimethylpropyl)-9-(1H-imidazol-2-ylmethoxy)-10-methoxy-1H,2H,3H,4H,6H,7H,11bH-pyrido[2,1-a]isoquinolin-2-ol | 400.3 |
| 4-111 | 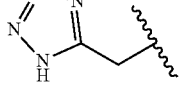 | (2R,3R,11bR)-3-(2,2-dimethylpropyl)-10-methoxy-9-(1H-1,2,3,4-tetrazol-5-ylmethoxy)-1H,2H,3H,4H,6H,7H,11bH-pyrido[2,1-a]isoquinolin-2-ol | 402.3 |
| 4-112 | 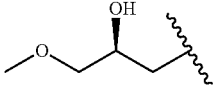 | (2R,3R,11bR)-3-(2,-dimethylpropyl)-9-[(2R)-2-hydroxy-3-methoxypropoxy]-10-methoxy-1H,2H,3H,4H,6H,7H,11bH-pyrido[2,1-a]isoquinolin-2-ol | 407.3 |
| 4-113 | 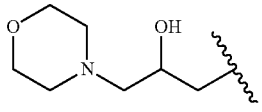 [SMILES: *CC(O)CN1CCOCC1] | (2R,3R,11bR)-3-(2,2-dimethylpropyl)-9-2-hydroxy-3-(morpholin-4-yl)propoxy]-10-methoxy-1H,2H,3H,4H,6H,7H,11bH-pyrido[2,1-a]isoquinolin-2-ol | 462.3 |

TABLE 10B-continued

| Cmpd. No. | —R¹ | Chemical Name | Obs. Ion (m/z) |
|---|---|---|---|
| 4-114 |  | (2R,3R,11bR)-3-(2,2-dimethylpropyl)-9-[(2S)-2-hydroxypropoxy]-10-methoxy-1H,2H,3H,4H,6H,7H,11bH-pyrido[2,1-a]isoquinolin-2-ol | 378.3 |
| 4-115 |  | (2R,3R,11bR)-3-(2,2-dimethylpropyl)-10-methoxy-9-[(5,5,5-trifluoropentyl)oxy]-1H,2H,3H,4H,6H,7H,11bH-pyrido[2,1-a]isoquinolin-2-ol | 444.4 |
| 4-116 |  | 3-({[(2R,3R,11bR)-3-(2,2-dimethylpropyl)-2-hydroxy-10-methoxy-1H,2H,3H,4H,6H,7H,11bH-pyrido[2,1-a]isoquinolin-9-yl]oxy}methyl)benzonitrile | 435.3 |
| 4-117 | 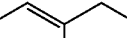 | (2R,3R,11bR)-3-(2,2-dimethylpropyl)-9-[2-(4-fluorophenyl)ethoxy]-10-methoxy-1H,2H,3H,4H,6H,7H,11bH-pyrido[2,1-a]isoquinolin-2-ol | 442.3 |
| 4-118 | 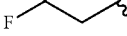 | (2R,3R,11bR)-3-(2,2-dimethylpropyl)-9-[(1-fluorocyclopropyl)methoxy]-10-methoxy-1H,2H,3H,4H,6H,7H,11bH-pyrido[2,1-a]isoquinolin-2-ol | 392.3 |
| 4-119 | 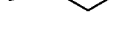 | (2R,3R,11bR)-9-(cyclobutylmethoxy)-3-(2,2-dimethylpropyl)-10-methoxy-1H,2H,3H,4H,6H,7H,11bH-pyrido[2,1-a]isoquinolin-2-ol | 388.4 |
| 4-120 |  | (2R,3R,11bR)-3-(2,2-dimethylpropyl)-10-methoxy-9-(4,4,4-trifluorobutoxy)-1H,2H,3H,4H,6H,7H,11bH-pyrido[2,1-a]isoquinolin-2-ol | 430.3 |
| 4-121 | 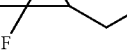 | (2R,3R,11bR)-9-[(2,2-difluorocyclopropyl)methoxy]-3-(2,2-dimethylpropyl)-10-methoxy-1H,2H,3H,4H,6H,7H,11bH-pyrido[2,1-a]isoquinolin-2-ol | 410.3 |

A summary of representative physical properties for Compound 4-1 prepared according to the methods disclosed herein are provided in Table 11 and Table 12, and a summary of representative physical properties for Compound 4-15 prepared according to the methods disclosed herein are provided in Table 13 and Table 14.

Example 6: Powder X-Ray Diffraction (PXRD), Differential Scanning Calorimetry (DSC), and Thermal Gravimetric (TGA) Analyses for (2R,3R,11bR)-3-(2,2-Dimethylpropyl)-10-methoxy-9-(2,2,2-trifluoroethoxy)-1H,2H,3H,4H,6H,7H,11bH-pyrido[2,1-a]isoquinolin-2-ol (Compound 4-1) and (2R,3R,11bR)-3-(2,2-dimethylpropyl)-10-methoxy-9-(3,3,3-trifluoropropoxy)-1H,2H,3H,4H,6H,7H,11bH-pyrido[2,1-a]isoquinolin-2-ol (Compound 4-15)

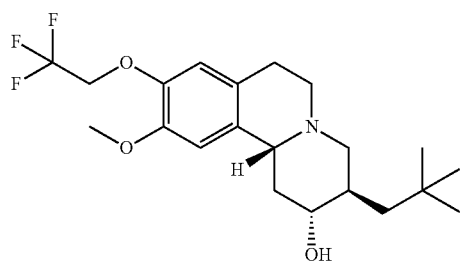

4-1

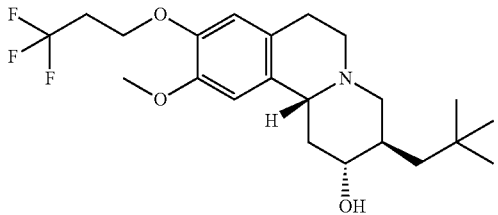

4-15

Powder X-Ray Diffraction (Pxrd)

The powder X-ray powder diffraction (PXRD) analysis was performed on a Rigaku Powder X-Ray Diffractometer Miniflex 600 Serial Number BD66000190-01. For analysis, approximately 0.5-1 mg of sample was added to a zero-background sample holder. The powder was pressed down gently with a piece of weigh paper, and the sample holder was placed in the sample changer. Run Parameters: Miniflex Counter Detector, Kb Filter (×2), Scan Axis Theta/2-Theta, Mode Continuous, Start (deg) 2.0, Stop (deg) 45.0, Step (deg) 0.020, Speed (deg/min) 10.0, Spin-yes, Voltage (kV) 40, Current (mA) 15. The reported 2θ values can vary by plus or minus 0.2° (i.e., ±0.2°).

It is understood that peak intensities can vary from one diffractogram to another for the same crystalline form based on any number of factors that are known to those skilled in the art, such as, preferred orientation effects, preparation technique, the sample mounting procedure, the instrument employed, sample purity, etc. One skilled in the art would understand that despite the differences in the peak intensities, a particular crystal form can be identified by its characteristic peak(s).

Differential Scanning Calorimetry (Dsc) and Thermal Gravimetric Analysis (Tga):

The DSC and TGA analyses were performed on TA Instruments Discovery 2500 calorimeter with serial number: 2500-00547 (DSC) and Discovery 5500 with serial number: 5500-0126 (TGA). For the DSC analysis, obtained and recorded the weight of a Tzero pan and a Tzero lid. ~1-3 mg of material was weighed into the Tzero Pan and the Tzero lid was pressed on with tweezers. The pan was transferred to the DSC autosampler for analysis. The method for analysis was a ramp at 10° C./min to 275° C. The reference pan was prepared with the same procedures, absent of material.

For TGA analysis, a standard aluminum sample pan was placed into the platinum TGA pan and the blank was tared with the instrument. Approximately 1-5 mg of material was added to the standard aluminum pan and analyzed at 10° C./min up to ~400° C. For TGA and DSC, the temperature features reported herein may vary by plus or minus 3° C. (i.e., +3° C.).

Table 11 provides select powder X-ray diffraction (PXRD) diffractogram peak positions at 2θ, DSC and TGA data for (2R,3R,11bR)-3-(2,2-dimethylpropyl)-10-methoxy-9-(2,2,2-trifluoroethoxy)-1H,2H,3H,4H,6H,7H,11bH-pyrido[2,1-a]isoquinolin-2-ol (Compound 4-1) free base crystalline Form I.

TABLE 11

Figure 2:
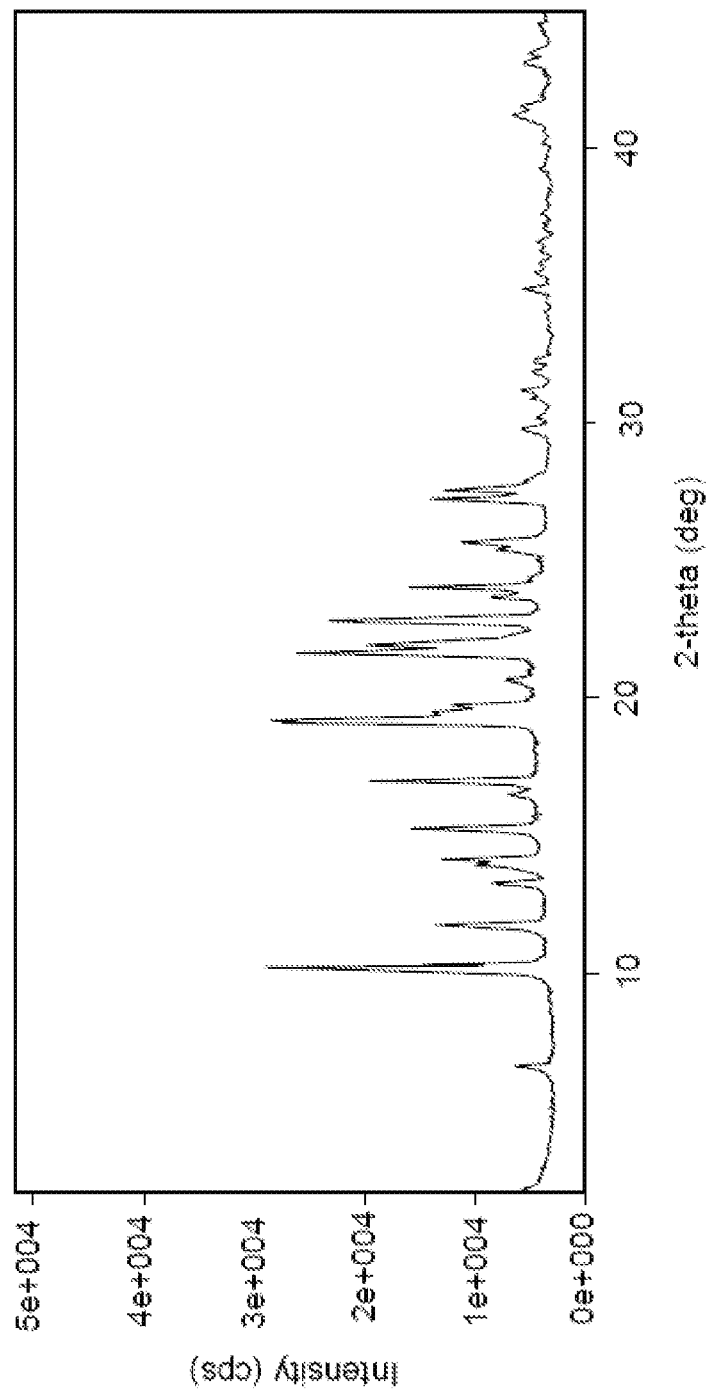
FIG. 2 shows a powder X-ray diffraction (PXRD) diffractogram of (2R,3R,11bR)-3-(2,2-dimethylpropyl)-10-methoxy-9-(2,2,2-trifluoroethoxy)-1H,2H,3H,4H,6H,7H,11bH-pyrido[2,1-a]isoquinolin-2-ol (Compound 4-1) free base crystalline Form I.
Figure 3:
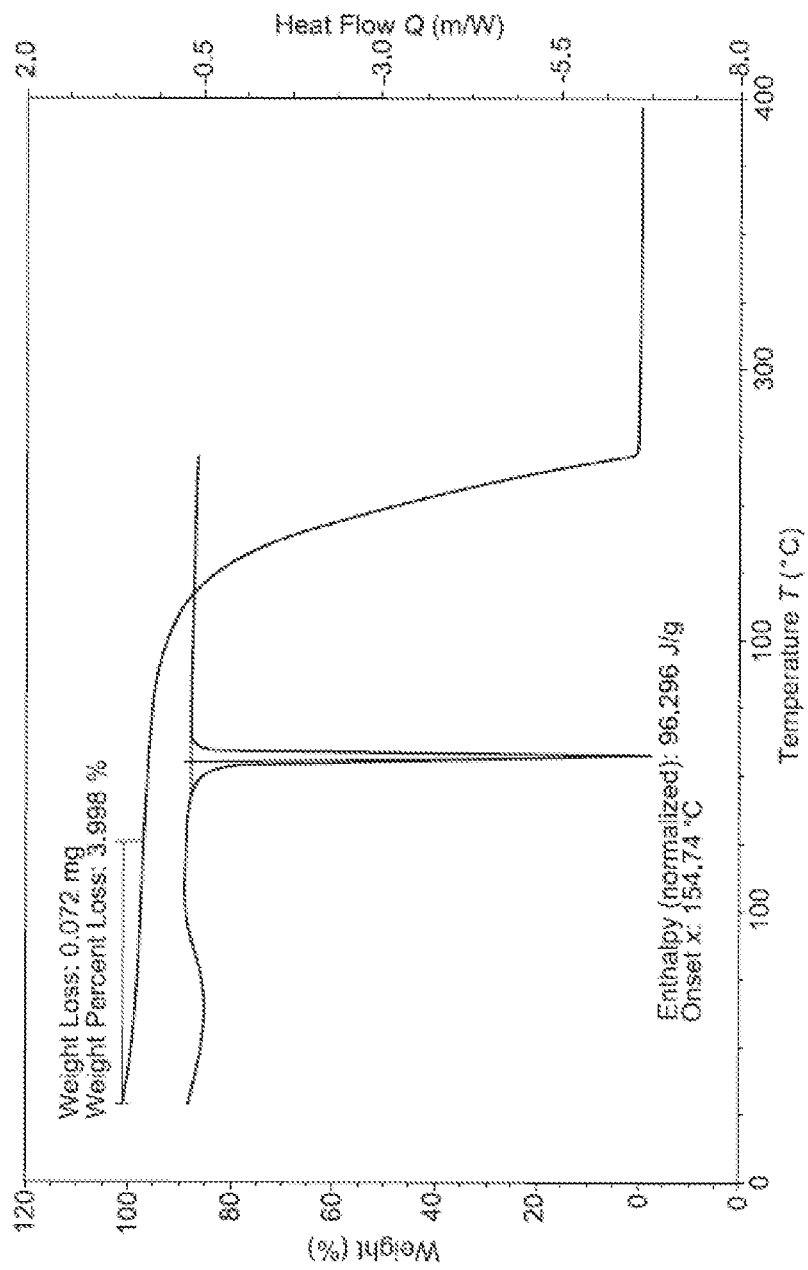
FIG. 3 shows a DSC and TGA thermogram of (2R,3R,11bR)-3-(2,2-dimethylpropyl)-10-methoxy-9-(2,2,2-trifluoroethoxy)-1H,2H,3H,4H,6H,7H,11bH-pyrido[2,1-a]isoquinolin-2-ol (Compound 4-1) free base crystalline Form I.

| (2R,3R,11bR)-3-(2,2-Dimethylpropyl)-10-methoxy-9-(2,2,2-trifluoroethoxy)-1H,2H,3H,4H,6H,7H,11bH-pyrido[2,1-a]isoquinolin-2-ol (Compound 4-1) | |
|---|---|
| PXRD | FIG. 2: Peaks at 10.2 ± 0.2°, 11.7 ± 0.2°, 15.2 ± 0.2° and 17.0 ± 0.2° 2θ |
| DSC | FIG. 3: Apparent onset temperature: about 154.7° C. |
| TGA | FIG. 3: Weight percent loss: about 4.0% |

Table 12 provides powder X-ray diffraction (PXRD) diffractogram peak positions at 2θ for (2R,3R,11bR)-3-(2,2-dimethylpropyl)-10-methoxy-9-(2,2,2-trifluoroethoxy)-1H,2H,3H,4H,6H,7H,11bH-pyrido[2,1-a]isoquinolin-2-ol (Compound 4-1) free base crystalline Form I.

TABLE 12

| Angle 2θ (2-theta) | Height (cps) |
|---|---|
| 6.6 ± 0.2° | 2546 (146) |
| 10.2 ± 0.2° | 17569 (383) |
| 11.7 ± 0.2° | 6874 (239) |
| 13.2 ± 0.2° | 3069 (160) |
| 13.9 ± 0.2° | 2883 (155) |
| 14.1 ± 0.2° | 5957 (223) |
| 15.2 ± 0.2° | 8497 (266) |
| 16.4 ± 0.2° | 1461 (110) |
| 17.0 ± 0.2° | 10114 (290) |
| 19.1 ± 0.2° | 15522 (360) |
| 19.5 ± 0.2° | 5227 (209) |
| 19.7 ± 0.2° | 4430 (192) |
| 20.6 ± 0.2° | 1622 (116) |
| 21.6 ± 0.2° | 14740 (350) |
| 21.9 ± 0.2° | 9609 (283) |
| 22.8 ± 0.2° | 13213 (332) |
| 23.7 ± 0.2° | 3139 (162) |
| 24.0 ± 0.2° | 8568 (267) |
| 25.4 ± 0.2° | 2646 (148) |
| 25.6 ± 0.2° | 5154 (207) |
| 27.2 ± 0.2° | 7410 (248) |
| 27.6 ± 0.2° | 6166 (227) |
| 27.9 ± 0.2° | 1120 (97) |
| 29.8 ± 0.2° | 1596 (115) |
| 30.3 ± 0.2° | 642 (73) |
| 31.2 ± 0.2° | 1408 (108) |
| 31.9 ± 0.2° | 1120 (97) |
| 32.3 ± 0.2° | 1013 (92) |
| 34.0 ± 0.2° | 380 (56) |
| 34.9 ± 0.2° | 1948 (127) |
| 35.4 ± 0.2° | 750 (79) |

TABLE 12-continued

| Angle 2θ (2-theta) | Height (cps) |
|---|---|
| 35.8 ± 0.2° | 617 (72) |
| 37.6 ± 0.2° | 431 (60) |
| 39.3 ± 0.2° | 566 (69) |
| 40.2 ± 0.2° | 251 (46) |
| 41.2 ± 0.2° | 1987 (129) |
| 41.6 ± 0.2° | 1642 (117) |
| 42.0 ± 0.2° | 550 (68) |
| 43.1 ± 0.2° | 1155 (98) |
| 44.4 ± 0.2° | 507 (65) |

Table 13 provides select powder X-ray diffraction (PXRD) diffractogram peak positions at 2θ, DSC and TGA data for (2R,3R,11bR)-3-(2,2-dimethylpropyl)-10-methoxy-9-(3,3,3-trifluoropropoxy)-1H,2H,3H,4H,6H,7H,11bH-pyrido[2,1-a]isoquinolin-2-ol (Compound 4-15) free base crystalline Form I.

TABLE 13

(2R,3R,11bR)-3-(2,2-Dimethylpropyl)-10-methoxy-9-(3,3,3-trifluoropropoxy)-1H,2H,3H,4H,6H,7H,11bH-pyrido[2,1-a]isoquinolin-2-ol (Compound 4-15)

Figure 4:
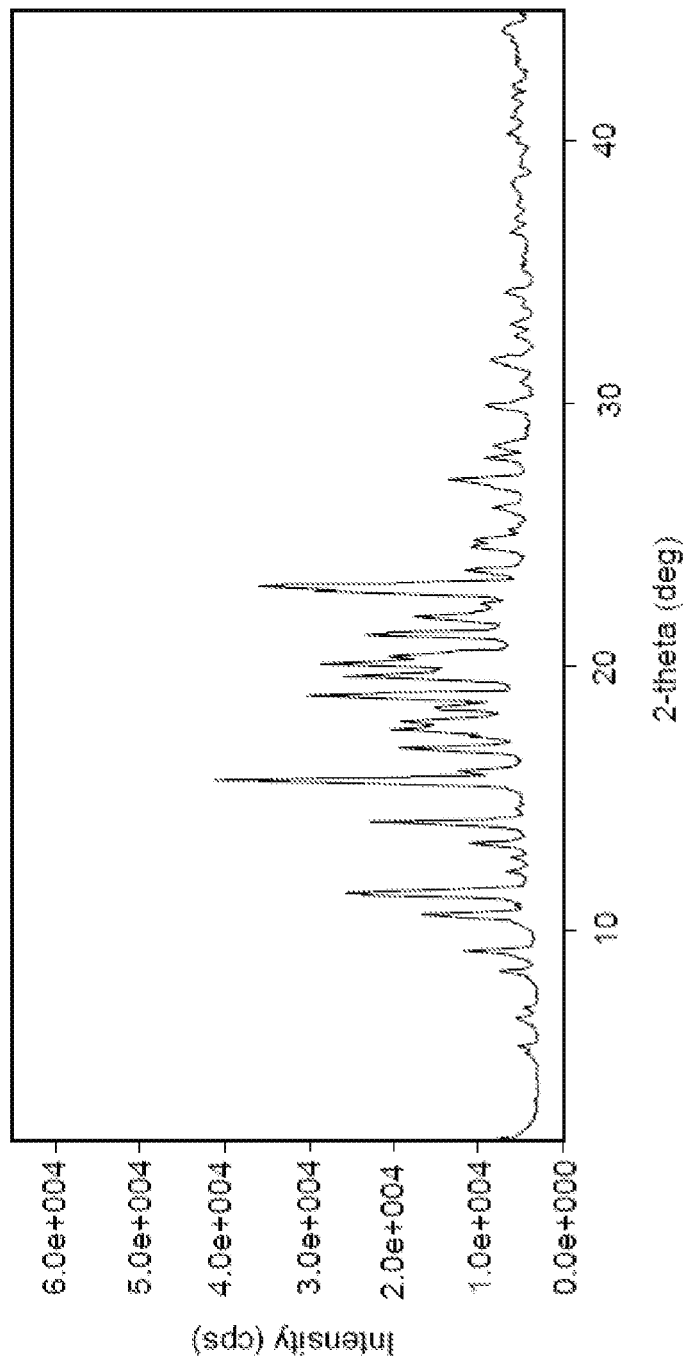
FIG. 4 shows a powder X-ray diffraction (PXRD) diffractogram of (2R,3R,11bR)-3-(2,2-dimethylpropyl)-10-methoxy-9-(3,3,3-trifluoropropoxy)-1H,2H,3H,4H,6H,7H,11bH-pyrido[2,1-a]isoquinolin-2-ol (Compound 4-15) free base crystalline Form I.
Figure 5:
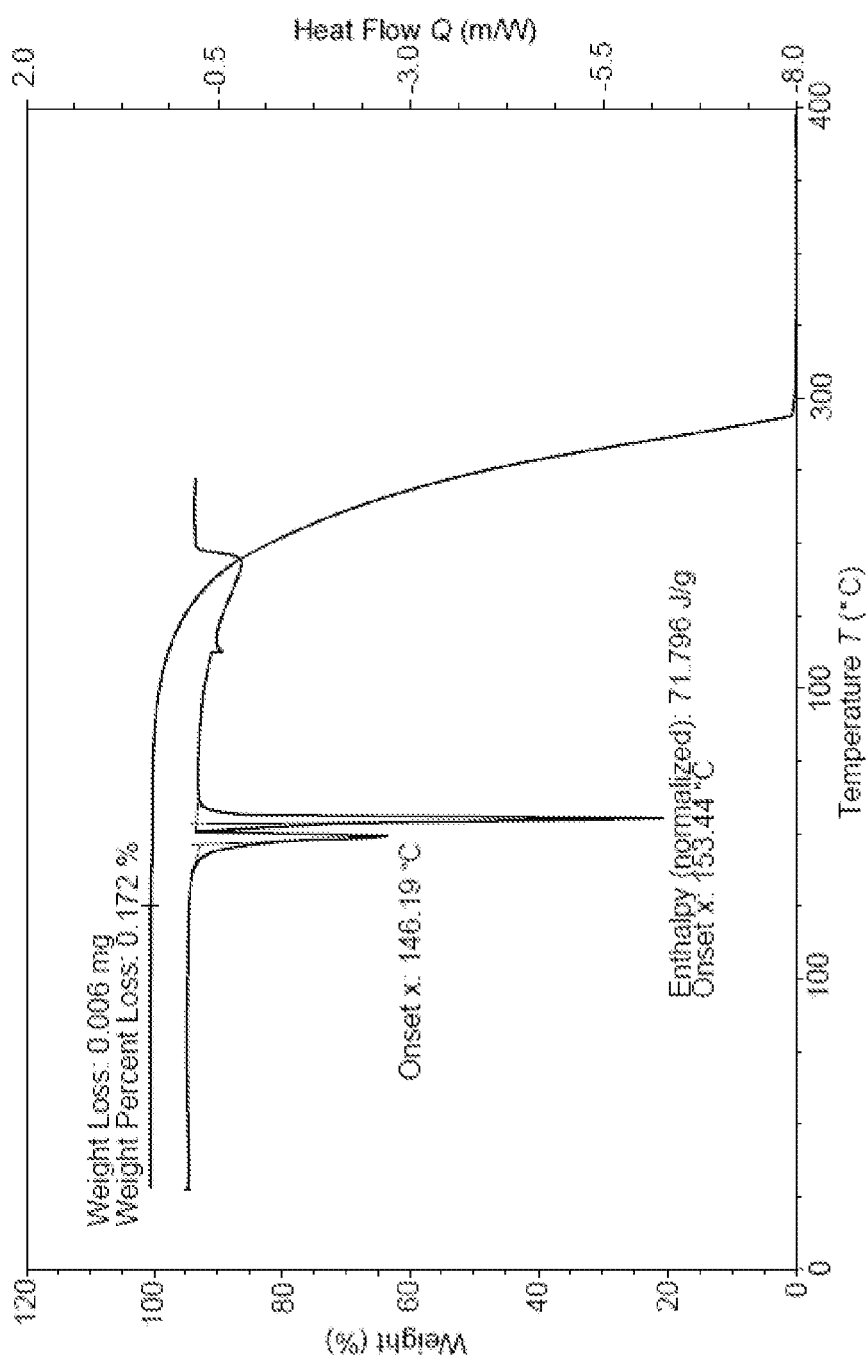
FIG. 5 shows a DSC and TGA thermogram of (2R,3R,11bR)-3-(2,2-dimethylpropyl)-10-methoxy-9-(3,3,3-trifluoropropoxy)-1H,2H,3H,4H,6H,7H,11bH-pyrido[2,1-a]isoquinolin-2-ol (Compound 4-15) free base crystalline Form I.

| PXRD | FIG. 4: Peaks at 11.4 ± 0.2°, 14.1 ± 0.2°, 15.7 ± 0.2° and 18.9 ± 0.2° 2θ |
|---|---|
| DSC | FIG. 5: Apparent onset temperature: about 146.2° C., and about 153.4° C. |
| TGA | FIG. 5: Weight percent loss: about 0.17% |

Table 14 provides powder X-ray diffraction (PXRD) diffractogram peak positions at 2θ for (2R,3R,11bR)-3-(2,2-dimethylpropyl)-10-methoxy-9-(3,3,3-trifluoropropoxy)-1H,2H,3H,4H,6H,7H,11bH-pyrido[2,1-a]isoquinolin-2-ol (Compound 4-15) free base crystalline Form I.

TABLE 14

| Angle 2θ (2-theta) | Height (cps) |
|---|---|
| 5.6 ± 0.2° | 1248 (102) |
| 6.7 ± 0.2° | 1744 (121) |
| 7.1 ± 0.2° | 1151 (98) |
| 8.4 ± 0.2° | 2630 (148) |
| 9.2 ± 0.2° | 5583 (216) |
| 10.6 ± 0.2° | 8271 (263) |
| 11.4 ± 0.2° | 13856 (340) |
| 12.3 ± 0.2° | 1809 (123) |
| 12.8 ± 0.2° | 1234 (101) |
| 13.3 ± 0.2° | 4742 (199) |
| 14.1 ± 0.2° | 12229 (319) |
| 14.6 ± 0.2° | 489 (64) |
| 15.7 ± 0.2° | 24533 (452) |
| 16.0 ± 0.2° | 4993 (204) |
| 16.9 ± 0.2° | 8830 (271) |
| 17.3 ± 0.2° | 2584 (147) |
| 17.6 ± 0.2° | 8835 (271) |
| 17.9 ± 0.2° | 8446 (265) |
| 18.5 ± 0.2° | 5690 (218) |
| 18.9 ± 0.2° | 16374 (369) |
| 19.6 ± 0.2° | 11400 (308) |
| 20.1 ± 0.2° | 13479 (335) |
| 20.4 ± 0.2° | 6903 (240) |
| 21.2 ± 0.2° | 10829 (300) |
| 21.9 ± 0.2° | 6742 (237) |
| 22.4 ± 0.2°°° | 1919 (126) |
| 22.9 ± 0.2° | 15091 (355) |
| 23.1 ± 0.2° | 19640 (405) |
| 23.7 ± 0.2° | 3951 (181) |
| 24.6 ± 0.2° | 3618 (174) |
| 24.9 ± 0.2° | 3464 (170) |
| 25.2 ± 0.2° | 957 (89) |
| 26.1 ± 0.2° | 2206 (136) |
| 27.1 ± 0.2° | 6631 (235) |

TABLE 14-continued

| Angle 2θ (2-theta) | Height (cps) |
|---|---|
| 27.9 ± 0.2° | 3317 (166) |
| 28.4 ± 0.2° | 2722 (151) |
| 29.9 ± 0.2° | 3566 (172) |
| 30.9 ± 0.2° | 794 (81) |
| 31.7 ± 0.2° | 2852 (154) |
| 32.6 ± 0.2° | 1383 (107) |
| 33.1 ± 0.2° | 1610 (116) |
| 33.8 ± 0.2° | 558 (68) |
| 34.3 ± 0.2° | 1942 (127) |
| 35.2 ± 0.2° | 418 (59) |
| 36.6 ± 0.2° | 1069 (94) |
| 37.1 ± 0.2° | 921 (88) |
| 37.7 ± 0.2° | 481 (63) |
| 38.4 ± 0.2° | 1013 (92) |
| 40.0 ± 0.2° | 675 (75) |
| 40.3 ± 0.2° | 989 (91) |
| 41.0 ± 0.2° | 563 (68) |
| 42.1 ± 0.2° | 854 (84) |
| 44.2 ± 0.2° | 1678 (118) |

Example 7: Preparation of (2R,3R,11bR)-3-(2,2-dimethylpropyl)-9,10-dimethoxy-1H,2H,3H,4H,6H,7H,11bH-pyrido[2,1-a]isoquinolin-2-ol (Compound 5-1), See FIG. 13

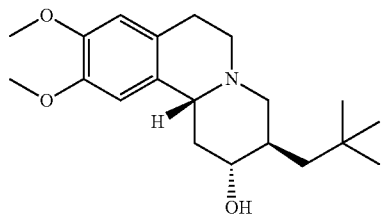

5-1

Step 1: Synthesis of (3R,11bR)-3-(2,2-dimethylpropyl)-9,10-dimethoxy-1H,2H,3H,4H,6H,7H,11bH-pyrido[2,1-a]isoquinolin-2-one (Compound 5-A (3R,11bR))

To a solution of (3R,11bR)-3-(2,2-dimethylpropyl)-9-hydroxy-10-methoxy-1H,2H,3H,4H,6H,7H,11bH-pyrido[2,1-a]isoquinolin-2-one (Compound 2-B (3R,11bR), 95 mg, 0.30 mmol, 1.0 eq) in acetone (1.5 mL) was added cesium carbonate (0.19 g, 0.60 mmol, 2.0 eq) and the resulting mixture stirred at RT for 10 min. Then, dimethyl sulfate (17 μL, 0.18 mmol, 0.6 eq) was added and the resulting mixture stirred at RT for 1 h. An additional 0.1 eq of dimethyl sulfate was added and the mixture was stirred an additional 30 min. The resulting suspension was filtered to remove solids and concentrated in vacuo. The crude material was re-dissolved in DCM, quenched with 1M aq. NaOH and extracted with DCM. The combined organic layers were dried over MgSO₄, filtered to remove solids, and concentrated in vacuo. Silica gel column (12 g) was loaded using DCM and run with an increasing gradient of EtOAc (0-40% over 25 min) in hexanes to provide (3R,11bR)-3-(2,2-dimethylpropyl)-9,10-dimethoxy-1H,2H,3H,4H,6H,7H,11bH-pyrido[2,1-a]isoquinolin-2-one (Compound 5-A (3R,11bR), 75 mg, 0.23 mmol, 77%).

Step 2: Synthesis of (2R,3R,11bR)-3-(2,2-dimethyl-propyl)-9,10-dimethoxy-1H,2H,3H,4H,6H,7H,11bH-pyrido[2,1-a]isoquinolin-2-ol (Compound 5-1)

To a solution of (3R,11bR)-3-(2,2-dimethylpropyl)-9,10-dimethoxy-1H,2H,3H,4H,6H,7H,11bH-pyrido[2,1-a]isoquinolin-2-one (Compound 5-A (3R,11bR), 33 mg, 0.10 mmol, 1.0 eq) in EtOH (0.6 mL) cooled to 0° C. was added sodium borohydride (7.4 mg, 0.20 mmol, 2.0 eq). The resulting mixture was stirred at 0° C. for 30 min, warmed to RT and stirred for 1 h. The mixture was diluted with DCM, washed twice with sat. aq. $K_2CO_3$ and the aqueous layer was further extracted with DCM. The combined organic layers were dried over $MgSO_4$, filtered to remove solid and concentrated in vacuo. Silica gel column (12 g) was loaded using DCM and run with an increasing gradient of EtOAc (0-60%) in hexanes over 15 min to provide (2R,3R,11bR)-3-(2,2-dimethylpropyl)-9,10-dimethoxy-1H,2H,3H,4H,6H,7H,11bH-pyrido[2,1-a]isoquinolin-2-ol (Compound 5-1, 20 mg, 0.06 mmol, 60%) as a white solid. 10 mg was dissolved in MeOH (1 mL) and submitted for additional purification by preparative HPLC. $^1$H NMR (400 MHz, DMSO-d$_6$): δ (ppm) 6.72 (s, 1H), 6.64 (s, 1H), 4.55 (d, J=6.4 Hz, 1H), 3.72 (s, 3H), 3.71 (s, 3H), 3.13-3.05 (m, 1H), 3.01 (d, J=11.2 Hz, 1H), 2.95 (dd, J=11.8, 4.2 Hz, 1H), 2.91-2.82 (m, 2H), 2.58-2.54 (m, 1H), 2.48-2.43 (m, 1H), 2.33-2.25 (m, 1H), 1.93 (t, J=11.4 Hz, 1H), 1.70 (d, J=12.8 Hz, 1H), 1.48-1.39 (m, 1H), 1.25 (q, J=12.8 Hz, 1H), 0.91 (s, 9H), 0.81 (dd, J=13.6, 7.6 Hz, 1H). The observed (Obs) ion m/z ratio for Compound 5-1 was 334.2.

Example 8: Preparation of (2S,3S,11bS)-3-(2,2-dimethylpropyl)-9,10-dimethoxy-1H,2H,3H,4H,6H,7H,11bH-pyrido[2,1-a]isoquinolin-2-ol (Compound 5-3), See FIG. 13

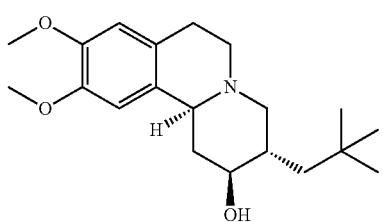

5-3

Step 1: Synthesis of (3S,11bS)-3-(2,2-dimethylpropyl)-9,10-dimethoxy-1H,2H,3H,4H,6H,7H,11bH-pyrido[2,1-a]isoquinolin-2-one (Compound 5-A (3S,11bS))

Figure 13:
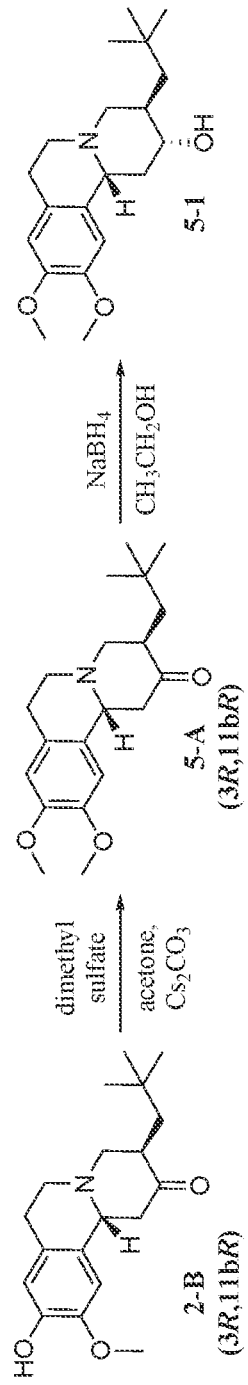
FIG. 13 shows a representative reaction scheme used in the preparation of (2R,3R,11bR)-3-(2,2-dimethylpropyl)-9,10-dimethoxy-1H,2H,3H,4H,6H,7H,11bH-pyrido[2,1-a]isoquinolin-2-ol (Compound 5-1), see Example 7; and a representative reaction scheme used in the preparation of (2S,3S,11bS)-3-(2,2-dimethylpropyl)-9,10-dimethoxy-1H,2H,3H,4H,6H,7H,11bH-pyrido[2,1-a]isoquinolin-2-ol (Compound 5-3), see Example 8; both reactions utilize dimethyl sulfate as the methylating agent and sodium borohydride as the reducing agent.
Figure 13:
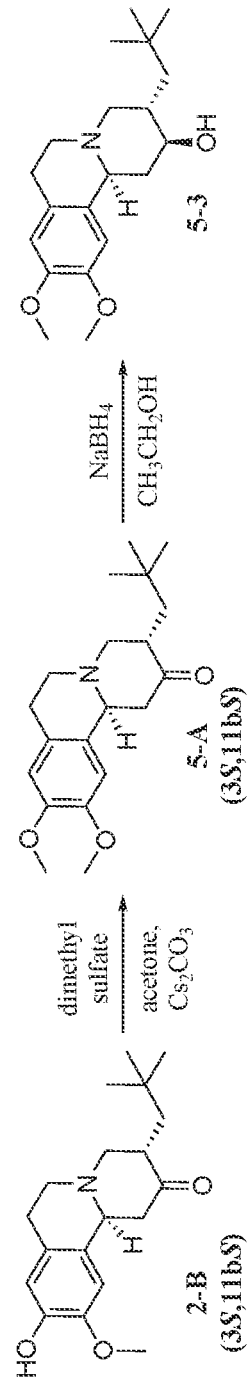

Compound 5-A (3S,11bS) was prepared according to the same procedure used to prepare Compound 5-A (3R,11bR) (see Example 7, Step 1) using Compound 2-B (3S,11bS) in place of Compound 2-B (3R,11bR), see FIG. 13.

Step 2: Synthesis of (2S,3S,11bS)-3-(2,2-dimethyl-propyl)-9,10-dimethoxy-1H,2H,3H,4H,6H,7H,11bH-pyrido[2,1-a]isoquinolin-2-ol (Compound 5-3)

Compound 5-3 was prepared according to the same procedure used to prepare Compound 5-1 (see Example 7, Step 2) using Compound 5-A (3S,11bS) in place of Compound 5-A (3R,11bR). The observed (Obs) ion m/z ratio for Compound 5-3 was 334.2.

Figure 14:
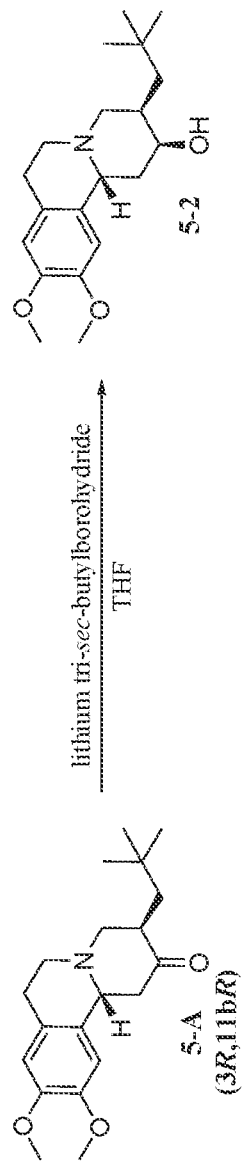
FIG. 14 shows a representative reduction reaction used in the preparation of (2S,3R,11bR)-3-(2,2-dimethylpropyl)-9,10-dimethoxy-1H,2H,3H,4H,6H,7H,11bH-pyrido[2,1-a]isoquinolin-2-ol (Compound 5-2), see Example 9; and a representative reduction reaction used in the preparation of (2R,3S,11bS)-3-(2,2-dimethylpropyl)-9,10-dimethoxy-1H,2H,3H,4H,6H,7H,11bH-pyrido[2,1-a]isoquinolin-2-ol (Compound 5-4), see Example 10; both reactions utilize lithium tri-sec-butylborohydride as the reducing agent in THF.
Figure 14:
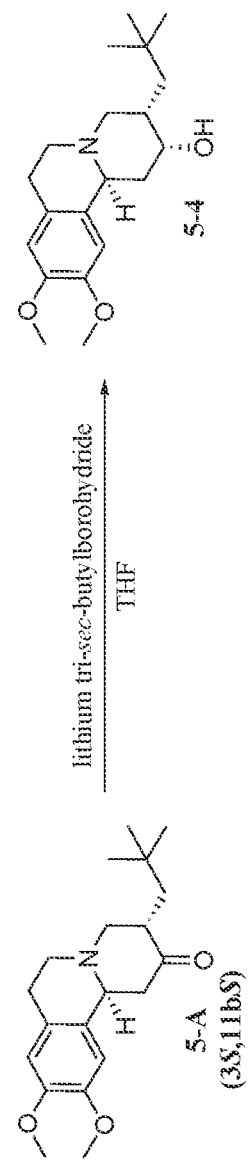
Figure 17:
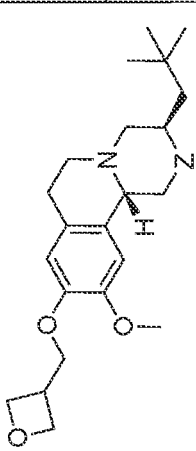
FIG. 17 shows the VMAT2 $K_i$ values (nM) between compounds provided herein (i.e., Compound 4-22, Compound 4-26, and Compound 4-28) and comparator compounds (i.e., Compound 4-22C, Compound 4-26C, and Compound 4-28C).
Figure 17:
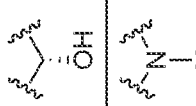
Figure 17:
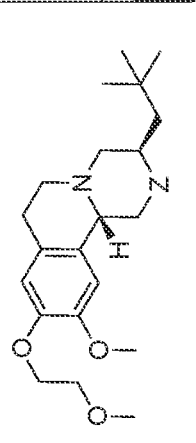
Figure 19:
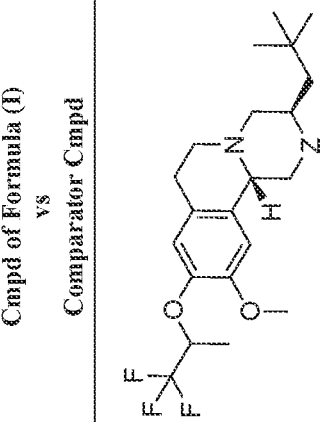
FIG. 19 shows the VMAT2 $K_i$ values (nM) between compounds provided herein (i.e., Compound 4-39 and Compound 5-1) and comparator compounds (i.e., Compound 4-39C and Compound 5-1C).
Figure 19:
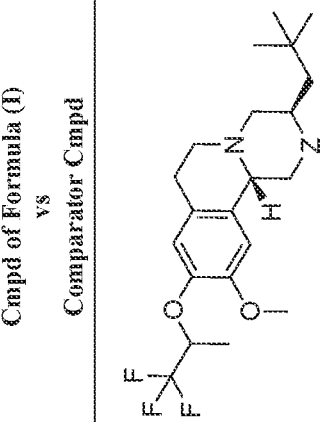
Figure 19:
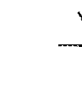
Figure 19:
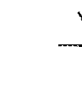
Figure 19:
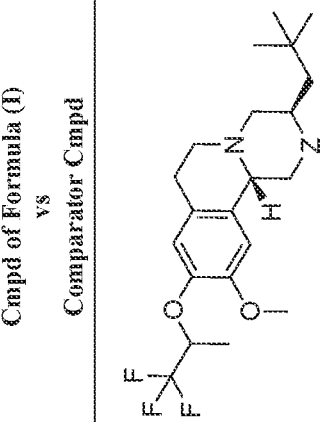
Figure 19:
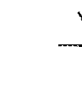

Example 9: Preparation of (2S,3R,11bR)-3-(2,2-dimethylpropyl)-9,10-dimethoxy-1H,2H,3H,4H,6H,7H,11bH-pyrido[2,1-a]isoquinolin-2-ol (Compound 5-2), See FIG. 14

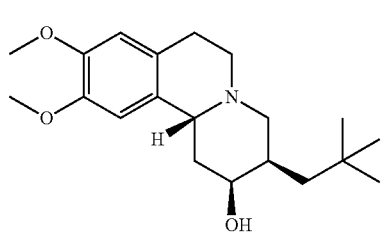

5-2

A solution of (3R,11bR)-3-(2,2-dimethylpropyl)-9,10-dimethoxy-1H,2H,3H,4H,6H,7H,11bH-pyrido[2,1-a]isoquinolin-2-one (Compound 5-A (3R,11bR), 27 mg, 0.08 mmol, 1.0 eq) in THF (0.6 mL) was prepared and cooled to 0° C. Then, lithium tri-sec-butylborohydride (1M THF, 0.16 mL, 0.16 mmol, 2.0 eq) was added dropwise. The excess reagent was quenched with water. The resulting aqueous mixture was extracted with DCM. The combined organic layers were dried over $MgSO_4$, filtered to removed solids and concentrated in vacuo. Silica gel column (4 g) was loaded using DCM and run with an increasing gradient of EtOAc in hexanes to provide (2S,3R,11bR)-3-(2,2-dimethylpropyl)-9,10-dimethoxy-1H,2H,3H,4H,6H,7H,11bH-pyrido[2,1-a]isoquinolin-2-ol (Compound 5-2, 17 mg, 0.05 mmol, 63%). $^1$H NMR (400 MHz, DMSO-d$_6$): δ (ppm) 6.64 (s, 1H), 6.63 (s, 1H), 4.46 (d, J=4.0 Hz, 1H), 3.84-3.80 (m, 1H), 3.70 (s, 6H), 3.38 (d, J=11.2 Hz, 1H), 2.94-2.83 (m, 2H), 2.56-2.46 (m, 2H), 2.41-2.26 (m, 3H), 1.72-1.65 (m, 1H), 1.50-1.43 (m, 2H), 0.90 (s, 9H), 0.84 (dd, J=14.2, 4.6 Hz, 1H). The observed (Obs) ion m/z ratio for Compound 5-2 was 334.2.

Example 10: Preparation of (2R,3S,11bS)-3-(2,2-dimethylpropyl)-9,10-dimethoxy-1H,2H,3H,4H,6H,7H,11bH-pyrido[2,1-a]isoquinolin-2-ol (Compound 5-4), See FIG. 14

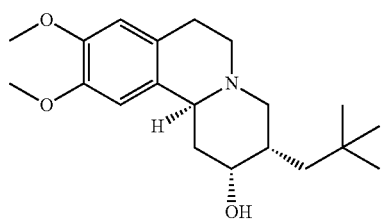

5-4

(2R,3S,11bS)-3-(2,2-Dimethylpropyl)-9,10-dimethoxy-1H,2H,3H,4H,6H,7H,11bH-pyrido[2,1-a]isoquinolin-2-ol (Compound 5-4) was prepared according to the same procedure to prepare Compound 5-2 (see Example 9) using Compound 5-A (3S,11bS) in place of Compound 5-A (3R,11bR). The observed (Obs) ion m/z ratio for Compound 5-4 was 334.2.

Example 11: Methods for Determining VMAT2 Inhibitory Activity of a Compound

Examples of techniques for determining the capability of a compound to inhibit VMAT2 are provided below. The procedure was adapted from that described previously (see, e.g., Near, (1986), Mol. Pharmacol. 30: 252-57; Teng, et al., J. Neurochem. 71, 258-65, 1998). Homogenates from human platelets were prepared by homogenization and then washed by centrifugation as described previously (see, e.g., Hoare et al., (2003) Peptides 24:1881-97).

The human VMAT2 Ki values for the compounds listed in Table 15A and Table 15B were determined using the following procedures. Compound dilution series in DMSO were generated from either powder stocks by hand, or from DMSO stocks using serial dilution on a Vantage (Hamilton), or direct dilution using an Echo 655 (Beckman). In a total volume of 0.145 to 0.150 mL in low-binding 96-well plates (Corning #3605), twelve concentrations of test compound were competed against 10 nM $^3$H-dihydrotetrabenezine (American Radiolabeled Chemicals) on human platelet homogenate (30 μg membrane protein per well) in VMAT2 binding buffer (Dulbecco's phosphate buffered saline, 1 mM EDTA, pH 7.4). Following incubation at 25° C. for 90 minutes, bound radioligand was collected by rapid filtration onto either GF/B or GF/C glass fiber filters, pretreated with 0.100 polyethylenimine, using either a Unifilter-96 Harvester (PerkinElmer) or Microlab Star (Hamilton). Following harvesting the filter plates were washed with 0.8 mL VMAT2 binding buffer, and bound radioligand was quantified by scintillation counting using a Topcount NXT or Microplate Counter Microbeta (PerkinElmer). Data from 12-point concentration response curves were analyzed to calculate an $IC_{50}$ using a four-parameter logistic regression algorithm, where top was constrained to 100 and bottom was constrained to 0. The Ki value for each compound was calculated using the Cheng-Prusoff equation, utilizing a Kd of 2.5 nM or 4.06 nM for $^3$H-dihydrotetrabenezine, depending on the batch of platelets and radiolabel used in each experiment.

Compound $K_i$ (nM) values are provided in Table 15A and Table 15B.

TABLE 15A

| Cmpd. No. | VMAT2 $K_i$ (nM) |
| --- | --- |
| 4-1 | 2.4 |
| 4-2 | 467 |
| 4-3 | 152 |
| 4-4 | 170 |
| 4-5 | 135 |
| 4-6 | 860 |
| 4-7 | 539 |
| 4-8 | 597 |
| 4-9 | 277 |
| 4-10 | 15 |
| 4-11 | 14 |
| 4-12 | 3.4 |
| 4-13 | 2.2 |
| 4-14 | 2.6 |
| 4-15 | 1.1 |
| 4-16 | 22 |
| 4-17 | 1.1 |
| 4-18 | 5.5 |
| 4-19 | 8.1 |
| 4-20 | 336 |
| 4-21 | 28 |
| 4-22 | 14 |
| 4-23 | 0.41 |
| 4-24 | 35 |
| 4-25 | 5.5 |
| 4-26 | 14 |
| 4-27 | 1.0 |
| 4-28 | 0.48 |
| 4-29 | 83 |
| 4-30 | 12 |
| 4-31 | 1.6 |
| 4-32 | 0.59 |
| 4-33 | >10,000 |
| 4-34 | >10,000 |
| 4-35 | >10,000 |
| 4-36 | 51 |
| 4-37 | >10,000 |
| 4-38 | 3.7 |
| 4-39 | 12 |
| 4-40 | 1.4 |
| 4-41 | 238 |
| 4-42 | 35 |
| 4-43 | 4.8 |
| 4-44 | 2.4 |
| 4-45 | 7.3 |
| 4-46 | 25 |
| 4-47 | 15 |
| 4-48 | 313 |
| 4-49 | 20 |
| 4-50 | 1.4 |
| 4-51 | 9.4 |
| 4-52 | 2.5 |
| 4-53 | 12 |
| 4-54 | 12 |
| 4-55 | 4.8 |
| 5-1 | 6.6 |
| 5-2 | 50 |
| 5-3 | 700 |
| 5-4 | >10,000 |

TABLE 15B

| Cmpd. No. | VMAT2 $K_i$ (nM) |
| --- | --- |
| 4-56 | 0.52 |
| 4-57 | 0.93 |
| 4-58 | 1.1 |
| 4-59 | 1.5 |
| 4-60 | 3.1 |
| 4-61 | 3.5 |
| 4-62 | 3.7 |
| 4-63 | 4.2 |
| 4-64 | 5.5 |
| 4-65 | 8.7 |
| 4-66 | 10 |
| 4-67 | 14 |
| 4-68 | 29 |
| 4-69 | 32 |
| 4-70 | 36 |
| 4-71 | 37 |
| 4-72 | 51 |
| 4-73 | 51 |
| 4-74 | 65 |
| 4-75 | 76 |
| 4-76 | 82 |
| 4-77 | 85 |
| 4-78 | 92 |
| 4-79 | 99 |
| 4-80 | 133 |
| 4-81 | 177 |
| 4-82 | 198 |
| 4-83 | 207 |
| 4-84 | 272 |
| 4-85 | 276 |
| 4-86 | 287 |
| 4-87 | 650 |

TABLE 15B-continued

| Cmpd. No. | VMAT2 $K_i$ (nM) |
|---|---|
| 4-88 | 0.68 |
| 4-89 | 140 |
| 4-90 | 0.29 |
| 4-91 | 28 |
| 4-92 | 51 |
| 4-93 | 281 |
| 4-94 | 387 |
| 4-95 | >10,000 |
| 4-96 | >10,000 |
| 4-97 | >10,000 |
| 4-98 | NT |
| 4-99 | NT |
| 4-100 | NT |
| 4-101 | NT |
| 4-102 | NT |
| 4-103 | NT |
| 4-104 | NT |
| 4-105 | NT |
| 4-106 | NT |
| 4-107 | NT |
| 4-108 | NT |
| 4-109 | NT |
| 4-110 | NT |
| 4-111 | NT |
| 4-112 | NT |
| 4-113 | NT |
| 4-114 | 70 |
| 4-115 | 6.1 |
| 4-116 | 56 |
| 4-117 | 2.2 |
| 4-118 | 13 |
| 4-119 | 0.29 |
| 4-120 | 1.5 |
| 4-121 | 0.82 |

NT = Not Tested

FIG. 15 to FIG. 21 provide VMAT2 $K_i$ (nM) values for representative compounds of Formula (I) and comparator compounds. The VMAT2 $K_i$ values were determined according to Example 11. The comparator compounds were prepared as described in Intl. Pub. No. WO 2018/195121 A1, which is incorporated herein by reference in its entirety. Representative compounds of Formula (I) are more potent than the comparator compounds in terms of VMAT2 $K_i$ values (e.g., 4.1-times to 20.9-times).

Figure 22:
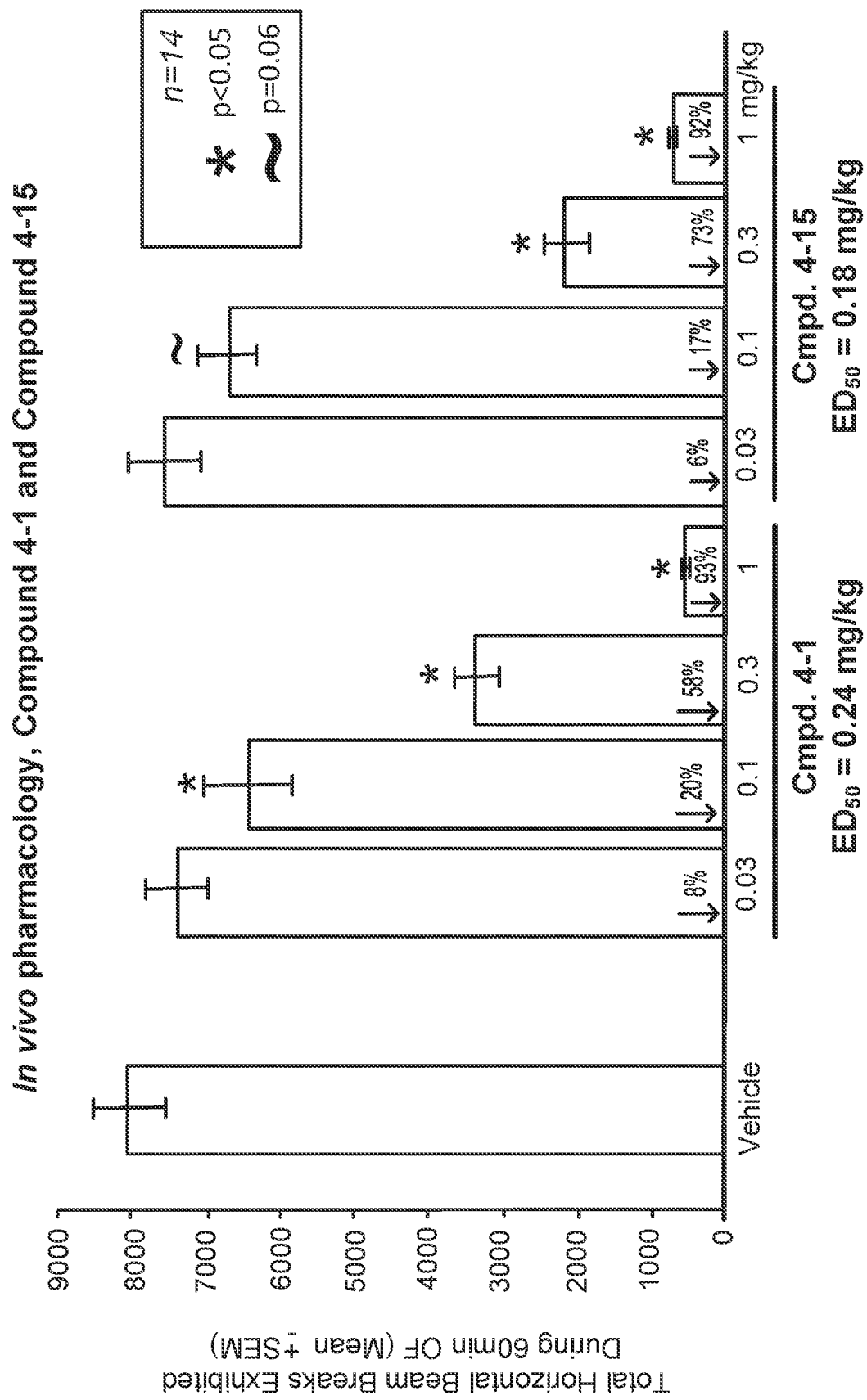
FIG. 22 shows in vivo pharmacology in Sprague Dawley rats for Compound 4-1 and Compound 4-15 in the Open Field Hypolocomotion model as described in Example 12.
Figure 23:
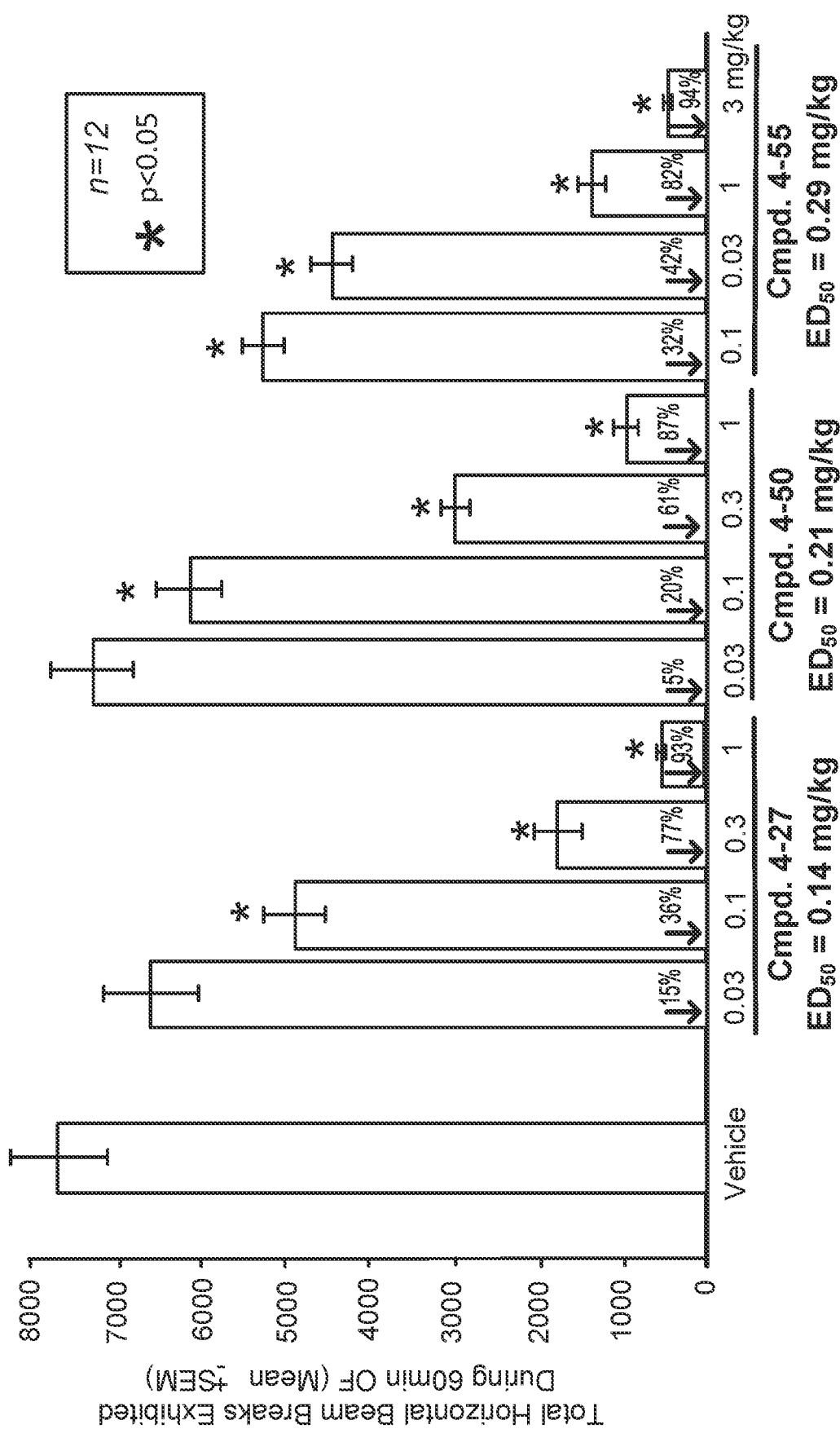
FIG. 23 shows in vivo pharmacology in Sprague Dawley rats for Compound 4-27, Compound 4-50, and Compound 4-55 in the Open Field Hypolocomotion model as described in Example 12.
Figure 24:
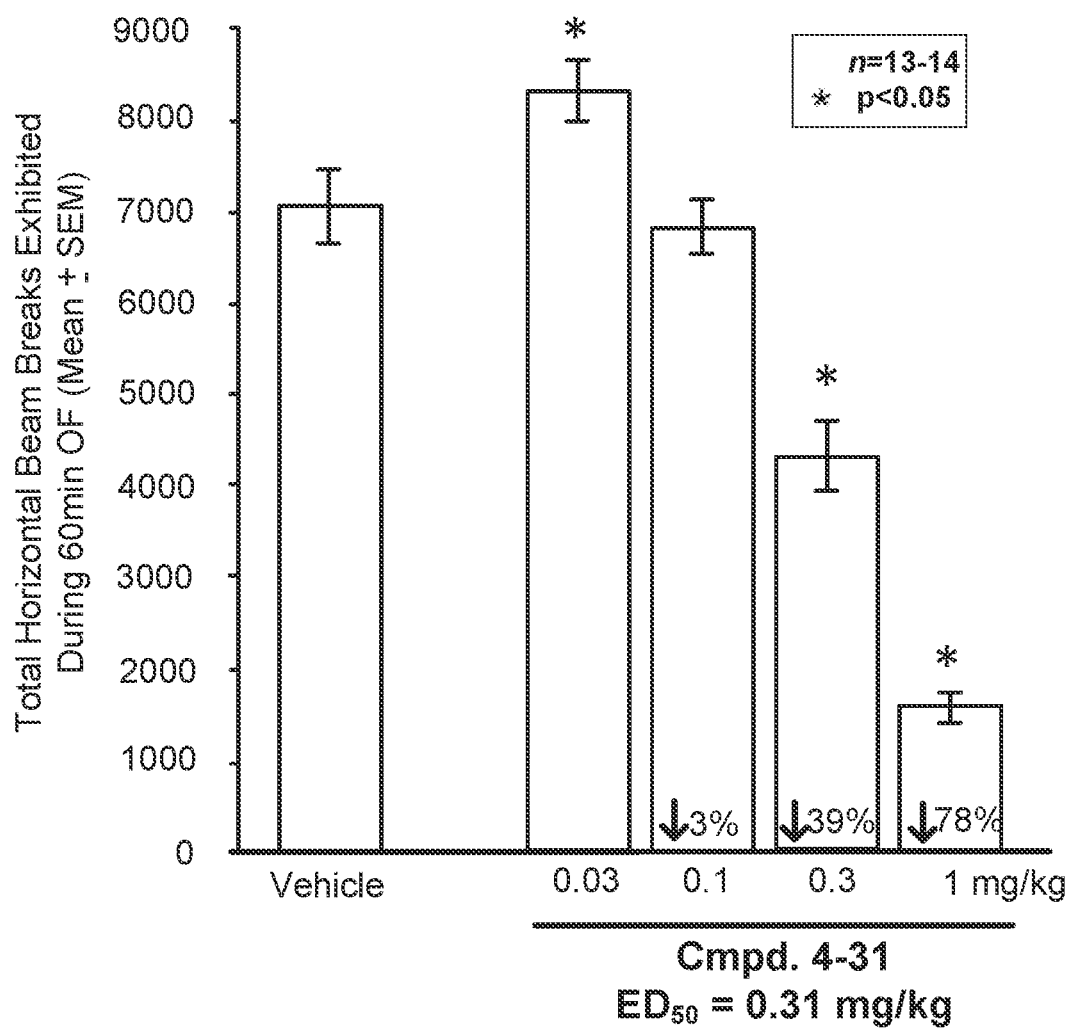
FIG. 24 shows in vivo pharmacology in Sprague Dawley rats for Compound 4-31 in the Open Field Hypolocomotion model as described in Example 12.

Example 12: VMAT2 Inhibitor-Induced Reduction of Open-Field Hypolocomotor Activity The effect of VMAT2 inhibitors on dopamine depletion was measured using the locomotor activity (LMA) assay. Following a pre-treatment time of 60 or 120 minutes, male Sprague-Dawley rats (200-250 g) were placed in a clear cage surrounded by photocell detectors (San Diego Instruments). Rat locomotor activity was detected by breaks in the photocell beams and activity is defined as the number of beam breaks in 30 min. Data was analyzed by one-way analysis of variance (ANOVA; SigmaStat version 3.0.1, SPSS, Chicago, Ill.) followed by the Student Newman Keuls post-hoc test for significance. The $ED_{50}$ was calculated for Compound 4-1 (0.24 mg/kg, see FIG. 22), Compound 4-15 (0.18 mg/kg, see FIG. 22), Compound 4-27 (0.14 mg/kg, see FIG. 23), Compound 4-31 (0.31 mg/kg, see FIG. 24), Compound 4-50 (0.21 mg/kg, see FIG. 23), and Compound 4-55 (0.29 mg/kg, see FIG. 23).

Example 13A: Conditioned Avoidance Response Assay of Antipsychotic Activity

The conditioned avoidance response (CAR) test has been shown to be an effective and reliable preclinical model for assessing the antipsychotic activity of compounds. In the CAR paradigm, a rat is trained in a two-chamber shuttle box to respond to a conditioned stimulus (auditory) by negative reinforcement. If the animal fails to move to the other chamber upon presentation of an auditory stimulus, a mild foot shock is applied to the side where the rat is located. The rat learns to avoid the mild foot shock by moving to the other chamber upon initiation of the auditory signal, termed a conditioned avoidance response. Crossing to the other chamber during administration of the shock is termed an escape response. If a rat fails to move to the other chamber even upon administration of the foot shock, the rat is considered to have an escape failure. Numerous studies have shown that typical and atypical antipsychotic drugs selectively suppress CAR, thus making it an ideal assay to screen potential antipsychotic compounds (see, e.g., Wadenberg et al., Biobehav. Rev. (1999) 23: 851-62).

Male Wistar rats are trained every day for 3 to 4 weeks. In the training session, rats are placed in the CAR two-way shuttle box and the training period of 20 trials ensued. A trial consisted of a 10-sec presentation of an 80 dB white noise followed by a scrambled 0.6 mA foot shock lasting up to 20 sec. The inter-trial interval ranged from 20-60 sec. The rat learns to avoid shock by moving from one compartment to the other when the conditioned stimulus is presented (a conditioned avoidance response). A rat is deemed sufficiently trained if it avoided the shock when presented with the conditioned stimulus at least 19 times out of the 20 trials. Rats that do not pass these criteria are not used.

On test day, trained animals are acclimated in the test room for 30 minutes prior to testing. They were then dosed with compound and are placed in the CAR two-way shuttle box. In the test, 20 trials are performed on each rat. In each trial the conditioned stimulus is applied (10-sec presentation of 80 dB white noise), followed by the foot shock (a scrambled 0.6 mA foot shock lasting up to 20 sec). If the animal moves to the other chamber on presentation of the conditioned stimulus, it is scored as a conditioned avoidance response. If it moved upon presentation of the foot shock, it is scored as an escape. If it fails to move upon presentation of the foot shock, it is scored as an escape failure. Antipsychotic efficacy is evident by an increase in the number of escapes. Data are analyzed by analysis of variance (ANOVA) followed by post-hoc comparisons with the Bonferroni Test when appropriate. An effect is considered significant if p<0.05. Outliers defined as two standard deviations above or below the mean are detected and are removed from all analysis.

Example 13B: Conditioned Avoidance Response (CAR) Assay of Antipsychotic Activity Material and Methods Animals: Adult male Wistar rats from Envigo (Indianapolis, Ind.) were used in this study. Rats were received at approximately 150 g, assigned unique identification numbers and group housed 2-3 per cage in ventilated cages. All rats were examined, handled, and weighed prior to initiation of the study to assure adequate health and suitability. During the course of the study, 12/12 light/dark cycles were maintained. The RT was maintained between 20° C. and 23° C. with a relative humidity around 50%. Chow and water were provided ad libitum for the duration of the study. All testing was conducted during the light cycle of the rats.

Compound Formulation

Compound 4-1 (0.03, 0.1, 0.3, and 1 mg/kg) was formulated in 0.25% methyl cellulose and administered orally at a dose volume of 3 mL/kg 120 minutes prior to test.

Compound 4-15 (0.03, 0.1, 0.3, and 1 mg/kg) was formulated in 0.25% methyl cellulose and administered orally at a dose volume of 3 mL/kg 120 minutes prior to test.

Behavioral Testing—Conditioned Avoidance Response

The conditioned avoidance response (CAR) test has been shown to be a very reliable animal model for screening antipsychotic drugs (see Wadenberg & Hicks, Neuroscience and Biobehavioral Reviews, (1999) 23:851-862). In the CAR paradigm, an animal is trained to respond to a conditioned stimulus (auditory and visual) by negative reinforcement (foot shock). Numerous studies have shown that typical and atypical antipsychotic drugs selectively suppress CAR, thus making it an ideal assay to screen potential antipsychotic compounds (Wadenberg & Hicks, Neuroscience and Biobehavioral Reviews, (1999) 23:851-862).

Rats were placed in the CAR two-way shuttle box and the training period of 20 trials ensued. A trial consisted of a 10-sec presentation of an 80 dB white noise followed by a scrambled 0.6 mA foot shock lasting up to 20 sec. The inter-trial interval ranged from 20-60 sec. The rat learned to avoid shock by moving from one compartment to the other when the cue is presented. If it failed to do so, it received the foot-shock, during which it most likely crossed compartments to escape the shock. Finally, if the rat failed to leave the compartment, it endures the full 20 s foot-shock. The following measures were captured from the assay:

Avoidance response: If the rat moved from one compartment to the other during the cued-stimulus (CS) presentation. Decreased avoidance responding is the typical signature of an efficacious dose of an antipsychotic.

Escape Failure: If the rat failed to move into the other compartment during the 20-sec foot-shock.

Data Analysis

Avoidance response data were expressed as the number of avoidance responses as well as percent of avoidance responses based on the three baseline responses prior to drug test. Escape failures were expressed as the total number of failures during the test session.
Body weight and avoidance data were analyzed by analysis of variance (ANOVA) followed by Dunnett's post-hoc comparisons when appropriate. Escape failures were analyzed by Kruskal-Wallis nonparametric analysis followed by Dunn's post hoc comparisons when appropriate. Results are reported as mean SEM. An effect was considered statistically significant if $p<0.05$.

The $ED_{50}$ was calculated for Compound 4-1 (0.55 mg/kg). The $ED_{50}$ (mg/kg) was also calculated for Compound 4-15 (0.44 mg/kg). In addition, rats treated with either Compound 4-1 or Compound 4-15 were observed to display a reduction in avoidance without significant increase in escape failures at 0.3 mg/kg.

Example 14: Method to Determine Stability of Compounds in Human Liver Microsomes A test compound (0.5 µM) was incubated with pooled mixed gender liver microsomes from humans (0.5 mg/mL total protein) at 37° C. in the presence of an NADPH-generating system containing 50 mM, pH 7.4 potassium phosphate buffer, 3 mM magnesium chloride, 1 mM EDTA, 1 mM NADP, 5 mM glucose-6-phosphate, and 1 Unit/mL glucose-6-phosphate dehydrogenase. All concentrations were relative to the final incubation volume of 125 µL. Incubations were conducted at 37° C. for 0, 5, 10, 20, 40, and 60 minutes in a water bath and terminated by rapid mixing with 150 µL of ice-cold acetonitrile containing internal standard. Precipitated proteins were removed by centrifugation prior to LC-MS/MS analysis. Aliquots of the resulting supernatant fractions were analyzed by LC-MS/MS monitoring for depletion of parent compound. The resultant peak area ratio versus time data was fitted to a non-linear regression using XLfit Scientific Curve Fitting Software (IDBS Ltd., Surrey, UK) and the elimination half-life ($t_{1/2}$, min) was calculated from the slope. Pharmacokinetic parameters were predicted using the method described by Obach et al. (J. Pharmcol. Exp. Ther. 1997; 283: 46.58). Briefly, the values for intrinsic clearance were calculated from the elimination half-life data and were then scaled to represent the clearance expected in the entire animal, see Table 16 (human). Additional values calculated included predicted extraction ratio and predicted maximum bioavailability.

For very stable compounds the in vitro half-life calculated from the HLM method is maxed at 420 minutes. Accordingly, for these stable compounds the in vitro half-life is at least 420 minutes but could be greater. Further, for these stable compounds the predicted systemic clearance and scaled intrinsic clearance is at least 2.59 and 2.97 respectively but could be lower, and the predicted maximum bioavailability (%₀F) is at least 87 but could be higher.

TABLE 16

(Human LM)

| Cmpd. No. | HLM Elimination half-life ($t_{1/2}$, min) | HLM Predicted Systemic Clearance (ml/min/kg) | HLM Scaled Intrinsic Clearance (ml/min/kg) | Predicted Max. Bioavailability (% F) |
|---|---|---|---|---|
| 4-1 | ≥420 | ≤2.59 | ≤2.97 | ≥87 |
| 4-9 | ≥420 | ≤2.59 | ≤2.97 | ≥87 |
| 4-10 | 342 | 3.09 | 3.65 | 85 |
| 4-11 | ≥420 | ≤2.59 | ≤2.97 | ≥87 |
| 4-12 | ≥420 | ≤2.59 | ≤2.97 | ≥87 |
| 4-13 | ≥420 | ≤2.59 | ≤2.97 | ≥87 |
| 4-14 | ≥420 | ≤2.59 | ≤2.97 | ≥87 |
| 4-15 | 308 | 3.37 | 4.05 | 83 |
| 4-16 | ≥420 | ≤2.59 | ≤2.97 | ≥87 |
| 4-17 | 38 | 12.44 | 32.9 | 38 |
| 4-18 | 155 | 5.74 | 8.05 | 71 |
| 4-19 | 88 | 8.3 | 14.18 | 59 |
| 4-22 | 130 | 6.49 | 9.6 | 68 |
| 4-23 | 21 | 14.9 | 58.49 | 25 |
| 4-24 | 117 | 6.97 | 10.7 | 65 |
| 4-25 | 109 | 7.26 | 11.41 | 64 |
| 4-26 | 88 | 8.32 | 14.24 | 58 |
| 4-27 | ≥420 | ≤2.59 | ≤2.97 | ≥87 |
| 4-28 | 39 | 12.28 | 31.79 | 39 |
| 4-29 | ≥420 | ≤2.59 | ≤2.97 | ≥87 |
| 4-30 | ≥420 | ≤2.59 | ≤2.97 | ≥87 |
| 4-31 | ≥420 | ≤2.59 | ≤2.97 | ≥87 |
| 4-32 | 19 | 15.38 | 66.53 | 23 |
| 4-36 | 93 | 8.02 | 13.39 | 60 |
| 4-38 | 58 | 10.35 | 21.46 | 48 |
| 4-40 | 52 | 10.88 | 23.86 | 46 |
| 4-41 | 28 | 13.87 | 45.21 | 31 |
| 4-42 | 51 | 10.98 | 24.33 | 45 |
| 4-43 | 18 | 15.5 | 68.8 | 23 |
| 4-44 | 46 | 11.47 | 26.9 | 43 |
| 4-45 | 129 | 6.53 | 9.7 | 67 |
| 4-46 | 28 | 13.86 | 45.1 | 31 |
| 4-47 | ≥420 | ≤2.59 | ≤2.97 | ≥87 |
| 4-49 | ≥420 | ≤2.59 | ≤2.97 | ≥87 |
| 4-50 | ≥420 | ≤2.59 | ≤2.97 | ≥87 |
| 4-51 | ≥420 | ≤2.59 | ≤2.97 | ≥87 |
| 4-52 | ≥420 | ≤2.59 | ≤2.97 | ≥87 |

TABLE 16-continued (Human LM)

| Cmpd. No. | HLM Elimination half-life ($t_{1/2}$, min) | HLM Predicted Systemic Clearance (ml/min/kg) | HLM Scaled Intrinsic Clearance (ml/min/kg) | Predicted Max. Bioavailability (% F) |
|---|---|---|---|---|
| 4-53 | 146 | 6 | 8.57 | 70 |
| 4-54 | 164 | 5.5 | 7.59 | 73 |
| 4-55 | ≥420 | ≤2.59 | ≤2.97 | ≥87 |
| 4-56 | 10 | 17.16 | 120.93 | 14 |
| 4-57 | ≥420 | ≤2.59 | ≤2.97 | ≥87 |
| 4-58 | 208 | 4.61 | 5.99 | 77 |
| 4-59 | 50 | 11.08 | 24.82 | 45 |
| 4-60 | 37 | 12.58 | 33.93 | 37 |
| 4-61 | 30 | 13.55 | 42.02 | 32 |
| 4-62 | ≥420 | ≤2.59 | ≤2.97 | ≥87 |
| 4-63 | 29 | 13.58 | 42.33 | 32 |
| 4-64 | 33 | 13.1 | 37.96 | 35 |
| 4-65 | 227 | 4.31 | 5.5 | 78 |
| 4-66 | ≥420 | ≤2.59 | ≤2.97 | ≥87 |
| 4-67 | ≥420 | ≤2.59 | ≤2.97 | ≥87 |
| 4-68 | 196 | 4.83 | 6.37 | 76 |
| 4-69 | 80 | 8.74 | 15.51 | 56 |
| 4-70 | 110 | 7.25 | 11.37 | 64 |
| 4-71 | 33 | 13.15 | 38.38 | 34 |
| 4-72 | 80 | 8.77 | 15.62 | 56 |
| 4-73 | 119 | 6.88 | 10.48 | 66 |
| 4-74 | 36 | 12.68 | 34.62 | 37 |
| 4-75 | 104 | 7.48 | 11.94 | 63 |
| 4-76 | ≥420 | ≤2.59 | ≤2.97 | ≥87 |
| 4-77 | 156 | 5.72 | 8.01 | 71 |
| 4-78 | 195 | 4.86 | 6.41 | 76 |
| 4-79 | 212 | 4.54 | 5.88 | 77 |
| 4-88 | 44 | 11.68 | 28.05 | 42 |
| 4-90 | 8 | 17.72 | 155.72 | 11 |
| 4-91 | 63 | 9.92 | 19.7 | 50 |
| 4-92 | 49 | 11.2 | 25.46 | 44 |
| 4-114 | ≥420 | ≤2.59 | ≤2.97 | ≥87 |
| 4-115 | 133 | 6.39 | 9.38 | 68 |
| 4-116 | 57 | 10.44 | 21.84 | 48 |
| 4-117 | 11 | 16.98 | 112.26 | 15 |
| 4-118 | 189 | 4.96 | 6.6 | 75 |
| 4-119 | 9 | 17.4 | 133.88 | 13.00 |
| 4-120 | ≥420 | ≤2.59 | ≤2.97 | ≥87 |
| 4-121 | 280 | 3.64 | 4.46 | 82 |
| 5-1 | 80 | 8.77 | 15.63 | 56 |
| 5-2 | 38 | 12.39 | 32.56 | 38 |

The various embodiments described above can be combined to provide further embodiments. All U.S. patents, U.S. patent application publications, U.S. patent applications, foreign patents, foreign patent applications, and non-patent publications referred to in this specification and/or listed in the Application Data Sheet are incorporated herein by reference in their entirety. Aspects of the embodiments can be modified, if necessary, to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A compound of Formula (Ia):

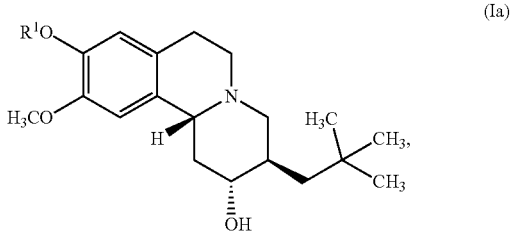

or a pharmaceutically acceptable salt thereof; wherein:

$R^1$ is:

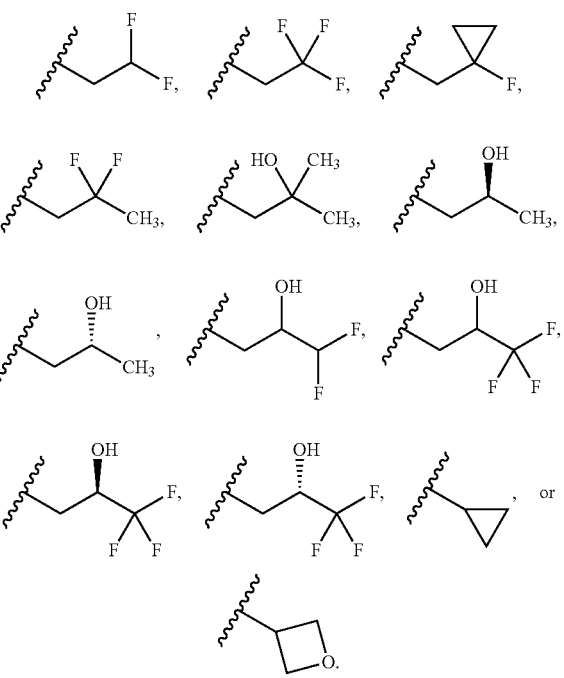

2. The compound according to claim 1, wherein the compound is:

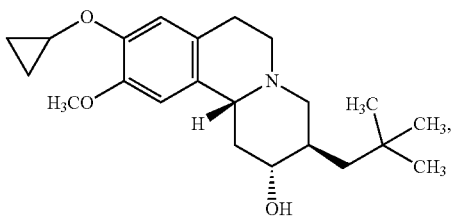

(Compound 4-27)

or a pharmaceutically acceptable salt thereof.

3. The compound according to claim 1, wherein the compound is:

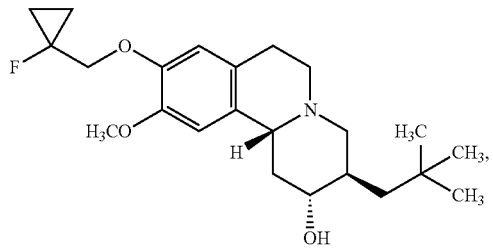

(Compound 4-31)

or a pharmaceutically acceptable salt thereof.

4. The compound according to claim 1, wherein the compound is:

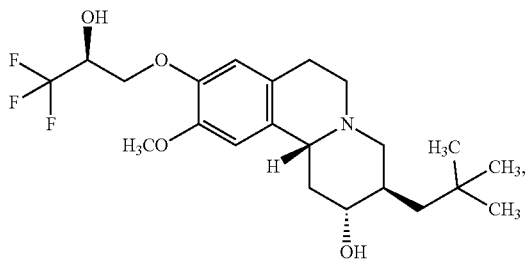

(Compound 4-50)

or a pharmaceutically acceptable salt thereof.

5. The compound according to claim 1, wherein the compound is:

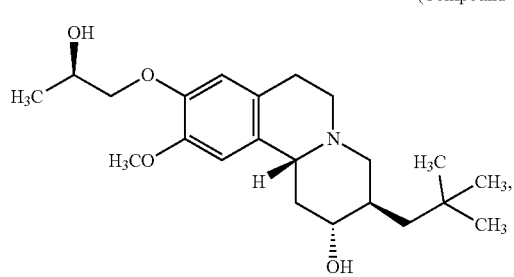

(Compound 4-55)

or a pharmaceutically acceptable salt thereof.

6. A pharmaceutical product comprising at least one pharmaceutically acceptable excipient and a compound according to claim 1, or a pharmaceutically acceptable salt thereof;
wherein the pharmaceutical product is selected from the group consisting of a kit, a pharmaceutical composition, a pharmaceutical formulation, and a pharmaceutical unit dosage form.

7. A pharmaceutical composition comprising at least one pharmaceutically acceptable excipient and a compound according to claim 1, or a pharmaceutically acceptable salt thereof.

8. A pharmaceutical composition comprising at least one pharmaceutically acceptable excipient and the compound according to claim 2, or a pharmaceutically acceptable salt thereof.

9. A pharmaceutical composition comprising at least one pharmaceutically acceptable excipient and the compound according to claim 3, or a pharmaceutically acceptable salt thereof.

10. A pharmaceutical composition comprising at least one pharmaceutically acceptable excipient and the compound according to claim 4, or a pharmaceutically acceptable salt thereof.

11. A pharmaceutical composition comprising at least one pharmaceutically acceptable excipient and the compound according to claim 5, or a pharmaceutically acceptable salt thereof.

12. A method for treating a neurological disease, a neurological disorder, a psychiatric disease, or a psychiatric disorder in a subject in need thereof, wherein the method comprises administering to the subject a compound according to claim 1, or a pharmaceutically acceptable salt thereof;
wherein the neurological disease, neurological disorder, psychiatric disease, or psychiatric disorder is selected from the group consisting of:
an agitation associated with Alzheimer's disease, an agitation associated with fragile X syndrome, an agitation associated with fragile X-associated tremor-ataxia syndrome, an autism spectrum disorder, chorea-acanthocytosis, a hyperkinetic movement disorder, a mood disorder, a neurological dysfunction associated with Lesch-Nyhan syndrome, Rett syndrome, schizoaffective disorder, schizophrenia, and treatment-refractory obsessive-compulsive disorder.

13. The method according to claim 12, wherein the neurological disease, neurological disorder, psychiatric disease, or psychiatric disorder is an autism spectrum disorder.

14. The method according to claim 13, wherein the compound is:

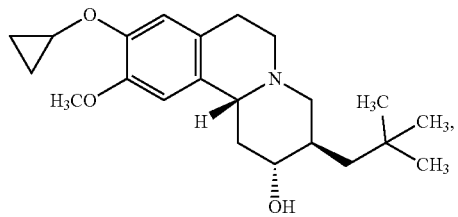

(Compound 4-27)

or a pharmaceutically acceptable salt thereof.

15. The method according to claim 13, wherein the compound is:

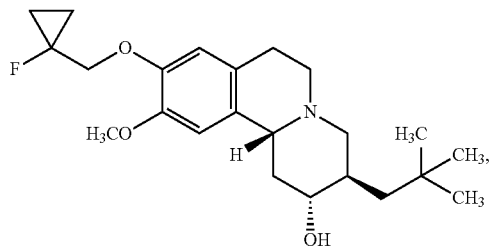

(Compound 4-31)

or a pharmaceutically acceptable salt thereof.

16. The method according to claim 13, wherein the compound is:

(Compound 4-50)

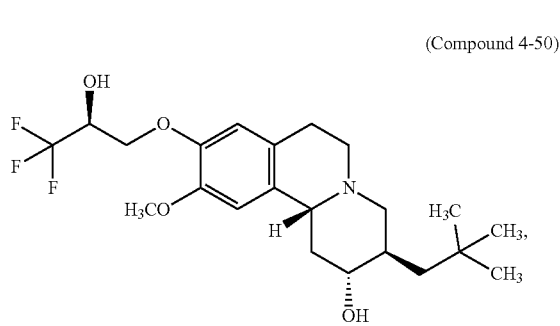 [SMILES: COc1cc2c(cc1OC[C@H](O)C(F)(F)F)CCN1C[C@@H](CC(C)(C)C)[C@H](O)C[C@H]21]

or a pharmaceutically acceptable salt thereof.

17. The method according to claim 13, wherein the compound is:

(Compound 4-55)

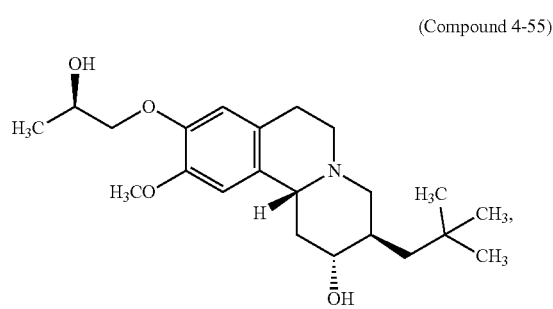 [SMILES: COc1cc2c(cc1OC[C@@H](C)O)CCN1C[C@@H](CC(C)(C)C)[C@H](O)C[C@H]21]

or a pharmaceutically acceptable salt thereof.

18. The method according to claim 12, wherein the neurological disease, neurological disorder, psychiatric disease, or psychiatric disorder is a hyperkinetic movement disorder.

19. The method according to claim 18, wherein the hyperkinetic movement disorder is tardive dyskinesia.

20. The method according to claim 19, wherein the compound is:

(Compound 4-27)

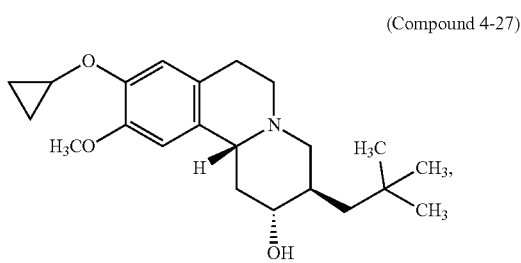 [SMILES: COc1cc2c(cc1OC1CC1)CCN1C[C@@H](CC(C)(C)C)[C@H](O)C[C@H]21]

or a pharmaceutically acceptable salt thereof.

21. The method according to claim 19, wherein the compound is:

(Compound 4-31)

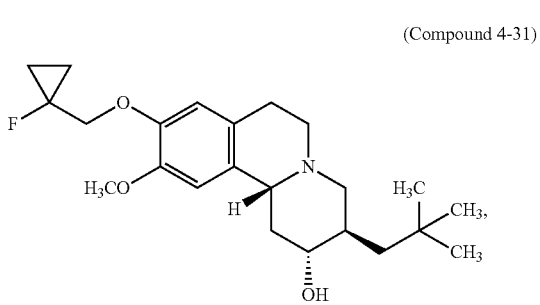 [SMILES: COc1cc2c(cc1OCC1(F)CC1)CCN1C[C@@H](CC(C)(C)C)[C@H](O)C[C@H]21]

or a pharmaceutically acceptable salt thereof.

22. The method according to claim 19, wherein the compound is:

(Compound 4-50)

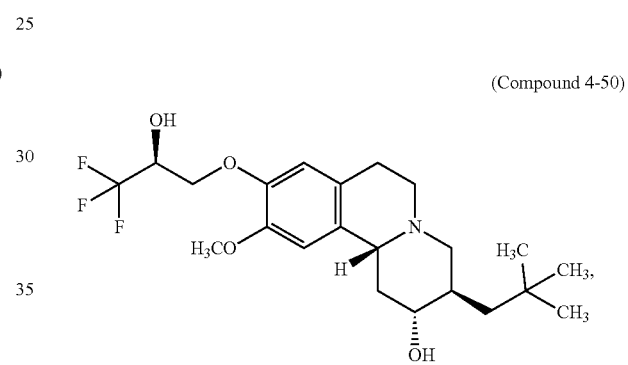

or a pharmaceutically acceptable salt thereof.

23. The method according to claim 19, wherein the compound is:

(Compound 4-55)

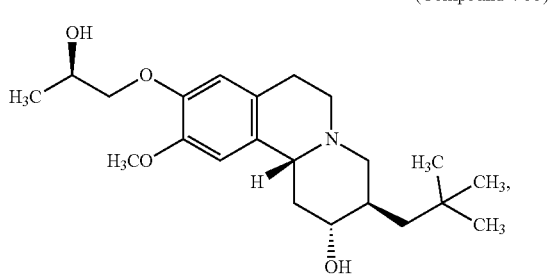

or a pharmaceutically acceptable salt thereof.

24. The method according to claim 12, wherein the neurological disease, neurological disorder, psychiatric disease, or psychiatric disorder is treatment-refractory obsessive-compulsive disorder.

25. The method according to claim 24, wherein the compound is:

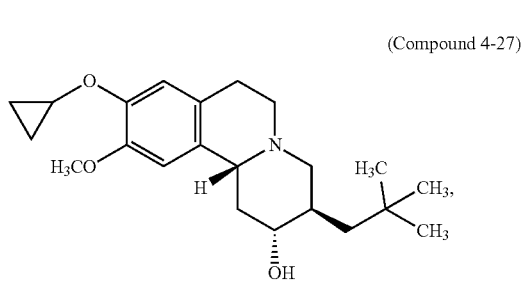 [SMILES: COc1cc2c(cc1OC1CC1)CCN1C[C@@H](CC(C)(C)C)[C@H](O)C[C@H]21]

(Compound 4-27)

or a pharmaceutically acceptable salt thereof.

26. The method according to claim 24, wherein the compound is:

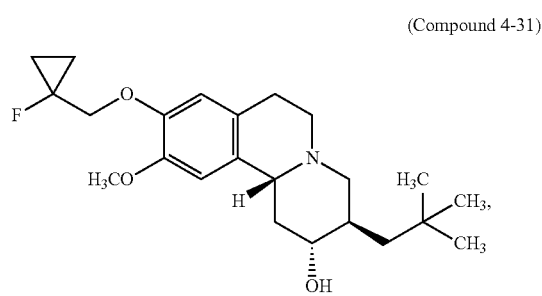 [SMILES: COc1cc2c(cc1OCC1(F)CC1)CCN1C[C@@H](CC(C)(C)C)[C@H](O)C[C@H]21]

(Compound 4-31)

or a pharmaceutically acceptable salt thereof.

27. The method according to claim 24, wherein the compound is:

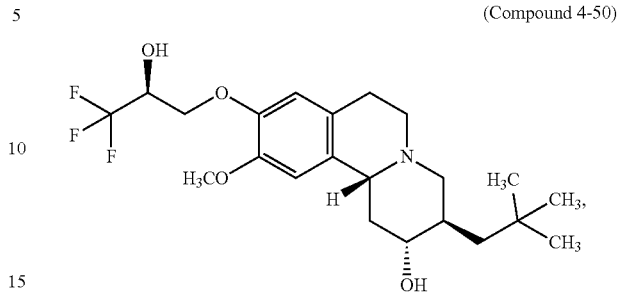

(Compound 4-50)

or a pharmaceutically acceptable salt thereof.

28. The method according to claim 24, wherein the compound is:

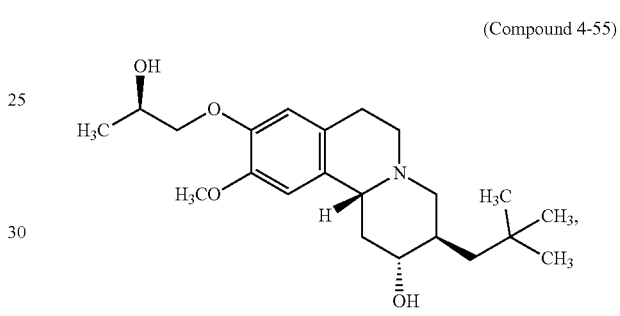

(Compound 4-55)

or a pharmaceutically acceptable salt thereof.

* * * * *